United States Patent
Bock et al.

(10) Patent No.: US 9,227,969 B2
(45) Date of Patent: Jan. 5, 2016

(54) COMPOUNDS AND COMPOSITIONS AS INHIBITORS OF MEK

(71) Applicants: Mark Gary Bock, Hatfield, PA (US); Henrik Moebitz, Freiburg (DE); Sunil Kumar Panigrahi, Odisha (IN); Ramulu Poddutoori, Karnataka (IN); Susanta Samajdar, Karnataka (IN)

(72) Inventors: Mark Gary Bock, Hatfield, PA (US); Henrik Moebitz, Freiburg (DE); Sunil Kumar Panigrahi, Odisha (IN); Ramulu Poddutoori, Karnataka (IN); Susanta Samajdar, Karnataka (IN)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/451,563

(22) Filed: Aug. 5, 2014

(65) Prior Publication Data

US 2015/0051209 A1 Feb. 19, 2015

(30) Foreign Application Priority Data

Aug. 14, 2013 (IN) ................... 2418/DEL/13
Jun. 24, 2014 (IN) ................... 1686/DEL/14

(51) Int. Cl.

| | |
|---|---|
| *C07D 471/04* | (2006.01) |
| *A61K 31/53* | (2006.01) |
| *A61K 31/4745* | (2006.01) |
| *A61K 31/506* | (2006.01) |
| *A61K 31/513* | (2006.01) |
| *A61K 31/437* | (2006.01) |
| *A61K 45/06* | (2006.01) |

(52) U.S. Cl.
CPC ............ *C07D 471/04* (2013.01); *A61K 31/437* (2013.01); *A61K 31/4745* (2013.01); *A61K 31/506* (2013.01); *A61K 31/513* (2013.01); *A61K 31/53* (2013.01); *A61K 45/06* (2013.01)

(58) Field of Classification Search
CPC ............... C07D 471/04; C07D 471/14; A61K 31/4375; A61K 31/4745
USPC ........................................... 546/81
See application file for complete search history.

(56) References Cited

U.S. PATENT DOCUMENTS

| | | | |
|---|---|---|---|
| 4,698,348 | A | 10/1987 | Gerster |
| 5,420,135 | A | 5/1995 | Brown et al. |

FOREIGN PATENT DOCUMENTS

| | | | |
|---|---|---|---|
| EP | 0 385 630 | A2 | 9/1990 |
| EP | 0 441 036 | A2 | 8/1991 |
| JP | 2004-161662 | A | 6/2004 |
| WO | 02/16370 | A1 | 2/2002 |
| WO | 03/097641 | A2 | 11/2003 |
| WO | 2005/054237 | A1 | 6/2005 |
| WO | 2005/054238 | A1 | 6/2005 |
| WO | 2005/094531 | A2 | 10/2005 |
| WO | 2006/091394 | A2 | 8/2006 |
| WO | 2006/122806 | A2 | 11/2006 |
| WO | 2007/035935 | A1 | 3/2007 |
| WO | 2007/075468 | A1 | 7/2007 |
| WO | 2007/079086 | A1 | 7/2007 |
| WO | 2008/103636 | A1 | 8/2008 |
| WO | 2010/006225 | A1 | 1/2010 |
| WO | 2012/007926 | A1 | 1/2012 |
| WO | 2012/034526 | A1 | 3/2012 |
| WO | 2013/052550 | A2 | 4/2013 |
| WO | 2013/147711 | A1 | 10/2013 |
| WO | 2013/178581 | A1 | 12/2013 |
| WO | 2015/022663 | A1 | 2/2015 |
| WO | 2015/022664 | A1 | 2/2015 |

*Primary Examiner* — Rita Desai
(74) *Attorney, Agent, or Firm* — Qian Zhang

(57) ABSTRACT

The present invention relates to compounds of formula I:

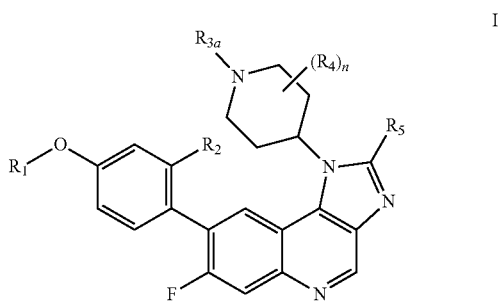

in which n, $R_1$, $R_2$, $R_{3a}$, $R_4$ and $R_5$ are defined in the Summary of the Invention; capable of inhibiting the activity of MEK. The invention further provides a process for the preparation of compounds of the invention, pharmaceutical preparations comprising such compounds and methods of using such compounds and compositions in the management of hyperproliferative diseases like cancer.

16 Claims, 1 Drawing Sheet

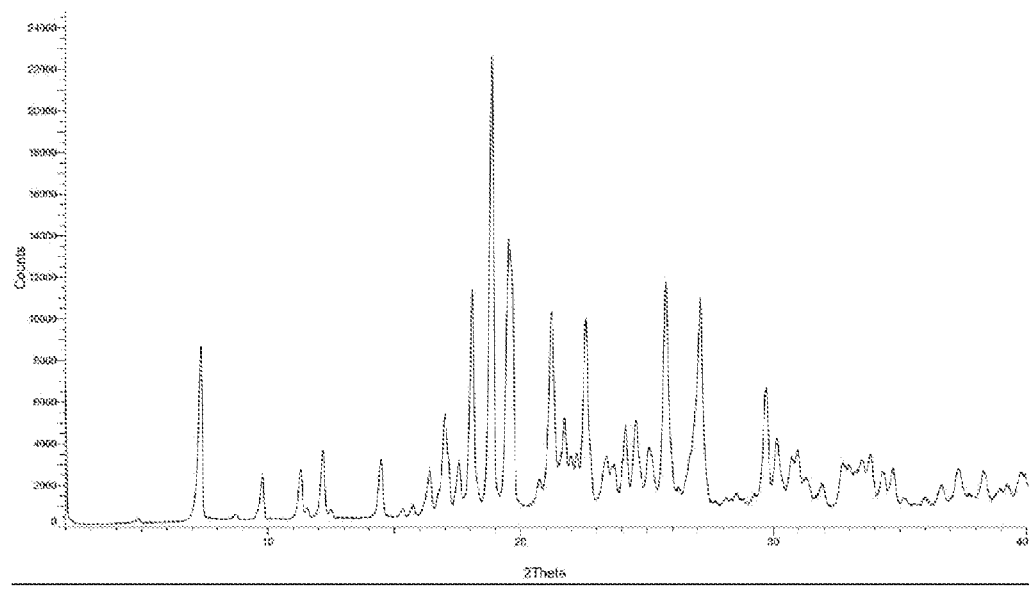

COMPOUNDS AND COMPOSITIONS AS INHIBITORS OF MEK

BACKGROUND

1. Field of the Invention

The present invention relates to compounds capable of selectively inhibiting the activity of MEK. The invention further provides a process for the preparation of compounds of the invention, pharmaceutical preparations comprising such compounds and methods of using such compounds and compositions in the management of hyperproliferative diseases like cancer and inflammation.

2. Background of the Invention

Over activation of the mitogen-activated protein (MAP) kinase cascade is known to play an important role in cell proliferation and differentiation. This pathway can be activated when a growth factor binds to its receptor tyrosine kinase. This interaction promotes RAS association with RAF and initiates a phosphorylation cascade through MEK (MAP kinase) to ERK. The only known substrates for MEK phosphorylation are the MAP kinases, ERK1 and ERK2. Phosphorylation of MEK increases its affinity and catalytic activity toward ERK as well as its affinity for ATP. Constitutive activation of the MAPK pathway has been found in a number of diseases, for example, melanoma, pancreatic, colon, lung, kidney and ovarian cancers; in particular pancreatic, colon, lung, kidney and ovarian cancers. Therefore, inhibition of this pathway, particularly inhibiting MEK activity, is known to be beneficial in treating hyperproliferative diseases.

Therefore, MEK represents a highly attractive target for the development of a novel therapy for the treatment of many forms of cancers. In particular, the need exists for small molecules that selectively inhibit the activity of MEK. The present invention fulfills this need.

SUMMARY OF THE INVENTION

In one aspect, the present invention provides compounds of formula I:

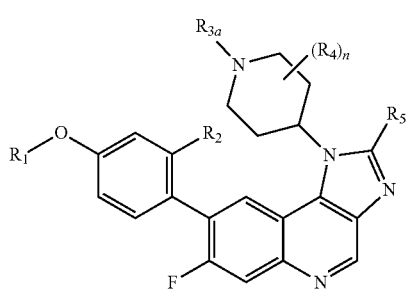

in which:
n is selected from 0, 1, 2 and 3;
$R_1$ is selected from:

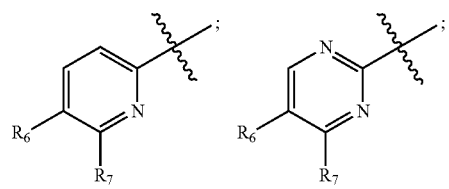

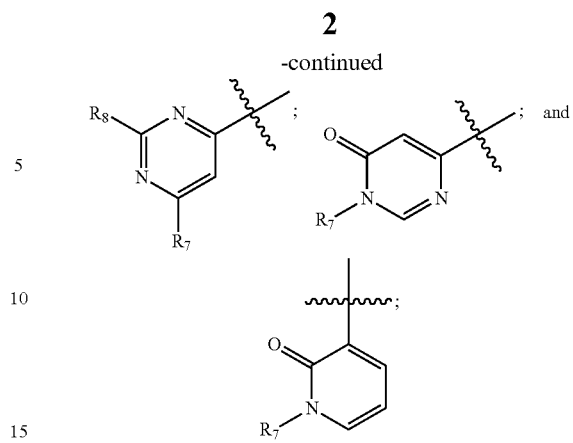

$R_2$ is selected from chloro and methoxy;
$R_{3a}$ is selected from cyano-methyl, 2-hydroxy-ethyl, 1-hydroxypropan-2-yl, 3-hydroxy-2-(hydroxy-methyl)propanoyl, 2-methoxy-ethyl, 2-fluoropropanoyl, (3-methyloxetan-3-yl)-methyl, methyl-sulfonyl, amino-carbonyl-methyl, cyclopropyl-sulfonyl, isopropyl-sulfonyl, dimethylcarbamoyl, 3-hydroxy-2-(hydroxy-methyl)propyl, 2-hydroxy-propyl, 2-hydroxyacetyl, 2-acetoxyacetyl, 2-methoxyacetyl, (2,2,2-trifluoroethyl)carbamoyl, oxetan-2-yl, 2-aminoacetyl, oxetan-3-ylmethyl, (S)-2-hydroxypropanoyl, 2-hydroxypropanoyl, acetyl, 2-amino-2-oxoethyl and carbamoyl;
$R_4$ is selected from hydrogen, halo, methyl and hydroxymethyl; and optionally two $R_4$ groups together with the carbon atoms to which they are attached form $—(CH_2)_{2-3}—$; (for example, 8-azabicyclo[3.2.1]octan-3-yl);
$R_5$ is selected from hydrogen and methyl;
$R_6$ is selected from hydrogen and halo;
$R_7$ is selected from hydrogen, fluoro, chloro, $CH_2F$, $CHF_2$, $CF_3$, $CH_2OH$, cyclopropyl and methyl; and
$R_8$ is selected from cyano.

In another aspect, the invention relates to a compound of the formula I

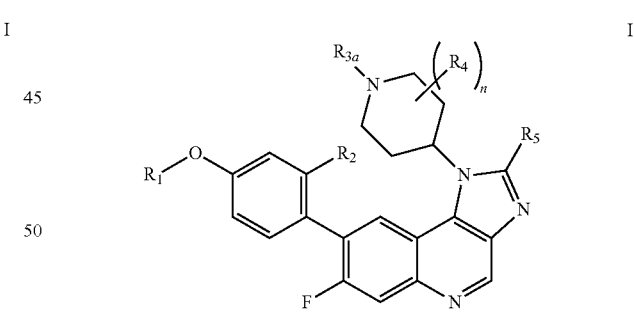

wherein
n is selected from 0, 1, 2 and 3;
$R_1$ is selected from:

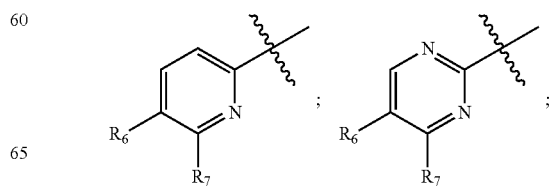

R₂ is selected from chloro, methyl, hydrogen, fluoro and methoxy;
R₃ₐ is selected from cyano-methyl, 2-hydroxy-ethyl, 1-hydroxypropan-2-yl, 3-hydroxy-2-(hydroxy-methyl)propanoyl, 2-methoxy-ethyl, 2-fluoropropanoyl, (3-methyloxetan-3-yl)-methyl, methyl-sulfonyl, amino-carbonyl-methyl, cyclopropyl-sulfonyl, isopropyl-sulfonyl, dimethylcarbamoyl, 3-hydroxy-2-(hydroxy-methyl)propyl, 2-hydroxy-propyl, 2-hydroxyacetyl, 2-acetoxyacetyl, 2-methoxyacetyl, (2,2,2-trifluoroethyl)carbamoyl, 2-aminoacetyl, oxetan-3-yl-methyl, (S)-2-hydroxypropanoyl, 2-hydroxypropanoyl, acetyl, 2-amino-2-oxoethyl, carbamoyl, (oxetan-2-yl)-methanoyl, 2-(sulfooxy)acetyl, 2-fluoroethanoyl, 3-hydroxypropanoyl, and N,N-dimethylsulfonamidyl;
each R₄ is independently selected from hydrogen, halo, methyl and hydroxy-methyl; and optionally two R₄ groups together with the carbon atoms to which they are attached form —(CH₂)₂₋₃—;
R₅ is selected from hydrogen and methyl;
R₆ is selected from hydrogen, methoxy and halo;
R₇ is selected from hydrogen, fluoro, CF₃, CH₂OH, cyclopropyl and methyl; and
R₈ is cyano;
or the pharmaceutically acceptable salts thereof.

In another aspect, the present invention provides a pharmaceutical composition which contains a compound of Formula I or a N-oxide derivative, tautomer, individual isomers and mixture of isomers thereof; or a pharmaceutically acceptable salt thereof, in admixture with one or more suitable excipients.

In another aspect, the present invention provides a method of treating a disease in an animal in which modulation of MEK activity can prevent, inhibit or ameliorate the pathology and/or symptomology of the diseases, which method comprises administering to the animal a therapeutically effective amount of a compound of Formula I or a N-oxide derivative, individual isomers and mixture of isomers thereof, or a pharmaceutically acceptable salt thereof.

In another aspect, the present invention provides the use of a compound of Formula I in the manufacture of a medicament for treating a disease in an animal in which MEK activity contributes to the pathology and/or symptomology of the disease.

In another aspect, the present invention provides a process for preparing compounds of Formula I and the N-oxide derivatives, prodrug derivatives, protected derivatives, individual isomers and mixture of isomers thereof, and the pharmaceutically acceptable salts thereof.

DEFINITIONS

The general terms used hereinbefore and hereinafter preferably have within the context of this disclosure the following meanings, unless otherwise indicated, where more general terms wherever used may, independently of each other, be replaced by more specific definitions or remain, thus defining more detailed embodiments of the invention:

"Halogen" (or "halo") preferably represents chloro or fluoro, in particular fluoro, but may also be bromo or iodo. The term "dimethylcarbamoyl" as used herein refers to "N,N-dimethylcarbamoyl" (i.e. Me₂NC(=O)—).

Compounds of formula I may have different isomeric forms. For example, any asymmetric carbon atom may be present in the (R)-, (S)- or (R,S)-configuration, preferably in the (R)- or (S)-configuration. Substituents at a double bond or especially a ring may be present in cis-(=Z—) or trans (=E—) form. The compounds may thus be present as mixtures of isomers or preferably as pure isomers, preferably as pure diastereomers or pure enantiomers.

Compounds of formula I are selective MEK inhibitors. Selectivity of the compounds for MEK is attributed to compounds of formula I contain a fluoro atom linked directly to the 1H-imidazo[4,5-c]quinolone as shown in compounds A and B below. In the absence of a fluoro group at this position, the selectivity for MEK over other kinases is reduced. For example, comparing the following compounds:

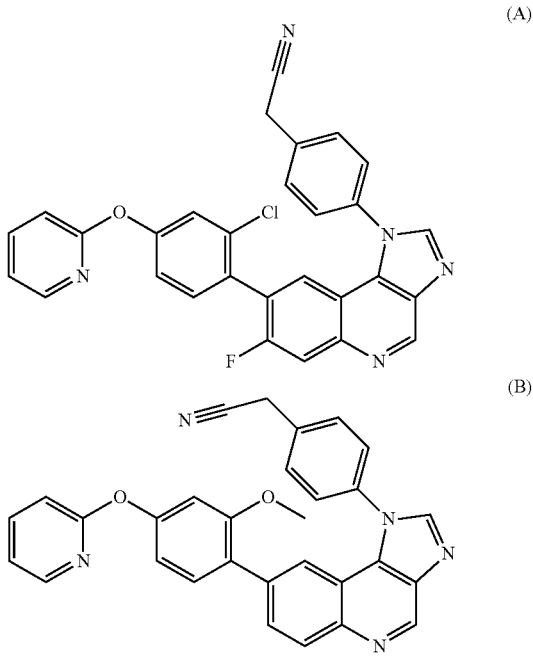

Both compounds inhibit MEK at less than 100 nM and are equipotent. However, when tested against a kinase panel, the number of kinases in the panel inhibited with an IC₅₀ of less than 100 nM is zero for compound (A) and 4 for compound (B). That is, compound (A) is selective for MEK while compound (B) is less selective for MEK. Compound (B) also inhibits ABL1, LCK, LYN and PDGFRa at an $IC_{50}$ of 20 nM, 7 nM, 30 nM and 50 nM, respectively.

A similar comparison shows that the following compounds selectively inhibit MEK and do not inhibit other kinases from the kinase panel with an $IC_{50}$ of less than 100 nM:

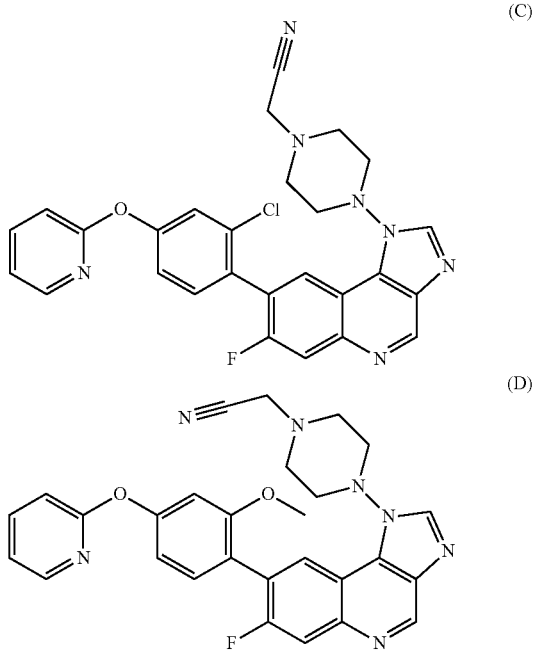

Compounds of the invention are screened, using assay conditions known in the art, against some or all of the "Kinase Panel" comprising ABL1, ABL1 (T315I), ACVR1, AKT1, ALK, AURKA, AXL, BTK, CAMK2D, CDK1B, CDK2A, CDK4D1, CSK, CSNK1G3, EGFR, EPHA4, EPHB4, ERBB4, FGFR1, FGFR2, FGFR3, FGFR3 (K650E), FGFR4, FLT3 (D835Y), IGF1R, GSK3B, INSR, IRAK4, JAK1, JAK2, JAK3, KDR, KIT, LCK, LYN, MAP3K8, MAPK1, MAPK10, MAPK14, MAPKAPK2, MAPKAPK5, MET, MKNK1, MKNK2, PAK2, PDGFRa, PDPK1, PIM2, PKN1, PKN2, PLK1, PRKACA, PRKCA, PRKCQ, RET, ROCK2, RPS6 KB1, SRC, SYK, TYK2, WNK1, ZAP70, PIKSCD, PIK3CG, MTOR, PIK3C3, PIK3CA, PIK3CB and PIK4CB.

The plural form (e.g. compounds, salts) is used, this includes the singular (e.g. a single compound, a single salt). "A compound" does not exclude that (e.g. in a pharmaceutical formulation) more than one compound of the formula I (or a salt thereof) is present, the "a" merely representing the indefinite article. "A" can thus preferably be read as "one or more", less preferably alternatively as "one".

Wherever a compound or compounds of the formula I are mentioned, this is further also intended to include N-oxides of such compounds and/or tautomers thereof.

The term "and/or an N-oxide thereof, a tautomer thereof and/or a (preferably pharmaceutically acceptable) salt thereof" especially means that a compound of the formula I may be present as such or in mixture with its N-oxide, as tautomer (e.g. due to keto-enol, lactam-lactim, amide-imidic acid or enamine-imine tautomerism) or in (e.g. equivalency reaction caused) mixture with its tautomer, or as a salt of the compound of the formula I and/or any of these forms or mixtures of two or more of such forms.

The present invention also includes all suitable isotopic variations of the compounds of the invention, or pharmaceutically acceptable salts thereof. An isotopic variation of a compound of the invention or a pharmaceutically acceptable salt thereof is defined as one in which at least one atom is replaced by an atom having the same atomic number but an atomic mass different from the atomic mass usually found in nature. Examples of isotopes that may be incorporated into the compounds of the invention and pharmaceutically acceptable salts thereof include, but are not limited to, isotopes of hydrogen, carbon, nitrogen and oxygen such as as $^{2}H$, $^{3}H$, $^{11}C$, $^{13}C$, $^{14}C$, $^{15}N$, $^{17}O$, $^{18}O$, $^{35}S$, $^{18}F$, $^{36}Cl$ and $^{123}I$. Certain isotopic variations of the compounds of the invention and pharmaceutically acceptable salts thereof, for example, those in which a radioactive isotope such as $^{3}H$ or $^{14}C$ is incorporated, are useful in drug and/or substrate tissue distribution studies. In particular examples, $^{3}H$ and $^{14}C$ isotopes may be used for their ease of preparation and detectability. In other examples, substitution with isotopes such as $^{2}H$ may afford certain therapeutic advantages resulting from greater metabolic stability, such as increased in vivo half-life or reduced dosage requirements. Isotopic variations of the compounds of the invention or pharmaceutically acceptable salts thereof can generally be prepared by conventional procedures using appropriate isotopic variations of suitable reagents.

BRIEF DESCRIPTION OF THE DRAWINGS

FIG. 1 shows the XRPD pattern for Form A of the free form of 1-((3S,4S)-4-(8-(2-chloro-4-(pyrimidin-2-yloxy)phenyl)-7-fluoro-2-methyl-1H-imidazo[4,5-c]quinolin-1-yl)-3-fluoropiperidin-1-yl)-2-hydroxyethanone.

DESCRIPTION OF PREFERRED EMBODIMENTS

The present invention relates to compounds capable of inhibiting the activity of MEK. In one embodiment, with respect to compounds of Formula I, are compounds of Formula Ia:

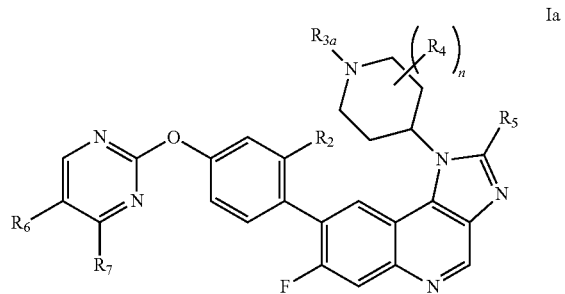

in which: $R_2$ is selected from chloro and methoxy; $R_{3a}$ is selected from 2-hydroxy-ethyl, 1-hydroxypropan-2-yl, 2-methoxy-ethyl, (3-methyloxetan-3-yl)-methyl, methylsulfonyl, 2-acetoxyacetyl, 2-fluoropropanoyl, 2-hydroxypropyl, cyclopropyl-sulfonyl, isopropyl-sulfonyl, 3-hydroxy-2-(hydroxy-methyl)propyl, 3-hydroxy-2-(hydroxymethyl)propanoyl, oxetan-2-yl, dimethylcarbamoyl, (2,2,2-trifluoroethyl)carbamoyl, (S)-2-hydroxypropanoyl, oxetan-3-ylmethyl, 2-aminoacetyl, 2-methoxyacetyl, 2-hydroxyacetyl, 2-hydroxypropanoyl, acetyl, 2-amino-2-oxoethyl and carbamoyl; $R_4$ is selected from hydrogen, methyl and hydroxy-methyl; $R_5$ is selected from hydrogen and methyl; R₆ is selected from hydrogen and fluoro; R₇ is selected from hydrogen, fluoro, chloro, $CH_2F$, $CHF_2$, $CF_3$, $CH_2OH$, cyclopropyl and methyl; and R₈ is selected from cyano; or the pharmaceutically acceptable salts thereof.
In an further embodiment are compounds or pharmaceutically acceptable salts thereof, selected from:
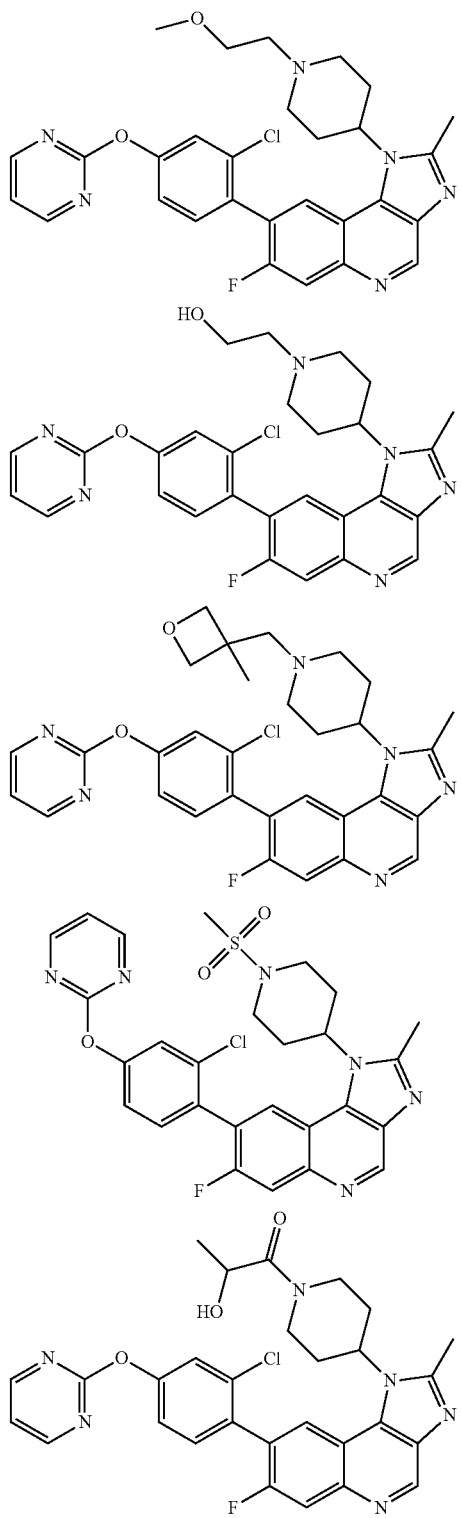
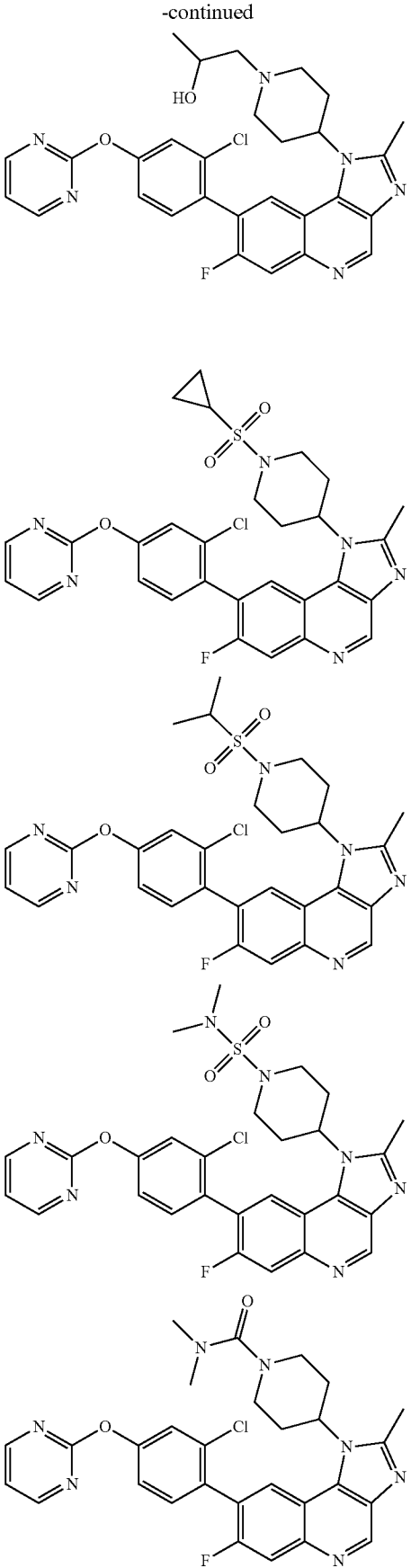

9
-continued
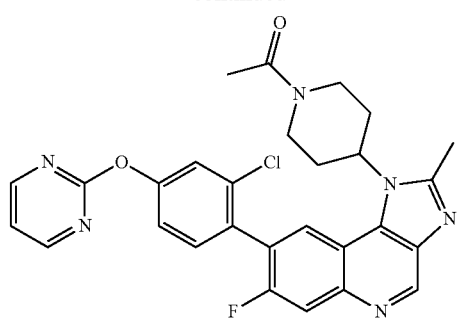
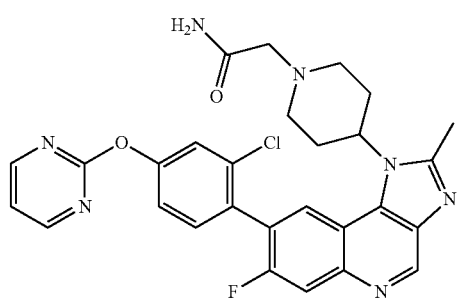
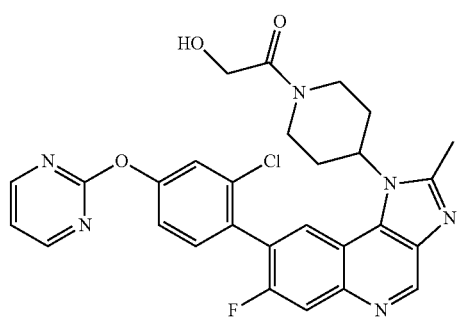
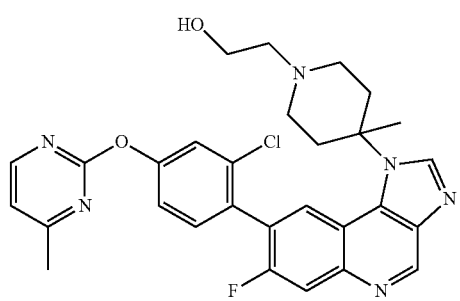
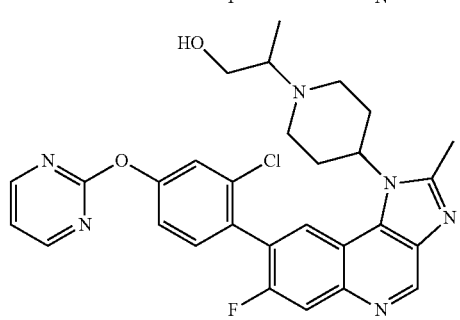
10
-continued
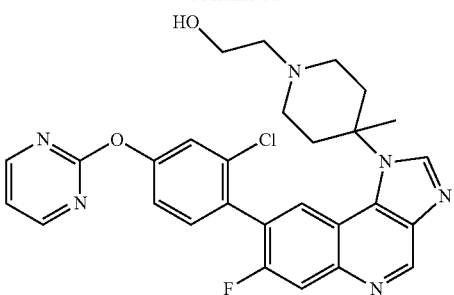
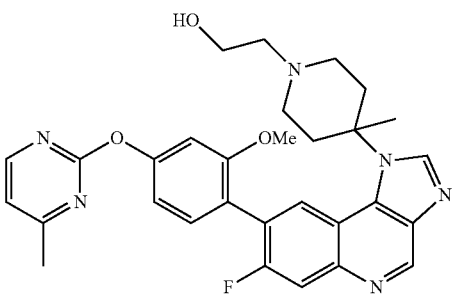
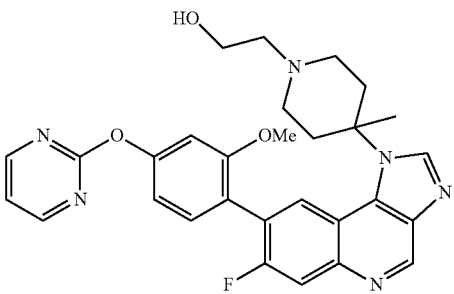
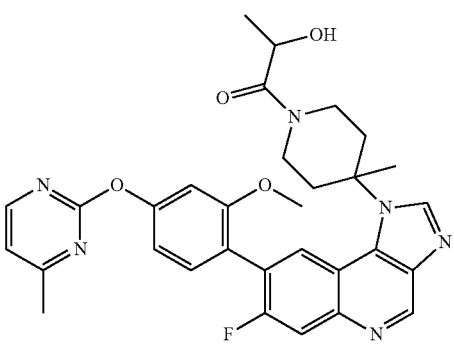
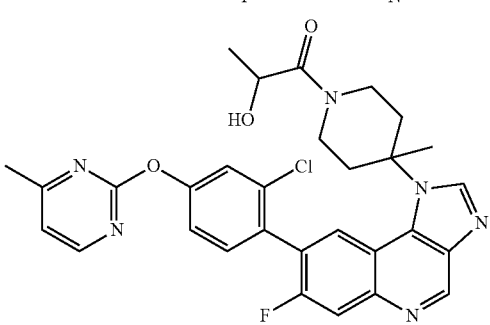

11
-continued
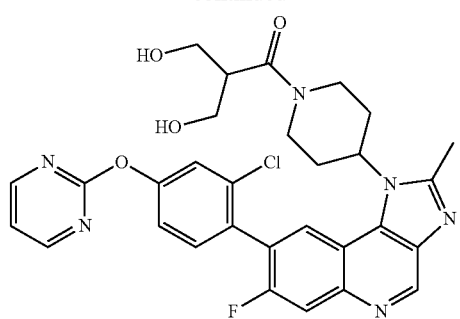
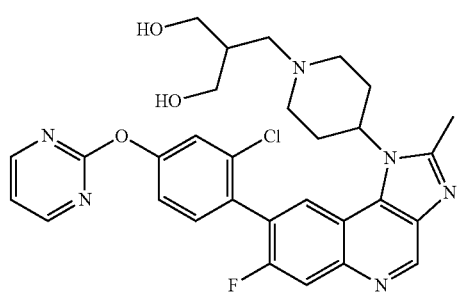
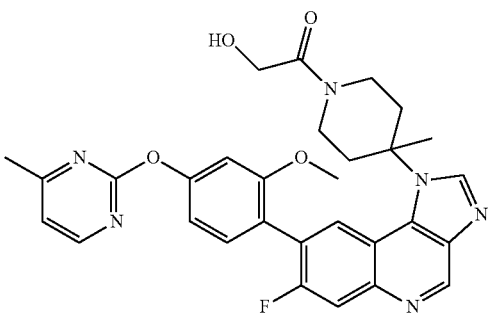
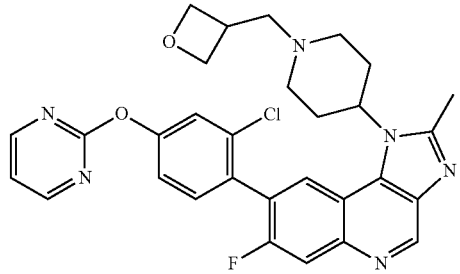
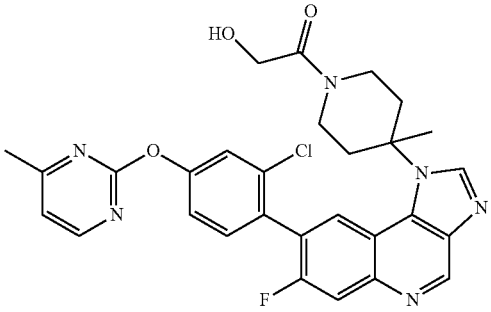
12
-continued
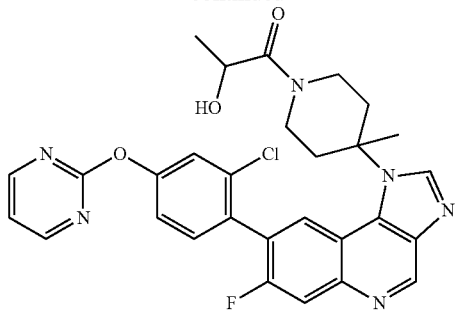
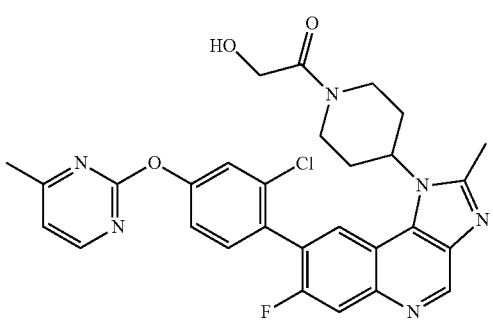
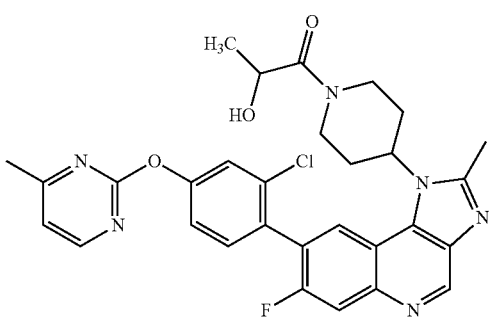
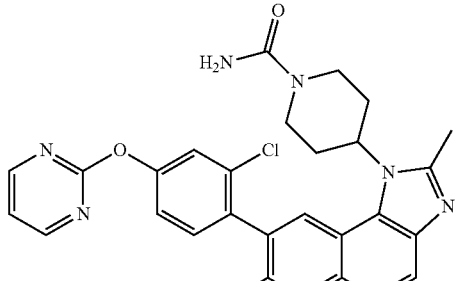
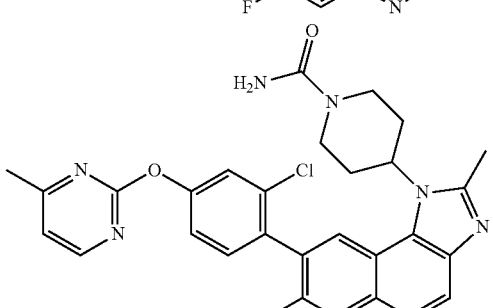

13
-continued
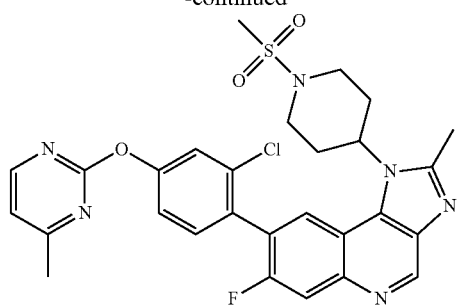
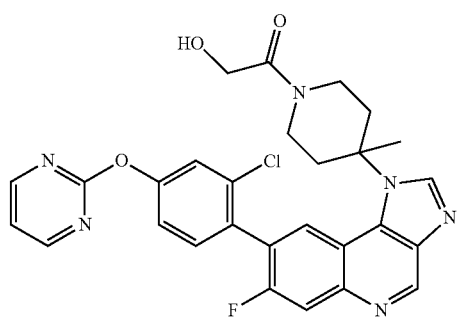
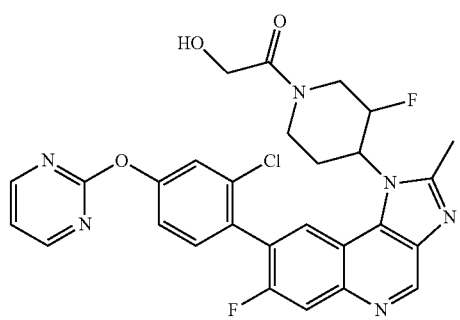
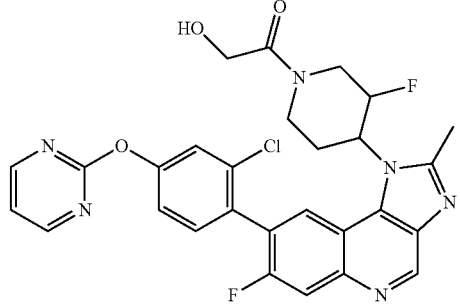
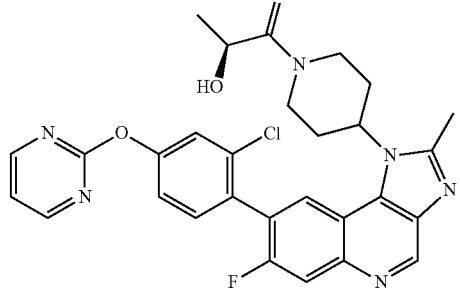
14
-continued
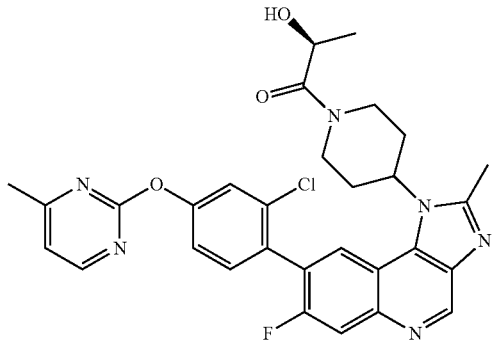
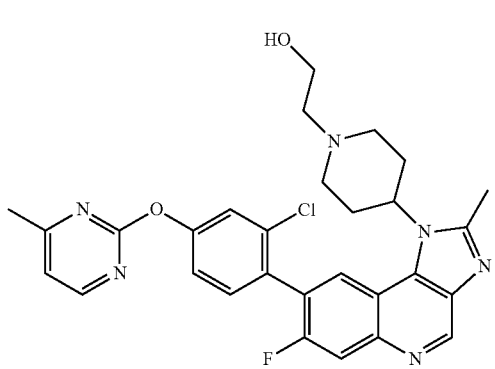
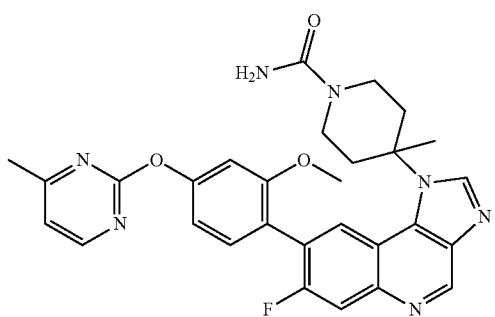
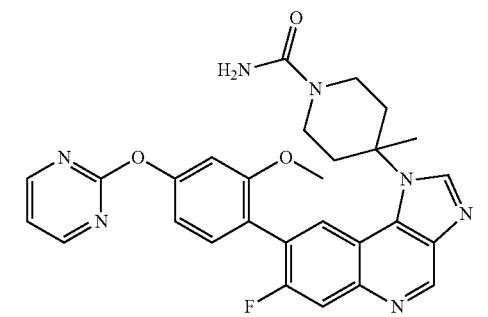
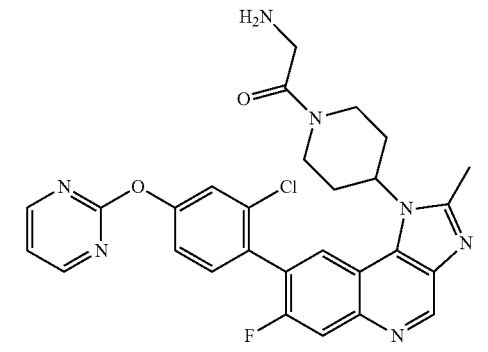

15
-continued
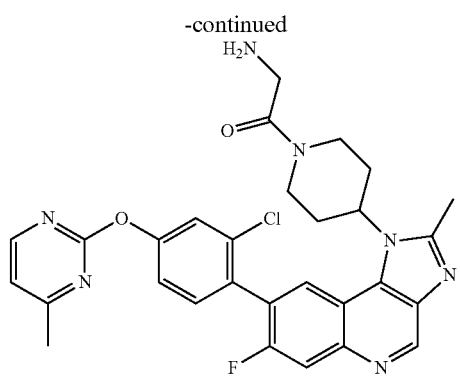
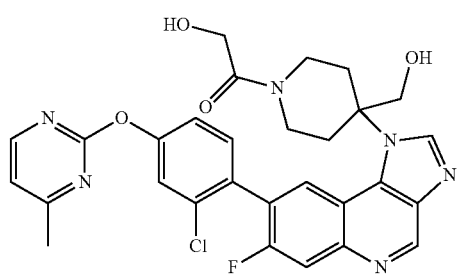
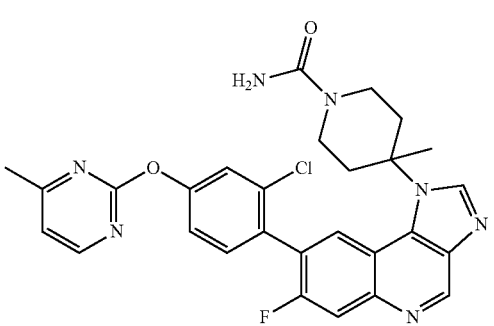
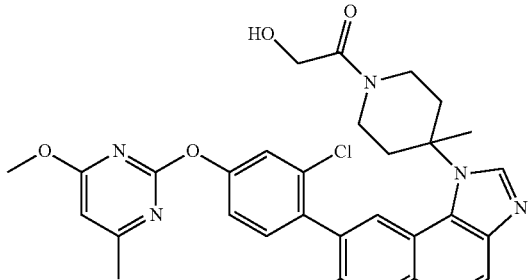
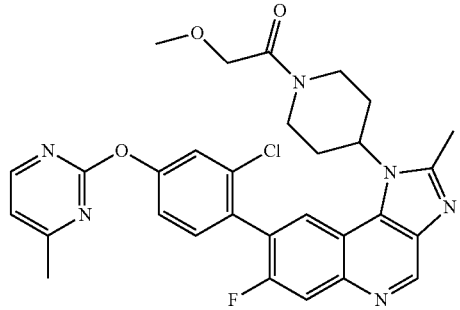
16
-continued
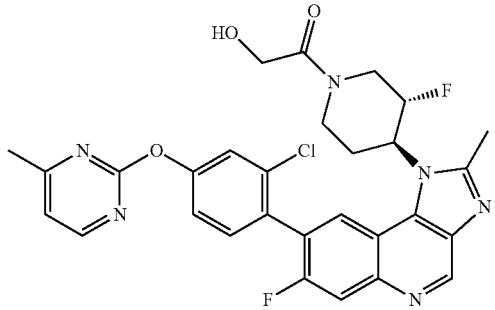
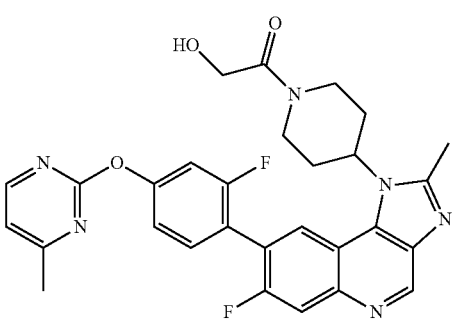
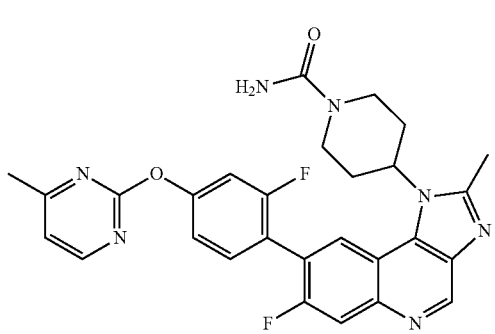
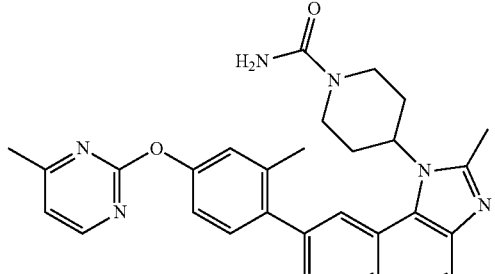
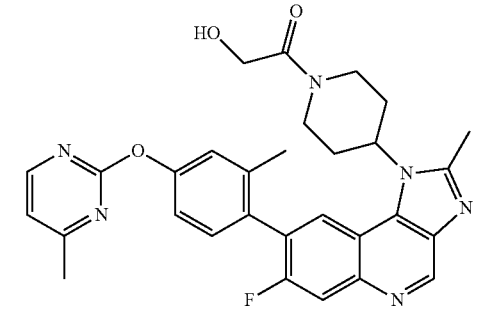

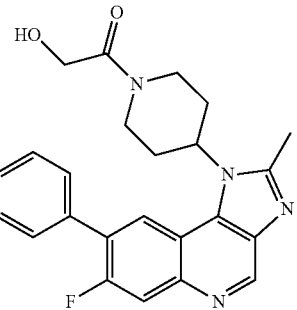
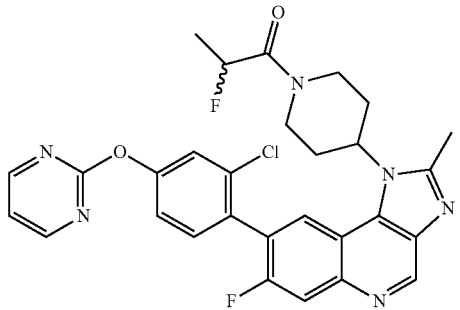
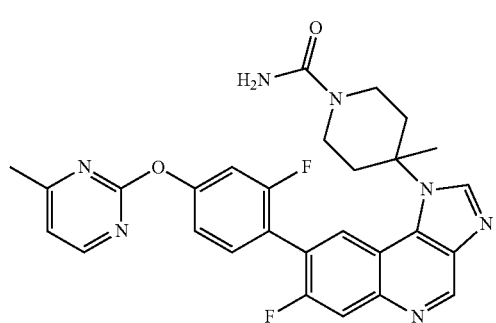
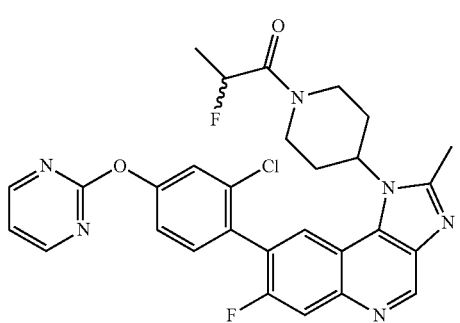
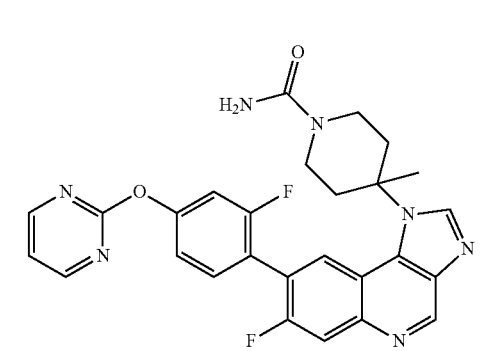
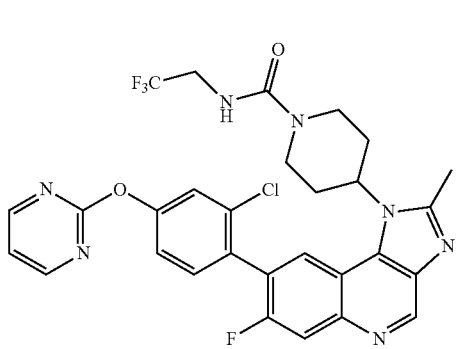
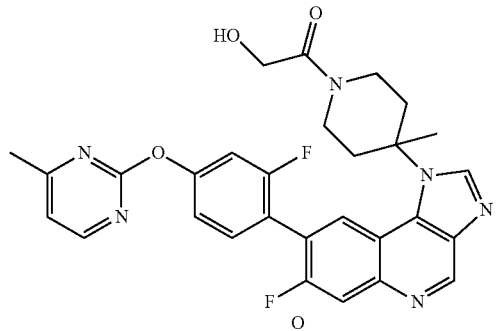
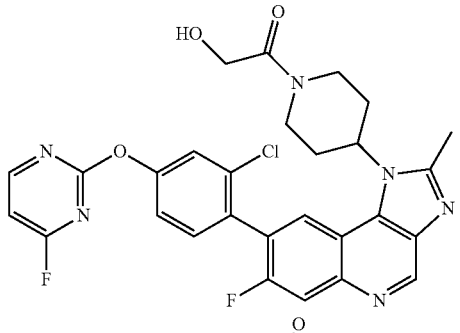
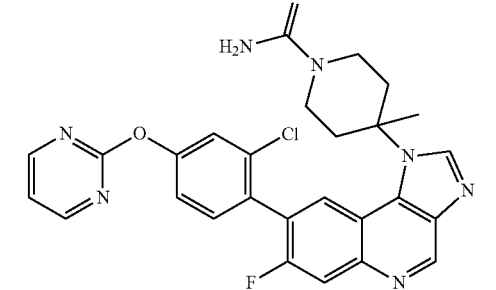
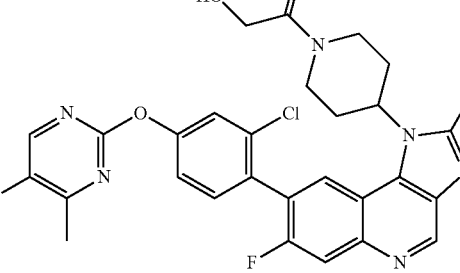

-continued

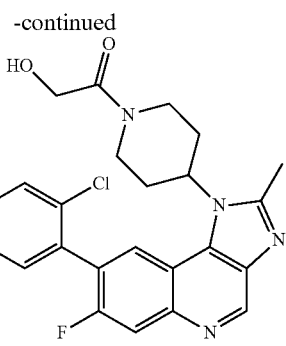

In another embodiment are compounds of formula Ib:

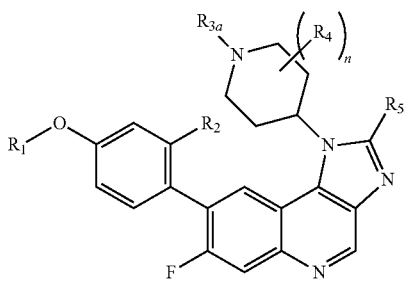

in which: n is selected from 0, 1 and 2; R₁ is selected from:

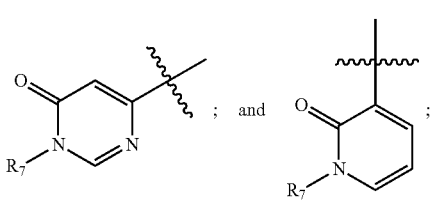

R₂ is selected from chloro and methoxy; R$_{3a}$ is selected from cyano-methyl, 2-hydroxy-ethyl, 1-hydroxypropan-2-yl, 2-methoxy-ethyl, (3-methyloxetan-3-yl)-methyl, methyl-sulfonyl, 2-fluoropropanoyl, 2-hydroxy-propyl, cyclopropyl-sulfonyl, isopropyl-sulfonyl, 3-hydroxy-2-(hydroxy-methyl) propyl, 2-acetoxyacetyl, 3-hydroxy-2-(hydroxy-methyl) propanoyl, dimethylcarbamoyl, (2,2,2-trifluoroethyl) carbamoyl, (S)-2-hydroxypropanoyl, oxetan-2-yl, oxetan-3-ylmethyl, 2-aminoacetyl, 2-methoxyacetyl, 2-hydroxyacetyl, 2-hydroxypropanoyl, acetyl, 2-amino-2-oxoethyl and carbamoyl; R₄ is selected from hydrogen, methyl and hydroxymethyl; R₅ is selected from hydrogen and methyl; and R₇ is selected from hydrogen, fluoro, chloro, CH₂F, CHF₂, CF₃, CH₂OH, cyclopropyl and methyl; or the pharmaceutically acceptable salts thereof.

In a further embodiment are compounds, or pharmaceutically acceptable salts thereof, selected from:

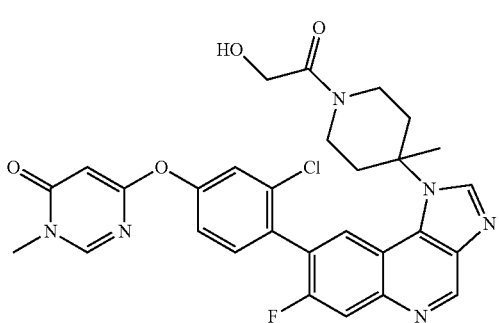

-continued

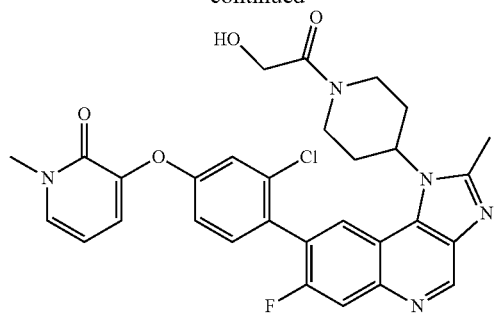

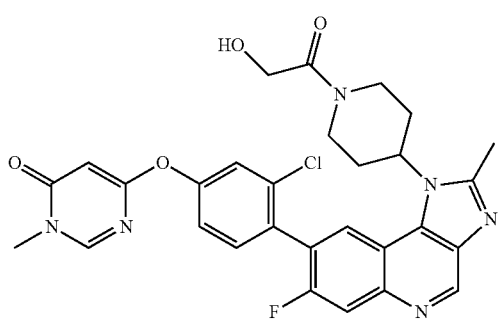

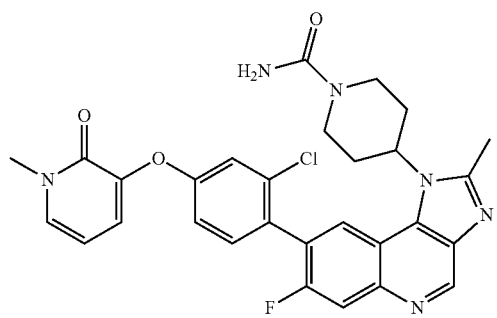

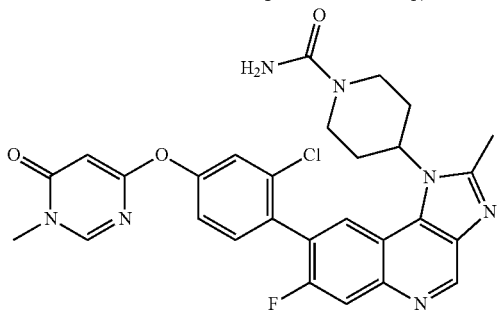

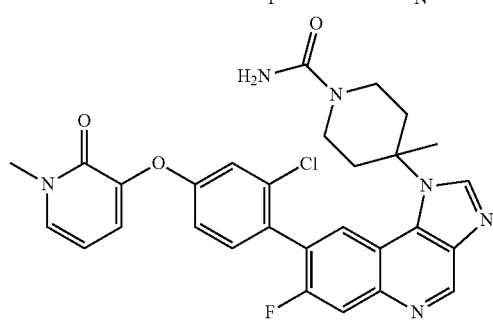

-continued

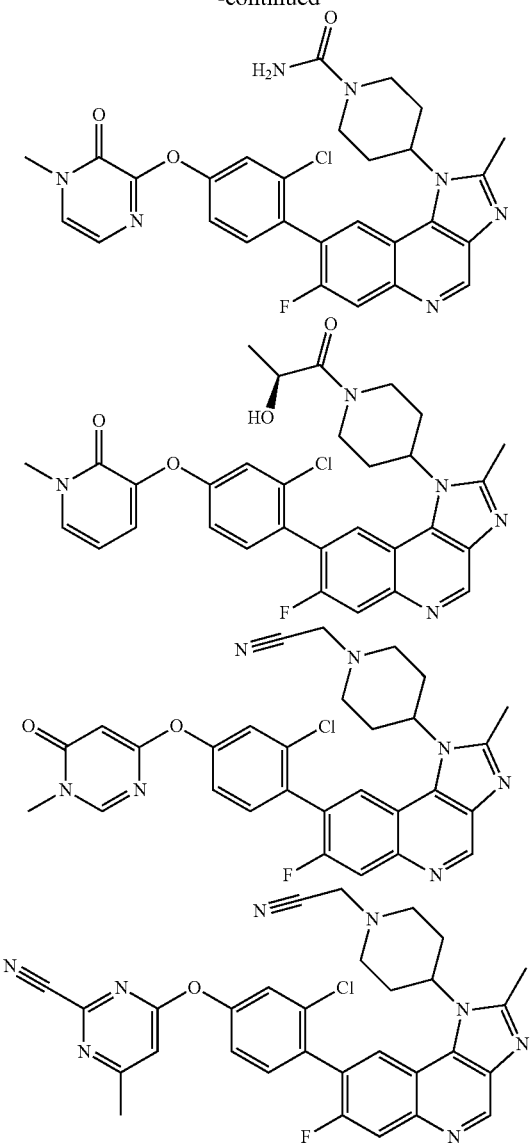

In another embodiment are compounds of formula Ic:

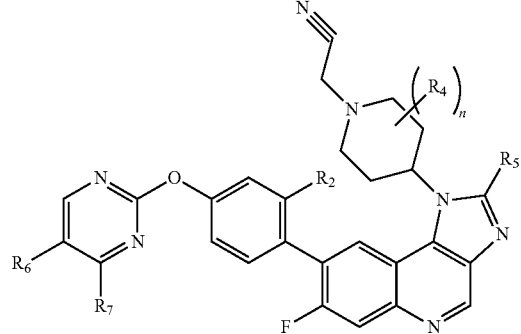

in which: n is selected from 0, 1, 2 and 3; $R_2$ is selected from chloro and methoxy; $R_4$ is selected from fluoro; and optionally two $R_4$ groups together with the carbon atoms to which they are attached form —$(CH_2)_{2-3}$—; (for example, 8-azabicyclo[3.2.1]octan-3-yl); $R_5$ is selected from hydrogen and methyl; $R_6$ is selected from hydrogen; and $R_7$ is selected from hydrogen, fluoro, chloro, $CH_2F$, $CHF_2$, $CF_3$, $CH_2OH$, cyclopropyl and methyl; or the pharmaceutically acceptable salts thereof.

In a further embodiment are compounds, or pharmaceutically acceptable salts thereof, selected from:

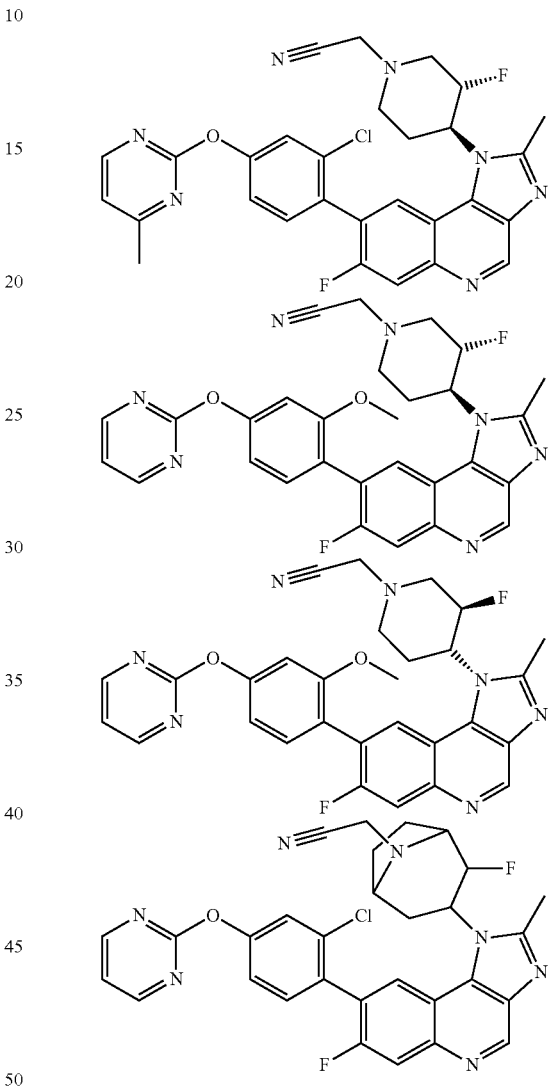

In another embodiment are compounds of formula Id:

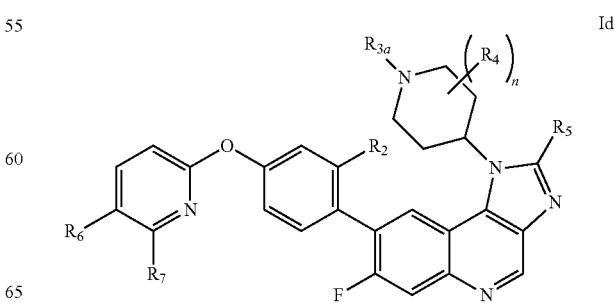

in which: n is selected from 0, 1, 2 and 3; R₂ is selected from chloro and methoxy; R_{3a} is selected from 2-hydroxy-ethyl, 1-hydroxypropan-2-yl, 2-methoxy-ethyl, (3-methyloxetan-3-yl)-methyl, methyl-sulfonyl, 2-hydroxy-propyl, 2-acetoxy-acetyl, 2-fluoropropanoyl, cyclopropyl-sulfonyl, oxetan-2-yl, isopropyl-sulfonyl, 3-hydroxy-2-(hydroxy-methyl)propyl, 3-hydroxy-2-(hydroxy-methyl)propanoyl, dimethylcarbamoyl, (2,2,2-trifluoroethyl)carbamoyl, (S)-2-hydroxypropanoyl, oxetan-3-ylmethyl, 2-aminoacetyl, 2-methoxyacetyl, 2-hydroxyacetyl, 2-hydroxypropanoyl, acetyl, 2-amino-2-oxoethyl and carbamoyl; R₄ is selected from fluoro; and optionally two R₄ groups together with the carbon atoms to which they are attached form —(CH₂)$_{2-3}$—, R₅ is selected from hydrogen and methyl; R₆ is selected from hydrogen and fluoro; and R₇ is selected from hydrogen, fluoro, chloro, CH₂F, CHF₂, CF₃, CH₂OH, cyclopropyl and methyl; or the pharmaceutically acceptable salts thereof.

In a further embodiment are compounds, or pharmaceutically acceptable salts thereof, selected from:

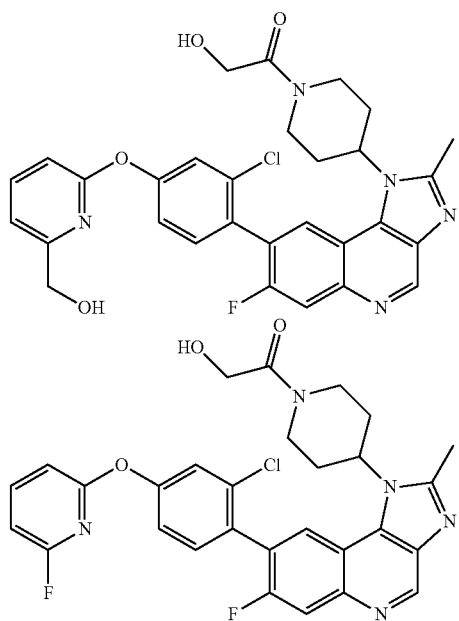

In another embodiment are compounds of formula Ie:

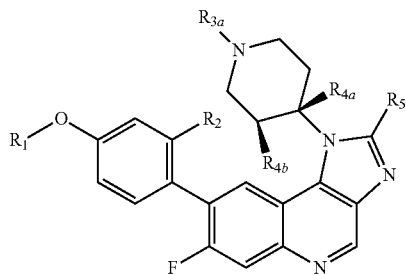

in which: R_{4a} and R_{4b} are derived from —(R₄)$_n$; wherein n is 2; and R₄ of the Summary of the Invention is defined by R_{4a} and R_{4b}; wherein R_{4a} is selected from hydrogen and methyl; and R_{4b} is selected from hydrogen and fluorine; R₁ is selected from:

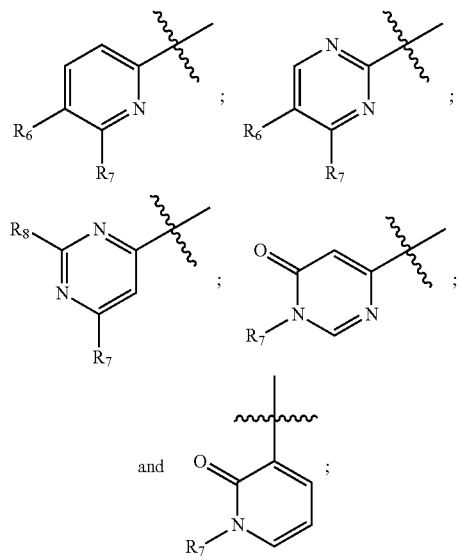

R₂ is selected from chloro and methoxy; R_{3a} is selected from 2-hydroxy-ethyl, 1-hydroxypropan-2-yl, 2-methoxy-ethyl, (3-methyloxetan-3-yl)-methyl, methyl-sulfonyl, 2-hydroxy-propyl, 2-acetoxyacetyl, 2-fluoropropanoyl, cyclopropyl-sulfonyl, oxetan-2-yl, isopropyl-sulfonyl, 3-hydroxy-2-(hydroxy-methyl)propyl, 3-hydroxy-2-(hydroxy-methyl)propanoyl, dimethylcarbamoyl, (2,2,2-trifluoroethyl)carbamoyl, (S)-2-hydroxypropanoyl, oxetan-3-ylmethyl, 2-aminoacetyl, 2-methoxyacetyl, 2-hydroxyacetyl, 2-hydroxypropanoyl, acetyl, 2-amino-2-oxoethyl and carbamoyl; R₅ is selected from hydrogen and methyl; R₆ is selected from hydrogen and fluoro; R₇ is selected from hydrogen, fluoro, chloro, CH₂F, CHF₂, CF₃, CH₂OH, cyclopropyl and methyl; and R₈ is selected from cyano; or the pharmaceutically acceptable salts thereof.

In a further embodiment are compounds, or a pharmaceutically acceptable salt thereof, selected from:

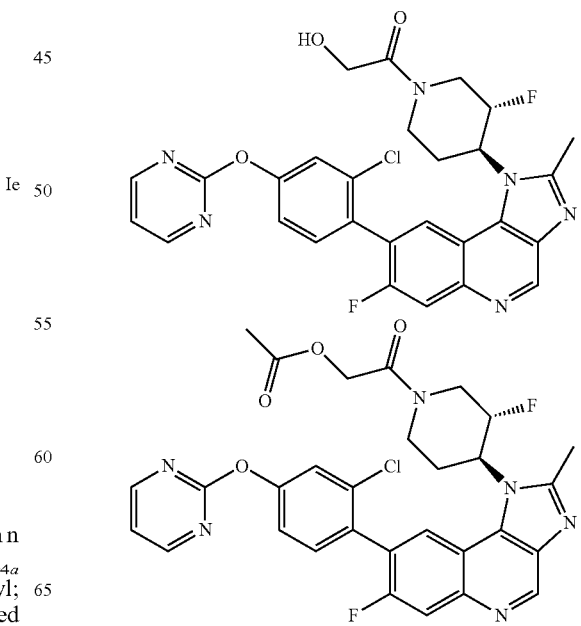

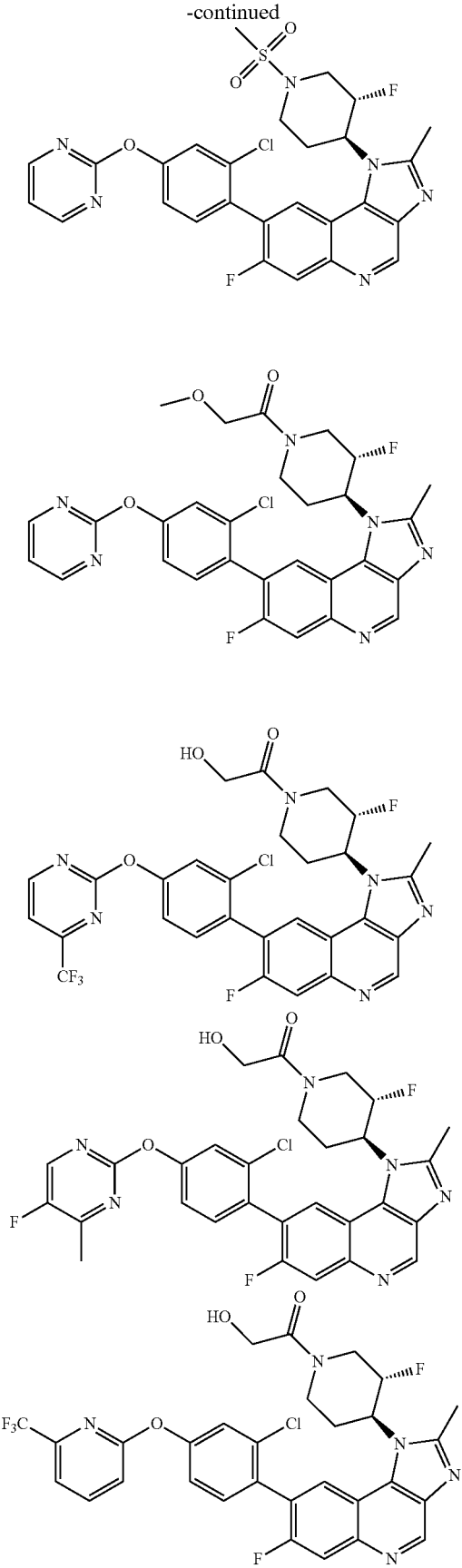

Further Embodiments of the Invention

Embodiment 1

A compound of formula I:

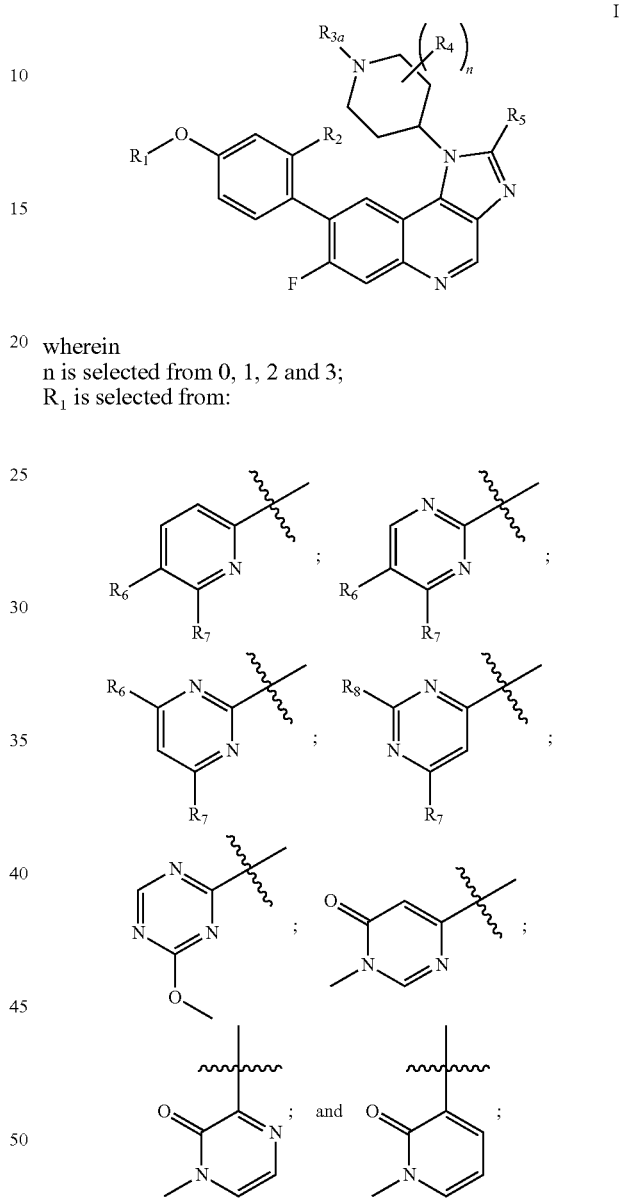

wherein
n is selected from 0, 1, 2 and 3;
$R_1$ is selected from:

$R_2$ is selected from chloro, methyl, hydrogen, fluoro and methoxy;
$R_{3a}$ is selected from cyano-methyl, 2-hydroxy-ethyl, 1-hydroxypropan-2-yl, 3-hydroxy-2-(hydroxy-methyl)propanoyl, 2-methoxy-ethyl, 2-fluoropropanoyl, (3-methyloxetan-3-yl)-methyl, methyl-sulfonyl, amino-carbonyl-methyl, cyclopropyl-sulfonyl, isopropyl-sulfonyl, dimethylcarbamoyl, 3-hydroxy-2-(hydroxy-methyl)propyl, 2-hydroxy-propyl, 2-hydroxyacetyl, 2-acetoxyacetyl, 2-methoxyacetyl, (2,2,2-trifluoroethyl)carbamoyl, 2-aminoacetyl, oxetan-3-yl-methyl, (S)-2-hydroxypropanoyl, 2-hydroxypropanoyl, acetyl, 2-amino-2-oxoethyl, carbamoyl, (oxetan-2-yl)-methanoyl, 2-(sulfooxy)acetyl, 2-fluoroethanoyl, 3-hydroxypropanoyl, and N,N-dimethylsulfonamidyl;

each R$_4$ is independently selected from hydrogen, halo, methyl and hydroxy-methyl; and optionally two R$_4$ groups together with the carbon atoms to which they are attached form —(CH$_2$)$_{2-3}$—;
R$_5$ is selected from hydrogen and methyl;
R$_6$ is selected from hydrogen, methoxy and halo;
R$_7$ is selected from hydrogen, fluoro, CF$_3$, CH$_2$OH, cyclopropyl and methyl; and
R$_8$ is selected from cyano;
or the pharmaceutically acceptable salts thereof.

Embodiment 2

The compound of formula I, according to embodiment 1, wherein
n is selected from 0 or 1;
R$_1$ is selected from:

R$_2$ is selected from chloro, methyl, hydrogen, fluoro and methoxy;
R$_{3a}$ is selected from cyano-methyl, 2-hydroxy-ethyl, 1-hydroxypropan-2-yl, 3-hydroxy-2-(hydroxy-methyl)propanoyl, 2-methoxy-ethyl, 2-fluoropropanoyl, (3-methyloxetan-3-yl)-methyl, methyl-sulfonyl, amino-carbonyl-methyl, cyclopropyl-sulfonyl, isopropyl-sulfonyl, dimethylcarbamoyl, 3-hydroxy-2-(hydroxy-methyl)propyl, 2-hydroxy-propyl, 2-hydroxyacetyl, 2-acetoxyacetyl, 2-methoxyacetyl, (2,2,2-trifluoroethyl)carbamoyl, 2-aminoacetyl, oxetan-3-yl-methyl, (S)-2-hydroxypropanoyl, 2-hydroxypropanoyl, acetyl, 2-amino-2-oxoethyl, carbamoyl, (oxetan-2-yl)-methanoyl, 2-(sulfooxy)acetyl, 2-fluoroethanoyl, 3-hydroxypropanoyl, and N,N-dimethylsulfonamidyl;
each R$_4$ is independently selected from halo, methyl and hydroxy-methyl;
R$_5$ is selected from hydrogen and methyl;
R$_6$ is selected from hydrogen, methoxy and halo;
R$_7$ is selected from hydrogen, fluoro, CF$_3$, CH$_2$OH, cyclopropyl and methyl; and
R$_8$ is selected from cyano;
or the pharmaceutically acceptable salts thereof.

Embodiment 3

The compound of formula I, according to embodiment 1, wherein
n is selected from 0 or 1;
R$_1$ is selected from:

R$_2$ is selected from chloro, methyl, hydrogen, fluoro and methoxy;
R$_{3a}$ is selected from cyano-methyl, 2-hydroxy-ethyl, 1-hydroxypropan-2-yl, 3-hydroxy-2-(hydroxy-methyl)propanoyl, 2-methoxy-ethyl, 2-fluoropropanoyl, (3-methyloxetan-3-yl)-methyl, methyl-sulfonyl, amino-carbonyl-methyl, cyclopropyl-sulfonyl, isopropyl-sulfonyl, dimethylcarbamoyl, 3-hydroxy-2-(hydroxy-methyl)propyl, 2-hydroxy-propyl, 2-hydroxyacetyl, 2-acetoxyacetyl, 2-methoxyacetyl, (2,2,2-trifluoroethyl)carbamoyl, 2-aminoacetyl, oxetan-3-yl-methyl, (S)-2-hydroxypropanoyl, 2-hydroxypropanoyl, acetyl, 2-amino-2-oxoethyl, carbamoyl, (oxetan-2-yl)-methanoyl, 2-(sulfooxy)acetyl, 2-fluoroethanoyl, 3-hydroxypropanoyl, and N,N-dimethylsulfonamidyl;
each R$_4$ is independently selected from halo, methyl and hydroxy-methyl;
R$_5$ is selected from hydrogen and methyl;
R$_6$ is selected from hydrogen and halo; and
R$_7$ is selected from hydrogen, fluoro, CF$_3$, CH$_2$OH, cyclopropyl and methyl;
or the pharmaceutically acceptable salts thereof.

Embodiment 4

The compound of formula I, according to embodiment 1, wherein
n is selected from 0 or 1;
R$_1$ is selected from:

R$_2$ is selected from chloro, methyl, hydrogen, fluoro and methoxy;
R$_{3a}$ is selected from cyano-methyl, 3-hydroxy-2-(hydroxy-methyl)propanoyl, 2-methoxy-ethyl, 2-fluoropropanoyl, (3-methyloxetan-3-yl)-methyl, methyl-sulfonyl, amino-carbonyl-methyl, cyclopropyl-sulfonyl, isopropyl-sulfonyl, dimethylcarbamoyl, 2-hydroxyacetyl, 2-acetoxyacetyl, 2-methoxyacetyl, (2,2,2-trifluoroethyl)carbamoyl, 2-aminoacetyl, oxetan-3-ylmethyl, (S)-2-hydroxypropanoyl, 2-hydroxypropanoyl, acetyl, 2-amino-2-oxoethyl, carbamoyl, (oxetan-2-yl)-methanoyl, 2-(sulfooxy)acetyl, 2-fluoroethanoyl, 3-hydroxypropanoyl, and N,N-dimethylsulfonamidyl;
each $R_4$ is independently from halo, methyl and hydroxy-methyl;
$R_5$ is selected from hydrogen and methyl;
$R_6$ is selected from hydrogen and halo; and
$R_7$ is selected from hydrogen, fluoro, $CF_3$, $CH_2OH$, cyclopropyl and methyl;
or the pharmaceutically acceptable salts thereof.

Embodiment 5

The compound of formula I, according to embodiment 1, wherein
n is selected from 0 or 1;
$R_1$ is selected from:

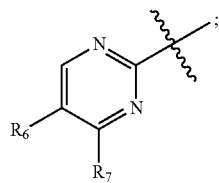

$R_2$ is selected from chloro, methyl, hydrogen, fluoro and methoxy;
$R_{3a}$ is selected from 3-hydroxy-2-(hydroxy-methyl)propanoyl, 2-fluoropropanoyl, (3-methyloxetan-3-yl)-methyl, methyl-sulfonyl, amino-carbonyl-methyl, cyclopropyl-sulfonyl, isopropyl-sulfonyl, dimethylcarbamoyl, 2-hydroxyacetyl, 2-acetoxyacetyl, 2-methoxyacetyl, (2,2,2-trifluoroethyl)carbamoyl, 2-aminoacetyl, oxetan-3-ylmethyl, (S)-2-hydroxypropanoyl, 2-hydroxypropanoyl, acetyl, 2-amino-2-oxoethyl, carbamoyl, (oxetan-2-yl)-methanoyl, 2-(sulfooxy)acetyl, 2-fluoroethanoyl, 3-hydroxypropanoyl, and N,N-dimethylsulfonamidyl;
each $R_4$ is independently selected from halo, methyl and hydroxy-methyl;
$R_5$ is selected from hydrogen and methyl;
$R_6$ is selected from hydrogen and halo; and
$R_7$ is selected from hydrogen, fluoro, $CF_3$, $CH_2OH$, cyclopropyl and methyl;
or the pharmaceutically acceptable salts thereof.

Embodiment 6

The compound of formula I, according to embodiment 1, wherein
n is selected from 0 or 1;
$R_1$ is selected from:

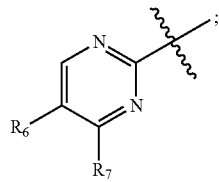

$R_2$ is selected from chloro, methyl, hydrogen, fluoro and methoxy;
$R_{3a}$ is selected from 3-hydroxy-2-(hydroxy-methyl)propanoyl, 2-fluoropropanoyl, methyl-sulfonyl, cyclopropyl-sulfonyl, isopropyl-sulfonyl, dimethylcarbamoyl, 2-hydroxyacetyl, 2-acetoxyacetyl, 2-methoxyacetyl, (2,2,2-trifluoroethyl)carbamoyl, 2-aminoacetyl, (S)-2-hydroxypropanoyl, 2-hydroxypropanoyl, acetyl, carbamoyl, 2-(sulfooxy)acetyl, 2-fluoroethanoyl, 3-hydroxypropanoyl, and N,N-dimethylsulfonamidyl;
each $R_4$ is independently selected from halo, methyl and hydroxy-methyl;
$R_5$ is selected from hydrogen and methyl;
$R_6$ is selected from hydrogen and halo; and
$R_7$ is selected from hydrogen, fluoro, $CF_3$, $CH_2OH$, cyclopropyl and methyl;
or the pharmaceutically acceptable salts thereof.

Embodiment 7

The compound of formula I, according to embodiment 1, wherein
n is selected from 0 or 1;
$R_1$ is selected from:

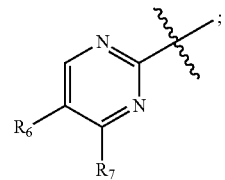

$R_2$ is selected from chloro, methyl, hydrogen, fluoro and methoxy;
$R_{3a}$ is selected from 3-hydroxy-2-(hydroxy-methyl)propanoyl, 2-fluoropropanoyl, dimethylcarbamoyl, 2-hydroxyacetyl, 2-acetoxyacetyl, 2-methoxyacetyl, (2,2,2-trifluoroethyl)carbamoyl, 2-aminoacetyl, (S)-2-hydroxypropanoyl, 2-hydroxypropanoyl, acetyl, carbamoyl, 2-(sulfooxy)acetyl, 2-fluoroethanoyl and 3-hydroxypropanoyl;
each $R_4$ is independently selected from halo, methyl and hydroxy-methyl;
$R_5$ is selected from hydrogen and methyl;
$R_6$ is selected from hydrogen and halo; and
$R_7$ is selected from hydrogen, fluoro, $CF_3$, $CH_2OH$, cyclopropyl and methyl;
or the pharmaceutically acceptable salts thereof.

Embodiment 8

The compound of formula I, according to embodiment 1, wherein
n is selected from 0 or 1;
$R_1$ is selected from:

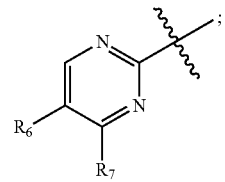

$R_2$ is selected from chloro and methoxy;
$R_{3a}$ is selected from 3-hydroxy-2-(hydroxy-methyl)propanoyl, 2-fluoropropanoyl, dimethylcarbamoyl, 2-hydroxyacetyl, 2-acetoxyacetyl, 2-methoxyacetyl, (2,2,2-trifluoroethyl)carbamoyl, 2-aminoacetyl, (S)-2-hydroxypropanoyl, 2-hydroxypropanoyl, acetyl, carbamoyl, 2-(sulfooxy)acetyl, 2-fluoroethanoyl and 3-hydroxypropanoyl;
each $R_4$ is independently selected from halo, methyl and hydroxy-methyl;
$R_5$ is selected from hydrogen and methyl;
$R_6$ is selected from hydrogen and halo; and
$R_7$ is selected from hydrogen, fluoro, $CF_3$, $CH_2OH$, cyclopropyl and methyl;
or the pharmaceutically acceptable salts thereof.

Embodiment 9

The compound of formula I, according to embodiment 1, wherein
n is selected from 0 or 1;
$R_1$ is selected from:

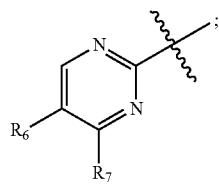

$R_2$ is selected from chloro and methoxy;
$R_{3a}$ is selected from 3-hydroxy-2-(hydroxy-methyl)propanoyl, 2-fluoropropanoyl, dimethylcarbamoyl, 2-hydroxyacetyl, 2-acetoxyacetyl, 2-methoxyacetyl, (2,2,2-trifluoroethyl)carbamoyl, 2-aminoacetyl, (S)-2-hydroxypropanoyl, 2-hydroxypropanoyl, acetyl, carbamoyl, 2-(sulfooxy)acetyl, 2-fluoroethanoyl and 3-hydroxypropanoyl;
each $R_4$ is independently selected from halo, methyl and hydroxy-methyl;
$R_5$ is selected from hydrogen and methyl;
$R_6$ is hydrogen; and
$R_7$ is hydrogen;
or the pharmaceutically acceptable salts thereof.

Embodiment 10

The compound of formula I, according to embodiment 1, wherein
n is selected from 0 or 1;
$R_1$ is selected from:

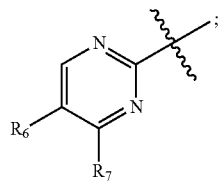

$R_2$ is selected from chloro and methoxy;
$R_{3a}$ is selected from 3-hydroxy-2-(hydroxy-methyl)propanoyl, 2-fluoropropanoyl, dimethylcarbamoyl, 2-hydroxyacetyl, 2-acetoxyacetyl, 2-methoxyacetyl, (2,2,2-trifluoroethyl)carbamoyl, 2-aminoacetyl, (S)-2-hydroxypropanoyl, 2-hydroxypropanoyl, acetyl, carbamoyl, 2-(sulfooxy)acetyl, 2-fluoroethanoyl and 3-hydroxypropanoyl;
each $R_4$ is independently selected from halo, methyl and hydroxy-methyl;
$R_5$ is methyl;
$R_6$ is hydrogen; and
$R_7$ is hydrogen;
or the pharmaceutically acceptable salts thereof.

Embodiment 11

The compound of formula I, according to embodiment 1, wherein
n is selected from 0 or 1;
$R_1$ is selected from:

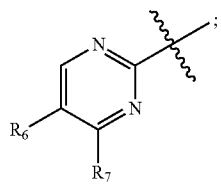

$R_2$ is chloro;
$R_{3a}$ is selected from 3-hydroxy-2-(hydroxy-methyl)propanoyl, 2-fluoropropanoyl, dimethylcarbamoyl, 2-hydroxyacetyl, 2-acetoxyacetyl, 2-methoxyacetyl, (2,2,2-trifluoroethyl)carbamoyl, 2-aminoacetyl, (S)-2-hydroxypropanoyl, 2-hydroxypropanoyl, acetyl, carbamoyl, 2-(sulfooxy)acetyl, 2-fluoroethanoyl and 3-hydroxypropanoyl;
each $R_4$ is independently selected from halo, methyl and hydroxy-methyl;
$R_5$ is methyl;
$R_6$ is hydrogen; and
$R_7$ is hydrogen;
or the pharmaceutically acceptable salts thereof.

Embodiment 12

The compound of formula I, according to embodiment 1, wherein
n is selected from 0 or 1;
$R_1$ is selected from:

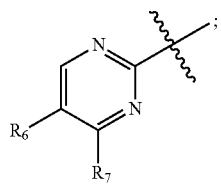

$R_2$ is chloro;
$R_{3a}$ is selected from 3-hydroxy-2-(hydroxy-methyl)propanoyl, 2-fluoropropanoyl, 2-hydroxyacetyl, 2-acetoxyacetyl, 2-methoxyacetyl, 2-aminoacetyl, (S)-2-hydroxypropanoyl, 2-hydroxypropanoyl, acetyl, 2-(sulfooxy)acetyl, 2-fluoroethanoyl and 3-hydroxypropanoyl;
each $R_4$ is independently selected from halo, methyl and hydroxy-methyl;
$R_5$ is methyl;
$R_6$ is hydrogen; and
$R_7$ is hydrogen;
or the pharmaceutically acceptable salts thereof.

Embodiment 13

A compound of formula Ie:

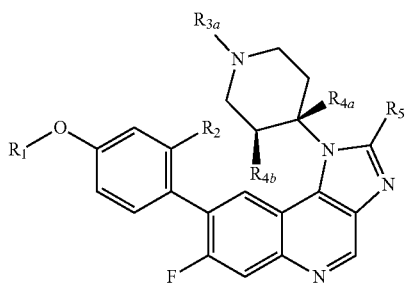

Ie wherein
$R_1$ is selected from:

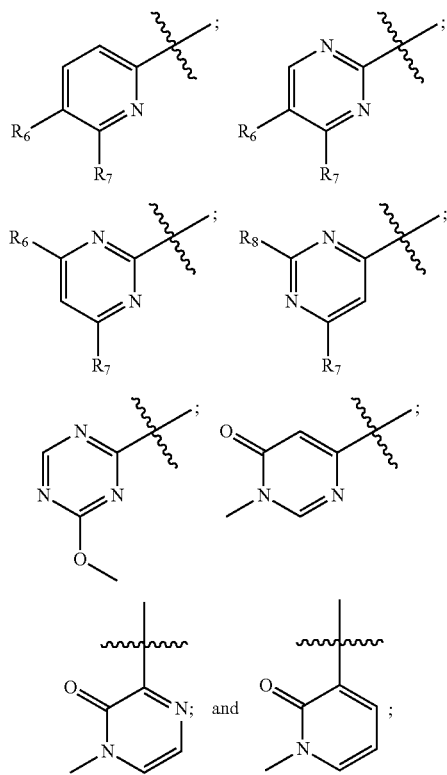

$R_2$ is selected from chloro, methyl, fluoro and methoxy;
$R_{3a}$ is selected from cyano-methyl, 2-hydroxy-ethyl, 1-hydroxypropan-2-yl, 3-hydroxy-2-(hydroxy-methyl)propanoyl, 2-methoxy-ethyl, 2-fluoropropanoyl, (3-methyloxetan-3-yl)-methyl, methyl-sulfonyl, amino-carbonyl-methyl, cyclopropyl-sulfonyl, isopropyl-sulfonyl, dimethylcarbamoyl, 3-hydroxy-2-(hydroxy-methyl)propyl, 2-hydroxy-propyl, 2-hydroxyacetyl, 2-acetoxyacetyl, 2-methoxyacetyl, (2,2,2-trifluoroethyl)carbamoyl, 2-aminoacetyl, oxetan-3-yl-methyl, (S)-2-hydroxypropanoyl, 2-hydroxypropanoyl, acetyl, 2-amino-2-oxoethyl, carbamoyl, (oxetan-2-yl)-methanoyl, 2-(sulfooxy)acetyl, 2-fluoroethanoyl, 3-hydroxypropanoyl, and N,N-dimethylsulfonamidyl;
$R_{4a}$ is hydrogen;
$R_{4b}$ is selected from hydrogen and fluorine;
$R_5$ is selected from hydrogen and methyl;
$R_6$ is selected from hydrogen and fluoro;
$R_7$ is selected from hydrogen, fluoro, $CF_3$, $CH_2OH$, cyclopropyl and methyl; and
$R_8$ is cyano;
or the pharmaceutically acceptable salts thereof.

Embodiment 14

The compound of formula Ie, according to embodiment 13, wherein
$R_1$ is selected from:

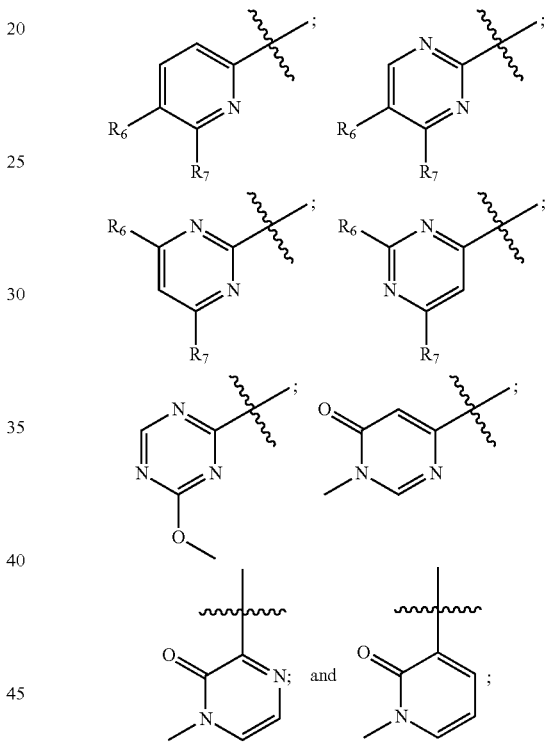

$R_2$ is selected from chloro, methyl, fluoro and methoxy;
$R_{3a}$ is selected from cyano-methyl, 2-hydroxy-ethyl, 1-hydroxypropan-2-yl, 3-hydroxy-2-(hydroxy-methyl)propanoyl, 2-methoxy-ethyl, 2-fluoropropanoyl, (3-methyloxetan-3-yl)-methyl, methyl-sulfonyl, amino-carbonyl-methyl, cyclopropyl-sulfonyl, isopropyl-sulfonyl, dimethylcarbamoyl, 3-hydroxy-2-(hydroxy-methyl)propyl, 2-hydroxy-propyl, 2-hydroxyacetyl, 2-acetoxyacetyl, 2-methoxyacetyl, (2,2,2-trifluoroethyl)carbamoyl, 2-aminoacetyl, oxetan-3-yl-methyl, (S)-2-hydroxypropanoyl, 2-hydroxypropanoyl, acetyl, 2-amino-2-oxoethyl, carbamoyl, (oxetan-2-yl)-methanoyl, 2-(sulfooxy)acetyl, 2-fluoroethanoyl, 3-hydroxypropanoyl, and N,N-dimethylsulfonamidyl;
$R_{4a}$ is hydrogen;
$R_{4b}$ is fluorine;
$R_5$ is methyl;
$R_6$ is selected from hydrogen and fluoro;
$R_7$ is selected from hydrogen, fluoro, $CF_3$, $CH_2OH$, cyclopropyl and methyl; and R$_8$ is cyano;
or the pharmaceutically acceptable salts thereof.

Embodiment 15

The compound of formula Ie, according to embodiment 13, wherein
R$_1$ is selected from:

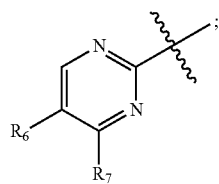

R$_2$ is selected from chloro, methyl, fluoro and methoxy;
R$_{3a}$ is selected from cyano-methyl, 2-hydroxy-ethyl, 1-hydroxypropan-2-yl, 3-hydroxy-2-(hydroxy-methyl)propanoyl, 2-methoxy-ethyl, 2-fluoropropanoyl, (3-methyloxetan-3-yl)-methyl, methyl-sulfonyl, amino-carbonyl-methyl, cyclopropyl-sulfonyl, isopropyl-sulfonyl, dimethylcarbamoyl, 3-hydroxy-2-(hydroxy-methyl)propyl, 2-hydroxy-propyl, 2-hydroxyacetyl, 2-acetoxyacetyl, 2-methoxyacetyl, (2,2,2-trifluoroethyl)carbamoyl, 2-aminoacetyl, oxetan-3-ylmethyl, (S)-2-hydroxypropanoyl, 2-hydroxypropanoyl, acetyl, 2-amino-2-oxoethyl, carbamoyl, (oxetan-2-yl)-methanoyl, 2-(sulfooxy)acetyl, 2-fluoroethanoyl, 3-hydroxypropanoyl, and N,N-dimethylsulfonamidyl;
R$_{4a}$ is hydrogen;
R$_{4b}$ is fluorine;
R$_5$ is methyl;
R$_6$ is selected from hydrogen and fluoro; and
R$_7$ is selected from hydrogen, CF$_3$, CH$_2$OH, and methyl;
or the pharmaceutically acceptable salts thereof.

Embodiment 16

The compound of formula Ie, according to embodiment 13, wherein
R$_1$ is selected from:

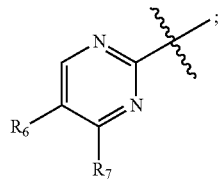

R$_2$ is selected from chloro, methyl, fluoro and methoxy;
R$_{3a}$ is selected from cyano-methyl, 3-hydroxy-2-(hydroxymethyl)propanoyl, 2-methoxy-ethyl, 2-fluoropropanoyl, (3-methyloxetan-3-yl)-methyl, methyl-sulfonyl, amino-carbonyl-methyl, cyclopropyl-sulfonyl, isopropyl-sulfonyl, dimethylcarbamoyl, 2-hydroxyacetyl, 2-acetoxyacetyl, 2-methoxyacetyl, (2,2,2-trifluoroethyl)carbamoyl, 2-aminoacetyl, oxetan-3-ylmethyl, (S)-2-hydroxypropanoyl, 2-hydroxypropanoyl, acetyl, 2-amino-2-oxoethyl, carbamoyl, (oxetan-2-yl)-methanoyl, 2-(sulfooxy)acetyl, 2-fluoroethanoyl, 3-hydroxypropanoyl, and N,N-dimethylsulfonamidyl;
R$_{4a}$ is hydrogen;
R$_{4b}$ is fluorine;
R$_5$ is methyl;
R$_6$ is selected from hydrogen and fluoro; and
R$_7$ is selected from hydrogen, CF$_3$, CH$_2$OH, and methyl;
or the pharmaceutically acceptable salts thereof.

Embodiment 17

The compound of formula Ie, according to embodiment 13, wherein
R$_1$ is selected from:

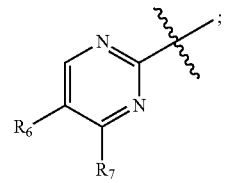

R$_2$ is selected from chloro, methyl, fluoro and methoxy;
R$_{3a}$ is selected from cyano-methyl, 3-hydroxy-2-(hydroxymethyl)propanoyl, 2-fluoropropanoyl, methyl-sulfonyl, cyclopropyl-sulfonyl, isopropyl-sulfonyl, dimethylcarbamoyl, 2-hydroxyacetyl, 2-acetoxyacetyl, 2-methoxyacetyl, (2,2,2-trifluoroethyl)carbamoyl, 2-aminoacetyl, (S)-2-hydroxypropanoyl, 2-hydroxypropanoyl, acetyl, carbamoyl, (oxetan-2-yl)-methanoyl, 2-(sulfooxy)acetyl, 2-fluoroethanoyl, 3-hydroxypropanoyl, and N,N-dimethylsulfonamidyl;
R$_{4a}$ is hydrogen;
R$_{4b}$ is fluorine;
R$_5$ is methyl;
R$_6$ is selected from hydrogen and fluoro; and
R$_7$ is selected from hydrogen, CF$_3$, CH$_2$OH, and methyl;
or the pharmaceutically acceptable salts thereof.

Embodiment 18

The compound of formula Ie, according to embodiment 13, wherein
R$_1$ is selected from:

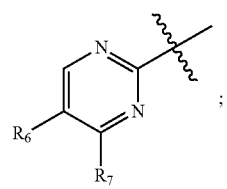

R$_2$ is selected from chloro, methyl, fluoro and methoxy;
R$_{3a}$ is selected from cyano-methyl, methyl-sulfonyl, 2-hydroxyacetyl, 2-acetoxyacetyl, 2-methoxyacetyl, (S)-2-hydroxypropanoyl, acetyl, carbamoyl, (oxetan-2-yl)-methanoyl, 2-(sulfooxy)acetyl, 2-fluoroethanoyl and 3-hydroxypropanoyl;
R$_{4a}$ is hydrogen;
R$_{4b}$ is fluorine;
R$_5$ is methyl;
R$_6$ is selected from hydrogen and fluoro; and
R$_7$ is selected from hydrogen, CF$_3$, CH$_2$OH, and methyl;
or the pharmaceutically acceptable salts thereof.

Embodiment 19

A pharmaceutical composition comprising a compound according to any one of embodiments 1 to 18, or a pharmaceutically acceptable salt thereof, and at least one pharmaceutically acceptable carrier.

Embodiment 20

A combination comprising a compound according to any one of embodiments 1 to 18, or a pharmaceutically acceptable salt thereof, and one or more therapeutically active agents, for example selected from:
i) PI3K inhibitors, such as BKM120 [i.e. 5-(2,6-dimorpholinopyrimidin-4-yl)-4-(trifluoromethyl)pyridin-2-amine] or BYL719 [i.e. (S)—N-1-(4-methyl-5-(2-(1,1,1-trifluoro-2-methylpropan-2-yl)pyridin-4-yl)thiazol-2-yl)pyrrolidine-1,2-dicarboxamide];
ii) compounds targeting, decreasing or inhibiting the activity of members of the protein kinase C (PKC) and Raf family of serine/threonine kinases, members of the MEK, ERK, SRC, JAK, FAK, PDK1, PKB/Akt, and Ras/MAPK family members, and/or members of the cyclin-dependent kinase family (CDK); such as Dabrafenib, Encorafenib ot LEE011 (i.e., 7-cyclopentyl-N,N-dimethyl-2-(5-(piperazin-1-yl)pyridin-2-yl)amino)-7H-pyrrolo[2,3-d]pyrimidine-6-carboxamide); and
iii) mTOR inhibitors, such as Everolimus.

Embodiment 20a

A combination comprising a compound according to any one of embodiments 1 to 18, or a pharmaceutically acceptable salt thereof, and one or more therapeutically active agents, such as PI3K inhibitors, such as BKM120 [i.e. 5-(2,6-dimoipholinopyrimidin-4-yl)-4-(trifluoromethyl)pyridin-2-amine] or BYL719 [i.e. (S)—N-1-(4-methyl-5-(2-(1,1,1-trifluoro-2-methylpropan-2-yl)pyridin-4-yl)thiazol-2-yl)pyrrolidine-1,2-dicarboxamide].

Embodiment 20b

A combination comprising a compound according to any one of embodiments 1 to 18, or a pharmaceutically acceptable salt thereof, and one or more therapeutically active agents, such as compounds targeting, decreasing or inhibiting the activity of members of the protein kinase C(PKC) and Raf family of serine/threonine kinases, members of the MEK, ERK, SRC, JAK, FAK, PDK1, PKB/Akt, and Ras/MAPK family members, and/or members of the cyclin-dependent kinase family (CDK); such as Dabrafenib, Encorafenib ot LEE011 (i.e., 7-cyclopentyl-N,N-dimethyl-2-(5-(piperazin-1-yl)pyridin-2-yl)amino)-7H-pyrrolo[2,3-d]pyrimidine-6-carboxamide).

Embodiment 20c

A combination comprising a compound according to any one of embodiments 1 to 18, or a pharmaceutically acceptable salt thereof, and one or more therapeutically active agents, such as mTOR inhibitors, such as Everolimus.

Embodiment 21

A compound according to any one of embodiments 1 to 18, or a pharmaceutically acceptable salt thereof, for use as a medicament.

Embodiment 22

A compound according to any one of embodiments 1 to 18, or a pharmaceutically acceptable salt thereof, for use in the treatment of a disorder or disease which is mediated by the activity of MEK, for example a disease or disorder selected from ovarian carcinoma, kidney cancer, prostate cancer, breast carcinoma, lymphomas, myeloma, bladder carcinoma, colon cancer, cutaneous melanoma, hepatocellular carcinoma, endometrial cancer, lung cancer, pancreatic cancer, gastric cancer and soft tissue sarcomas selected from rhabdomyosarcoma, synovial sarcoma and Ewing sarcoma; in particular melanoma, pancreatic, colon, lung, kidney and ovarian cancers.

Embodiment 23

Use of a compound according to any one of embodiments 1 to 18, or a pharmaceutically acceptable salt thereof, for the manufacture of a medicament for the treatment of a disorder or disease which is mediated by the activity of MEK, for example a disease or disorder selected from ovarian carcinoma, kidney cancer, prostate cancer, breast carcinoma, lymphomas, myeloma, bladder carcinoma, colon cancer, cutaneous melanoma, hepatocellular carcinoma, endometrial cancer, lung cancer, pancreatic cancer, gastric cancer and soft tissue sarcomas selected from rhabdomyosarcoma, synovial sarcoma and Ewing sarcoma; in particular melanoma, pancreatic, colon, lung, kidney and ovarian cancers.

Embodiment 24

A pharmaceutical composition according to embodiment 19 for use in the treatment of a disorder or disease which is mediated by the activity of MEK, for example a disease or disorder selected from ovarian carcinoma, kidney cancer, prostate cancer, breast carcinoma, lymphomas, myeloma, bladder carcinoma, colon cancer, cutaneous melanoma, hepatocellular carcinoma, endometrial cancer, lung cancer, pancreatic cancer, gastric cancer and soft tissue sarcomas selected from rhabdomyosarcoma, synovial sarcoma and Ewing sarcoma; in particular melanoma, pancreatic, colon, lung, kidney and ovarian cancers.

Embodiment 25

A method of treatment an MEK-mediated disorder comprising the step of administering to a patient in need thereof a therapeutically effective amount of a compound according to any one of embodiments 1 to 18, or a pharmaceutically acceptable salt thereof.

Embodiment 26

The method of embodiment 25 wherein said MEK-mediated disorders are selected from ovarian carcinoma, kidney cancer, prostate cancer, breast carcinoma, lymphomas, myeloma, bladder carcinoma, colon cancer, cutaneous melanoma, hepatocellular carcinoma, endometrial cancer, lung cancer, pancreatic cancer, gastric cancer and soft tissue sarcomas selected from rhabdomyosarcoma, synovial sarcoma and Ewing sarcoma; in particular melanoma, pancreatic, colon, lung, kidney and ovarian cancers.

Further Embodiments

Preferred substituents present in compounds of the formula I, or of formula (Ie), are defined below. The definition of the substituents applies to the end-products as well as to the corresponding intermediates. In addition, the definitions of the substituent, as provided below, may be combined at will, e.g. preferred substituents $R_{3a}$ and preferred substituents $R_4$.

In one embodiment, the compound of the invention is a compound of formula (I), as defined herein, wherein n is 0.

In one embodiment, the compound of the invention is a compound of formula (I), as defined herein, wherein n is 1.

In one embodiment, the compound of the invention is a compound of formula (I), as defined herein, wherein $R_1$ is

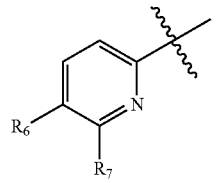

In one embodiment, the compound of the invention is a compound of formula (I), or of formula (Ie), as defined herein, wherein $R_1$ is

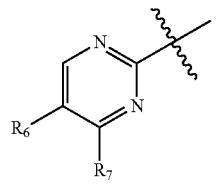

In one embodiment, the compound of the invention is a compound of formula (I), or of formula (Ie), as defined herein, wherein $R_1$ is

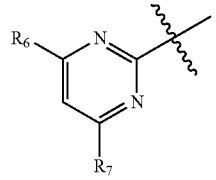

In one embodiment, the compound of the invention is a compound of formula (I), or of formula (Ie), as defined herein, wherein $R_1$ is

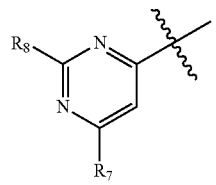

In one embodiment, the compound of the invention is a compound of formula (I), or of formula (Ie), as defined herein, wherein $R_1$ is

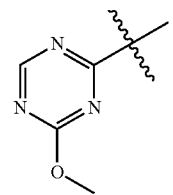

In one embodiment, the compound of the invention is a compound of formula (I), or of formula (Ie), as defined herein, wherein $R_1$ is

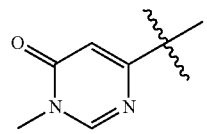

In one embodiment, the compound of the invention is a compound of formula (I), or of formula (Ie), as defined herein, wherein $R_1$ is

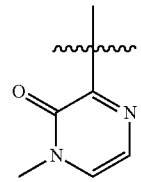 [SMILES: *c1nccn(C)c1=O]

In one embodiment, the compound of the invention is a compound of formula (I), or of formula (Ie), as defined herein, wherein $R_1$ is

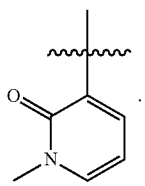

In one embodiment, the compound of the invention is a compound of formula (I), or of formula (Ie), as defined herein, wherein $R_2$ is chloro.

In one embodiment, the compound of the invention is a compound of formula (I), or of formula (Ie), as defined herein, wherein $R_2$ is methyl.

In one embodiment, the compound of the invention is a compound of formula (I), or of formula (Ie), as defined herein, wherein $R_2$ is hydrogen.

In one embodiment, the compound of the invention is a compound of formula (I), or of formula (Ie), as defined herein, wherein $R_2$ is fluoro.

In one embodiment, the compound of the invention is a compound of formula (I), or of formula (Ie), as defined herein, wherein $R_2$ is methoxy.

In one embodiment, the compound of the invention is a compound of formula (I), or of formula (Ie), as defined herein, wherein $R_{3a}$ is selected from cyano-methyl, 2-hydroxy-ethyl, 1-hydroxypropan-2-yl, 2-methoxy-ethyl, (3-methyloxetan-3-yl)-methyl, amino-carbonyl-methyl, 3-hydroxy-2-(hydroxy-methyl)propyl, 2-hydroxy-propyl, oxetan-3-ylmethyl and 2-amino-2-oxoethyl; in particular cyano-methyl, 2-methoxy-ethyl, (3-methyloxetan-3-yl)-methyl, amino-carbonyl-methyl, oxetan-3-ylmethyl and 2-amino-2-oxoethyl; such as cyano-methyl.

In one embodiment, the compound of the invention is a compound of formula (I), or of formula (Ie), as defined herein, wherein $R_{3a}$ is selected from 3-hydroxy-2-(hydroxy-methyl)propanoyl, 2-fluoropropanoyl, dimethylcarbamoyl, 2-hydroxyacetyl, 2-acetoxyacetyl, 2-methoxyacetyl, (2,2,2-trifluoroethyl)carbamoyl, 2-aminoacetyl, (S)-2-hydroxypropanoyl, 2-hydroxypropanoyl, acetyl, carbamoyl, (oxetan-2-yl)-methanoyl, 2-(sulfooxy)acetyl, 2-fluoroethanoyl and 3-hydroxypropanoyl; in particular 3-hydroxy-2-(hydroxy-methyl)propanoyl, 2-hydroxyacetyl, (S)-2-hydroxypropanoyl, 2-hydroxypropanoyl, and 3-hydroxypropanoyl; such as 2-hydroxyacetyl.

In one embodiment, the compound of the invention is a compound of formula (I), or of formula (Ie), as defined herein, wherein $R_{3a}$ is selected from methyl-sulfonyl, cyclopropyl-sulfonyl, isopropyl-sulfonyl and N,N-dimethylsulfonamidyl.

In one embodiment, the compound of the invention is a compound of formula (I), or of formula (Ie), as defined herein, wherein $R_{3a}$ is selected from methyl-sulfonyl, cyclopropyl-sulfonyl, isopropyl-sulfonyl and N,N-dimethylsulfonamidyl.

In one embodiment, the compound of the invention is a compound of formula (I), or of formula (Ie), as defined herein, wherein $R_{3a}$ is selected from dimethylcarbamoyl, (2,2,2-trifluoroethyl)carbamoyl and carbamoyl.

In one embodiment, the compound of the invention is a compound of formula (I), as defined herein, wherein $R_4$ is hydrogen.

In one embodiment, the compound of the invention is a compound of formula (I), as defined herein, wherein $R_4$ is halo, in particular fluoro.

In one embodiment, the compound of the invention is a compound of formula (I), as defined herein, wherein $R_4$ is methyl or hydroxy-methyl.

In one embodiment, the compound of the invention is a compound of formula (I), or of formula (Ie), as defined herein, wherein $R_5$ is hydrogen.

In one embodiment, the compound of the invention is a compound of formula (I), or of formula (Ie), as defined herein, wherein $R_5$ is methyl.

In one embodiment, the compound of the invention is a compound of formula (I), or of formula (Ie), as defined herein, wherein $R_6$ is hydrogen.

In one embodiment, the compound of the invention is a compound of formula (I), or of formula (Ie), as defined herein, wherein $R_6$ is methoxy.

In one embodiment, the compound of the invention is a compound of formula (I), or of formula (Ie), as defined herein, wherein $R_6$ is halo, in particular fluoro.

In one embodiment, the compound of the invention is a compound of formula (I), or of formula (Ie), as defined herein, wherein $R_7$ is selected from fluoro, cyclopropyl, $CF_3$ and $CH_2OH$.

In one embodiment, the compound of the invention is a compound of formula (I), or of formula (Ie), as defined herein, wherein $R_7$ is hydrogen.

In one embodiment, the compound of the invention is a compound of formula (I), or of formula (Ie), as defined herein, wherein $R_7$ is methyl.

In one embodiment, the compound of the invention is a compound of formula (Ie), as defined herein, wherein $R_{4a}$ is hydrogen.

In one embodiment, the compound of the invention is a compound of formula (Ie), as defined herein, wherein $R_{4a}$ is methyl.

In one embodiment, the compound of the invention is a compound of formula (Ie), as defined herein, wherein $R_{4b}$ is fluorine.

Yet Further Embodiments

Embodiment 1"

A compound of formula I:

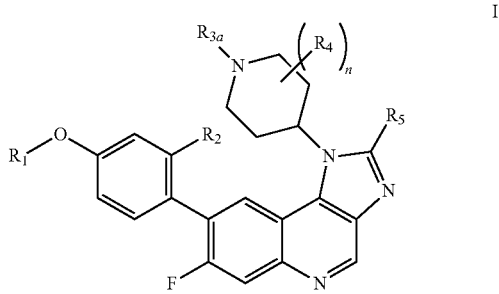

n is selected from 0, 1, 2 and 3;
$R_1$ is selected from:

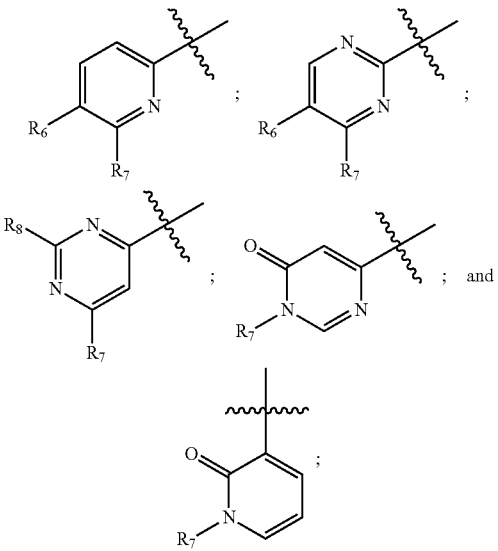

$R_2$ is selected from chloro and methoxy;
$R_{3a}$ is selected from cyano-methyl, 2-hydroxy-ethyl, 1-hydroxypropan-2-yl, 3-hydroxy-2-(hydroxy-methyl)propanoyl, 2-methoxy-ethyl, 2-fluoropropanoyl, (3-methyloxetan-3-yl)-methyl, methyl-sulfonyl, amino-carbonyl-methyl, cyclopropyl-sulfonyl, isopropyl-sulfonyl, dimethylcarbamoyl, 3-hydroxy-2-(hydroxy-methyl)propyl, 2-hydroxy-propyl, 2-hydroxyacetyl, 2-acetoxyacetyl, 2-methoxyacetyl, (2,2,2-trifluoroethyl)carbamoyl, oxetan-2-yl, 2-aminoacetyl, oxetan-3-ylmethyl, (S)-2-hydroxypropanoyl, 2-hydroxypropanoyl, acetyl, 2-amino-2-oxoethyl and carbamoyl;

R4 is selected from hydrogen, halo, methyl and hydroxymethyl; and optionally two R4 groups together with the carbon atoms to which they are attached form —(CH2)2-3—;
R5 is selected from hydrogen and methyl;
R6 is selected from hydrogen and halo;
R7 is selected from hydrogen, fluoro, chloro, CH2F, CHF2, CF3, CH2OH, cyclopropyl and methyl; and
R8 is selected from cyano; or the pharmaceutically acceptable salts thereof.

Embodiment 2"

The compound of embodiment 1" of formula Ia:

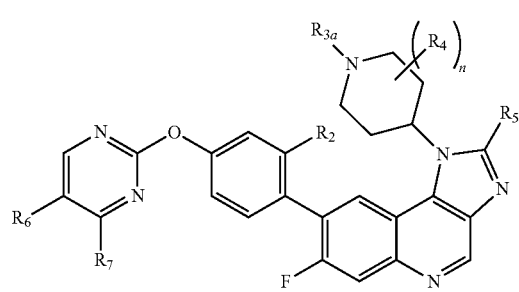

in which:
R2 is selected from chloro and methoxy;
R3a is selected from 2-hydroxy-ethyl, 1-hydroxypropan-2-yl, 2-methoxy-ethyl, (3-methyloxetan-3-yl)-methyl, methylsulfonyl, 2-acetoxyacetyl, 2-fluoropropanoyl, 2-hydroxypropyl, cyclopropyl-sulfonyl, isopropyl-sulfonyl, 3-hydroxy-2-(hydroxy-methyl)propyl, 3-hydroxy-2-(hydroxymethyl)propanoyl, oxetan-2-yl, dimethylcarbamoyl, (2,2,2-trifluoroethyl)carbamoyl, (S)-2-hydroxypropanoyl, oxetan-3-ylmethyl, 2-aminoacetyl, 2-methoxyacetyl, 2-hydroxyacetyl, 2-hydroxypropanoyl, acetyl, 2-amino-2-oxoethyl and carbamoyl;
R4 is selected from hydrogen, methyl and hydroxy-methyl;
R5 is selected from hydrogen and methyl;
R6 is selected from hydrogen and fluoro;
R7 is selected from hydrogen, fluoro, chloro, CH2F, CHF2, CF3, CH2OH, cyclopropyl and methyl; and
R8 is selected from cyano; or the pharmaceutically acceptable salts thereof.

Embodiment 3"

The compound of embodiment 2" selected from:

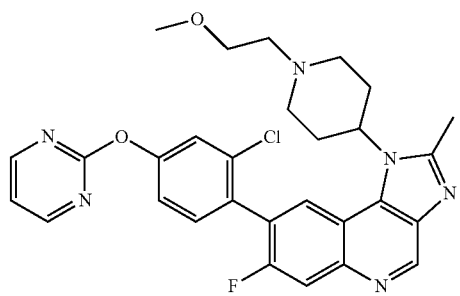

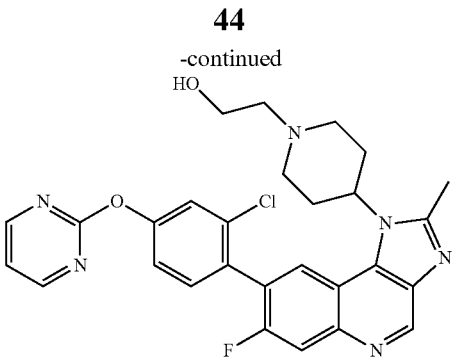

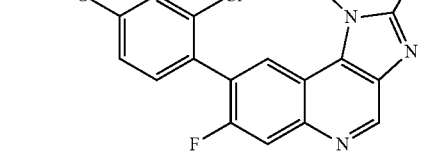

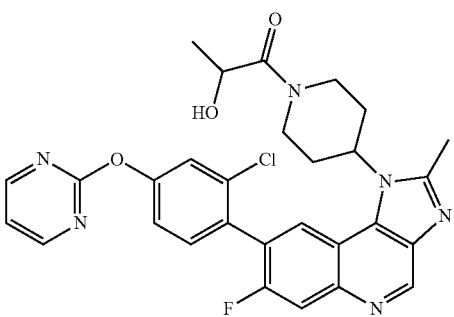

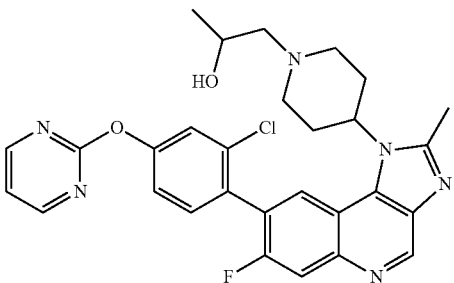

45
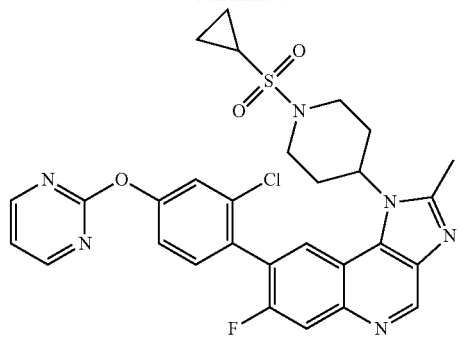
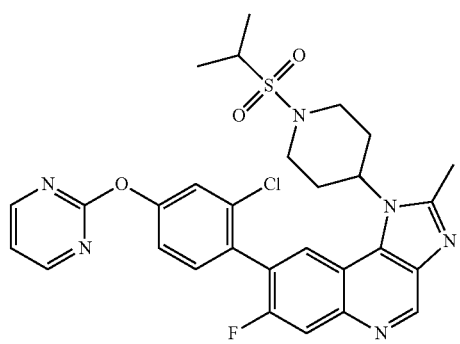
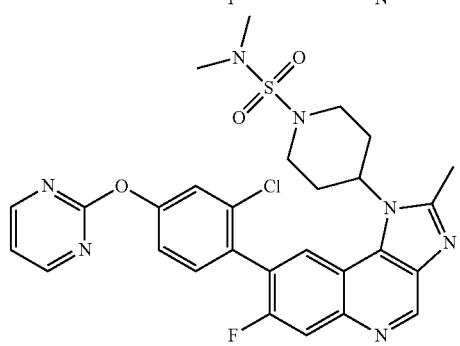
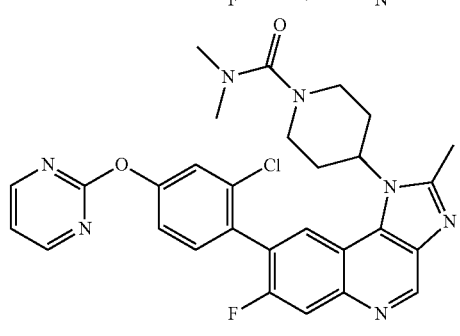
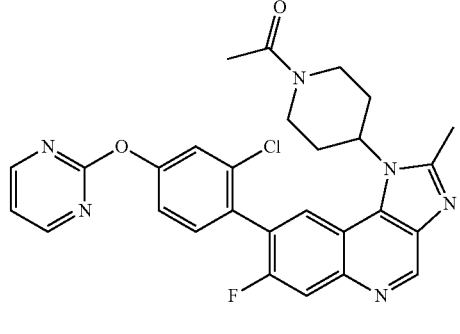
46
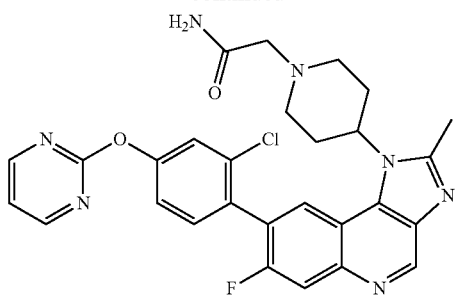
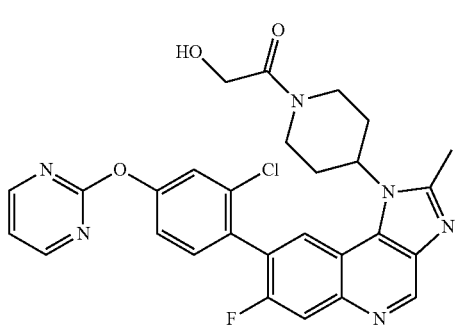
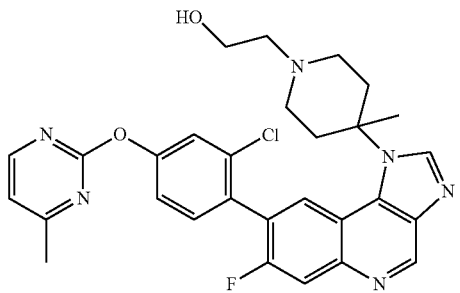
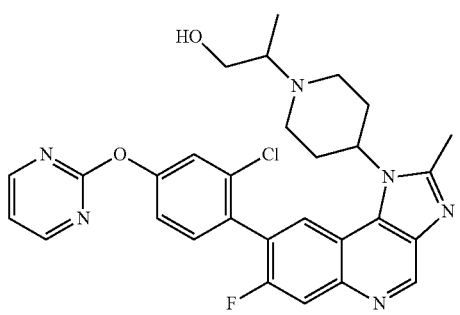
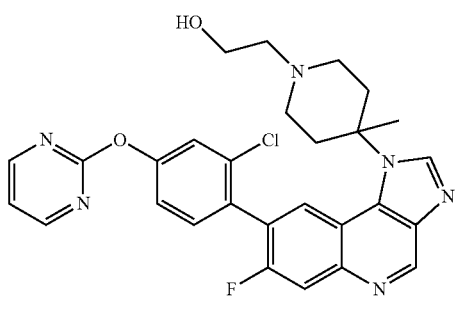

47
-continued
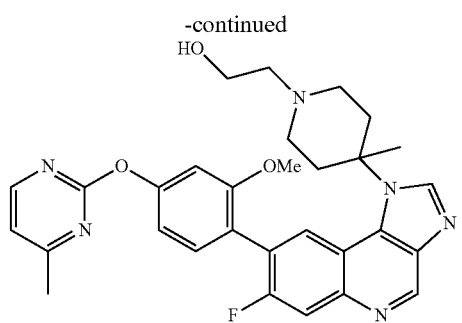
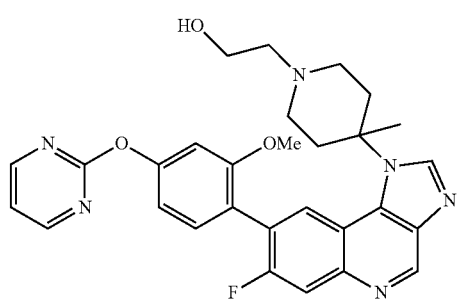
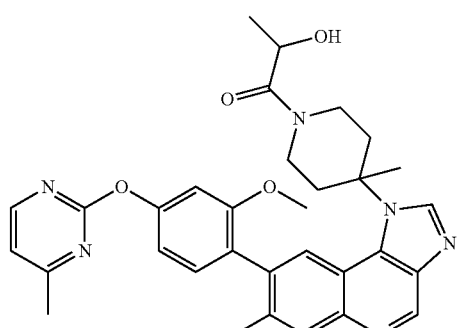
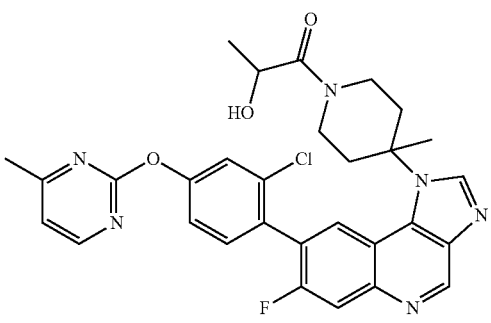
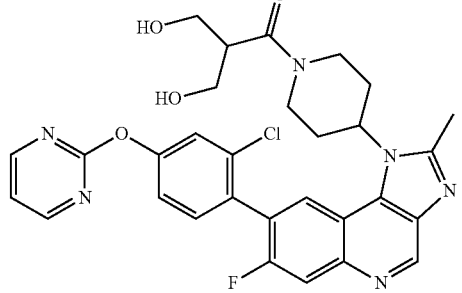
48
-continued
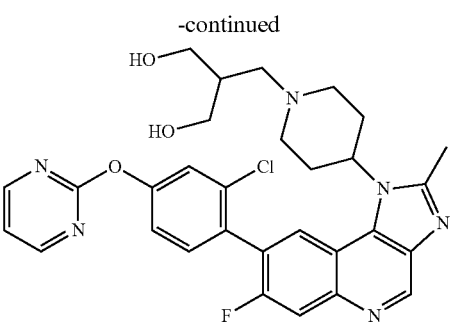
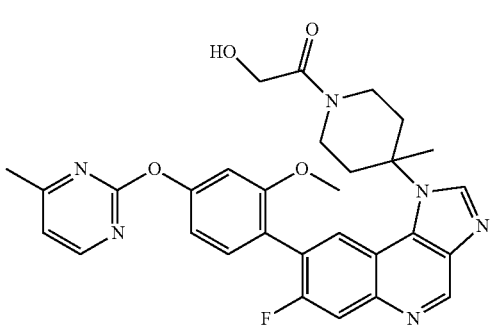
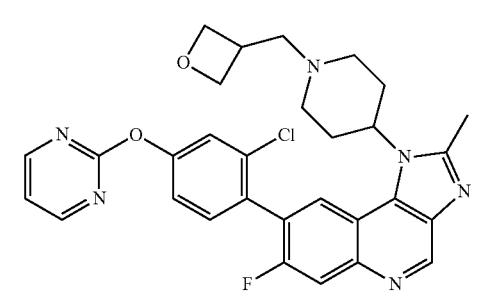
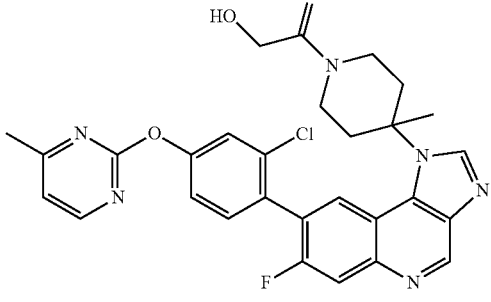
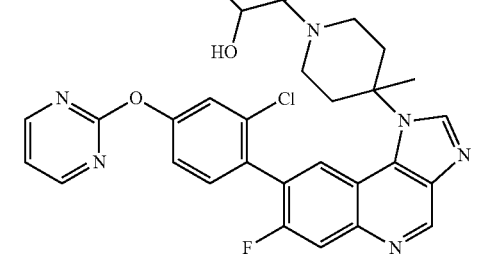

49
-continued
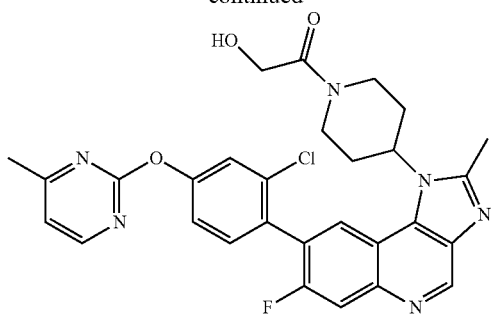
50
-continued
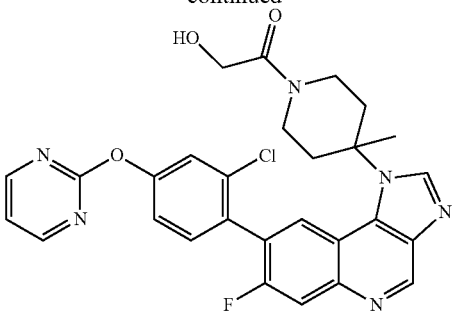
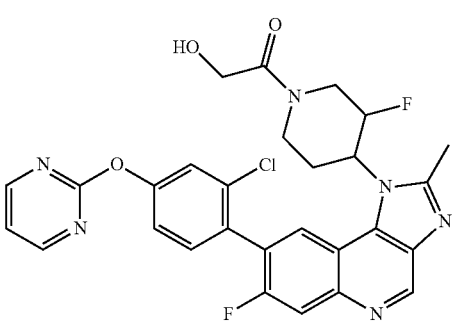
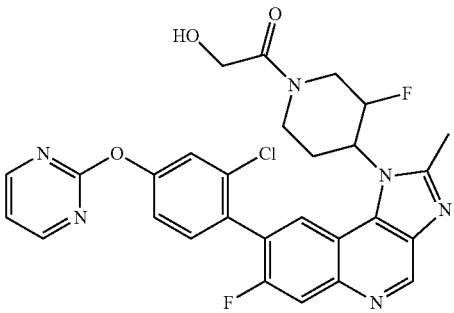
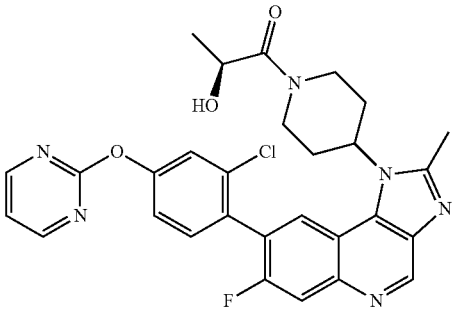
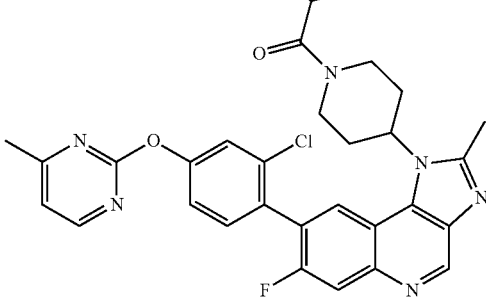

-continued
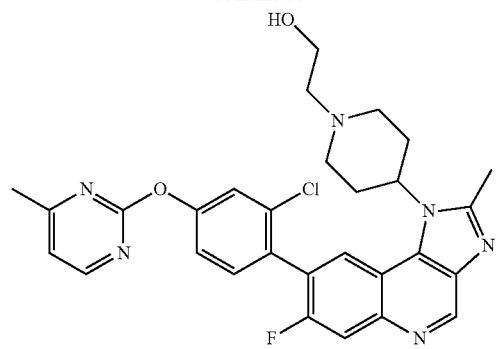
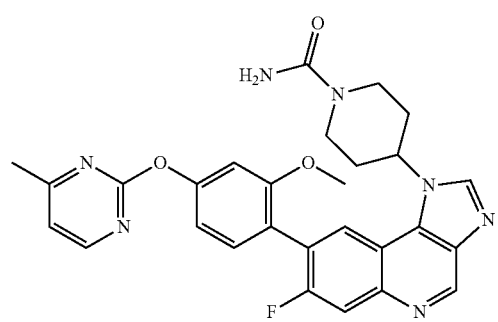
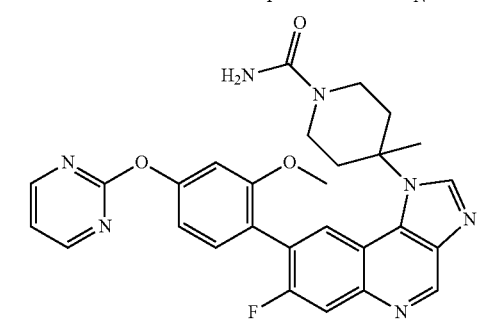
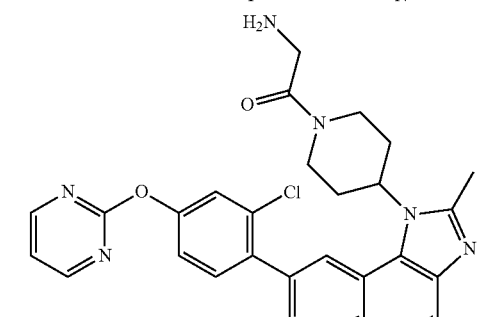
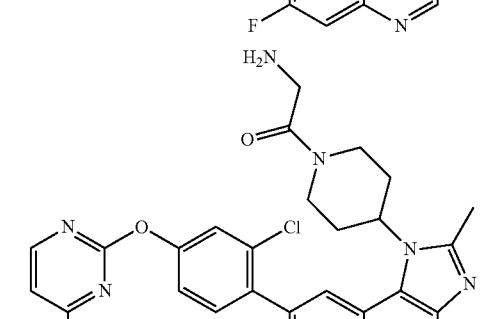
-continued
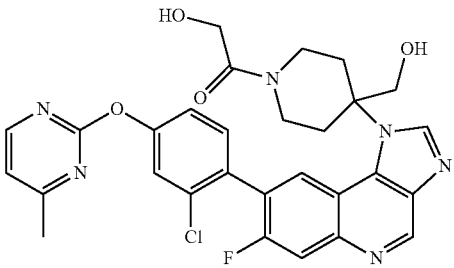
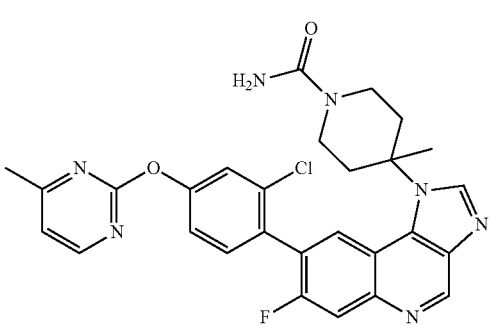
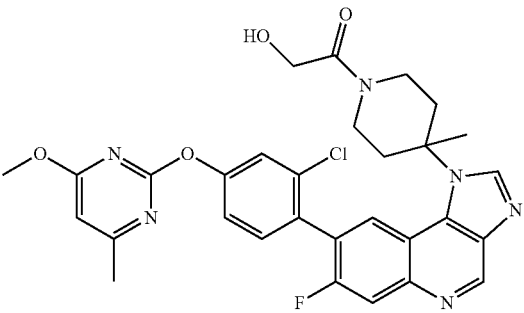
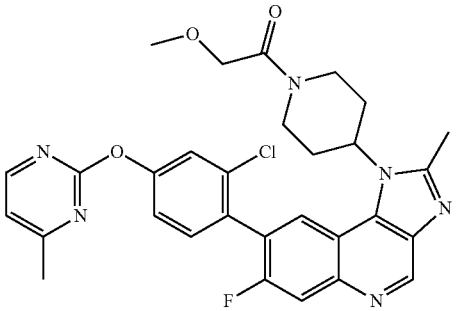
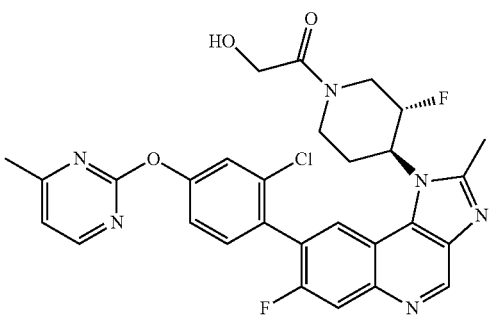

53
-continued
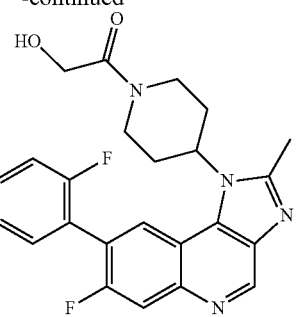
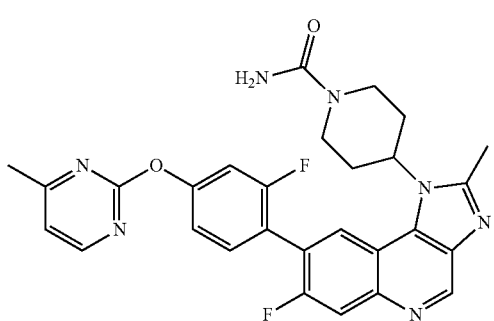
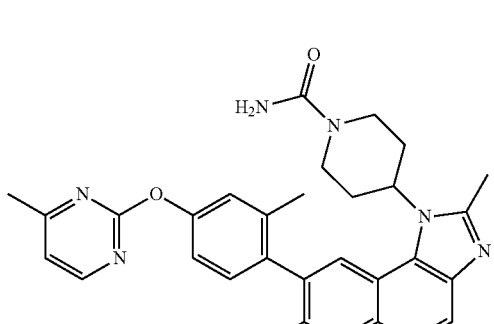
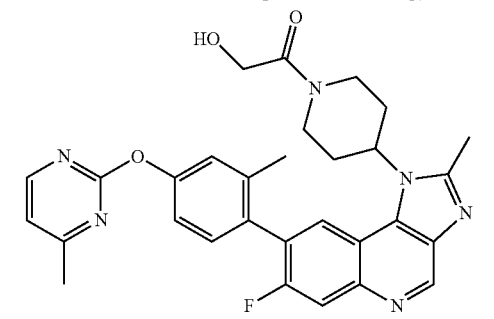
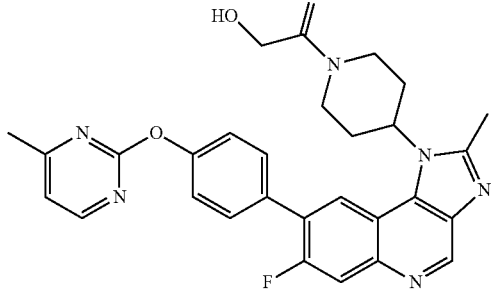
54
-continued
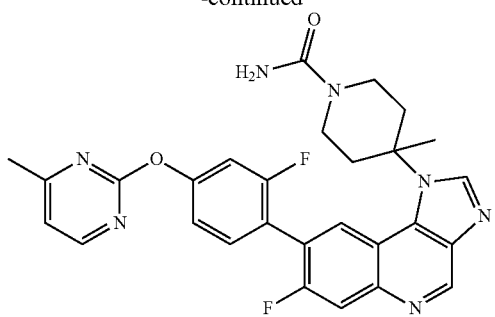
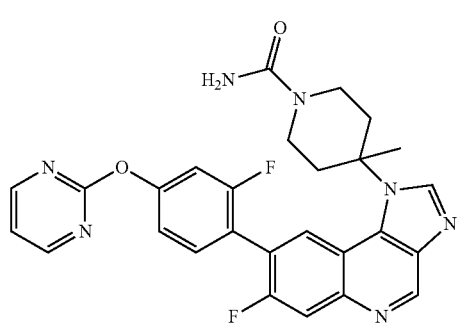
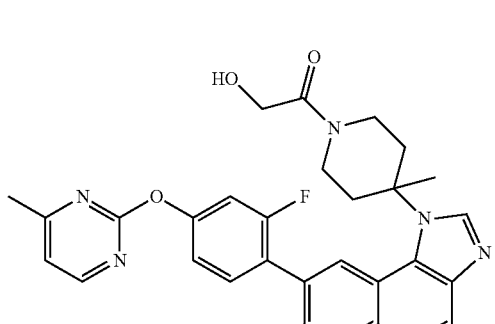
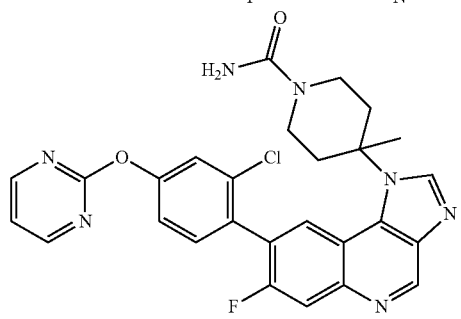
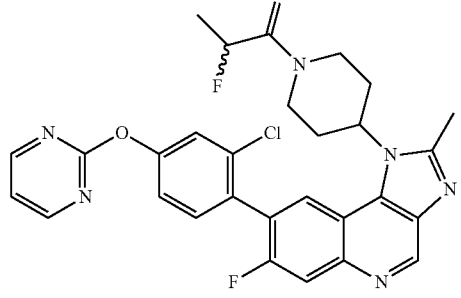

Embodiment 4″

The compound of embodiment 1″ of formula Ib:

in which:

n is selected from 0, 1 and 2;

R₁ is selected from:

$R_2$ is selected from chloro and methoxy;

$R_{3a}$ is selected from cyano-methyl, 2-hydroxy-ethyl, 1-hydroxypropan-2-yl, 2-methoxy-ethyl, (3-methyloxetan-3-yl)-methyl, methyl-sulfonyl, 2-fluoropropanoyl, 2-hydroxy-propyl, cyclopropyl-sulfonyl, isopropyl-sulfonyl, 3-hydroxy-2-(hydroxy-methyl)propyl, 2-acetoxyacetyl, 3-hydroxy-2-(hydroxy-methyl)propanoyl, dimethylcarbamoyl, (2,2,2-trifluoroethyl)carbamoyl, (S)-2-hydroxypropanoyl, oxetan-2-yl, oxetan-3-ylmethyl, 2-aminoacetyl, 2-methoxyacetyl, 2-hydroxyacetyl, 2-hydroxypropanoyl, acetyl, 2-amino-2-oxoethyl and carbamoyl;

$R_4$ is selected from hydrogen, methyl and hydroxy-methyl;

$R_5$ is selected from hydrogen and methyl;

$R_7$ is selected from hydrogen, fluoro, chloro, $CH_2F$, $CHF_2$, $CF_3$, $CH_2OH$, cyclopropyl and methyl; and $R_8$ is selected from cyano; or the pharmaceutically acceptable salts thereof.

57
Embodiment 5"
The compound of embodiment 4" selected from:
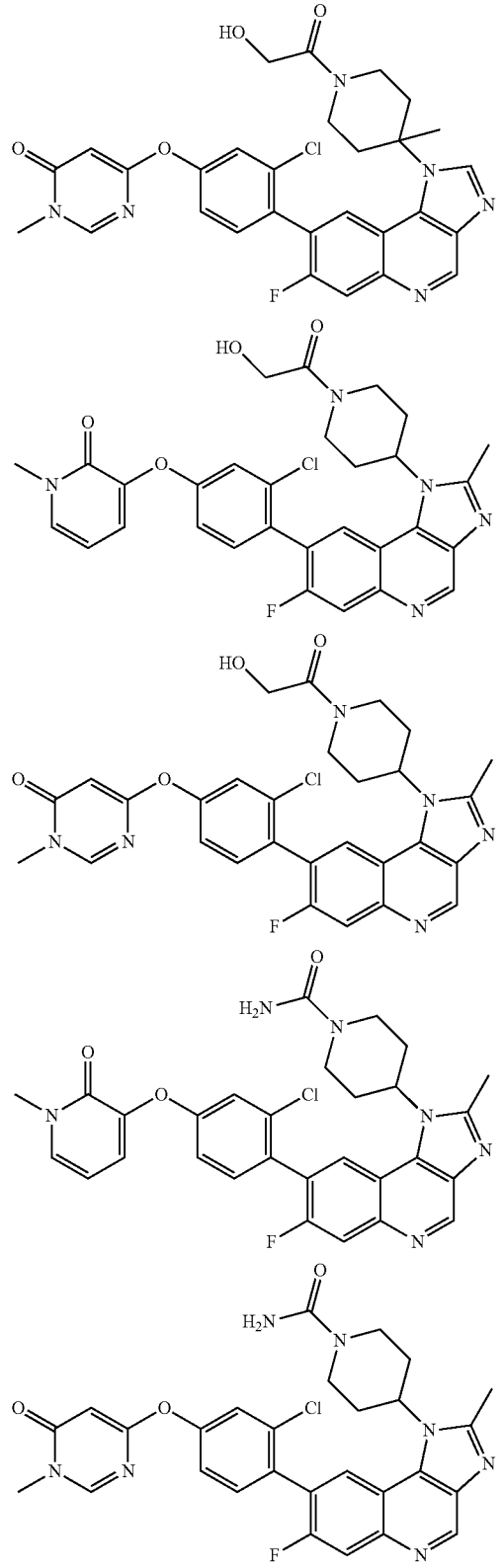
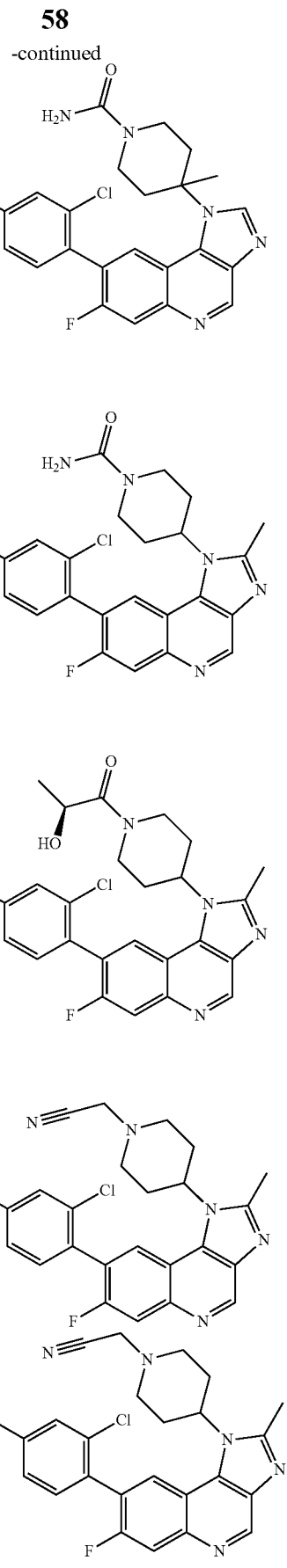

Embodiment 6"

The compound of embodiment 1" of formula Ic:

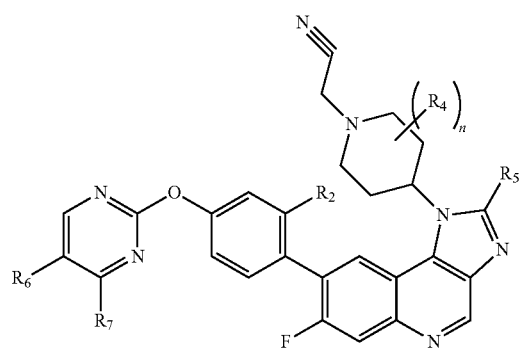

in which:

n is selected from 0, 1, 2 and 3;

$R_2$ is selected from chloro and methoxy;

$R_4$ is selected from fluoro; and optionally two $R_4$ groups together with the carbon atoms to which they are attached form —$(CH_2)_{2-3}$—;

$R_5$ is selected from hydrogen and methyl;

$R_6$ is selected from hydrogen and fluoro; and $R_7$ is selected from hydrogen, fluoro, chloro, $CH_2F$, $CHF_2$, $CF_3$, $CH_2OH$, cyclopropyl and methyl; or the pharmaceutically acceptable salts thereof.

Embodiment 7"

The compound of embodiment 6", or the pharmaceutically acceptable salts thereof, selected from:

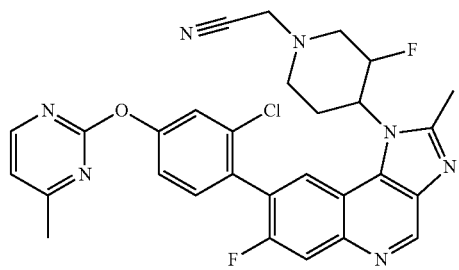

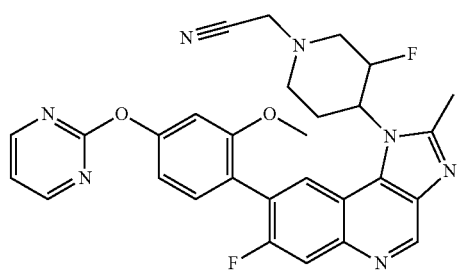

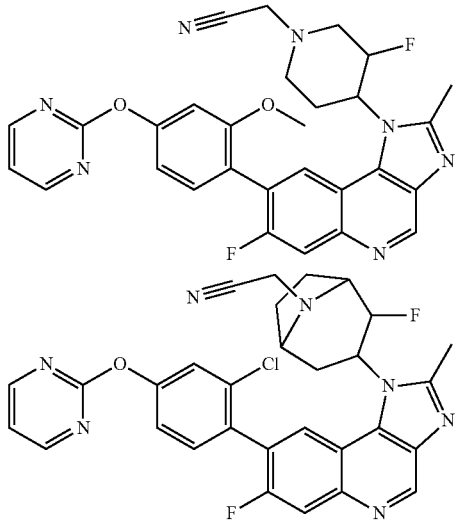

Embodiment 8"

The compound of embodiment 1" of formula Id:

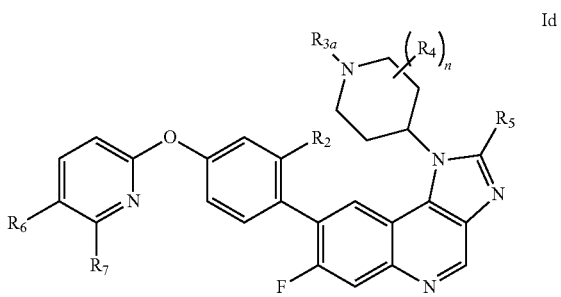

in which:

n is selected from 0, 1, 2 and 3;

$R_2$ is selected from chloro and methoxy;

$R_{3a}$ is selected from 2-hydroxy-ethyl, 1-hydroxypropan-2-yl, 2-methoxy-ethyl, (3-methyloxetan-3-yl)-methyl, methylsulfonyl, 2-hydroxy-propyl, 2-acetoxyacetyl, 2-fluoropropanoyl, cyclopropyl-sulfonyl, oxetan-2-yl, isopropyl-sulfonyl, 3-hydroxy-2-(hydroxy-methyl)propyl, 3-hydroxy-2-(hydroxy-methyl)propanoyl, dimethylcarbamoyl, (2,2,2-trifluoroethyl)carbamoyl, (S)-2-hydroxypropanoyl, oxetan-3-ylmethyl, 2-aminoacetyl, 2-methoxyacetyl, 2-hydroxyacetyl, 2-hydroxypropanoyl, acetyl, 2-amino-2-oxoethyl and carbamoyl;

$R_4$ is selected from fluoro; and optionally two $R_4$ groups together with the carbon atoms to which they are attached form —$(CH_2)_{2-3}$—;

$R_5$ is selected from hydrogen and methyl;

$R_6$ is selected from hydrogen and fluoro; and $R_7$ is selected from hydrogen, fluoro, chloro, $CH_2F$, $CHF_2$, $CF_3$, $CH_2OH$, cyclopropyl and methyl; or the pharmaceutically acceptable salts thereof.

Embodiment 9"

The compound of embodiment 8", or the pharmaceutically acceptable salts thereof, selected from:

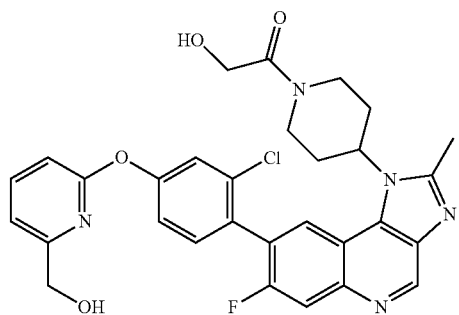

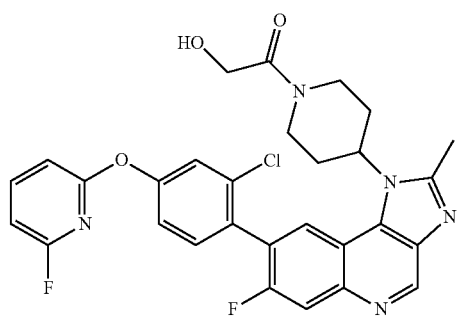

Embodiment 10"

The compound of embodiment 1" of formula Ie:

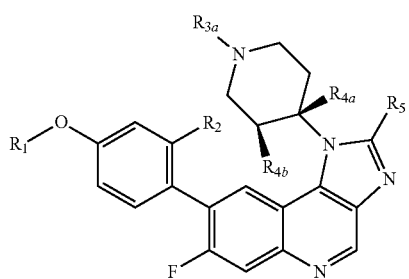

in which:
$R_1$ is selected from:

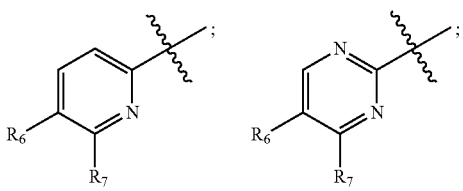

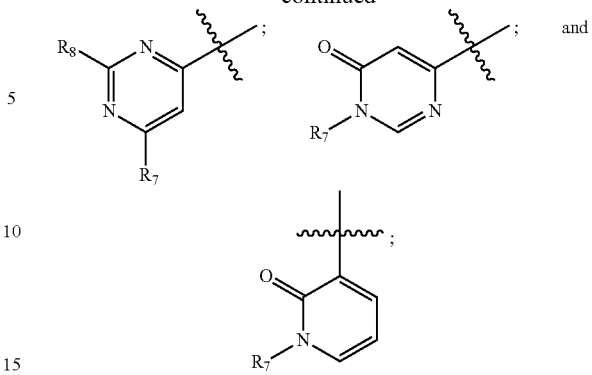

$R_2$ is selected from chloro and methoxy;
$R_{3a}$ is selected from 2-hydroxy-ethyl, 1-hydroxypropan-2-yl, 2-methoxy-ethyl, (3-methyloxetan-3-yl)-methyl, methylsulfonyl, 2-hydroxy-propyl, 2-acetoxyacetyl, 2-fluoropropanoyl, cyclopropyl-sulfonyl, oxetan-2-yl, isopropyl-sulfonyl, 3-hydroxy-2-(hydroxy-methyl)propyl, 3-hydroxy-2-(hydroxy-methyl)propanoyl, dimethylcarbamoyl, (2,2,2-trifluoroethyl)carbamoyl, (S)-2-hydroxypropanoyl, oxetan-3-ylmethyl, 2-aminoacetyl, 2-methoxyacetyl, 2-hydroxyacetyl, 2-hydroxypropanoyl, acetyl, 2-amino-2-oxoethyl and carbamoyl;
$R_{4a}$ is selected from hydrogen and methyl;
$R_{4b}$ is selected from hydrogen and fluorine;
$R_5$ is selected from hydrogen and methyl;
$R_6$ is selected from hydrogen and fluoro;
$R_7$ is selected from hydrogen, fluoro, chloro, $CH_2F$, $CHF_2$, $CF_3$, $CH_2OH$, cyclopropyl and methyl; and
$R_8$ is selected from cyano; or the pharmaceutically acceptable salts thereof.

Embodiment 11"

The compound of embodiment 10", or a pharmaceutically acceptable salt thereof, selected from:

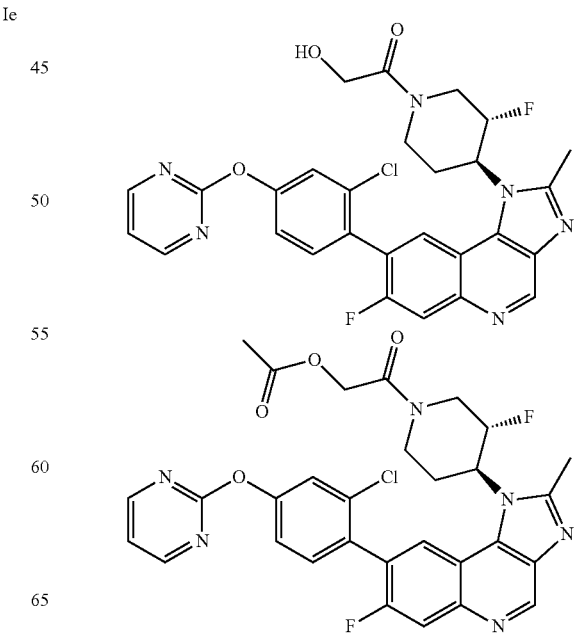

-continued

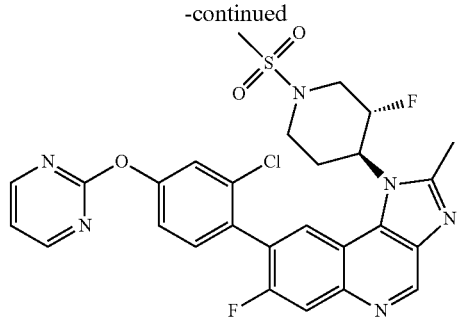

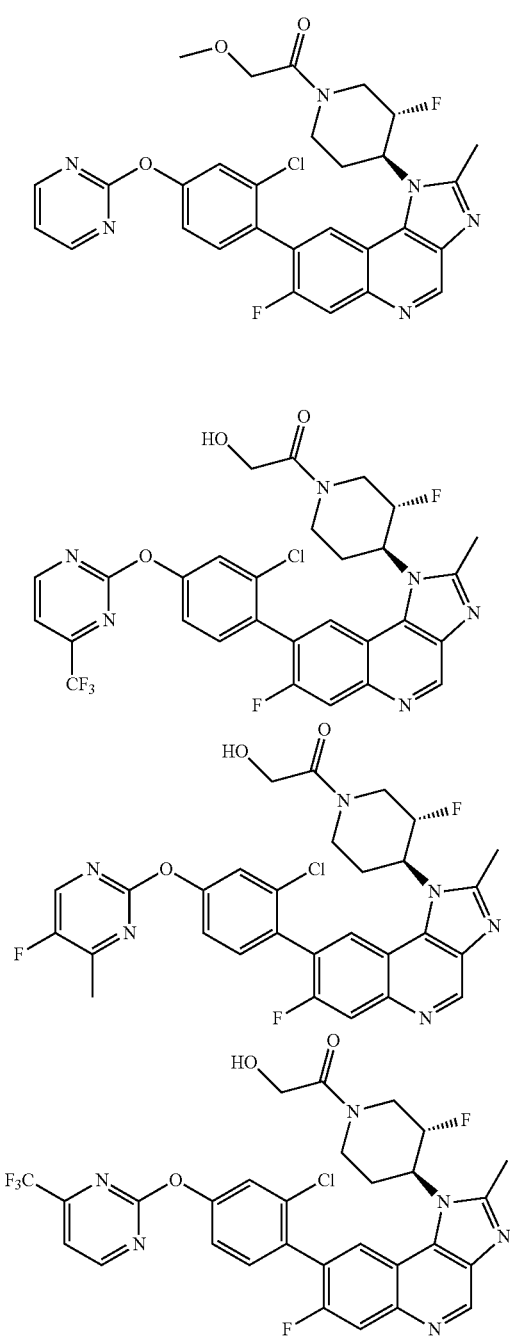

Embodiment 12"

A pharmaceutical composition comprising a compound of embodiment 1" or a pharmaceutically acceptable salt thereof, and at least one pharmaceutically acceptable carrier.

Embodiment 13"

A pharmaceutical composition according to embodiment 12" for use in the treatment of a disorder or disease which is mediated by the activity of MEK.

Embodiment 14"

A method of treatment an MEK-mediated disorder comprising the step of administering to a patient in need thereof a therapeutically effective amount of a compound of embodiment 1", or a pharmaceutically acceptable salt thereof.

Embodiment 15"

The method of embodiment 14" wherein said MEK-mediated disorders are selected from prostate cancer, breast carcinoma, lymphomas, myeloma, bladder carcinoma, colon cancer, cutaneous melanoma, hepatocellular carcinoma, endometrial cancer, lung cancer, pancreatic cancer, gastric cancer and soft tissue sarcomas selected from rhabdomyosarcoma, synovial sarcoma and Ewing sarcoma.

Pharmacology and Utility

Hyperproliferative diseases like cancer and inflammation are receiving a lot of attention from the scientific community and there is a strong desire to discover compounds that provide therapeutic benefits with regard to treating hyperproliferative diseases. In this regard efforts have been made to identify and target specific mechanisms which play a role in these diseases.

One target of interest is the over-activation of mitogen-activated protein (MAP) kinase cascade which is known to play an important role in cell proliferation and differentiation. This pathway can be activated when a growth factor binds to its receptor tyrosine kinase. This interaction promotes RAS association with RAF and initiates a phosphorylation cascade through MEK (MAP kinase) to ERK. Inhibition of this pathway is known to be beneficial in treating hyperproliferative diseases. MEK is an attractive therapeutic target because the only known substrates for MEK phosphorylation are the MAP kinases, ERK1 and ERK2. Constitutive activation of MEK/ERK has been found in pancreatic, colon, lung, kidney and ovarian primary tumor samples.

Phosphorylation of MEK increases its affinity and its catalytic activity toward ERK as well as its affinity for ATP. This invention describes compounds that inhibit MEK activity by modulating ATP binding and the association of MEK with ERK by a mechanism that is ATP-competitive.

Activation of MEK has been demonstrated in many disease models suggesting that inhibition of MEK could have potential therapeutic benefit in various diseases such as Pain (see, e.g., Evidence of efficacy in pain models described in J. Neurosci. 22:478, 2002; Acta Pharmacol Sin. 26:789 2005; Expert Opin Ther Targets. 9:699, 2005; and Mol. Pain. 2:2, 2006): Stroke (see, e.g., Evidence of efficacy in stroke models significant neuroprotection against ischemic brain injury by inhibition of the MEK described in J. Pharmacol. Exp. Ther. 304:172, 2003; and Brain Res. 996:55, 2004); Diabetes (see, e.g., Evidence in diabetic complications described in Am. J. Physiol. Renal. 286, F120 2004); Inflammation (see e.g., Evidence of efficacy in inflammation models described in Biochem Biophy. Res. Com. 268:647, 2000); and Arthritis (see, e.g, Evidence of efficacy in experimental osteoarthritis and arthritis as described in J. Clin. Invest. 116:163. 2006).

The present invention relates to compounds capable of inhibiting the activity of MEK. The invention further provides a process for the preparation of compounds of the invention and pharmaceutical preparations comprising such compounds. Another aspect of the present invention relates to a method of treating MEK-mediated disorders comprising the step of administering to a patient in need thereof a therapeutically effective amount of a compound of formula I as defined in the Summary of the Invention.

In certain embodiments, the present invention relates to the aforementioned method, wherein said MEK-mediated disorders are cancers selected from, but not limited to: angiosarcoma, fibrosarcoma, rhabdomyosarcoma, liposarcoma, myxoma, rhabdomyoma, fibroma, lipoma, teratoma; bronchogenic carcinoma, squamous cell carcinoma, undifferentiated small cell carcinoma, undifferentiated large cell carcinoma, alveolar (bronchiolar) carcinoma, bronchial adenoma, lymphoma, chondromatous hanlartoma, inesothelioma, esophageal squamous cell carcinoma, leiomyosarcoma, leiomyosarcoma, ductal adenocarcinoma, insulinorna, glucagonoma, gastrinoma, vipoma, stomach and small bowel carcinoid tumors, adenocarcinoma, Karposi's sarcoma, leiomyoma, hemangioma, lipoma, neurofibroma, fibroma, tubular adenoma, villous adenoma, hamartoma, Wilm's tumor [nephroblastoma, leukemia, bladder and urethra squamous cell carcinoma, transitional cell carcinoma, adenocarcinoma, seminoma, teratoma, embryonal carcinoma, teratocareinoma, choriocarcinoma, interstitial cell carcinoma, fibroadenoma, adenomatoid tumors, hepatoma (hepatocellular carcinoma), cholangiocarcinoma, hepatoblastoma, hepatocellular adenoma, hemangioma, osteogenic sarcoma (osteosarcoma), malignant fibrous histiocytoma, chondrosarcoma, Ewing's sarcoma, malignant lyinphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors, osteoma, granuloma, xanthoma, osteitis deformians, meningioma, meningiosarcoma, gliomatosis, astrocytoma, medulloblastoma, glioma, ependymoma, germinoma [pinealoma], glioblastoma multiform, oligodendroglioma, schwannoma, retinoblastoma, congenital tumors, spinal cord neurofibroma, meningioma, glioma, endometrial carcinoma, cervical carcinoma, pre-tumor cervical dysplasia, ovarian carcinoma, serous cystadenocarcinoma, mucinous cystadenocarcinoma, granulosa-thecal cell tumors, Sertoli-Leydig cell tumors, dysgerminoma, malignant teratoma, intraepithelial carcinoma, adenocarcinoma, melanoma), vaginal clear cell carcinoma, botryoid sarcoma (embryonal rhabdomyosarcoma), fallopian tube carcinoma, acute and chronic myeloid leukemia, acute lymphoblastic leukemia, chronic lymphocytic leukemia, myeloproliferative diseases, multiple myeloma, myelodysplastic syndrome, Hodgkin's disease, non-Hodgkin's lymphoma, malignant lymphoma, malignant melanoma, basal cell carcinoma, moles, dysplastic nevi, angioma, dermatofibroma, keloids, psoriasis, and neuroblastoma; in particular ovarian carcinoma, kidney cancer, prostate cancer, breast carcinoma, lymphomas, myeloma, bladder carcinoma, colon cancer, cutaneous melanoma, hepatocellular carcinoma, endometrial cancer, lung cancer, pancreatic cancer, gastric cancer and soft tissue sarcomas selected from rhabdomyosarcoma, synovial sarcoma and Ewing sarcoma; preferably pancreatic cancer, colon cancer, lung cancer, kidney cancer and ovarian carcinoma.

The compounds of the present invention may also be useful in the treatment of other diseases or conditions related to the hyperactivity of MEK. Thus, as a further aspect, the invention relates to a method of treatment of a disorder selected from: xenograft (cellos), skin, limb, organ or bone marrow transplant) rejection; osteoarthritis; rheumatoid arthritis; cystic fibrosis; complications of diabetes (including diabetic retinopathy and diabetic nephropathy); hepatomegaly; cardiomegaly; stroke (such as acute focal ischemic stroke and global cerebral ischemia); heart failure; septic shock; asthma; chronic obstructive pulmonary disorder; Alzheimer's disease; and chronic or neuropathic pain.

The term "chronic pain" for purposes of the present invention includes, but is not limited to, idiopathic pain, and pain associated with chronic alcoholism, vitamin deficiency, uremia, or hypothyroidism. Chronic pain is associated with numerous conditions including, but not limited to, inflammation, and post-operative pain.

As used herein, the term "neuropathic pain" is associated with numerous conditions which include, but are not limited to, inflammation, postoperative pain, phantom limb pain, burn pain, gout, trigeminal neuralgia, acute herpetic and postherpetic pain, causalgia, diabetic neuropathy, plexus avulsion, neuroma, vasculitis, viral infection, crush injury, constriction injury, tissue injury, limb amputation, and nerve injury between the peripheral nervous system and the central nervous system.

Compounds of the invention may also be useful as antiviral agents for treating viral infections such as HIV, hepatitis (B) virus (HBV) human papilloma virus (HPV), cytomegalovirus (CMV), and Epstein-Barr virus (EBV).

Compounds of the invention may also be useful in the treatment of restenosis, psoriasis, allergic contact dermatitis, autoimmune disease, atherosclerosis and inflammatory bowel diseases, e.g. Crohn's disease and ulcerative colitis.

A MEK inhibitor of the present invention may be usefully combined with another pharmacologically active compound, or with two or more other pharmacologically active compounds, particularly in the treatment of cancer. For example, a compound of the formula (I), or a pharmaceutically acceptable salt thereof, as defined above, may be administered simultaneously, sequentially or separately in combination with one or more agents selected from chemotherapy agents, for example, mitotic inhibitors such as a taxane, a vinca alkaloid, paclitaxel, docetaxel, vincristine, vinblastine, vinorelbine or vinflunine, and other anticancer agents, e.g. cisplatin, 5-fluorouracil or 5-fluoro-2-4(1H,3H)-pyrimidinedione (5FU), flutamide or gemcitabine.

Such combinations may offer significant advantages, including synergistic activity, in therapy.

In certain embodiments, the present invention relates to the aforementioned method, wherein said compound is administered parenterally.

In certain embodiments, the present invention relates to the aforementioned method, wherein said compound is administered intramuscularly, intravenously, subcutaneously, orally, pulmonary, intrathecally, topically or intranasally.

In certain embodiments, the present invention relates to the aforementioned method, wherein said compound is administered systemically.

In certain embodiments, the present invention relates to the aforementioned method, wherein said patient is a mammal.

In certain embodiments, the present invention relates to the aforementioned method, wherein said patient is a primate.

In certain embodiments, the present invention relates to the aforementioned method, wherein said patient is a human.

In another aspect, the present invention relates to a method of treating an MEK-mediated disorder, comprising the step of: administering to a patient in need thereof a therapeutically effective amount of a chemothereutic agent in combination with a therapeutically effective amount of a compound of formula I as defined in the Summary of the Invention.

Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) nasally; (9) pulmonary; or (10) intrathecally. In one embodiment, the pharmaceutical formulation comprises a solid dispersion having a compound of the present invention, or pharmaceutically acceptable salt thereof, as the active ingredient embedded in a polymer or mixture of polymers, optionally mixed with at least one excipient (eg a surfactant). Examples of suitable polymers are PVP k30, PVP-VA 64, HPMC E3, HPMC-ASLF, HPMC P, Eudragit EPO, Eudragit L100, Soluplus or PEG8000. Examples of suitable excipients are SLS, Cremophor EL, vitamine E TPGS, Poloxamer407, Poloxamer188 or Solutol HS15.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", J. Pharm. Sci. 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. Preferred dosing is one administration per day.

While it is possible for a compound of the present invention to be administered alone, it is preferable to administer the compound as a pharmaceutical formulation (composition).

The compounds according to the invention may be formulated for administration in any convenient way for use in human or veterinary medicine, by analogy with other pharmaceuticals.

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

Microemulsification technology can improve bioavailability of some lipophilic (water insoluble) pharmaceutical agents. Examples include Trimetrine (Dordunoo, S. K., et al., Drug Development and Industrial Pharmacy, 17(12), 1685-1713, 1991 and REV 5901 (Sheen, P. C., et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastrointestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Commercially available amphiphilic carriers are particularly contemplated, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

Hydrophilic polymers suitable for use in the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight of from about 100 or 120 daltons up to about 5,000 or 10,000 daltons, and more preferably from about 300 daltons to about 5,000 daltons. In a particularly preferred embodiment, the polymer is polyethyleneglycol having a molecular weight of from about 100 to about 5,000 daltons, and more preferably having a molecular weight of from about 300 to about 5,000 daltons. In a particularly preferred embodiment, the polymer is polyethyleneglycol of 750 daltons (PEG(750)). Polymers may also be defined by the number of monomers therein; a preferred embodiment of the present invention utilizes polymers of at least about three monomers, such PEG polymers consisting of three monomers (approximately 150 daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Cyclodextrins are cyclic oligosaccharides, consisting of 6, 7 or 8 glucose units, designated by the Greek letter .alpha., .beta. or .gamma., respectively. Cyclodextrins with fewer than six glucose units are not known to exist. The glucose units are linked by alpha-1,4-glucosidic bonds. As a consequence of the chair conformation of the sugar units, all secondary hydroxyl groups (at C-2, C-3) are located on one side of the ring, while all the primary hydroxyl groups at C-6 are situated on the other side. As a result, the external faces are hydrophilic, making the cyclodextrins water-soluble. In contrast, the cavities of the cyclodextrins are hydrophobic, since they are lined by the hydrogen of atoms C-3 and C-5, and by ether-like oxygens. These matrices allow complexation with a variety of relatively hydrophobic compounds, including, for instance, steroid compounds such as 17.beta.-estradiol (see, e.g., van Uden et al. Plant Cell Tiss. Org. Cult. 38:1-3-113 (1994)). The complexation takes place by Van der Waals interactions and by hydrogen bond formation. For a general review of the chemistry of cyclodextrins, see, Wenz, Agnew. Chem. Int. Ed. Engl., 33:803-822 (1994).

The physico-chemical properties of the cyclodextrin derivatives depend strongly on the kind and the degree of substitution. For example, their solubility in water ranges from insoluble (e.g., triacetyl-beta-cyclodextrin) to 147% soluble (w/v) (G-2-beta-cyclodextrin). In addition, they are soluble in many organic solvents. The properties of the cyclodextrins enable the control over solubility of various formulation components by increasing or decreasing their solubility.

Numerous cyclodextrins and methods for their preparation have been described. For example, Parmeter (I), et al. (U.S. Pat. No. 3,453,259) and Gramera, et al. (U.S. Pat. No. 3,459,731) described electroneutral cyclodextrins. Other derivatives include cyclodextrins with cationic properties [Parmeter (II), U.S. Pat. No. 3,453,257], insoluble crosslinked cyclodextrins (Solms, U.S. Pat. No. 3,420,788), and cyclodextrins with anionic properties [Parmeter (III), U.S. Pat. No. 3,426,011]. Among the cyclodextrin derivatives with anionic properties, carboxylic acids, phosphorous acids, phosphinous acids, phosphonic acids, phosphoric acids, thiophosphonic acids, thiosulphinic acids, and sulfonic acids have been appended to the parent cyclodextrin [see, Parmeter (III), supra]. Furthermore, sulfoalkyl ether cyclodextrin derivatives have been described by Stella, et al. (U.S. Pat. No. 5,134,127).

Liposomes consist of at least one lipid bilayer membrane enclosing an aqueous internal compartment. Liposomes may be characterized by membrane type and by size. Small unilamellar vesicles (SUVs) have a single membrane and typically range between 0.02 and 0.05 μm in diameter; large unilamellar vesicles (LUVS) are typically larger than 0.05 μm Oligolamellar large vesicles and multilamellar vesicles have multiple, usually concentric, membrane layers and are typically larger than 0.1 μm. Liposomes with several nonconcentric membranes, i.e., several smaller vesicles contained within a larger vesicle, are termed multivesicular vesicles.

One aspect of the present invention relates to formulations comprising liposomes containing a compound of the present invention, where the liposome membrane is formulated to provide a liposome with increased carrying capacity. Alternatively or in addition, the compound of the present invention may be contained within, or adsorbed onto, the liposome bilayer of the liposome. The compound of the present invention may be aggregated with a lipid surfactant and carried within the liposomes internal space; in these cases, the liposome membrane is formulated to resist the disruptive effects of the active agent-surfactant aggregate.

According to one embodiment of the present invention, the lipid bilayer of a liposome contains lipids derivatized with polyethylene glycol (PEG), such that the PEG chains extend from the inner surface of the lipid bilayer into the interior space encapsulated by the liposome, and extend from the exterior of the lipid bilayer into the surrounding environment.

Active agents contained within liposomes of the present invention are in solubilized form. Aggregates of surfactant and active agent (such as emulsions or micelles containing the active agent of interest) may be entrapped within the interior space of liposomes according to the present invention. A surfactant acts to disperse and solubilize the active agent, and may be selected from any suitable aliphatic, cycloaliphatic or aromatic surfactant, including but not limited to biocompatible lysophosphatidylcholines (LPCs) of varying chain lengths (for example, from about C.sub.14 to about C.sub.20). Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. Preferred are surfactants with CMCs in the micromolar range; higher CMC surfactants may be utilized to prepare micelles entrapped within liposomes of the present invention, however, micelle surfactant monomers could affect liposome bilayer stability and would be a factor in designing a liposome of a desired stability.

Liposomes according to the present invention may be prepared by any of a variety of techniques that are known in the art. See, e.g., U.S. Pat. No. 4,235,871; Published PCT applications WO 96/14057; New RRC, Liposomes: A practical approach, IRL Press, Oxford (1990), pages 33-104; Lasic D D, Liposomes from physics to applications, Elsevier Science Publishers BV, Amsterdam, 1993.

For example, liposomes of the present invention may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323 (Apr. 12, 1988).

The release characteristics of a formulation of the present invention depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Pore forming agents which add microstructure to the matrices (i.e., water soluble compounds such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

Pharmaceutical Combinations

The invention especially relates to the use of a compound of the formula I (or a pharmaceutical composition comprising a compound of the formula I) in the treatment of one or more of the diseases mentioned herein; wherein the response to treatment is beneficial as demonstrated, for example, by the partial or complete removal of one or more of the symptoms of the disease up to complete cure or remission.

A compound of formula (I) can also be used in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors, such as RAD001; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies, such as HCD122; heparanase inhibitors; inhibitors of Ras oncogenic isoforms; telomerase inhibitors; proteasome inhibitors; compounds used in the treatment of hematologic malignancies, such as FLUDARABINE; compounds which target, decrease or inhibit the activity of Flt-3, such as PKC412; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics and AUY922; temozolomide (TEMODAL®); kinesin spindle protein inhibitors, such as SB715992 or SB743921 from GlaxoSmithKline, or pentamidine/chlorpromazine from CombinatoRx; PI3K inhibitors, such as BEZ235, BKM120 [i.e. 5-(2,6-dimorpholinopyrimidin-4-yl)-4-(trifluoromethyl)pyridin-2-amine] or BYL719 [i.e. (S)—N-1-(4-methyl-5-(2-(1,1,1-trifluoro-2-methylpropan-2-yl)pyridin-4-yl)thiazol-2-yl)pyrrolidine-1,2-dicarboxamide]; in particular BEZ235; preferably BKM120 or BYL719; RAF inhibitors, such as LGX818 or RAF265; MEK inhibitors such as ARRY142886 from Array PioPharma, AZD6244 from AstraZeneca, PD181461 from Pfizer, leucovorin, EDG binders, antileukemia compounds, ribonucleotide reductase inhibitors, S-adenosylmethionine decarboxylase inhibitors, antiproliferative antibodies or other chemotherapeutic compounds. Further, alternatively or in addition they may be used in combination with other tumor treatment approaches, including surgery, ionizing radiation, photodynamic therapy, implants, e.g. with corticosteroids, hormones, or they may be used as radiosensitizers. Also, in anti-inflammatory and/or antiproliferative treatment, combination with anti-inflammatory drugs is included. Combination is also possible with antihistamine drug substances, bronchodilatatory drugs, NSAID or antagonists of chemokine receptors.

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketoconazole, vorozole, fadrozole, anastrozole and letrozole. Exemestane can be administered, e.g., in the form as it is marketed, e.g. under the trademark AROMASIN. Formestane can be administered, e.g., in the form as it is marketed, e.g. under the trademark LENTARON. Fadrozole can be administered, e.g., in the form as it is marketed, e.g. under the trademark AFEMA. Anastrozole can be administered, e.g., in the form as it is marketed, e.g. under the trademark ARIMIDEX. Letrozole can be administered, e.g., in the form as it is marketed, e.g. under the trademark FEMARA or FEMAR. Aminoglutethimide can be administered, e.g., in the form as it is marketed, e.g. under the trademark ORIMETEN. A combination of the invention comprising a chemotherapeutic agent which is an aromatase inhibitor is particularly useful for the treatment of hormone receptor positive tumors, e.g. breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX. Raloxifene hydrochloride can be administered, e.g., in the form as it is marketed, e.g. under the trademark EVISTA. Fulvestrant can be formulated as disclosed in U.S. Pat. No. 4,659,516 or it can be administered, e.g., in the form as it is marketed, e.g. under the trademark FASLODEX. A combination of the invention comprising a chemotherapeutic agent which is an antiestrogen is particularly useful for the treatment of estrogen receptor positive tumors, e.g. breast tumors.

The term "anti-androgen" as used herein relates to any substance which is capable of inhibiting the biological effects of androgenic hormones and includes, but is not limited to, bicalutamide (CASODEX), which can be formulated, e.g. as disclosed in U.S. Pat. No. 4,636,505.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX. Abarelix can be formulated, e.g. as disclosed in U.S. Pat. No. 5,843,901.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148 (compound A1 in WO99/17804). Irinotecan can be administered, e.g. in the form as it is marketed, e.g. under the trademark CAMPTOSAR. Topotecan can be administered, e.g., in the form as it is marketed, e.g. under the trademark HYCAMTIN.

The term "topoisomerase II inhibitor" as used herein includes, but is not limited to the anthracyclines such as doxorubicin (including liposomal formulation, e.g. CAELYX), daunorubicin, epirubicin, idarubicin and nemorubicin, the anthraquinones mitoxantrone and losoxantrone, and the podophillotoxines etoposide and teniposide. Etoposide can be administered, e.g. in the form as it is marketed, e.g. under the trademark ETOPOPHOS. Teniposide can be administered, e.g. in the form as it is marketed, e.g. under the trademark VM 26-BRISTOL. Doxorubicin can be administered, e.g. in the form as it is marketed, e.g. under the trademark ADRIBLASTIN or ADRIAMYCIN. Epirubicin can be administered, e.g. in the form as it is marketed, e.g. under the trademark FARMORUBICIN. Idarubicin can be administered, e.g. in the form as it is marketed, e.g. under the trademark ZAVEDOS. Mitoxantrone can be administered, e.g. in the form as it is marketed, e.g. under the trademark NOVANTRON.

The term "microtubule active compound" relates to microtubule stabilizing, microtubule destabilizing compounds and microtublin polymerization inhibitors including, but not limited to taxanes, e.g. paclitaxel and docetaxel, vinca alkaloids, e.g., vinblastine, especially vinblastine sulfate, vincristine especially vincristine sulfate, and vinorelbine, discodermolides, cochicine and epothilones and derivatives thereof, e.g. epothilone B or D or derivatives thereof. Paclitaxel may be administered e.g. in the form as it is marketed, e.g. TAXOL. Docetaxel can be administered, e.g., in the form as it is marketed, e.g. under the trademark TAXOTERE. Vinblastine sulfate can be administered, e.g., in the form as it is marketed, e.g. under the trademark VINBLASTIN R.P. Vincristine sulfate can be administered, e.g., in the form as it is marketed, e.g. under the trademark FARMISTIN. Discodermolide can be obtained, e.g., as disclosed in U.S. Pat. No. 5,010,099. Also included are Epothilone derivatives which are disclosed in WO 98/10121, U.S. Pat. No. 6,194,181, WO 98/25929, WO 98/08849, WO 99/43653, WO 98/22461 and WO 00/31247. Especially preferred are Epothilone A and/or B.

The term "alkylating compound" as used herein includes, but is not limited to, cyclophosphamide, ifosfamide, melphalan or nitrosourea (BCNU or Gliadel). Cyclophosphamide can be administered, e.g., in the form as it is marketed, e.g. under the trademark CYCLOSTIN. Ifosfamide can be administered, e.g., in the form as it is marketed, e.g. under the trademark HOLOXAN.

The term "histone deacetylase inhibitors" or "HDAC inhibitors" relates to compounds which inhibit the histone deacetylase and which possess antiproliferative activity. This includes compounds such as LDH589 disclosed in WO 02/22577, especially N-hydroxy-3-[4-[[[(2-hydroxyethyl)[2-(1H-indol-3-yl)ethyl]-amino]methyl]phenyl]-2E-2-propenamide, N-hydroxy-3-[4-[[[2-(2-methyl-1H-indol-3-yl)-ethyl]-amino]methyl]phenyl]-2E-2-propenamide and pharmaceutically acceptable salts thereof. It further especially includes Suberoylanilide hydroxamic acid (SAHA).

The term "antineoplastic antimetabolite" includes, but is not limited to, 5-Fluorouracil or 5-FU, capecitabine, gemcitabine, DNA demethylating compounds, such as 5-azacytidine and decitabine, methotrexate and edatrexate, and folic acid antagonists such as pemetrexed. Capecitabine can be administered, e.g., in the form as it is marketed, e.g. under the trademark XELODA. Gemcitabine can be administered, e.g., in the form as it is marketed, e.g. under the trademark GEMZAR.

The term "platin compound" as used herein includes, but is not limited to, carboplatin, cis-platin, cisplatinum and oxaliplatin. Carboplatin can be administered, e.g., in the form as it is marketed, e.g. under the trademark CARBOPLAT. Oxaliplatin can be administered, e.g., in the form as it is marketed, e.g. under the trademark ELOXATIN.

The term "compounds targeting/decreasing a protein or lipid kinase activity"; or a "protein or lipid phosphatase activity"; or "further anti-angiogenic compounds" as used herein includes, but is not limited to, protein tyrosine kinase and/or serine and/or threonine kinase inhibitors or lipid kinase inhibitors, for example:

a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g. a N-phenyl-2-pyrimidine-amine derivative, e.g. imatinib, SU101, SU6668 and GFB-111;

b) compounds targeting, decreasing or inhibiting the activity of the fibroblast growth factor-receptors (FGFR);

c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, such as those compounds disclosed in WO 02/092599, or antibodies that target the extracellular domain of IGF-I receptor or its growth factors;

d) compounds targeting, decreasing or inhibiting the activity of the Trk receptor tyrosine kinase family, or ephrin B4 inhibitors;

e) compounds targeting, decreasing or inhibiting the activity of the Axl receptor tyrosine kinase family;

f) compounds targeting, decreasing or inhibiting the activity of the Ret receptor tyrosine kinase;

g) compounds targeting, decreasing or inhibiting the activity of the Kit/SCFR receptor tyrosine kinase, i.e C-kit receptor tyrosine kinases—(part of the PDGFR family), such as compounds which target, decrease or inhibit the activity of the c-Kit receptor tyrosine kinase family, especially compounds which inhibit the c-Kit receptor, e.g. imatinib;

h) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, e.g. a N-phenyl-2-pyrimidine-amine derivative, e.g. imatinib or nilotinib (AMN107); PD180970; AG957; NSC 680410; PD173955 from ParkeDavis; or dasatinib (BMS-354825)

i) compounds targeting, decreasing or inhibiting the activity of members of the protein kinase C (PKC) and Raf family of serine/threonine kinases, members of the MEK, ERK, SRC, JAK, FAK, PDK1, PKB/Akt, and Ras/MAPK family members, such as members of the MEK, SRC, JAK, FAK, PDK1, PKB/Akt, and Ras/MAPK family members, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; LY333531/LY379196; isochinoline compounds such as those disclosed in WO 00/09495; FTIs; BEZ235 (a PI3K inhibitor) or AT7519 (CDK inhibitor); in particular compounds targeting, decreasing or inhibiting the activity of members of the protein kinase C (PKC) and Raf family of serine/threonine kinases, members of the MEK, ERK, SRC, JAK, FAK, PDK1, PKB/Akt, and Ras/MAPK family members, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; LY333531/LY379196; isochinoline compounds such as those disclosed in WO 00/09495; Dabrafenib, Vemurafenib, Encorafenib; FTIs; BEZ235 (a PI3K inhibitor) or AT7519 (CDK inhibitor) or NVP-LEE011 (i.e., 7-cyclopentyl-N,N-dimethyl-2-(5-(piperazin-1-yl)pyridin-2-yl)amino)-7H-pyrrolo[2,3-d]pyrimidine-6-carboxamide); GDC-0994 (i.e., (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one) or SCH900353 or BVD-523 (i.e., (S)-4-(5-chloro-2-(isopropylamino)pyridin-4-yl)-N-(1-(3-chlorophenyl)-2-hydroxyethyl)-1H-pyrrole-2-carboxamide); preferably Dabrafenib, NVP-LEE011 (i.e., 7-cyclopentyl-N,N-dimethyl-2-(5-(piperazin-1-yl)pyridin-2-yl)amino)-7H-pyrrolo[2,3-d]pyrimidine-6-carboxamide) or Encorafenib.

j) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC) or tyrphostin. A tyrphostin is preferably a low molecular weight (Mr<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin);

k) compounds targeting, decreasing or inhibiting the activity of the epidermal growth factor family of receptor tyrosine kinases (EGFR, ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180); e.g. trastuzumab (Herceptin™), cetuximab (Erbitux™), Iressa, Tarceva, OSI-774, CI-1033, EKB-569, GW-2016, E1.1, E2.4, E2.5, E6.2, E6.4, E2.11, E6.3 or E7.6.3, and 7H-pyrrolo-[2,3-d]pyrimidine derivatives which are disclosed in WO 03/013541; and l) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF.

Further anti-angiogenic compounds include compounds having another mechanism for their activity, e.g. unrelated to protein or lipid kinase inhibition e.g. thalidomide (THALOMID) and TNP-470.

Compounds which target, decrease or inhibit the activity of a protein or lipid phosphatase are e.g. inhibitors of phosphatase 1, phosphatase 2A, or CDC25, e.g. okadaic acid or a derivative thereof.

Compounds which induce cell differentiation processes are e.g. retinoic acid, α-γ- or δ-tocopherol or α-γ- or δ-tocotrienol.

The term cyclooxygenase inhibitor as used herein includes, but is not limited to, e.g. Cox-2 inhibitors, 5-alkyl substituted 2-arylaminophenylacetic acid and derivatives, such as celecoxib (CELEBREX), rofecoxib (VIOXX), etoricoxib, valdecoxib or a 5-alkyl-2-arylaminophenylacetic acid, e.g. 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. "Etridonic acid" can be administered, e.g., in the form as it is marketed, e.g. under the trademark DIDRONEL. "Clodronic acid" can be administered, e.g., in the form as it is marketed, e.g. under the trademark BONEFOS. "Tiludronic acid" can be administered, e.g., in the form as it is marketed, e.g. under the trademark SKELID. "Pamidronic acid" can be administered, e.g. in the form as it is marketed, e.g. under the trademark AREDIA™. "Alendronic acid" can be administered, e.g., in the form as it is marketed, e.g. under the trademark FOSAMAX. "Ibandronic acid" can be administered, e.g., in the form as it is marketed, e.g. under the trademark BONDRANAT. "Risedronic acid" can be administered, e.g., in the form as it is marketed, e.g. under the trademark ACTONEL. "Zoledronic acid" can be administered, e.g. in the form as it is marketed, e.g. under the trademark ZOMETA.

The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578; preferably everolimus.

The term "heparanase inhibitor" as used herein refers to compounds which target, decrease or inhibit heparin sulfate degradation. The term includes, but is not limited to, PI-88.

The term "biological response modifier" as used herein refers to a lymphokine or interferons, e.g. interferon γ.

The term "inhibitor of Ras oncogenic isoforms", e.g. H-Ras, K-Ras, or N-Ras, as used herein refers to compounds which target, decrease or inhibit the oncogenic activity of Ras e.g. a "farnesyl transferase inhibitor" e.g. L-744832, DK8G557 or R115777 (Zarnestra).

The term "telomerase inhibitor" as used herein refers to compounds which target, decrease or inhibit the activity of telomerase. Compounds which target, decrease or inhibit the activity of telomerase are especially compounds which inhibit the telomerase receptor, e.g. telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase are e.g. bengamide or a derivative thereof.

The term "proteasome inhibitor" as used herein refers to compounds which target, decrease or inhibit the activity of the proteasome. Compounds which target, decrease or inhibit the activity of the proteasome include e.g. Bortezomid (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors e.g. compounds targeting, decreasing or inhibiting the activity of FMS-like tyrosine kinase receptors (Flt-3R); interferon, 1-b-D-arabinofuransylcytosine (ara-c) and bisulfan; and ALK inhibitors e.g. compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, e.g. PKC412, TKI258, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90 e.g., 17-allylamino,17-demethoxygeldanamycin (17AAG), a geldanamycin derivative; other geldanamycin related compounds; radicicol and HDAC inhibitors. An example HSP90 inhibitor is AUY922.

The term "antiproliferative antibodies" as used herein includes, but is not limited to, trastuzumab (Herceptin™), Trastuzumab-DM1,erbitux, bevacizumab (Avastin™), rituximab (Rituxan), PRO64553 (anti-CD40), 2C4 Antibody and HCD122 antibody (anti-CD40). By antibodies is meant e.g. intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of formula (I) can be used in combination with standard leukemia therapies, especially in combination with therapies used for the treatment of AML. In particular, compounds of formula (I) can be administered in combination with, e.g., farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The term "antileukemic compounds" includes, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate.

Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065, in particular, N-hydroxy-3-[4-[[[2-(2-methyl-1H-indol-3-yl)-ethyl]-amino]-methyl]phenyl]-2E-2-propenamide, or a pharmaceutically acceptable salt thereof and N-hydroxy-3-[4-[(2-hydroxy-ethyl){2-(1H-indol-3-yl)ethyl]-amino]methyl]phenyl]-2E-2-propenamide, or a pharmaceutically acceptable salt thereof, especially the lactate salt.

Somatostatin receptor antagonists as used herein refers to compounds which target, treat or inhibit the somatostatin receptor such as octreotide, and SOM230 (pasireotide).

Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

The term "EDG binders" as used herein refers a class of immunosuppressants that modulates lymphocyte recirculation, such as FTY720.

The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives, such as PL-1, PL-2, PL-3, PL-4, PL-5, PL-6, PL-7 or PL-8 mentioned in Nandy et al., *Acta Oncologica, Vol.* 33, No. 8, pp. 953-961 (1994).

The term "S-adenosylmethionine decarboxylase inhibitors" as used herein includes, but is not limited to the compounds disclosed in U.S. Pat. No. 5,461,076.

Also included are in particular those compounds, proteins or monoclonal antibodies of VEGF disclosed in WO 98/35958, e.g. 1-(4-chloroanilino)-4-(4-pyridylmethyl)phthalazine or a pharmaceutically acceptable salt thereof, e.g. the succinate, or in WO 00/09495, WO 00/27820, WO 00/59509, WO 98/11223, WO 00/27819 and EP 0 769 947; those as described by Prewett et al, *Cancer Res, Vol.* 59, pp. 5209-5218 (1999); Yuan et al., *Proc Natl Acad Sci USA, Vol.* 93, pp. 14765-14770 (1996); Zhu et al., *Cancer Res, Vol.* 58, pp. 3209-3214 (1998); and Mordenti et al., *Toxicol Pathol, Vol.* 27, No. 1, pp. 14-21 (1999); in WO 00/37502 and WO 94/10202; ANGIOSTATIN, described by O'Reilly et al., *Cell, Vol.* 79, pp. 315-328 (1994); ENDOSTATIN, described by O'Reilly et al., *Cell, Vol.* 88, pp. 277-285 (1997); anthranilic acid amides; ZD4190; ZD6474; SU5416; SU6668; bevacizumab; or anti-VEGF antibodies or anti-VEGF receptor antibodies, e.g. rhuMAb and RHUFab, VEGF aptamer e.g. Macugon; FLT-4 inhibitors, FLT-3 inhibitors, VEGFR-2 IgG1 antibody, Angiozyme (RPI 4610) and Bevacizumab (Avastin™)

Photodynamic therapy as used herein refers to therapy which uses certain chemicals known as photosensitizing compounds to treat or prevent cancers. Examples of photodynamic therapy includes treatment with compounds, such as e.g. VISUDYNE and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as e.g. fluocinolone, dexamethasone.

"Other chemotherapeutic compounds" include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code nos., generic or trade names may be taken from the actual edition of the standard compendium "The Merck Index" or from databases, e.g. Patents International (e.g. IMS World Publications).

Some combinations might be particularly useful for the treatment of certain types of proliferative diseases. The following non-exhaustive list indicates some preferred combinations and the respective diseases: a compound of the present invention in combination with an inhibitor of EGFR (e.g. Iressa™), in particular for the treatment of NSCLC; a compound of the present invention in combination with an inhibitor of PI-3K, such as BEZ235 (CAS No. 915019-65-7) from Novartis, in particular for the treatment of Nasopharyngeal carcinoma (NPC) and some other cancers; a compound of the present invention in combination with an inhibitor of mTOR; a compound of the present invention in combination with a tyrosine protein kinase and/or Raf inhibitor such as Sorafenib, in particular for the treatment of primary kidney cancer (advanced renal cell carcinoma) and advanced primary liver cancer (hepatocellular carcinoma); a compound of the present invention in combination with an VEGFR inhibitor such as PTK787 or an antibody against the ligand VEGF such as Avastin®; a compound of the present invention in combination with an PDGFR inhibitor, e.g. imatinib (STI571 or Glivec®); a compound of the present invention in combination with an mTOR inhibitors, such as rapamycin and everolimus (RAD001).

In one embodiment, the other therapeutic agent is selected from: an EGFR inhibitor such as Iressa™; Raf inhibitor such as Sorafenib; PI-3K inhibitor such as BEZ235 (CAS No. 915019-65-7); VEGFR inhibitor such as PTK787; VEGF antibody such as Avastin®; PDGFR inhibitor such as STI571 (Glivec®); mTOR inhibitors such as rapamycin and everolimus; aromatase inhibitor such as letrozole (Femara®) or anastrozole; microtubule active compound such as paclitaxel or an epothilone; antineoplastic antimetabolite such as gemcitabine or capecitabine; platin compounds such as carboplatin or cis-platin; bisphosphonates such as AREDIAO or ZOMETAO; and HER2 antibodies such as trastuzumab.

None of the quotations of references made within the present disclosure is to be understood as an admission that the references cited are prior art that would negatively affect the patentability of the present invention.

Processes for Making Compounds of the Invention

Compounds of the invention can be prepared according to reaction Scheme 1, wherein n, R1, R2, R5, R4 and R3a are as defined for a compound of formula (I) herein and R3 is R3a and optionally comprises a hydroxyl or an amino protecting group.

In the present application the term "nitrogen protecting group" generally comprises any group which is capable of reversibly protecting a nitrogen functionality, preferably an amino and/or amide functionality. The term "hydroxylprotecting group" generally comprises any group which is capable of reversibly protecting the hydroxyl functionality. Suitable nitrogen protecting groups and hydroxylprotecting groups are described e.g. in the relevant chapters of standard reference works such as J. F. W. McOmie, "Protective Groups in Organic Chemistry", Plenum Press, London and New York 1973; T. W. Greene and P. G. M. Wuts, "Greene's Protective Groups in Organic Synthesis", Fourth Edition, Wiley, New York 2007; in "The Peptides"; Volume 3 (editors: E. Gross and J. Meienhofer), Academic Press, London and New York 1981, and in "*Methoden der organischen Chemie*" (Methods of Organic Chemistry), Houben Weyl, 4th edition, Volume 15/I, Georg Thieme Verlag, Stuttgart 1974.

Scheme 1:

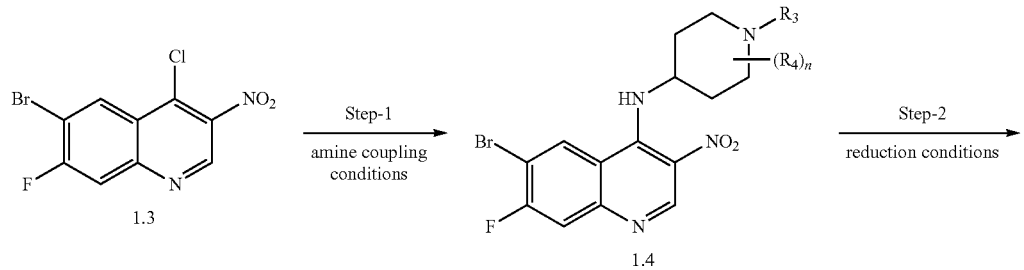

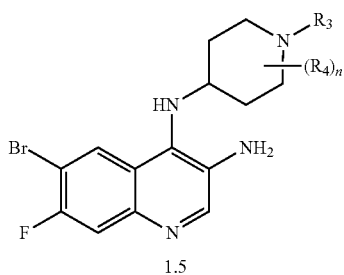 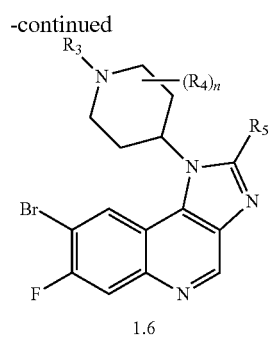
Step-3 cyclization conditions
Step-4 cross-coupling conditions
1.5 → 1.6
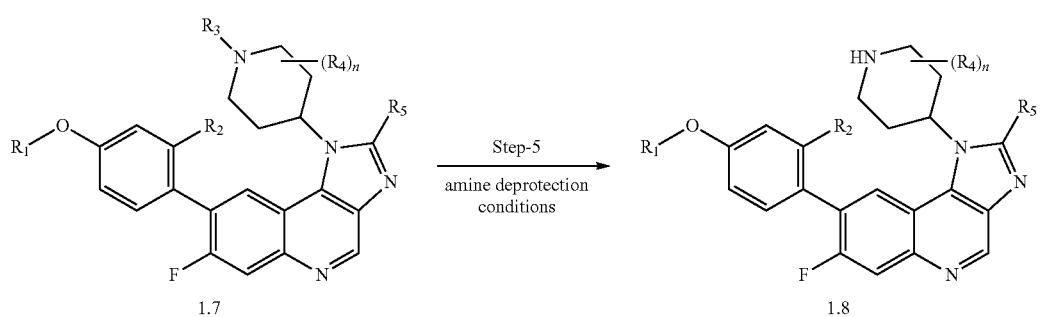
Step-5 amine deprotection conditions
1.7 → 1.8
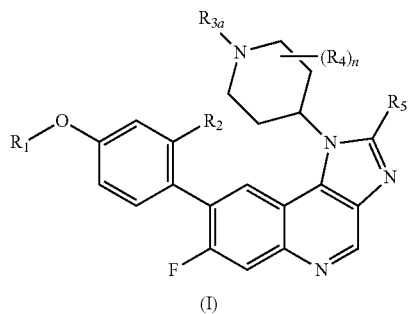
(I)
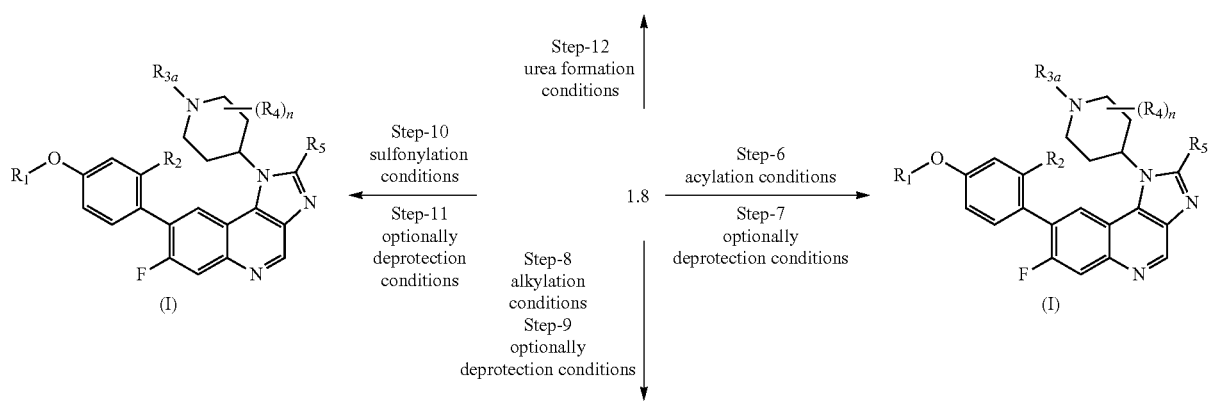
Step-12 urea formation conditions
Step-10 sulfonylation conditions
Step-11 optionally deprotection conditions
Step-6 acylation conditions
Step-7 optionally deprotection conditions
Step-8 alkylation conditions
Step-9 optionally deprotection conditions
1.8
(I)        (I)

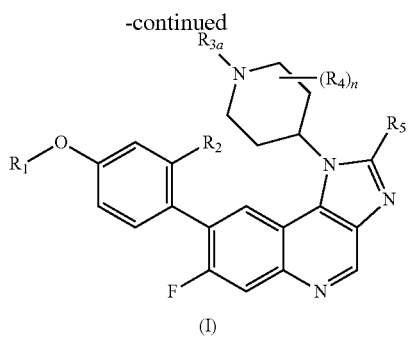

(I)

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Compounds of Formula I can be prepared by proceeding as in the following Reaction Scheme 2:

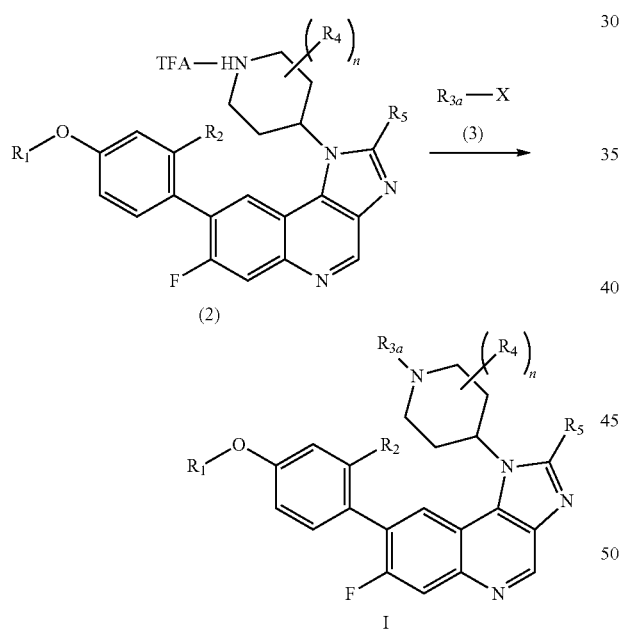

in which $R_1$, $R_2$, $R_{3a}$, $R_4$ and $R_5$ are as defined for Formula I in the Summary of the Invention and X represents a group, such as a leaving group, selected from bromine, chlorine, or the like.

A compound of Formula I can be prepared by reacting a compound of formula (2) with a compound of formula (3) in the presence of a suitable base (such as TEA, DIPEA, $K_2CO_3$, or the like), a suitable coupling reagent (such as EDCI, HOBt, HATU, or the like), a suitable reactant (such as alkyl halides, acid chlorides, sulfonyl chlorides, carbamoyl chlorides, sulfamoyl chlorides, isocyanate or the like, in particular such as alkyl halides, acid chlorides, sulfonyl chlorides) and a suitable solvent (such as dichlormethane, THF, ACN, DMF, or the like). The reaction takes place at about 0° C. to about 100° C. and can take from about 1 to about 24 hours to complete.

6-Bromo-4-chloro-7-fluoro-3-nitroquinoline (1.3 in Scheme 1) is prepared according to the synthesis described in WO 200505423, Example 54b. The diarylether boronic acid used in the cross-coupling Step-4 of Scheme 1 can be prepared according to the general scheme 3 below, either starting from commercially available phenol 3.1 or biarylether halide 3.2.

Scheme 3:

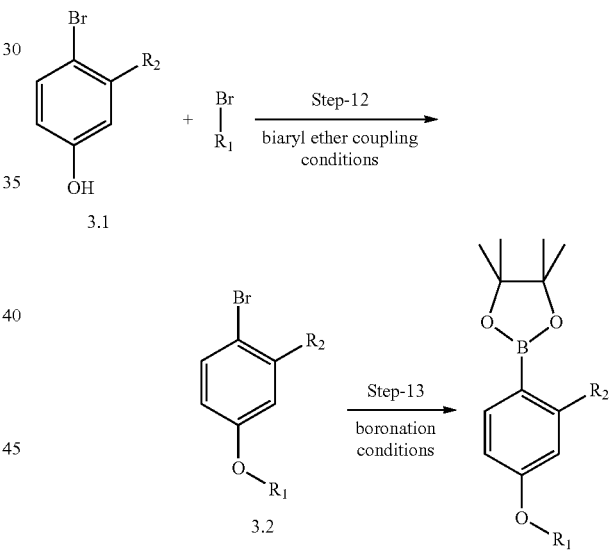

Detailed examples of the synthesis of compounds of Formula I can be found in the Examples, infra. Steps 1 to 12 in Scheme 1 and Steps 12 and 13 in Scheme 3 refer to specific reaction conditions which are described for example in the Experimental section herein and in standard reference works, such as in the relevant chapters in Richard C. Larock, "Comprehensive Organic Transformations: A Guide to Functional Group Preparations", Second Edition, Wiley-VCH Verlag GmbH, 2000 and in T. W. Greene and P. G. M. Wuts, "Greene's Protective Groups in Organic Synthesis", Fourth Edition, Wiley, New York 2007.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Compounds of the formula I can also be modified by appending appropriate functionalities to enhance selective biological properties. Modifications of this kind are known in the art and include those that increase penetration into a given biological system (e.g. blood, lymphatic system, central nervous system, testis), increase bioavailability, increase solubility to allow parenteral administration (e.g. injection, infusion), alter metabolism and/or alter the rate of secretion. Examples of this type of modifications include but are not limited to esterification, e.g. with polyethylene glycols, derivatisation with pivaloyloxy or fatty acid substituents, conversion to carbamates, hydroxylation of aromatic rings and heteroatom substitution in aromatic rings. Whereever compounds of the formula I, and/or N-oxides, tautomers and/or (preferably pharmaceutically acceptable) salts thereof are mentioned, this comprises such modified formulae, while preferably the molecules of the formula I, their N-oxides, their tautomers and/or their salts are meant.

Alternatively, the salt forms of the compounds of the invention can be prepared using salts of the starting materials or intermediates. In view of the close relationship between the novel compounds of the formula I in free form and those in the form of their salts, including those salts that can be used as intermediates, for example in the purification or identification of the novel compounds, any reference to the compounds or a compound of the formula I hereinbefore and hereinafter is to be understood as referring to the compound in free form and/or also to one or more salts thereof, as appropriate and expedient, as well as to one or more solvates, e.g. hydrates.

Salts are formed, for example, as acid addition salts, preferably with organic or inorganic acids, from compounds of formula I with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, malonic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 4-toluenesulfonic acid, 2-naphthalenesulfonic acid, 1,5-naphthalene-disulfonic acid, 2- or 3-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", $3^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:
  (a) those of reaction scheme I; and
  (b) optionally converting a compound of the invention into a pharmaceutically acceptable salt;
  (c) optionally converting a salt form of a compound of the invention to a non-salt form;
  (d) optionally converting an unoxidized form of a compound of the invention into a pharmaceutically acceptable N-oxide;

(e) optionally converting an N-oxide form of a compound of the invention to its unoxidized form;
(f) optionally resolving an individual isomer of a compound of the invention from a mixture of isomers;
(g) optionally converting a non-derivatized compound of the invention into a pharmaceutically acceptable prodrug derivative; and
(h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The following examples and intermediates serve to illustrate the invention without limiting the scope thereof. Some abbreviations used in the examples are as follows: acetic acid (AcOH); triethylamine (TEA); tetrahydrofuran (THF); aqueous (aq.); atmosphere (atm.); 2,2'-bis-diphenylphosphanyl-[1,1']binaphthalenyl (BINAP); 4-dimethylaminopyridine (DMAP); tert-butoxycarbonyl (Boc); 1,1-carbonyldiimidazole (CDI); di-tert-butyl dicarbonate ($BOC_2O$); benzotriazole-1-yl-oxy-tris-(dimethylamino)-phosphonium hexafluorophosphate (BOP); dichloromethane (DCM); diethyl ether ($Et_2O$); p-toluene sulfonic acid (PTSA); ethyl acetate (EtOAc); ethanol (EtOH); lithium bis(trimethylsilyl)amide (LHMDS); diisopropyl azodicarboxylate (DIAD); N,N-diisopropyl-ethylamine (DIEA or DIPEA); N,N-dimethylformamide (DMF); dimethyl sulfoxide (DMSO); diphenylphosphoryl azide (DPPA); hour(s) (h); 2-(1H-7-azabenzotriazol-1-yl)-1,1,3,3-tetramethyluronium hexafluorophosphate (HATU); High Performance Liquid Chromatography (HPLC); lithium aluminium hydride (LAH); liquid chromatography coupled with mass spectrometry (LCMS); lithium diisopropylamide (LDA); methanol (MeOH); milliliter(s) (mL); minute(s) (min); microwave (MW); n-butyllithium (n-BuLi); 1,1-bis(diphenylphosphino)-ferrocenedichloropalladium (II) ($PdCl_2(dppf)$); tris(dibenzylideneacetone)dipalladium (0) ($Pd_2(dba)_3$); dichlorobis(triphenylphosphine) palladium (II) ($PdCl_2(PPh_3)_2$); room temperature (RT); trifluoroacetic acid (TFA); tetrahydrofuran (THF); thin layer chromatography (TLC); retention time ($t_R$); & 4,5-bis(diphenylphosphino)-9,9-dimethylxanthene (Xantphos).

LCMS data for the compounds below were generated on a Synergi 2.5u MAX-RP 100A Mercury column with the mobile phase: A=0.1% Formic acid, B=ACN, applying a gradient: 0/30, 0.5/30, 1.5/95, 2.4/95, 3.0/30 at a flow of 2.0 ml/min and a temperature of 30.0° C. Five different HPLC methods were used and the method used is given for each individual compound in Table 1 below. Unless mentioned otherwise, the method used for the detailed examples is Method-1. Conditions were as follows:

Method-1 Information:
Column: Zorbax XDB C18 5u 4.6×150 mm
Mobile Phase: A=0.01% TFA in Water, B=MeOH:ACN (1:1)
Gradient Time % B: 0/30, 1/70, 6/100, 8/100, 10/30, 12/30
Flow: 1.0 ml/min.
Temperature: 40.0° C.

Method-2 Information:
Column. AG/C18/15-010
Mobile Phase: A=Water, B=ACN (1:1)
Gradient: 70/30
Flow: 1.0 ml/min.
Temperature: 40.0° C.

Method-3 Information:
Column. Kienetex 5u C18 100A 150×4.60 mm
Mobile Phase: A=0.01% TFA in Water, B=MeOH:ACN (1:1)
Gradient Time % B: 0/5, 1/5, 6/100, 8/100, 10/5, 12/5
Flow: 1.0 ml/min.
Temperature: 40.0° C.

Method-4 Information:
Column: Zorbax Eclipse Plus C18 RR HD 2.1-100 mm 18u
Mobile Phase: A=0.01% TFA in Water, B=MeOH:ACN (1:1)
Gradient Time % B: 0/10, 5/30, 1.5/100, 3/100, 4/10, 5/30
Flow: 0.5 ml/min.
Temperature: 40.0° C.

Method-5 Information:
Column. Kienetex 2.6u C18
Mobile Phase: A=0.01% TFA in Water, B=MeOH:ACN (1:1)
Gradient Time % B: 0/10, 0.5/30, 1.5/100, 3/100, 4/10, 5/10
Flow: 1.4 ml/min.
Temperature: 40.0° C.

Intermediate 1.1

5-bromo-4-fluoro-2-((2-nitrovinyl)amino)benzoic acid

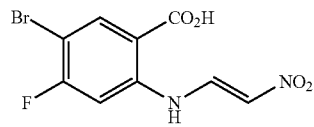

Step 1.1: Synthesis of intermediate 1.1; 5-bromo-4-fluoro-2-((2-nitrovinyl)amino)benzoic acid Part-a: HCl gas is purged through a solution of 2-amino-5-bromo-4-fluorobenzoic acid (38 g, 0.162 mol) in 570 ml of 1,4-dioxane for 1.5-2 hrs at 0° C. The mixture was stirred for 2 hrs and allowed to stand overnight at RT. The solid was filtered, washed with diethyl ether and dried under vacuum to afford an HCl salt (44.5 g) of 2-amino-5-bromo-4-fluorobenzoic acid.

Part-b: To a stirred solution of NaOH (22 g, 0.162 mol) in water (44 ml), cooled to 0-5° C., nitromethane (2×8.5 ml) was added drop wise so as to maintain an internal temperature of 25-30° C. After the addition was complete, the cooling bath was removed, causing a spontaneous rise in temperature to 70° C., and a red coloration to develop. The mixture was then cooled to 25-30° C. The resulting orange red solution was carefully poured on to ice (48 g) and conc. HCl (48 ml) to afford the methazonic acid.

Part-c: To a suspension of HCl salt (44 g) of 2-amino-5-bromo-4-fluorobenzoic (Part-a solid) in Con. HCl (140 ml) and water (800 ml) was added methazonic acid (Part-b). The resulting mixture was stirred for 30 mins. The solid that precipitated out was allowed to stand overnight before filtering, washing with excess of water and methanol (60 ml) and drying under vacuum for 3-4 hrs to afford the 5-bromo-4-fluoro-2-((2-nitrovinyl)amino)benzoic acid 44 g, 88.5% of yield. $^1$H NMR (DMSO-$d_6$, 300 MHz): δ 13.0 (d, 1H), 8.20 (d, 1H), 8.0 (m, 1H), 7.95 (d, 1H), 6.90 (d, 1H); LCMS: 77.7%, m/z=304.9 (M+1).

Intermediate 1.2

6-bromo-7-fluoro-3-nitroauinolin-4-ol

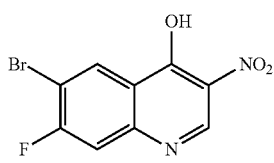 [SMILES: O=[N+]([O-])c1cnc2cc(F)c(Br)cc2c1O]

Step 1.2: Synthesis of intermediate-1.2; 6-bromo-7-fluoro-3-nitroquinolin-4-ol: 5-bromo-4-fluoro-2-((2-nitrovinyl)amino)benzoic acid (44 g, 0.144 mol) was heated in acetic anhydride, (220 ml) at 110° C. until dissolution was accomplished, and cooled to 40° C. Potassium acetate was (16.9 g) was added and the resulting mixture was heated to 140° C. for 45 min. The reaction mixture was cooled to RT. The resulting solid was filtered and washed with acetic acid (25 ml), water, methanol (30 ml) and dried under vacuum to afford the 6-bromo-7-fluoro-3-nitroquinolin-4-ol 18 g, 43.4% of yield. $^1$H NMR (DMSO-$d_6$, 300 MHz): δ 13.1 (bs, 1H), 9.25 (s, 1H), 8.41 (d, 1H), 7.61 (d, 1H); LCMS: 98.2%, m/z=286.9 (M+1).

Intermediate 1.3

6-bromo-4-chloro-7-fluoro-3-nitroquinoline

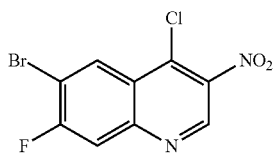 [SMILES: O=[N+]([O-])c1cnc2cc(F)c(Br)cc2c1Cl]

Step 1.3: Synthesis of intermediate-1.3; 6-bromo-4-chloro-7-fluoro-3-nitroquinoline: 6-bromo-7-fluoro-3-nitroquinolin-4-ol (20 g, 0.069 mol) was refluxed in POCl$_3$ (180 ml) and TEA (11.8 ml, 0.083 mol) for 24 h at 120° C. The reaction mixture was cooled to RT poured slowly into ice-water. The precipitated solid was filtered and washed with ice-cold water. The solid was dissolved in dichloromethane and washed with cold-brine solution. The organic layer was dried over sodium sulphate and evaporated under vacuum. The residue was purified by column chromatography on silica gel (10% EtOAc-Hexane) to afford 6-bromo-4-chloro-7-fluoro-3-nitroquinoline (19 g; 89.6% yield). $^1$H NMR (DMSO-$d_6$, 300 MHz): δ 9.4 (s, 1H), 8.76 (d, 1H), 8.22 (d, 1H); LCMS: 96.5%, m/z=304.9 (M+1).

Intermediate 1.4

Step-1 on Scheme 1 hereinabove: General rocedure for synthesis of intermediate 1.4:
Method-A: 6-bromo-4-chloro-7-fluoro-3-nitroquinoline (1 mmol) and desired aryl amine, 1 mmol) were stirred in AcOH for 2-3 hrs at RT. After completion of the reaction TLC (20% EtOAc-Hexane), the reaction mixture was diluted with water. The resultant yellow precipitate was filtered and washed with water. The solid was dissolved in EtOAc-THF (1:1) and washed with saturated NaHCO$_3$ solution. The organic layer was dried over Na$_2$SO$_4$ and evaporated to afford intermediate 1.4. The crude material was purified by column chromatography.
Method-B: 6-bromo-4-chloro-7-fluoro-3-nitroquinoline (1 mmol) and desired alkyl amines (1 mmol) are dissolved in DMF and added DIPEA at RT. The reaction mass is stirred at RT for 3-4 hrs. The reaction was monitored by TLC (20% EtOAc-Hexane). After completion, water was added to the reaction and the resultant yellow precipitate is filtered-off, washed with water and dried under vacuum for 1-2 hrs to afford Intermediate 1.4.

Intermediate 1.5

Step-2 on Scheme 1 hereinabove: General procedure for synthesis of intermediate 1.5

Method C: Intermediate 1.4 obtained from either method A or B was reduced with Raney-Ni under H$_2$ gas pressure (balloon) in a solvent mixture MeOH:THF (2:1) for 5-6 hrs. After completion of the reaction by TLC (60% EtOAc-Hexane), the reaction mass was filtered through a celite bed and washed with ethyl acetate. The filtrate was evaporated to dryness to give interemedaited 1.5.
Method D: Intermediate 1.4 (1 mol) obtained from either method A or B was treated with sodium dithionate (5 mol) in dioxane for 1-6 hrs. After completion of the reaction by TLC (60% EtOAc-Hexane), the reaction mixture was partitioned between EtOAc and water. The separated organic layer was washed with water, brine, dried over Na$_2$SO$_4$ and evaporated to dryness to get desired intermediate 1.5.

Intermediate 1.6

Step-3 on Scheme 1 hereinabove, General procedure for synthesis of intermediate 1.6:
Intermediate 1.5 obtained in step 1.5 was heated in triethyl orthoformate for 4 hrs at 105° C. After completion of the reaction by TLC (60% EtOAc-Hexane), the solvent was evaporated completely under reduced pressure and the residue was purified by column chromatography on silica gel (MeOH/DCM) to give interemediate 1.6.

Intermediate 1.7

Step-4 on Scheme 1 hereinabove: General procedure for synthesis of intermediate 1.7: To a stirred solution of intermediate 1.6 in a mixture of toluene:ethanol (8:2) in a seal tube, was added Pd(PPh$_3$)$_4$ (0.05 eq). The reaction mixture was purged with Organ gas for 10 mins before adding aryl/heteroaryl boronic acids/esters and 2M Na$_2$CO$_3$ solution (2 eq). The Organ gas purging was continued for an additional 15 mins before sealing the reaction vial. The reaction mass was heated at 95° C. for 4-16 hrs. The reaction was monitored by TLC (100% EtOAc). After completion of the reaction, the reaction mass was partitioned between EtOAc and water. The organic layers were separated, washed with water and brine, dried over Na₂SO₄ and evaporated under vacuum. The crude residue was purified by column chromatography on silica gel (MeOH/DCM) to give intermediate 1.7.
Example 1A
1-((3S,4S)-4-(8-(2-chloro-4-(pyrimidin-2-yloxy)phenyl)-7-fluoro-2-methyl-1H-imidazo[4,5-c]quinolin-1-yl)-3-fluoropiperidin-1-yl)-2-hydroxyethanone
Scheme 4:
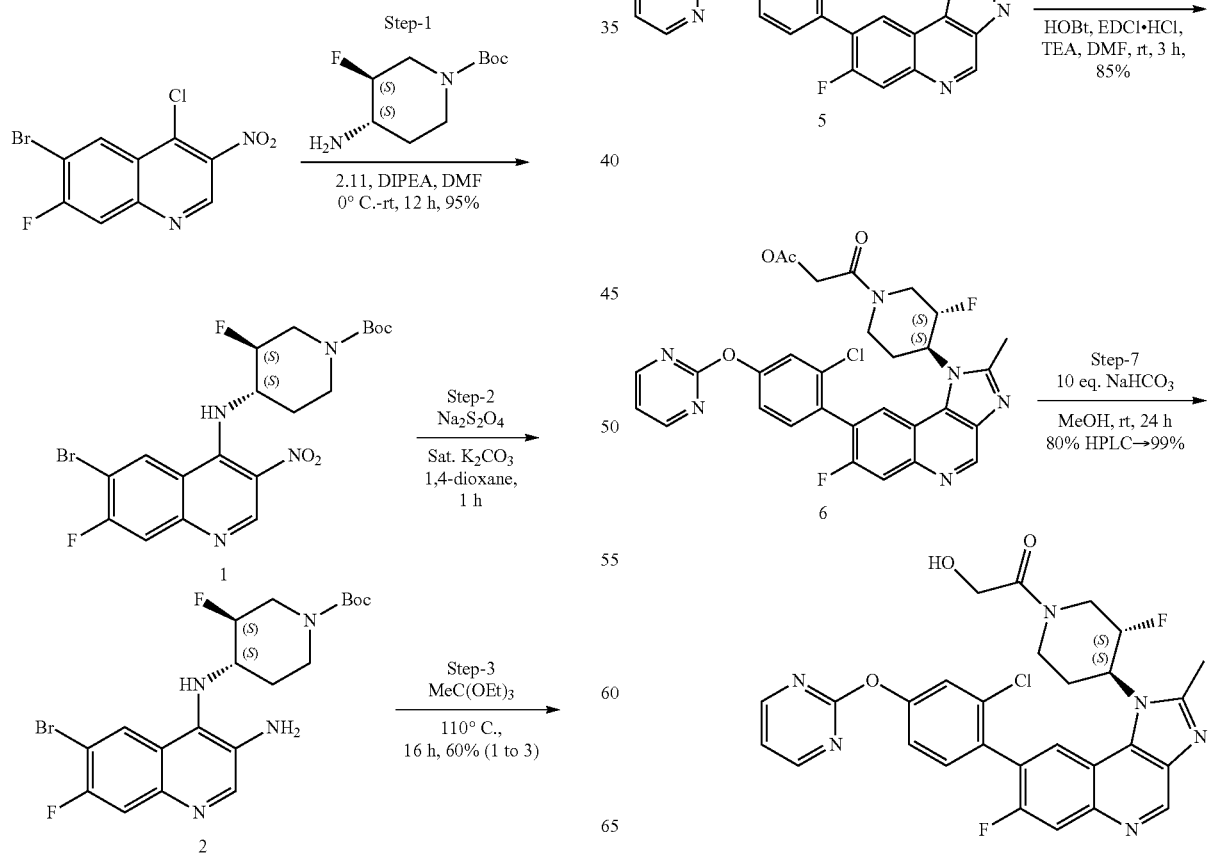
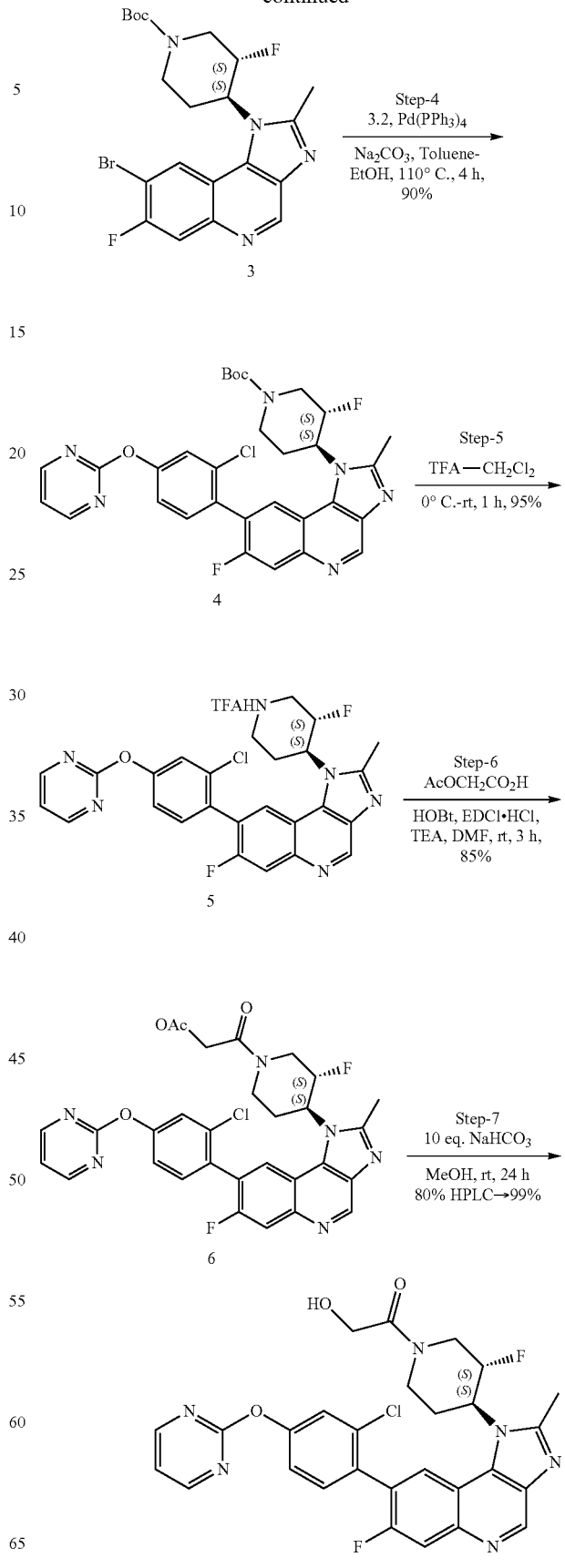

Step-1, Synthesis of (3S,4S)-tert-butyl 4-((6-bromo-7-fluoro-3-nitroquinolin-4-yl)amino)-3-fluoropiperidine-1-carboxylate, 1

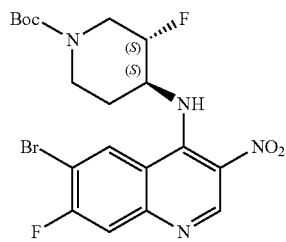

6-Bromo-4-chloro-7-fluoro-3-nitroquinoline (17.5 g, 0.0057 mol) was taken in dry DMF (200 mL) under N₂ atmosphere. DIPEA (14.8 g, 0.114 mol) and (3S,4S)-tert-butyl 4-amino-3-fluoropiperidine-1-carboxylate (12.5 g, 0.057 mol) in dry DMF (50 mL) was added sequentially at RT. The resulting mixture was stirred for overnight at RT. The reaction was monitored by TLC (30% EtOAc/Hexane), after completion of reaction, the reaction mixture poured into ice water and extracted with EtOAc (3×200 mL). The combined EtOAc layers were washed with brine solution and water, dried over sodium sulphate. The organic layer was evaporated under vacuum and the residue was purified by column chromatography on silica gel (10-50% EtOAc-Hexane) to afford the (3S,4S)-tert-butyl 4-((6-bromo-7-fluoro-3-nitroquinolin-4-yl)amino)-3-fluoropiperidine-1-carboxylate, 1 (27 g, 956% yield). ¹HNMR (CDCl₃, 400 MHz): δ 9.37 (s, 1H) 8.83-8.81 (d, 1H) 8.48-8.46 (d, 1H) 7.74-7.71 (d, 1H), 4-58-4.40 (m, 2H), 4.19-4.12 (m, 2H), 2.95-2.87 (m, 2H) 2.27-2.23 (m, 1H) 1.79-1.66 (m, 1H), 1.47 (s, 9H); LCMS: 98.84%, (M+2) 488.7; HPLC: 99.47%.

Step-2, Synthesis of (3S,4S)-tert-butyl 4-((3-amino-6-bromo-7-fluoroquinolin-4-yl)amino)-3-fluoropiperidine-1-carboxylate, 2

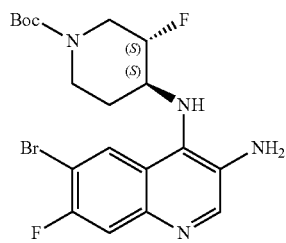

(3S,4S)-tert-butyl 4-((6-bromo-7-fluoro-3-nitroquinolin-4-yl)amino)-3-fluoropiperidine-1-carboxylate (27 g, 0.055 mol) was taken in 1,4-dioxane (150 mL). Solution of sodium dithionite (29 g, 0.166 mol in 150 mL water) was added at RT and the resulting mixture was stirred for 5 h at RT. The reaction was monitored by TLC (50% EtOAc/hexane), after completion of reaction the reaction mixture was poured into ice water and extracted with EtOAc (3×200 mL). The combined organic layers were washed with brine and water, dried over sodium sulphate. The organic layer was evaporated under vacuum, to afford the (3S,4S)-tert-butyl 4-((3-amino-6-bromo-7-fluoroquinolin-4-yl)amino)-3-fluoropiperidine-1-carboxylate, 2 (27 g). This material used directly in next step without purification. LCMS: 99.5%, m/z=456.7 (M⁺).

Step-3, Synthesis of (3S,4S)-tert-butyl 4-(8-bromo-7-fluoro-2-methyl-1H-imidazo[4,5-c]quinolin-1-yl)-3-fluoropiperidine-1-carboxylate, 3

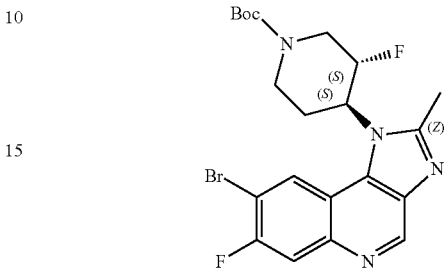

(3S,4S)-tert-butyl 4-((3-amino-6-bromo-7-fluoroquinolin-4-yl)amino)-3-fluoropiperidine-1-carboxylate (27 g, 0.059 mol) was heated in triethylorthoacetate (150 mL) under N₂ atmosphere for 5 h at 120° C. The reaction was monitored by TLC (5% MeOH/DCM). The volatiles were concentrated under vacuum, the obtained crude product was purified by column chromatography on silica gel (0-3% MeOH/DCM) to afford (3S,4S)-tert-butyl 4-(8-bromo-7-fluoro-2-methyl-1H-imidazo[4,5-c]quinolin-1-yl)-3-fluoropiperidine-1-carboxylate (15 g, yield from two steps). ¹HNMR (CDCl₃, 400 MHz): δ 9.28-9.23 (d, 1H), 8.43-8.34 (dd, 1H), 8.01-7.99 (d, 1H), 5.60-5.35 (m, 1H), 5.25-4.85 (m, 1H), 4.75-4.35 (m, 2H), 3.15-2.95 (m, 2H), 2.79 (s, 3H), 2.40-2.05 (m, 2H), 1.57 (s, 9H); LCMS: 100%, m/z=480.8 (M⁺); HPLC: 97.31%.

Step-4, Synthesis of (3S,4S)-tert-butyl 4-(8-(2-chloro-4-(pyrimidin-2-yloxy)phenyl)-7-fluoro-2-methyl-1H-imidazo[4,5-c]quinolin-1-yl)-3-fluoropiperidine-1-carboxylate, 4

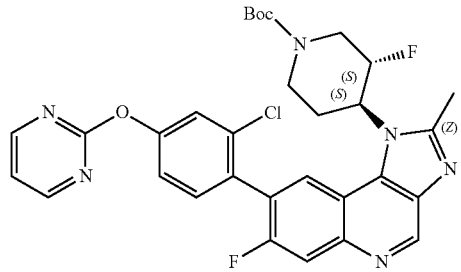

Chemical Formula $C_{31}H_{29}ClF_2N_6O_3$
Molecular Weight: 607.06 tert-Butyl 4-(8-bromo-7-fluoro-2-methyl-1H-imidazo[4,5-c]quinolin-1-yl)-3-fluoropiperidine-1-carboxylate (9 g, 0.018 mol) was dissolved in toluene:ethanol (8:2, 50 ml) in a 250 ml seal tube and degasified the reaction mixture with argon gas for 15 minutes. Tetrakis (2.1 g, 0.0018 mol) was added and degasified the reaction mixture with argon gas for 5 minutes, 2-(3-chloro-4-(4,4,5,5-tetramethyl-1,3,2-dioxaborolan-2-yl)phenoxy)pyrimidine (8 g, 0.024 .mol), followed by 2M Na₂CO₃(5 ml) was added and finally degasified the reaction mixture with argon gas for 10 minutes. The resulting reaction mixture was heated 5 h at 90° C. The reaction was monitored by TLC (5% MeOH/DCM), after completion of reaction by TLC the reaction mixture poured into ice water and extracted with EtOAc (3×100 mL). The combined organic layers were washed water, brine solution, dried over sodium sulphate and evaporated under vacuum. The residue was purified by column chromatography on silica gel (0-3% MeOH/DCM) to afford (3S,4S)-tert-butyl 4-(8-(2-chloro-4-(pyrimidin-2-yloxy)phenyl)-7-fluoro-2-methyl-1H-imidazo[4,5-c]quinolin-1-yl)-3-fluoropiperidine-1-carboxylate, 4 (10.2 g, 95% yield). $^1$HNMR (CDCl$_3$, 400 MHz): δ 9.28 (d, 1H), 8.68-8.60 (m, 2H), 8.34-8.31 (d, 0.8H), 8.17 (d, 0.2H), 8.09-8.02 (m, 1H), 7.58-7.44 (m, 2H), 7.30 (dd, 1H), 7.16-7.10 (m, 1H), 5.62-5.04 (m, 1H), 4.89-4.25 (m, 3H), 3.10-2.75 (m, 5H), 2.40-2.20 (m, 2H), 1.51 (s, 9H); LCMS: 98.99%, m/z=607.45 (M+1); HPLC: 96.89%, rt: 4.32 min.

Step-5, Synthesis of 8-(2-chloro-4-(pyrimidin-2-yloxy)phenyl)-7-fluoro-1-((3S,4S)-3-fluoropiperidin-4-yl)-2-methyl-1H-imidazo[4,5-c]quinoline TFA salt, 5

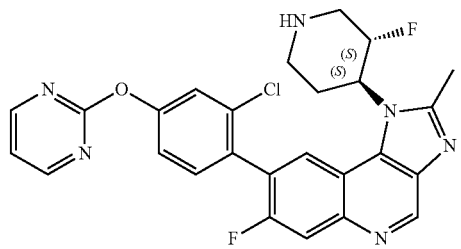

TFA (20 ml) was added drop wise to a solution of (3S,4S)-tert-butyl-4-(8-(2-chloro-4-(pyrimidin-2-yloxy)phenyl)-7-fluoro-2-methyl-1H-imidazo[4,5-c]quinolin-1-yl)-3-fluoropiperidine-1-carboxylate (10 g, 0.0164 mol) in dry DCM (150 mL) at 0° C. under N2 atmosphere. After addition completed, the reaction mixture allowed to RT and stirred for 3 h. The reaction was monitored by TLC (5% MeOH/DCM), after completion of reaction by TLC, the volatiles were concentrated under vacuum. The obtained residue was triturated with diethyl ether. The solid was filtered and dried under vacuum to afford TFA salt of 8-(2-chloro-4-(pyrimidin-2-yloxy)phenyl)-7-fluoro-1-((3S,4S)-3-fluoropiperidin-4-yl)-2-methyl-1H-imidazo[4,5-c]quinoline (11 g, quantitative). LCMS: 99.41%, m/z=507.1 (M+1) (Free base); HPLC: 96.43%, 6.002 min.

Step-6, Synthesis of 2-((3S,4S)-4-(8-(2-chloro-4-(pyrimidin-2-yloxy)phenyl)-7-fluoro-2-methyl-1H-imidazo[4,5-c]quinolin-1-yl)-3-fluoropiperidin-1-yl)-2-oxoethyl acetate, 6

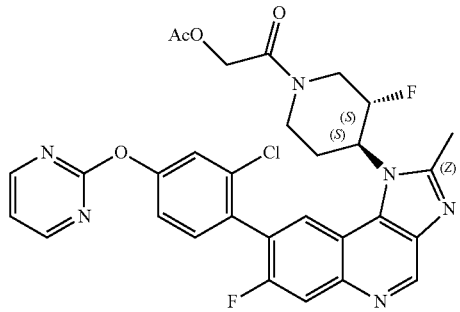

Chemical Formula C$_{30}$H$_{25}$ClF$_2$N$_6$O$_4$
Molecular Weight: 607.01

HOBT (5.4.g, 0.040 mol) and EDCI.HCl (7.64 g, 0.040 mol) was sequentially added to a solution of 2-acetoxyacetic acid (4.3.g, 0.036 mol) in dry DMF (100 mL) under N$_2$ atmosphere at 0° C. The resulting mixture was stirred at RT for 30 min. A solution of 8-(2-chloro-4-(pyrimidin-2-yloxy)phenyl)-7-fluoro-1-((3S,4S)-3-fluoropiperidin-4-yl)-2-methyl-1H-imidazo[4,5-c]quinoline. TFA salt (11.0 g, 0.0178 mol) in dry DMF (50 ml) and TEA (5.4 g, 0.053 mol) was added to the reaction mixture. The resulting reaction mixture was allowed to RT and stirred for 3 h. The reaction was monitored by TLC (5% MeOH/DCM). After completion of reaction, the reaction mixture was poured into saturated ice cold NaHCO$_3$ solution and extracted with EtOAc (3×200 mL). The combined EtOAc layers were washed with brine solution and water, dried over sodium sulphate and evaporated under vacuum. The residue was purified by column chromatography on silica gel (0-3% MeOH/DCM) to afford the 2-((3S,4S)-4-(8-(2-chloro-4-(pyrimidin-2-yloxy)phenyl)-7-fluoro-2-methyl-1H-imidazo[4,5-c]quinolin-1-yl)-3-fluoropiperidin-1-yl)-2-oxoethyl acetate, 6 (8 g, 85% yield). $^1$HNMR (CDCl$_3$, 400 MHz): δ 9.31 (d, 1H), 8.68-8.60 (m, 2H), 8.34 (d, 0.5H), 8.12-8.01 (m, 1.5H), 7.59 (d, 0.5H), 7.54-7.45 (m, 1.5H), 7.37-7.30 (m, 1H), 7.18-7.11 (m, 1H), 5.69-5.16 (m, 2H), 4.99-4.61 (m, 3H), 4.37-4.25 (m, 0.5H), 4.01-3.88 (m, 0.5H), 3.50 (d, 1H), 3.03-2.90 (m, 2H), 2.88 (s, 1.5H), 2.81 (s, 1.5H), 2.50-2.33 (m, 1H), 2.22 (s, 1.5H), 2.07 (s, 1.5H); LCMS: 98.99%, m/z=607.45 (M+1); HPLC: 96.89%, rt: 4.32 min.

Step-7, Synthesis of 1-((3S,4S)-4-(8-(2-chloro-4-(pyrimidin-2-yloxy)phenyl)-7-fluoro-2-methyl-1H-imidazo[4,5-c]quinolin-1-yl)-3-fluoropiperidin-1-yl)-2-hydroxyethanone

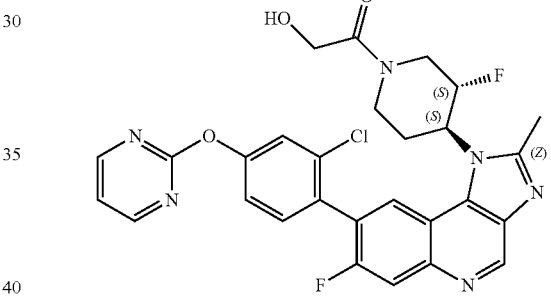

Chemical Formula: C$_{28}$H$_{23}$ClF$_2$N$_6$O$_3$
Molecular Weight: 564.98

NaHCO$_3$ (11 g, 0.1309 mol) was added to a stirred solution of 2-((3S,4S)-4-(8-(2-chloro-4-(pyrimidin-2-yloxy)phenyl)-7-fluoro-2-methyl-1H-imidazo[4,5-c]quinolin-1-yl)-3-fluoropiperidin-1-yl)-2-oxoethylacetate (8 g, 0.013 mol) in MeOH (300 mL) at RT and stirred for 24 h. The reaction was monitored by TLC (5% MeOH/DCM), after completion of reaction, the reaction mixture was filtered and wand washed with MeOH (100 mL). The filtrate was concentrated to remove methanol and the residue was dissolved in DCM (200 mL) and washed with water, brine solution, dried over sodium sulphate and evaporated under vacuum. The residue was purified by column chromatography on silica gel (0-4% MeOH/DCM) to afford the 1-((3S,4S)-4-(8-(2-chloro-4-(pyrimidin-2-yloxy)phenyl)-7-fluoro-2-methyl-1H-imidazo[4,5-c]quinolin-1-yl)-3-fluoropiperidin-1-yl)-2-hydroxyethanone (6.0 g, 81% yield). Obtained solid was recrystallized in EtOH (alternatively in MeOH) $^1$HNMR (CDCl$_3$, 400 MHz): δ 9.33 (s, 1H), 8.65-8.64 (d, 2H), 8.08-8.05 (d, 1H), 8.00-7.85 (m, 1H), 7.51-7.30 (m, 2H), 7.30-7.28 (dd, 1H), 7.15-7.13 (m, 1H), 5.65-5.25 (m, 1H), 4.96-4.75 (m, 1H), 4.35-4.15 (m, 2H), 3.92-3.74 (m, 2H), 3.35-3.15 (m, 1H), 3.05-2.85 (m, 2H), 2.80 (s, 3H), 2.45-2.15 (m, 2H); LCMS: 100%, m/z=565.1 (M+1); HPLC (Method-3): 99.80%, Chiral HPLC: 99.48%, rt=20.38 min., Column. AG/CHIRALPAK AD-H/03.

Free Form

A free form of 1-((3S,4S)-4-(8-(2-chloro-4-(pyrimidin-2-yloxy)phenyl)-7-fluoro-2-methyl-1H-imidazo[4,5-c]quinolin-1-yl)-3-fluoropiperidin-1-yl)-2-hydroxyethanone in crystalline form (Form A of the free form) was produced from cooling crystallization of a supersaturated solution of the compound in ethanol at concentrations of about 110 mg/ml. 17.6 g of compound 1A was heated in 500 ml of ethanol under nitrogen atmosphere to reflux temperature. Approx. 1100 mL ethanol was added drop wise at reflux temperature, until the entire solid dissolved and a clear solution was obtained. The clear solution was cooled to room temperature and kept under slow stirring for 48 h. The precipitated solid was filtered and washed with ethanol. Wt: 16.1 g, HPLC: 99.20%, ¹HNMR shown residual ethanol was trapped. The obtained crystalline solid of Ex. 1A (16 g) was heated to reflux with 200 mL of HPLC grade toluene (compound not soluble in toluene) for 2 h. Then the reaction mixture was slowly cooled to room temperature, the solid was filtered and washed with toluene and dried under vacuum. Wt: 15.1 g, HPLC: 99.80%, LCMS: 99.39%, ¹HNMR was clean and showed no residual EtOH peaks. The XRPD pattern of a sample prepared according to such a method is shown in FIG. 1. Measurements were performed performed at a temperature of about 22° C. and an x-ray wavelength, λ, of 1.54006 Å. (CuKα 1.54006 Å.). The following xray method was used:

| Instrument | Bruker D8 advantage |
|---|---|
| Geometry | Reflection |
| Detector | Vantec |
| Generator parameter | 30 kV; 40 mA |
| San range | 2-40° 2-Theta |
| San rate | 107.1 s |
| Step size | 0.0170 |
| Slits (from left to right) | U12 |

Summary of XRPD Pattern

| Degrees 2-Theta (±0.1) | Relative Intensity |
|---|---|
| 7.324 | Medium |
| 9.758 | Low |
| 11.285 | Low |
| 12.165 | Low |
| 18.073 | Medium |
| 18.845 | High |
| 19.569 | Medium |
| 21.219 | Medium |
| 22.564 | Medium |

In one embodiment, Form A of the free form of 1-((3S,4S)-4-(8-(2-chloro-4-(pyrimidin-2-yloxy)phenyl)-7-fluoro-2-methyl-1H-imidazo[4,5-c]quinolin-1-yl)-3-fluoropiperidin-1-yl)-2-hydroxyethanone in crystalline form is characterized by an XRPD pattern with at least four, more preferably five, most preferably all of the following peaks at an angle of refraction 2 theta (2θ) of 7.3, 18.1, 18.8, 19.6, 21.2 and 22.6, ±0.1, respectively.

In one embodiment, Form A of the free form of 1-((3S,4S)-4-(8-(2-chloro-4-(pyrimidin-2-yloxy)phenyl)-7-fluoro-2-methyl-1H-imidazo[4,5-c]quinolin-1-yl)-3-fluoropiperidin-1-yl)-2-hydroxyethanone in crystalline form is characterized by an XRPD pattern substantially the same as the XRPD pattern shown in FIG. 1.

The melting point of Form A of the free from was determined by heating at 10° C./minute to be about 238° C.

The following are further embodiments of the invention:

Embodiment 1a

A free form of 1-((3S,4S)-4-(8-(2-chloro-4-(pyrimidin-2-yloxy)phenyl)-7-fluoro-2-methyl-1H-imidazo[4,5-c]quinolin-1-yl)-3-fluoropiperidin-1-yl)-2-hydroxyethanone in solid form.

Embodiment 2a

The free form according to embodiment 1a, wherein the free form is in crystalline form.

Embodiment 3a

The free form according to embodiment 2a, wherein the free form is characterized by an XRPD pattern substantially the same as the XRPD pattern shown in FIG. 1.

Embodiment 4a

The free form according to embodiments 2a or 3a, wherein the free form is in substantially pure form.

Embodiment 5a

The free form according to embodiments 2a or 3a, wherein the free form has a purity greater than 90 weight %.

Example 2

8-(2-chloro-4-(pyrimidin-2-yloxy)phenyl)-7-fluoro-1-(1-(2-methoxyethyl)piperidin-4-yl)-2-methyl-1H-imidazo[4,5-c]quinoline

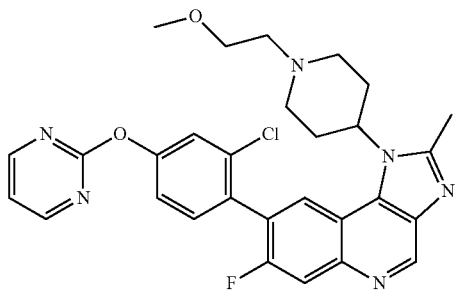

To a stirred solution of 7-fluoro-8-(2-fluoro-4-(pyrimidin-2-yloxy)phenyl)-2-methyl-1-(piperidin-4-yl)-1H-imidazo[4,5-c]quinolone. TFA salt (0.2 g, 0.408 mmol) in dry DMF (2 ml) at 0° C., was added DIPEA (0.2 mL, 1.2 mmol) followed by 1-bromo-2-methoxyethane (0.08 g, 0.61 mmol). The reaction mixture was stirred at room temperature for 48 h and monitored by TLC (10% MeOH in DCM). The reaction mixture was poured into ice water, extracted with ethyl acetate (3×25 mL). The combined organic layers were washed with ice-cold water, brine solution, dried over $Na_2SO_4$ and concentrated purified by silica-gel chromatography using 2% MeOH in DCM as eluent to afford 8-(2-chloro-4-(pyrimidin-2-yloxy)phenyl)-7-fluoro-1-(1-(2-methoxyethyl)piperidin-4-yl)-2-methyl-1H-imidazo[4,5-c]quinoline, (0.1 g, 46%). ¹H NMR (DMSO-$d_6$, 400 MHz): δ 9.21 (s, 1H), 8.73 (d, 2H), 8.42-8.35 (m, 1H), 8.07 (d, 1H), 7.73 (d, 1H), 7.67 (d, 1H), 7.43 (dd, 1H), 7.37 (t, 1H), 4.85-4.65 (m, 1H), 3.16 (s, 3H), 3.15-3.02 (m, 3H), 2.77 (s, 3H), 2.68 (t, 2H), 2.34 (t, 2H), 2.32-2.22 (m, 3H), 2.10-1.95 (m, 2H); LCMS: 90.41%, m/z=547.10 (M+1); HPLC: 96.15%, rt: 3.01 min.

Example 5

8-(2-chloro-4-(pyrimidin-2-yloxy)phenyl)-7-fluoro-2-methyl-1-(1-(methylsulfonyl)piperidin-4-yl)-1H-imidazo[4,5-c]quinoline

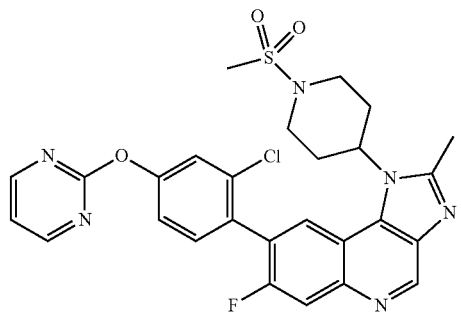 [SMILES: Cc1nc2cnc3cc(F)c(-c4ccc(Oc5ncccn5)cc4Cl)cc3c2n1C1CCN(S(C)(=O)=O)CC1]

To a stirred solution of 7-fluoro-8-(2-fluoro-4-(pyrimidin-2-yloxy)phenyl)-2-methyl-1-(piperidin-4-yl)-1H-imidazo[4,5-c]quinolone. TFA salt (0.05 g, 0.102 mmol) in dry DCM (2 ml) at 0° C., was added DIPEA (0.2 mL) followed by methanesulfonyl chloride (0.1 mL). The reaction mixture was stirred at room temperature for 4 h and monitored by TLC (5% MeOH in DCM). The reaction mixture was poured into ice water, extracted with ethyl acetate (3×15 mL). The combined organic layers were washed with ice-cold water, brine solution, dried over $Na_2SO_4$ and concentrated purified by silica-gel chromatography using 2% MeOH in DCM as eluent to afford 8-(2-chloro-4-(pyrimidin-2-yloxy)phenyl)-7-fluoro-2-methyl-1-(1-(methylsulfonyl)piperidin-4-yl)-1H-imidazo[4,5-c]quinoline (0.025 g, 46%). $^1$H NMR (DMSO-$d_6$, 400 MHz): δ 9.20 (s, 1H), 8.71 (d, 2H), 8.55-8.47 (m, 1H), 8.06 (d, 1H), 7.74 (d, 1H), 7.61 (s, 1H), 7.41-7.32 (m, 2H), 5.45-5.33 (m, 1H), 3.85-3.77 (m, 2H), 3.09-2.92 (m, 2H), 2.89 (s, 3H), 2.79 (s, 3H), 2.35-2.17 (m, 4H); LCMS: 98.33%, m/z=567.4 (M+1); HPLC: 94.22%, rt: 6.80 min.

Example 31

Synthesis of 4-(8-(2-chloro-4-((4-methylpyrimidin-2-yl)oxy)phenyl)-7-fluoro-2-methyl-1H-imidazo[4,5-c]quinolin-1-yl)piperidine-1-carboxamide

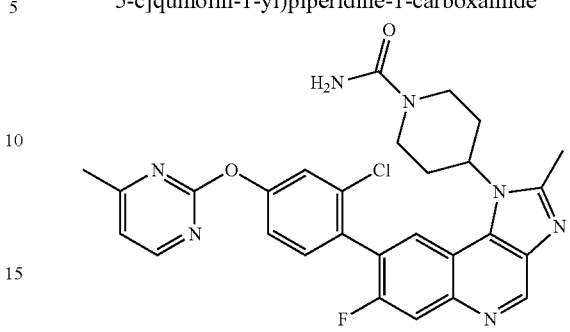

To a stirred solution of 8-(2-chloro-4-((4-methylpyrimidin-2-yl)oxy)phenyl)-7-fluoro-2-methyl-1-(piperidin-4-yl)-1H-imidazo[4,5-c]quinolone. TFA salt (0.25 g, 0.491 mmol) in dry DCM (5 ml) at 0° C., was added TEA (0.276 mL, 1.964 mmol) followed by trimethylsilyl isocyaante (0.085 mL, 0.744 mmol). The reaction mixture was stirred at room temperature for 4 h and monitored by TLC (10% MeOH in DCM). The reaction mixture was poured into ice water, extracted with ethyl acetate (3×15 mL). The combined organic layers were washed with ice-cold water, brine solution, dried over $Na_2SO_4$ and concentrated purified by silica-gel chromatography using 8% MeOH in DCM as eluent to afford 4-(8-(2-chloro-4-((4-methylpyrimidin-2-yl)oxy)phenyl)-7-fluoro-2-methyl-1H-imidazo[4,5-c]quinolin-1-yl)piperidine-1-carboxamide (0.08 g, 16%). $^1$HNMR (DMSO-$d_6$, 400 MHz): δ 9.19 (s, 1H), 8.51 (d, 1H), 8.40 (m, 1H), 8.05 (d, 1H), 7.72-7.54 (m, 2H), 7.42-7.36 (m, 1H), 7.22 (d, 1H), 6.10-5.50 (m, 3H), 5.10-4.80 (m, 1H), 4.20 (m, 2H), 2.92 (t, 2H), 2.77 (s, 3H), 2.46 (s, 3H), 2.10-1.90 (m, 3H); LCMS: 99.6%, m/z=546.5 (M+1); HPLC: 96.6%, rt: 6.26 min.

By repeating the procedures described in the above examples, using appropriate starting materials, the following compounds of Formula I, as identified by their chemical name in Table 1.1, are obtained. Examples 55 and 56 can be prepared in analoguous manner from the commercial building blocks 4-aminotetrahydro-2H-thiopyran 1,1-dioxide (CAS 210240-20-3) and 3-fluorotetrahydro-2H-pyran-4-amine (CAS 1416371-97-5).

TABLE 1.1

| Ex. | Steps | Chemical name |
|---|---|---|
| 1A | Step 1-5, 6 | 1-((3S,4S)-4-(8-(2-chloro-4-(pyrimidin-2-yloxy)phenyl)-7-fluoro-2-methyl-1H-imidazo[4,5-c]quinolin-1-yl)-3-fluoropiperidin-1-yl)-2-hydroxyethanone |
| 1B | Step 1-5, 6 | 1-((3R,4R)-4-(8-(2-chloro-4-(pyrimidin-2-yloxy)phenyl)-7-fluoro-2-methyl-1H-imidazo[4,5-c]quinolin-1-yl)-3-fluoropiperidin-1-yl)-2-hydroxyethanone |
| 2 | Step 1-5, 8 | 8-(2-chloro-4-(pyrimidin-2-yloxy)phenyl)-7-fluoro-1-(1-(2-methoxyethyl)piperidin-4-yl)-2-methyl-1H-imidazo[4,5-c]quinoline |
| 3 | Step 1-5, 8 | 2-(4-(8-(2-chloro-4-(pyrimidin-2-yloxy)phenyl)-7-fluoro-2-methyl-1H-imidazo[4,5-c]quinolin-1-yl)piperidin-1-yl)ethanol |
| 4 | Step 1-5, 8 | 8-(2-chloro-4-(pyrimidin-2-yloxy)phenyl)-7-fluoro-2-methyl-1-(1-((3-methyloxetan-3-yl)methyl)piperidin-4-yl)-1H-imidazo[4,5-c]quinoline |
| 5 | Step 1-5, 10 | 8-(2-chloro-4-(pyrimidin-2-yloxy)phenyl)-7-fluoro-2-methyl-1-(1-(methylsulfonyl)piperidin-4-yl)-1H-imidazo[4,5-c]quinoline |
| 6 | Step 1-5, 6 | 1-(4-(8-(2-chloro-4-(pyrimidin-2-yloxy)phenyl)-7-fluoro-2-methyl-1H-imidazo[4,5-c]quinolin-1-yl)piperidin-1-yl)-2-hydroxypropan-1-one |
| 7 | Step 1-5, 8 | 1-(4-(8-(2-chloro-4-(pyrimidin-2-yloxy)phenyl)-7-fluoro-2-methyl-1H-imidazo[4,5-c]quinolin-1-yl)piperidin-1-yl)propan-2-ol |
| 8 | Step 1-5, 10 | 8-(2-chloro-4-(pyrimidin-2-yloxy)phenyl)-1-(1-(cyclopropylsulfonyl)piperidin-4-yl)-7-fluoro-2-methyl-1H-imidazo[4,5-c]quinoline |
| 9 | Step 1-5, 10 | 8-(2-chloro-4-(pyrimidin-2-yloxy)phenyl)-7-fluoro-1-(1-(isopropylsulfonyl)piperidin-4-yl)-2-methyl-1H-imidazo[4,5-c]quinoline |

TABLE 1.1-continued

| Ex. | Steps | Chemical name |
|---|---|---|
| 10 | Step 1-5, 10 | 4-(8-(2-chloro-4-(pyrimidin-2-yloxy)phenyl)-7-fluoro-2-methyl-1H-imidazo[4,5-c]quinolin-1-yl)-N,N-dimethylpiperidine-1-sulfonamide |
| 11 | Step 1-5, 6 | 4-(8-(2-chloro-4-(pyrimidin-2-yloxy)phenyl)-7-fluoro-2-methyl-1H-imidazo[4,5-c]quinolin-1-yl)-N,N-dimethylpiperidine-1-carboxamide |
| 12 | Step 1-5, 6 | 1-(4-(8-(2-chloro-4-(pyrimidin-2-yloxy)phenyl)-7-fluoro-2-methyl-1H-imidazo[4,5-c]quinolin-1-yl)piperidin-1-yl)ethanone |
| 13 | Step 1-5, 8 | 2-(4-(8-(2-chloro-4-(pyrimidin-2-yloxy)phenyl)-7-fluoro-2-methyl-1H-imidazo[4,5-c]quinolin-1-yl)piperidin-1-yl)acetamide |
| 14 | Step 1-5, 6 | 1-(4-(8-(2-chloro-4-(pyrimidin-2-yloxy)phenyl)-7-fluoro-2-methyl-1H-imidazo[4,5-c]quinolin-1-yl)piperidin-1-yl)-2-hydroxyethanone |
| 15 | Step 1-5, 8 | 2-(4-(8-(2-chloro-4-((4-methylpyrimidin-2-yl)oxy)phenyl)-7-fluoro-1H-imidazo[4,5-c]quinolin-1-yl)-4-methylpiperidin-1-yl)ethanol |
| 16 | Step 1-5, 8 | 2-(4-(8-(2-chloro-4-(pyrimidin-2-yloxy)phenyl)-7-fluoro-2-methyl-1H-imidazo[4,5-c]quinolin-1-yl)piperidin-1-yl)propan-1-ol |
| 17 | Step 1-5, 8 | 2-(4-(8-(2-chloro-4-(pyrimidin-2-yloxy)phenyl)-7-fluoro-1H-imidazo[4,5-c]quinolin-1-yl)-4-methylpiperidin-1-yl)ethanol |
| 18 | Step 1-5, 8 | 2-(4-(7-fluoro-8-(2-methoxy-4-((4-methylpyrimidin-2-yl)oxy)phenyl)-1H-imidazo[4,5-c]quinolin-1-yl)-4-methylpiperidin-1-yl)ethanol |
| 19 | Step 1-5, 8 | 2-(4-(7-fluoro-8-(2-methoxy-4-(pyrimidin-2-yloxy)phenyl)-1H-imidazo[4,5-c]quinolin-1-yl)-4-methylpiperidin-1-yl)ethanol |
| 20 | Step 1-5, 6 | 1-(4-(7-fluoro-8-(2-methoxy-4-((4-methylpyrimidin-2-yl)oxy)phenyl)-1H-imidazo[4,5-c]quinolin-1-yl)-4-methylpiperidin-1-yl)-2-hydroxypropan-1-one |
| 21 | Step 1-5, 6 | 1-(4-(8-(2-chloro-4-((4-methylpyrimidin-2-yl)oxy)phenyl)-7-fluoro-1H-imidazo[4,5-c]quinolin-1-yl)-4-methylpiperidin-1-yl)-2-hydroxypropan-1-one |
| 22 | Step 1-5, 8 | 1-(4-(8-(2-chloro-4-(pyrimidin-2-yloxy)phenyl)-7-fluoro-2-methyl-1H-imidazo[4,5-c]quinolin-1-yl)piperidin-1-yl)-3-hydroxy-2-(hydroxymethyl)propan-1-one |
| 23 | Step 1-5, 8 | 2-((4-(8-(2-chloro-4-(pyrimidin-2-yloxy)phenyl)-7-fluoro-2-methyl-1H-imidazo[4,5-c]quinolin-1-yl)piperidin-1-yl)methyl)propane-1,3-diol |
| 24 | Step 1-5, 6 | 1-(4-(7-fluoro-8-(2-methoxy-4-((4-methylpyrimidin-2-yl)oxy)phenyl)-1H-imidazo[4,5-c]quinolin-1-yl)-4-methylpiperidin-1-yl)-2-hydroxyethanone |
| 25 | Step 1-5, 8 | 8-(2-chloro-4-(pyrimidin-2-yloxy)phenyl)-7-fluoro-2-methyl-1-(1-(oxetan-3-ylmethyl)piperidin-4-yl)-1H-imidazo[4,5-c]quinoline |
| 26 | Step 1-5, 6 | 1-(4-(8-(2-chloro-4-((4-methylpyrimidin-2-yl)oxy)phenyl)-7-fluoro-1H-imidazo[4,5-c]quinolin-1-yl)-4-methylpiperidin-1-yl)-2-hydroxyethanone |
| 27 | Step 1-5, 6 | 1-(4-(8-(2-chloro-4-(pyrimidin-2-yloxy)phenyl)-7-fluoro-1H-imidazo[4,5-c]quinolin-1-yl)-4-methylpiperidin-1-yl)-2-hydroxypropan-1-one |
| 28 | Step 1-5, 6 | 1-(4-(8-(2-chloro-4-((4-methylpyrimidin-2-yl)oxy)phenyl)-7-fluoro-2-methyl-1H-imidazo[4,5-c]quinolin-1-yl)piperidin-1-yl)-2-hydroxyethanone |
| 29 | Step 1-5, 6 | 1-(4-(8-(2-chloro-4-((4-methylpyrimidin-2-yl)oxy)phenyl)-7-fluoro-2-methyl-1H-imidazo[4,5-c]quinolin-1-yl)piperidin-1-yl)-2-hydroxypropan-1-one |
| 30 | Step 1-5, 6 | 4-(8-(2-chloro-4-(pyrimidin-2-yloxy)phenyl)-7-fluoro-2-methyl-1H-imidazo[4,5-c]quinolin-1-yl)piperidine-1-carboxamide |
| 31 | Step 1-5, 6 | 4-(8-(2-chloro-4-((4-methylpyrimidin-2-yl)oxy)phenyl)-7-fluoro-2-methyl-1H-imidazo[4,5-c]quinolin-1-yl)piperidine-1-carboxamide |
| 32 | Step 1-5, 10 | 8-(2-chloro-4-((4-methylpyrimidin-2-yl)oxy)phenyl)-7-fluoro-2-methyl-1-(1-(methylsulfonyl)piperidin-4-yl)-1H-imidazo[4,5-c]quinoline |
| 33 | Step 1-5, 6 | 1-(4-(8-(2-chloro-4-(pyrimidin-2-yloxy)phenyl)-7-fluoro-1H-imidazo[4,5-c]quinolin-1-yl)-4-methylpiperidin-1-yl)-2-hydroxyethanone |
| 34 | Step 1-5, 6 | (S)-1-(4-(8-(2-chloro-4-(pyrimidin-2-yloxy)phenyl)-7-fluoro-2-methyl-1H-imidazo[4,5-c]quinolin-1-yl)piperidin-1-yl)-2-hydroxypropan-1-one |
| 35 | Step 1-5, 6 | (S)-1-(4-(8-(2-chloro-4-((4-methylpyrimidin-2-yl)oxy)phenyl)-7-fluoro-2-methyl-1H-imidazo[4,5-c]quinolin-1-yl)piperidin-1-yl)-2-hydroxypropan-1-one |
| 36 | Step 1-5, 8 | 2-(4-(8-(2-chloro-4-((4-methylpyrimidin-2-yl)oxy)phenyl)-7-fluoro-2-methyl-1H-imidazo[4,5-c]quinolin-1-yl)piperidin-1-yl)ethanol |
| 37 | Step 1-5, 6 | 4-(7-fluoro-8-(2-methoxy-4-((4-methylpyrimidin-2-yl)oxy)phenyl)-1H-imidazo[4,5-c]quinolin-1-yl)-4-methylpiperidine-1-carboxamide |
| 38 | Step 1-5, 6 | 4-(7-fluoro-8-(2-methoxy-4-(pyrimidin-2-yloxy)phenyl)-1H-imidazo[4,5-c]quinolin-1-yl)-4-methylpiperidine-1-carboxamide |
| 39 | Step 1-5, 6 | 2-amino-1-(4-(8-(2-chloro-4-(pyrimidin-2-yloxy)phenyl)-7-fluoro-2-methyl-1H-imidazo[4,5-c]quinolin-1-yl)piperidin-1-yl)ethanone |
| 40 | Step 1-5, 6 | 2-amino-1-(4-(8-(2-chloro-4-((4-methylpyrimidin-2-yl)oxy)phenyl)-7-fluoro-2-methyl-1H-imidazo[4,5-c]quinolin-1-yl)piperidin-1-yl)ethanone |
| 41 | Step 1-5, 6 | 1-(4-(8-(2-chloro-4-((4-methylpyrimidin-2-yl)oxy)phenyl)-7-fluoro-1H-imidazo[4,5-c]quinolin-1-yl)-4-(hydroxymethyl)piperidin-1-yl)-2-hydroxyethanone |
| 42 | Step 1-5, 6 | 1-(4-(8-(2-chloro-4-(pyrimidin-2-yloxy)phenyl)-7-fluoro-2-methyl-1H-imidazo[4,5-c]quinolin-1-yl)piperidin-1-yl)-2-methoxyethanone |
| 43A | Step 1-5, 6 | (R or S)-1-(4-(8-(2-chloro-4-(pyrimidin-2-yloxy)phenyl)-7-fluoro-2-methyl-1H-imidazo[4,5-c]quinolin-1-yl)piperidin-1-yl)-2-fluoropropan-1-one (Peak 1) |
| 43B | Step 1-5, 6 | (R or S)-1-(4-(8-(2-chloro-4-(pyrimidin-2-yloxy)phenyl)-7-fluoro-2-methyl-1H-imidazo[4,5-c]quinolin-1-yl)piperidin-1-yl)-2-fluoropropan-1-one (Peak 2) |
| 44 | Step 1-5, 6 | 1-(4-(8-(2-chloro-4-((6-(hydroxymethyl)pyridin-2-yl)oxy)phenyl)-7-fluoro-2-methyl-1H-imidazo[4,5-c]quinolin-1-yl)piperidin-1-yl)-2-hydroxyethanone |
| 45 | Step 1-5, 6 | 4-(8-(2-chloro-4-(pyrimidin-2-yloxy)phenyl)-7-fluoro-2-methyl-1H-imidazo[4,5-c]quinolin-1-yl)-N-(2,2,2-trifluoroethyl)piperidine-1-carboxamide |

TABLE 1.1-continued

| Ex. | Steps | Chemical name |
|---|---|---|
| 46 | Step 1-5, 6 | 1-(4-(8-(2-chloro-4-((4-fluoropyrimidin-2-yl)oxy)phenyl)-7-fluoro-2-methyl-1H-imidazo[4,5-c]quinolin-1-yl)piperidin-1-yl)-2-hydroxyethanone |
| 47 | Step 1-5, 6 | 1-(4-(8-(2-chloro-4-((6-fluoropyridin-2-yl)oxy)phenyl)-7-fluoro-2-methyl-1H-imidazo[4,5-c]quinolin-1-yl)piperidin-1-yl)-2-hydroxyethanone |
| 48 | Step 1-5, 6 | 1-(4-(8-(2-chloro-4-((5-fluoro-4-methylpyrimidin-2-yl)oxy)phenyl)-7-fluoro-2-methyl-1H-imidazo[4,5-c]quinolin-1-yl)piperidin-1-yl)-2-hydroxyethanone |
| 49 | Step 1-5, 6 | 2-((3S,4S)-4-(8-(2-chloro-4-(pyrimidin-2-yloxy)phenyl)-7-fluoro-2-methyl-1H-imidazo[4,5-c]quinolin-1-yl)-3-fluoropiperidin-1-yl)-2-oxoethyl acetate |
| 50 | Step 1-5, 10 | 8-(2-chloro-4-(pyrimidin-2-yloxy)phenyl)-7-fluoro-1-((3S,4S)-3-fluoro-1-(methylsulfonyl)piperidin-4-yl)-2-methyl-1H-imidazo[4,5-c]quinoline |
| 51 | Step 1-5, 6 | 1-((3S,4S)-4-(8-(2-chloro-4-((4-(trifluoromethyl)pyrimidin-2-yl)oxy)phenyl)-7-fluoro-2-methyl-1H-imidazo[4,5-c]quinolin-1-yl)-3-fluoropiperidin-1-yl)-2-hydroxyethanone |
| 52 | Step 1-5, 6 | 1-((3S,4S)-4-(8-(2-chloro-4-(pyrimidin-2-yloxy)phenyl)-7-fluoro-2-methyl-1H-imidazo[4,5-c]quinolin-1-yl)-3-fluoropiperidin-1-yl)-2-methoxyethanone |
| 53 | Step 1-5, 6 | 1-((3S,4S)-4-(8-(2-chloro-4-((5-fluoro-4-methylpyrimidin-2-yl)oxy)phenyl)-7-fluoro-2-methyl-1H-imidazo[4,5-c]quinolin-1-yl)-3-fluoropiperidin-1-yl)-2-hydroxyethanone |
| 54 | Step 1-5, 6 | 1-(4-(8-(2-chloro-4-((4-cyclopropylpyrimidin-2-yl)oxy)phenyl)-7-fluoro-2-methyl-1H-imidazo[4,5-c]quinolin-1-yl)piperidin-1-yl)-2-hydroxyethanone |
| 55 | NA | 4-(8-(2-chloro-4-((4-methylpyrimidin-2-yl)oxy)phenyl)-7-fluoro-2-methyl-1H-imidazo[4,5-c]quinolin-1-yl)tetrahydro-2H-thiopyran 1,1-dioxide |
| 56 | NA | 8-(2-chloro-4-(pyrimidin-2-yloxy)phenyl)-7-fluoro-1-(3-fluorotetrahydro-2H-pyran-4-yl)-2-methyl-1H-imidazo[4,5-c]quinoline |
| 57 | Step 1-5, 8 | 2-((3R,4R)-4-(8-(2-chloro-4-((4-methylpyrimidin-2-yl)oxy)phenyl)-7-fluoro-2-methyl-1H-imidazo[4,5-c]quinolin-1-yl)-3-fluoropiperidin-1-yl)acetonitrile |
| 58 | Step 1-5, 8 | 2-((3S,4S)-4-(8-(2-chloro-4-((4-methylpyrimidin-2-yl)oxy)phenyl)-7-fluoro-2-methyl-1H-imidazo[4,5-c]quinolin-1-yl)-3-fluoropiperidin-1-yl)acetonitrile |
| 59 | Step 1-5, 8 | 4-(3-chloro-4-(1-(1-(cyanomethyl)piperidin-4-yl)-7-fluoro-2-methyl-1H-imidazo[4,5-c]quinolin-8-yl)phenoxy)-6-methylpyrimidine-2-carbonitrile |
| 60 | Step 1-5, 8 | 2-(4-(8-(2-chloro-4-((1-methyl-6-oxo-1,6-dihydropyrimidin-4-yl)oxy)phenyl)-7-fluoro-2-methyl-1H-imidazo[4,5-c]quinolin-1-yl)piperidin-1-yl)acetonitrile |
| 61 | Step 1-5, 8 | 2-((3R,4R)-3-fluoro-4-(7-fluoro-8-(2-methoxy-4-(pyrimidin-2-yloxy)phenyl)-2-methyl-1H-imidazo[4,5-c]quinolin-1-yl)piperidin-1-yl)acetonitrile |
| 62 | Step 1-5, 8 | 2-((3S,4S)-3-fluoro-4-(7-fluoro-8-(2-methoxy-4-(pyrimidin-2-yloxy)phenyl)-2-methyl-1H-imidazo[4,5-c]quinolin-1-yl)piperidin-1-yl)acetonitrile |
| 63 | Step 1-5, 6 | 3-(3-chloro-4-(7-fluoro-1-(1-(2-hydroxyacetyl)piperidin-4-yl)-2-methyl-1H-imidazo[4,5-c]quinolin-8-yl)phenoxy)-1-methylpyridin-2(1H)-one |
| 64 | Step 1-5, 6 | 4-(8-(2-chloro-4-(pyrimidin-2-yloxy)phenyl)-7-fluoro-1H-imidazo[4,5-c]quinolin-1-yl)-4-methylpiperidine-1-carboxamide |
| 65 | Step 1-5, 6 | 4-(8-(2-chloro-4-((4-methylpyrimidin-2-yl)oxy)phenyl)-7-fluoro-1H-imidazo[4,5-c]quinolin-1-yl)-4-methylpiperidine-1-carboxamide |
| 66 | Step 1-5, 6 | 1-(4-(8-(2-chloro-4-((4-methoxy-6-methylpyrimidin-2-yl)oxy)phenyl)-7-fluoro-1H-imidazo[4,5-c]quinolin-1-yl)-4-methylpiperidin-1-yl)-2-hydroxyethanone |
| 67 | Step 1-5, 6 | 1-(4-(8-(2-chloro-4-((4-methylpyrimidin-2-yl)oxy)phenyl)-7-fluoro-2-methyl-1H-imidazo[4,5-c]quinolin-1-yl)piperidin-1-yl)-2-methoxyethanone |
| 68 | Step 1-5, 6 | 1-((3S,4S)-4-(8-(2-chloro-4-((4-methylpyrimidin-2-yl)oxy)phenyl)-7-fluoro-2-methyl-1H-imidazo[4,5-c]quinolin-1-yl)-3-fluoropiperidin-1-yl)-2-hydroxyethanone |
| 69 | Step 1-5, 6 | 6-(3-chloro-4-(7-fluoro-1-(1-(2-hydroxyacetyl)-4-methylpiperidin-4-yl)-1H-imidazo[4,5-c]quinolin-8-yl)phenoxy)-3-methylpyrimidin-4(3H)-one |
| 70 | Step 1-5, 6 | 4-(7-fluoro-8-(2-fluoro-4-((4-methylpyrimidin-2-yl)oxy)phenyl)-2-methyl-1H-imidazo[4,5-c]quinolin-1-yl)piperidine-1-carboxamide |
| 71 | Step 1-5, 6 | 1-(4-(7-fluoro-8-(2-fluoro-4-((4-methylpyrimidin-2-yl)oxy)phenyl)-2-methyl-1H-imidazo[4,5-c]quinolin-1-yl)piperidin-1-yl)-2-hydroxyethanone |
| 72 | Step 1-5, 6 | 6-(3-chloro-4-(7-fluoro-1-(1-(2-hydroxyacetyl)piperidin-4-yl)-2-methyl-1H-imidazo[4,5-c]quinolin-8-yl)phenoxy)-3-methylpyrimidin-4(3H)-one |
| 73 | Step 1-5, 6 | 4-(8-(2-chloro-4-((1-methyl-2-oxo-1,2-dihydropyridin-3-yl)oxy)phenyl)-7-fluoro-2-methyl-1H-imidazo[4,5-c]quinolin-1-yl)piperidine-1-carboxamide |
| 74 | Step 1-5, 6 | 4-(8-(2-chloro-4-((1-methyl-6-oxo-1,6-dihydropyrimidin-4-yl)oxy)phenyl)-7-fluoro-2-methyl-1H-imidazo[4,5-c]quinolin-1-yl)piperidine-1-carboxamide |
| 75 | Step 1-5, 6 | 4-(8-(2-chloro-4-((1-methyl-2-oxo-1,2-dihydropyridin-3-yl)oxy)phenyl)-7-fluoro-1H-imidazo[4,5-c]quinolin-1-yl)-4-methylpiperidine-1-carboxamide |
| 76 | Step 1-5, 6 | 4-(7-fluoro-2-methyl-8-(2-methyl-4-((4-methylpyrimidin-2-yl)oxy)phenyl)-1H-imidazo[4,5-c]quinolin-1-yl)piperidine-1-carboxamide |
| 77 | Step 1-5, 6 | 1-(4-(7-fluoro-2-methyl-8-(2-methyl-4-((4-methylpyrimidin-2-yl)oxy)phenyl)-1H-imidazo[4,5-c]quinolin-1-yl)piperidin-1-yl)-2-hydroxyethanone |
| 78 | Step 1-5, 6 | 1-(4-(7-fluoro-2-methyl-8-(4-((4-methylpyrimidin-2-yl)oxy)phenyl)-1H-imidazo[4,5-c]quinolin-1-yl)piperidin-1-yl)-2-hydroxyethanone |
| 79 | Step 1-5, 6 | 4-(7-fluoro-8-(2-fluoro-4-((4-methylpyrimidin-2-yl)oxy)phenyl)-1H-imidazo[4,5-c]quinolin-1-yl)-4-methylpiperidine-1-carboxamide |
| 80 | Step 1-5, 6 | 4-(7-fluoro-8-(2-fluoro-4-(pyrimidin-2-yloxy)phenyl)-1H-imidazo[4,5-c]quinolin-1-yl)-4-methylpiperidine-1-carboxamide |
| 81 | Step 1-5, 6 | (S)-3-(3-chloro-4-(7-fluoro-1-(1-(2-hydroxypropanoyl)piperidin-4-yl)-2-methyl-1H-imidazo[4,5-c]quinolin-8-yl)phenoxy)-1-methylpyridin-2(1H)-one |
| 82 | Step 1-5, 6 | 4-(8-(2-chloro-4-((4-methyl-3-oxo-3,4-dihydropyrazin-2-yl)oxy)phenyl)-7-fluoro-2-methyl-1H-imidazo[4,5-c]quinolin-1-yl)piperidine-1-carboxamide |

TABLE 1.1-continued

| Ex. | Steps | Chemical name |
|---|---|---|
| 83 | Step 1-5, 6 | 1-(4-(7-fluoro-8-(2-fluoro-4-((4-methylpyrimidin-2-yl)oxy)phenyl)-1H-imidazo[4,5-c]quinolin-1-yl)-4-methylpiperidin-1-yl)-2-hydroxyethanone |
| 84 | Step 1-5, 8 | 2-(4-(8-(2-chloro-4-(pyrimidin-2-yloxy)phenyl)-7-fluoro-2-methyl-1H-imidazo[4,5-c]quinolin-1-yl)piperidin-1-yl)acetonitrile |
| 85 | Step 1-5, 8 | 2-((3S,4S)-4-(8-(2-chloro-4-(pyrimidin-2-yloxy)phenyl)-7-fluoro-2-methyl-1H-imidazo[4,5-c]quinolin-1-yl)-3-fluoropiperidin-1-yl)acetonitrile |
| 86 | Step 1-5, 6 | ((3S,4S)-4-(8-(2-chloro-4-(pyrimidin-2-yloxy)phenyl)-7-fluoro-2-methyl-1H-imidazo[4,5-c]quinolin-1-yl)-3-fluoropiperidin-1-yl)(oxetan-2-yl)methanone |
| 87 | Step 1-5, 6 | 1-((3S,4S)-4-(8-(2-chloro-4-((5-fluoro-4-methylpyrimidin-2-yl)oxy)phenyl)-7-fluoro-2-methyl-1H-imidazo[4,5-c]quinolin-1-yl)-3-fluoropiperidin-1-yl)-2-hydroxyethanone |
| 88 | Step 1-5, 6 | 1-((3S,4S)-3-fluoro-4-(7-fluoro-8-(2-methoxy-4-(pyrimidin-2-yloxy)phenyl)-2-methyl-1H-imidazo[4,5-c]quinolin-1-yl)piperidin-1-yl)-2-hydroxyethanone |
| 89 | Step 1-5, 6 | 1-((3S,4S)-4-(8-(2-chloro-4-((4-(hydroxymethyl)pyrimidin-2-yl)oxy)phenyl)-7-fluoro-2-methyl-1H-imidazo[4,5-c]quinolin-1-yl)-3-fluoropiperidin-1-yl)-2-hydroxyethanone |
| 90 | Step 1-5, 6 | 1-((3S,4S)-3-fluoro-4-(7-fluoro-2-methyl-8-(2-methyl-4-(pyrimidin-2-yloxy)phenyl)-1H-imidazo[4,5-c]quinolin-1-yl)piperidin-1-yl)-2-hydroxyethanone |
| 91 | Step 1-5, 6 | 2-((3S,4S)-4-(8-(2-chloro-4-(pyrimidin-2-yloxy)phenyl)-7-fluoro-2-methyl-1H-imidazo[4,5-c]quinolin-1-yl)-3-fluoropiperidin-1-yl)-2-oxoethyl hydrogen sulfate |
| 92 | Step 1-5, 6 | 1-((3S,4S)-3-fluoro-4-(7-fluoro-8-(2-fluoro-4-(pyrimidin-2-yloxy)phenyl)-2-methyl-1H-imidazo[4,5-c]quinolin-1-yl)piperidin-1-yl)-2-hydroxyethanone |
| 93 | Step 1-5, 6 | 1-((3S,4S)-4-(8-(2-chloro-4-(pyrimidin-2-yloxy)phenyl)-7-fluoro-2-methyl-1H-imidazo[4,5-c]quinolin-1-yl)-3-fluoropiperidin-1-yl)ethanone |
| 94 | Step 1-5, 6 | (3S,4S)-4-(8-(2-chloro-4-(pyrimidin-2-yloxy)phenyl)-7-fluoro-2-methyl-1H-imidazo[4,5-c]quinolin-1-yl)-3-fluoropiperidine-1-carboxamide |
| 95 | Step 1-5, 6 | (S)-1-((3S,4S)-4-(8-(2-chloro-4-(pyrimidin-2-yloxy)phenyl)-7-fluoro-2-methyl-1H-imidazo[4,5-c]quinolin-1-yl)-3-fluoropiperidin-1-yl)-2-hydroxypropan-1-one |
| 96 | Step 1-5, 6 | 1-(4-(8-(2-chloro-4-(pyrimidin-2-yloxy)phenyl)-7-fluoro-2-methyl-1H-imidazo[4,5-c]quinolin-1-yl)piperidin-1-yl)-2-fluoroethanone |
| 97 | Step 1-5, 6 | 1-((3S,4S)-4-(8-(2-chloro-4-(pyrimidin-2-yloxy)phenyl)-7-fluoro-2-methyl-1H-imidazo[4,5-c]quinolin-1-yl)-3-fluoropiperidin-1-yl)-2-fluoroethanone |
| 98 | Step 1-5, 6 | 1-((3S,4S)-4-(8-(2-chloro-4-(pyrimidin-2-yloxy)phenyl)-7-fluoro-2-methyl-1H-imidazo[4,5-c]quinolin-1-yl)-3-fluoropiperidin-1-yl)-3-hydroxypropan-1-one |
| 99 | Step 1-5, 6 | 1-((3S,4S)-4-(8-(2-chloro-4-((4-methoxy-1,3,5-triazin-2-yl)oxy)phenyl)-7-fluoro-2-methyl-1H-imidazo[4,5-c]quinolin-1-yl)-3-fluoropiperidin-1-yl)-2-hydroxyethanone |

Intermediate 1.8

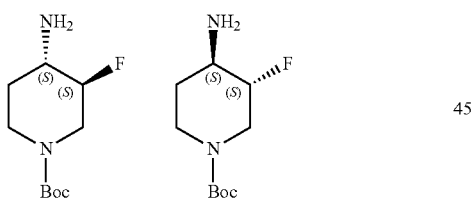

Scheme 5:

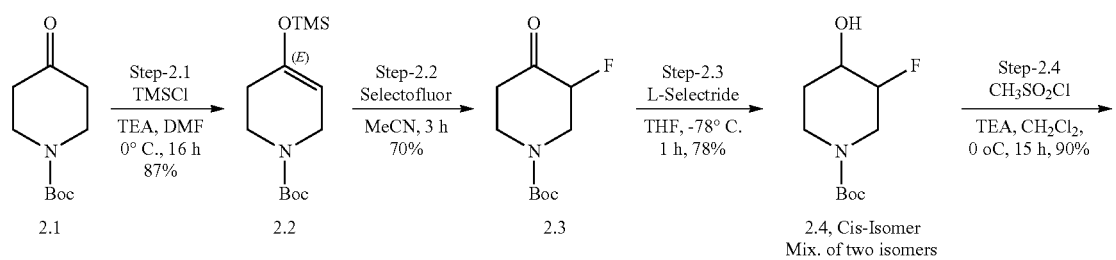

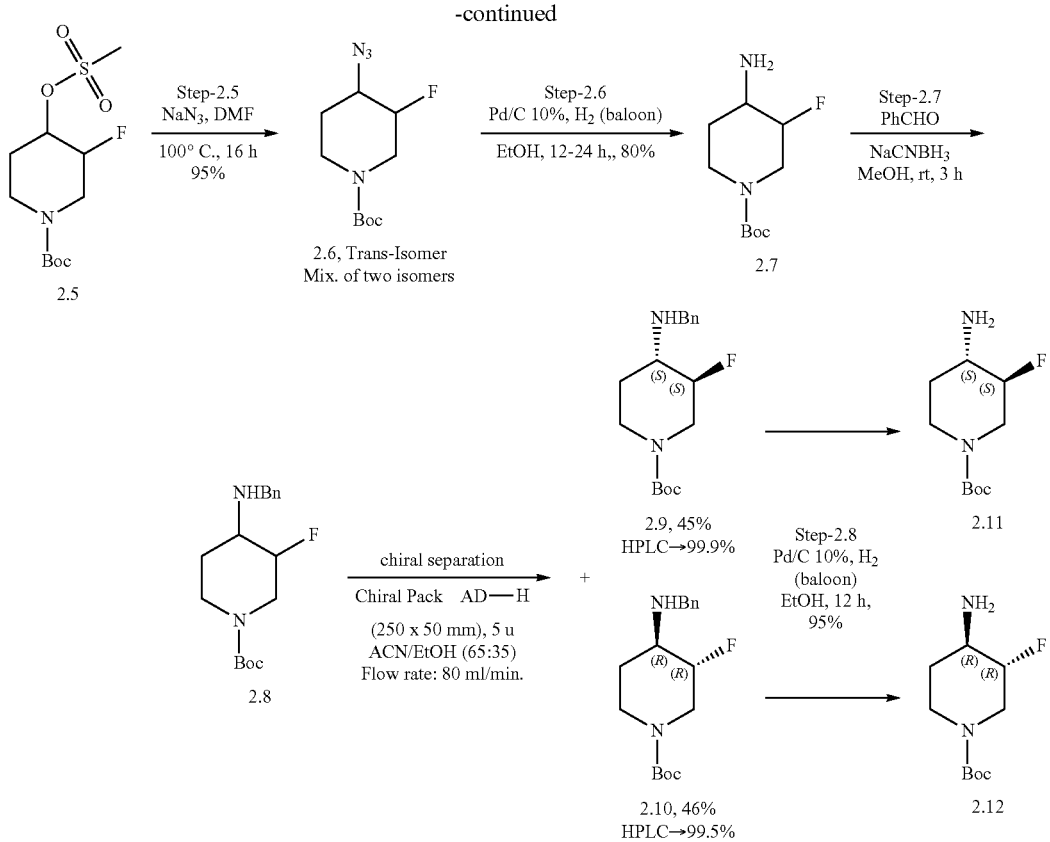

Step-2.1: Synthesis of tert-butyl 4-((trimethylsilyl)oxy)-5,6-dihydropyridine-1(2H)-carboxylate, 2.2

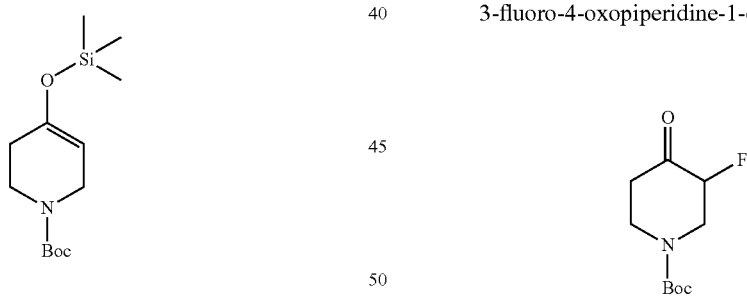

Tert-butyl 4-oxopiperidine-1-carboxylate, 1.1 (250 g, 1.256 mol) was taken in dry DMF (150 mL) under $N_2$ atmosphere and added TEA (230 g, 2.27 mmol) at room temperature. The reaction mixture was cooled to 0° C., added trimethylsilyl chloride (178 g, 1.64 mol) drop wise for 30 minutes. After addition completed the reaction mixture heated at 80° C. for 16 h. The reaction was monitored by TLC (20% EtOAc/hexane), and allowed to cool the reaction mixture to room temperature, poured into ice water and extracted with EtOAc (3×200 mL). The combined organic layers were washed with water, brine solution, dried over $Na_2SO_4$ and evaporated under vacuum. The residue was purified by column chromatography on silica gel (5-10% EtOAc-Hexane) to afford tert-butyl 4-((trimethylsilyl)oxy)-5,6-dihydropyridine-1(2H)-carboxylate, 2.2 (300 g, 87.79%). $^1$HNMR (CDCl$_3$, 400 MHz): δ 4.78 (s, 1H), 3.87-3.80 (m, 2H), 3.55 (t, 2H), 2.15-2.05 (m, 2H), 1.45 (s, 9H), 0.19 (s, 9H).

Step-2.2: Synthesis of tert-butyl 3-fluoro-4-oxopiperidine-1-carboxylate, 2.3

Tert-butyl 4-((trimethylsilyl)oxy)-5,6-dihydropyridine-1 (2H)-carboxylate, 2.2 (300 g, 1.102 mol) was dissolved in dry Acetonitrile (300 mL) and cooled to 0° C. and Selectfluor (430 g, 1.21 mol) was added in portion wise over a period of 45 min. under $N_2$ atmosphere. After addition completed, the reaction mixture was allowed to room temperature and stirred for 2 h. The reaction was monitored by TLC (50% EtOAc/hexane). After completion of reaction by TLC the reaction mixture poured into ice cold saturated brine solution (300 mL) and extracted with EtOAc (2×200 mL). The combined EtOAc layers were washed with brine solution, water, dried over $Na_2SO_4$ and evaporated under vacuum. The residue was purified by column chromatography on silica gel (10-40% EtOAc-Hexane) to afford tert-butyl 3-fluoro-4-oxopiperidine-1-carboxylate 2.3 (170 g; 70.7%). $^1$HNMR (CDCl$_3$, 400

MHz): δ 4.88 (dd, 0.5H), 4.77 (dd, 0.5H), 4.47 (brs, 1H), 4.17 (ddd, 1H), 3.25 (brs, 1H), 3.23 (ddd, 1H), 2.58 (m, 1H), 2.51 (m, 1H), 1.49 (s, 9H).

Step-2.3: Synthesis of tert-butyl 3-fluoro-4-hydroxypiperidine-1-carboxylate, 2.4

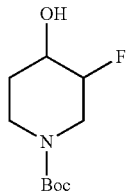

A solution of tert-butyl 3-fluoro-4-oxopiperidine-1-carboxylate, 2.3 (80 g, 0.368 mol) in THF (800 mL) was treated with L-Selectride (405 mL, 0.405 mol, drop wise) at −78° C. under nitrogen atmosphere. The resulting reaction mixture was stirred for 30 min. at the same temperature, MeOH (45.1 mL, 1.105 mol) 1M NaOH (1104 mL, 1.105 mol) were added and the reaction was allowed to warm to 0° C. The reaction was quenched by drop wise addition of $H_2O_2$ (125.1 mL, 1.843 mol). The volatiles were removed under vacuume and diluted with water (500 mL) and methylene chloride (500 mL). After separation, the organic layer was washed brine, dried over $Na_2SO_4$ and concentrated in vacuum to provide the desired product tert-butyl 3-fluoro-4-hydroxypiperidine-1-carboxylate, 2.4 (63 g, 78%). $^1$HNMR (CDCl$_3$, 400 MHz): δ 4.70-4.65 (m, 0.5H), 4.58-4.52 (m, 0.5H), 3.99-3.84 (m, 2H), 3.82-3.58 (m, 1H), 3.55-3.27 (m, 1H), 3.18 (brs, 1H), 2.06 (brs, 1H), 1.89-1.70 (m, 2H), 1.47 (s, 9H).

Step-2.4: Synthesis of tert-butyl 3-fluoro-4-((methylsulfonyl)oxy)piperidine-1-carboxylate, 2.5

A solution of tert-butyl 3-fluoro-4-hydroxypiperidine-1-carboxylate, 2.4 (63 g, 0.287 mol) in anhydrous methylene chloride (630 mL) was treated with triethylamine (60 mL, 0.43 μmol) followed by methane sulfonyl chloride (26.7 mL, 0.345 mol) at 0° C. under N2 atmosphere. The solution was allowed to warm slowly to ambient temperature and stirred for 14 hours. The mixture was partitioned between saturated NaHCO$_3$ (400 mL) and methylene chloride (400 mL). The aqueous layer was extracted with methylene chloride (2×500 mL). The combined organic phases were washed with 1N HCl, brine, dried over $Na_2SO_4$, filtered and concentrated under vacuum. The residue was purified by silica gel chromatography, eluting with 20-30% EtOAc/Hexane to provide the tert-butyl 3-fluoro-4-((methylsulfonyl)oxy)piperidine-1-carboxylate, 2.5 (78 g, 91%). $^1$HNMR (CDCl$_3$, 400 MHz): δ 4.98-4.86 (m, 1H), 4.80-4.74 (m, 0.5H), 4.67-4.63 (m, 0.5H), 3.92-3.45 (m, 3H), 3.44-3.25 (m, 1H), 3.08 (s, 3H), 2.20-2.07 (m, 1H), 1.93-1.80 (m, 1H), 1.45 (s, 9H).

Step-2.5: Synthesis of tert-butyl 4-azido-3-fluoropiperidine-1-carboxylate, 2.6

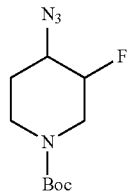

Sodium azide (68.2 g, 1.050 mol) was added to a solution of tert-butyl 3-fluoro-4-((methylsulfonyl)oxy)piperidine-1-carboxylate, 2.5 (78 g, 0.262 mol) in DMF (620 mL). The reaction mixture was heated at 100° C. for overnight. The mixture was cooled and diluted with 500 mL) water and methylene chloride (500 mL). After separation, the organic layer was washed with brine, dried over $Na_2SO_4$, filtered and concentrated in vacuum to provide the desired product tert-butyl 4-azido-3-fluoropiperidine-1-carboxylate, 2.6 (62 g, 96% yield), which was used for the next reaction without any purification.

Step-2.6: Synthesis of tert-butyl 4-amino-3-fluoropiperidine-1-carboxylate, 2.7

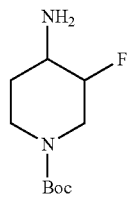

Pd/C 10% (12 g) was added to a solution of tert-butyl 4-azido-3-fluoropiperidine-1-carboxylate, 2.6 (62 g, 0.254 mol) in EtOH (600 mL). The reaction was stirred under a hydrogen atmosphere (balloon pressure) for 48 hours. The mixture was filtered through celite-bed and concentrated under reduced pressure to obtain the title compound tert-butyl4-amino-3-fluoropiperidine-1-carboxylate, 2.7 (42 g, 75% yield). LCMS: m/z 218.8 (M+1).

Step-2.7: Synthesis of tert-butyl 4-(benzylamino)-3-fluoropiperidine-1-carboxylate, 2.8

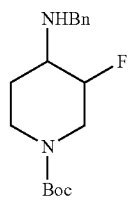

Benzaldehyde (34.0 g, 0.321 mol) was added to a solution of tert-butyl 4-amino-3-fluoropiperidine-1-carboxylate, 2.7 (70 g, 0.32 mol) and acetic acid (10 mL) in ethanol (500 mL) and stirred for 30 min at room temperature. Sodiumcyanoborohydride (26.23 g, 0.417 mol) was added and stirred for 3 h. Reaction was quenched with saturated sodium bicarbonate solution (200 mL) and extracted with dichloromethane (2×250 mL). The combined organic layers were washed with brine, dried over anhydrous sodium sulfate, filtered and concentrated under reduced pressure. The residue was dissolved in a minimum amount of dichloromethane (200 mL) and pH adjusted to 3-4 by adding aqueous citric acid (124 g, 0.645 mol in 1000 mL water). Layers were separated and aqueous layer was washed with dichloromethane (3×250 mL). Separated aqueous layer pH was then adjusted to 9-10 by using saturated $Na_2CO_3$ and extract with diethyl ether (2×500 mL). The combined organic layers were washed with brine, dried over anhydrous sodium sulfate, filtered and concentrated to obtain the crude product which was purified by as light yellow oil. The residue was purified by silica gel chromatography by eluting with 10-15% EtOAc/hexane to provide the desired product tert-butyl 4-(benzylamino)-3-fluoropiperidine-1-carboxylate, 2.8 (51 g, 51.52% yield). $^1$HNMR (400 MHz, $CDCl_3$): δ 7.39-7.29 (m, 5H), 4.44-4.35 (m, 0.5H), 4.32-4-10 (m, 1.5H), 3.98-3.85 (m, 2H), 3.80 (d, 1H), 2.97-2.77 (m, 4H), 2.04-1.93 (m, 1H), 1.46 (s, 9H); LCMS: 92.34%, m/z=309.2 (M+1); HPLC: 95.46%; Chiral HPLC: 47.2% at 9.56 min. and 48.3% at 12.34 min. Column. AG/Chiral Pak AD-H/03, n-Hexane/EtOH (80:20).

Two enantiomers were separated by chiral preparative HPLC from Compound 2.8. Amount: 42.5 g (load: 50 mg/ml). Conditions: Column: CHIRALPAK AD-H (250×50) mm.5 micron; Mobile Phase: ACN/EtOH (65:35); Parameters: flow rate 80 ml/min, column temp 25° C.

Peak-1: (3S,4S) tert-butyl 4-(benzylamino)-3-fluoropiperidine-1-carboxylate, 2.9:

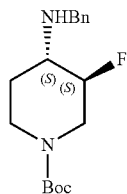

Peak-1

19.3 g, 45% yield. $^1$HNMR ($CDCl_3$, 400 MHz): δ 7.35-7.25 (m, 5H), 4.37-4.28 (m, 2H), 3.91-3.79 (dd, 3H), 2.86-2.82 (m, 3H), 1.99-1.97 (m, 1H), 1.45 (s, 9H), 1.37-1.34 (m, 1H); LCMS: 99.43% m/z=309 (M+1); HPLC: 99.9%, rt=10.0 min., (Column: CHIRALPAK AD-H (250×4.6) mm.5 micron, Mobile Phase: n-Hexane/EtOH/DEA 80/20/0.1, Parameters: flow rate 1 ml/min, column temp 25° C., Detection: DAD220 nm).

Peak 2: (3R,4R) tert-butyl 4-(benzylamino)-3-fluoropiperidine-1-carboxylate, 2.10

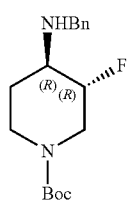

Peak-2

19.3 g, 46% yield. $^1$HNMR ($CDCl_3$, 400 MHz,): δ 7.35-7.25 (m, 5H), 4.37-4.28 (m, 2H), 3.91-3.79 (dd, 3H), 2.86-2.82 (m, 3H), 1.99-1.97 (m, 1H), 1.45 (s, 9H), 1.37-1.34 (m, 1H); 99.64% m/z=309 (M+1); HPLC: 99.5%, rt=12.8 min. (Column: CHIRALPAK AD-H (250×4.6) mm.5 micron, Mobile Phase: n-Hexane/EtOH/DEA 80/20/0.1, Parameters: flow rate 1 ml/min, column temp 25° C., Detection: DAD220 nm)

Step-2.8: Synthesis of (3S,4S)-tert-butyl 4-amino-3-fluoropiperidine-1-carboxylate, 2.11

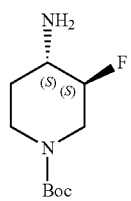

Pd/C 10% (4.5 g) was added to a solution of (3S,4S) tert-butyl 4-(benzyl amino)-3-fluoropiperidine-1-carboxylate, 2.9 (19.1 g, 0.062 mol) in EtOH (500 mL). The reaction was stirred under hydrogen atmosphere (balloon pressure) for 16 hours at room temperature. After completion of reaction by TLC, the mixture was filtered through celite-bed and concentrated under reduced pressure to obtain the title compound (3S,4S) tert-butyl 4-amino-3-fluoropiperidine-1-carboxylate, 2.11 (12.6 g, 93% yield). $^1$HNMR ($CDCl_3$, 400 MHz): δ 4.33-4.14 (m, 1H), 4.13-4.02 (m, 2H), 2.94-2.78 (m, 3H), 1.89-1.86 (m, 1H), 1.48 (s, 9H), 1.42-1.34 (m, 1H); LCMS: 100%, m/z 163.1 (M−55, tert-But); HPLC: 99.17%, rt=5.146 min.

Synthesis of (3R,4R)-tert-butyl 4-amino-3-fluoropiperidine-1-carboxylate, 2.12

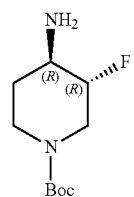

Pd/C 10% (4.5 g) was added to a solution of (3R,4R) tert-butyl 4-(benzyl amino)-3-fluoropiperidine-1-carboxylate, 2.10 (19.6 g, 0.063 mol) in EtOH (500 mL). The reaction was stirred under hydrogen atmosphere (balloon pressure) for 16 hour. After completion of reaction by TLC, the mixture was filtered through celite-bed and concentrated under reduced pressure to obtain the title compound (3R,4R) tert-butyl 4-amino-3-fluoropiperidine-1-carboxylate, 2.12 (12.6 g, 92% yield). $^1$HNMR ($CDCl_3$, 400 MHz): δ 4.33-4.14 (m, 1H), 4.13-4.02 (m, 2H), 2.94-2.78 (m, 3H), 1.89-1.86 (m, 1H), 1.48 (s, 9H), 1.42-1.34 (m, 1H); LCMS: 100%, m/z 163.1 (M−55, tert-But), HPLC: 99.62%, rt=5.214 min.

Alternative synthesis of tert-butyl (3S,4S)-4-amino-3-fluoropiperidine-1-carboxylate, 4.6

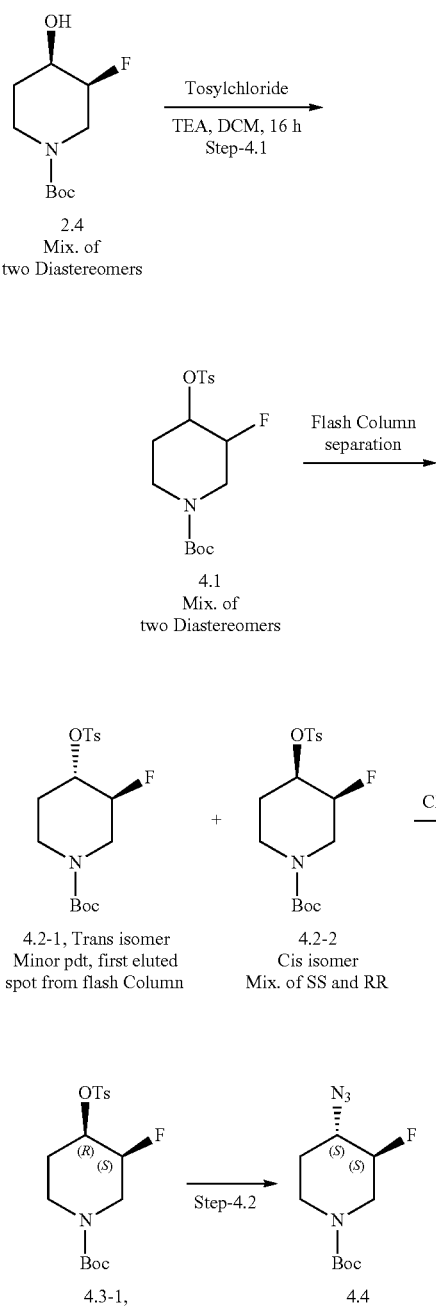

Scheme-6

Step-6.1: Synthesis of tert-butyl (3S,4R)-3-fluoro-4-(tosyloxy)piperidine-1-carboxylate, 4.3-1

Tert-butyl 3-fluoro-4-hydroxypiperidine-1-carboxylate, 2.4 (6 g, 0.0273 mol) in anhydrous DCM (100 mL) was treated with triethylamine (5.6 g, 0.055 mol) and DMAP (0.35 g, 0.029 mol) followed by p-toluene sulfonyl chloride (5.7 g, 0.03 mol) at 0° C. under nitrogen atmosphere. The resulting mixture was allowed slowly to ambient temperature and stirred for 16 h. The reaction mixture was poured into ice water, separated the organic layer, washed with saturated $NaHCO_3$, brine solution, dried over $Na_2SO_4$, filtered and concentrated under vacuum. The residue was purified by silica gel chromatography (10-30% EtOAc/hexane), as the second eluted product 4.2-2, 4.1 g (major product, mixture of two enantiomers). HPLC (ZORBAX XDB): 98.35% at rt 5.3 min. Chiral HPLC: [(LUX AMYLOSE 5 micron 2(250×4.60 mm), Hexane:EtOH (50:50)] shows two peaks at 7.27 min (Peak-1: 49.19% at rt) and at 11.406 min (Peak-2: 49.61% at rt). 1.6 g of the cis-isomer 4.2.2 was separated by chiral HPLC (column LUX AMYLOSE-2, flow rate: 20 ml/min, Solvent: n-Hexane/Ethanol (60:40)) and 0.7 g of the 3S,4R-isomer 4.3-1 and 0.75 g of the 3R,4S-isomer 4.3-2 were obtained.

Peak-1, 4.3-1: $^1$H NMR (400 MHz, $CDCl_3$): δ 7.81-7.79 (d, 2H), 7.35-7.33 (d, 2H), 4.83-4.52 (m, 2H), 4.05-3.55 (m, 2H), 3.50-3.05 (m, 2H), 2.44 (s, 3H), 2.07-2.05 (m, 1H), 1.71-1.68 (m, 1H), 1.43 (s, 9H); LCMS: 96.00%, m/z 274.1 (M-Boc+1); HPLC: 99.62%.

Peak-2, 4.3-2: $^1$H NMR (400 MHz, $CDCl_3$): δ 7.81-7.79 (d, 2H), 7.35-7.33 (d, 2H), 4.83-4.52 (m, 2H), 4.05-3.55 (m, 2H), 3.50-3.05 (m, 2H), 2.44 (s, 3H), 2.07-2.05 (m, 1H), 1.71-1.68 (m, 1H), 1.43 (s, 9H); LCMS: 94.48.0%, m/z 274 (M-Boc+1); HPLC: 97.64%.

Step-6.2: Synthesis of tert-butyl (3S,4S)-4-azido-3-fluoropiperidine-1-carboxylate, 4.4

Sodium azide (0.48 g, 0.0073 mol) was added to a solution of tert-butyl (3S,4R)-3-fluoro-4-(tosyloxy)piperidine-1-carboxylate, 4.3-1, Peak-1 (0.7 g, 0.00187 mol) dissolved in DMF (15 mL). The reaction mixture was heated at 100° C. for 4 h. The mixture was cooled and diluted with water and methylene chloride. After separation, the organic layer was dried over Na$_2$SO$_4$, filtered and concentrated in vacuum to provide the desired product, 4.4 (0.4 g). The obtained product was taken for the next reaction without any purification.

Step-6.3: Synthesis of tert-butyl (3S,4S)-4-amino-3-fluoropiperidine-1-carboxylate, 4.6

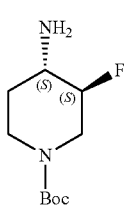
4.6

Palladium on carbon 10% (0.1 g) was added to a solution of tert-butyl (3S,4S)-4-azido-3-fluoropiperidine-1-carboxylate, 4.4 (0.4 g, 0.00163 mol) dissolved in EtOH (60 mL). The reaction was placed under a hydrogen atmosphere (40 psi pressure) for 16 h. The mixture was filtered through celite-bed and concentrated under reduced pressure to obtain the title compound tert-butyl (3S,4S)-4-amino-3-fluoropiperidine-1-carboxylate, 4.6 (0.4 g crude).

The obtained product was taken for the next reaction without any purification. After conversion of 4.6 with 6-bromo-4-chloro-7-fluoro-3-nitroquinoline according to the procedure detailed above in Step-1, (3S,4S)-tert-butyl 4-((6-bromo-7-fluoro-3-nitroquinolin-4-yl)amino)-3-fluoropiperidine-1-carboxylate was obtained with identical analytical data as provided above (i.e. HPLC, chiral HPLC and LCMS).

TABLE 1.2

| Example | Structure | 1H NMR, LCMS, HPLC, rt | IC50 µM Cascade MEK1 | HPLC method |
|---|---|---|---|---|
| 1A | 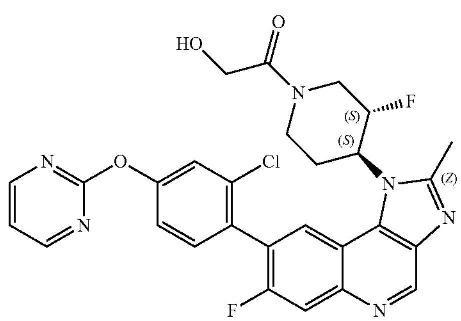 | $^1$H NMR (CDCl$_3$, 400 MHz): δ 9.33 (s, 1H), 8.65-8.64 (d, 2H), 8.08-8.05 (d, 1H), 8.00-7.85 (m, 1H), 7.51-7.30 (m, 2H), 7.30-7.28 (dd, 1H), 7.15-7.13 (m, 1H), 5.65-5.25 (m, 1H), 4.96-4.75 (m, 1H), 4.35-4.15 (m, 2H), 3.92-3.74 (m, 2H), 3.35-3.15 (m, 1H), 3.05-2.85 (m, 2H), 2.80 (s, 3H), 2.45-2.15 (m, 2H); LCMS: 97.59%, m/z = 565.1 (M + 1); HPLC: 98.80%, rt: 3.61 min., Column: ZORBAX XDB C18, 5 micro (4.6 × 150 mm); Chiral HPLC: 95.97%, rt = 21.37 min., Column: AG/CHIRALPAK AD-H/03. | 0.005 | 1 |
| 1B | 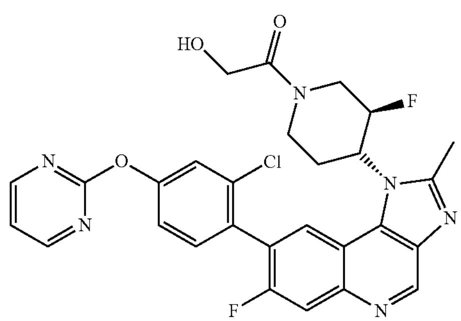 | $^1$H NMR (CDCl$_3$, 400 MHz): δ 9.32 (s, 1H), 8.65-8.64 (d, 2H), 8.08-8.05 (d, 1H), 7.95-7.85 (m, 1H), 7.50-7.40 (m, 2H), 7.31-7.28 (m, 1H), 7.15-7.13 (m, 1H), 5.65-5.20 (m, 1H), 4.95-4.70 (m, 1H), 4.25-4.15 (m, 2H), 3.90-3.70 (m, 2H), 3.35-3.15 (m, 1H), 3.01-2.85 (m, 2H), 2.80 (s, 3H), 2.45-2.15 (m, 2H); LCMS: 99.77%, m/z = 564.90 (M + 1); HPLC: 97.14%, rt: 3.61 min., Column: ZORBAX XDB C18, 5 micro (4.6 × 150 mm); Chiral HPLC: 97.23%, rt = 8.53 min., Column: AG/CHIRALPAK AD-H/03. | 0.138 | 1 |
| 2 | 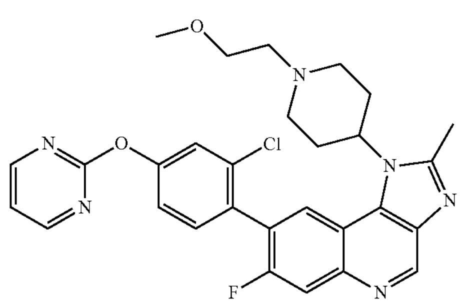 [SMILES: COCCN1CCC(n2c(C)nc3cnc4cc(F)c(-c5ccc(Oc6ncccn6)cc5Cl)cc4c32)CC1] | $^1$H NMR (DMSO-d$_6$, 400 MHz): δ 9.21 (s, 1H), 8.73 (d, 2H), 8.42-8.35 (m, 1H), 8.07 (d, 1H), 7.73 (d, 1H), 7.67 (d, 1H), 7.43 (dd, 1H), 7.37 (t, 1H), 4.85-4.65 (m, 1H), 3.16 (s, 3H), 3.15-3.02 (m, 3H), 2.77 (s, 3H), 2.68 (t, 2H), 2.34 (t, 2H), 2.32-2.22 (m, 3H), 2.10-1.95 (m, 2H); LCMS: 90.41%, m/z = 547.10 (M + 1); HPLC: 96.15%, rt: 3.01 min. | 0.726 | 1 |

TABLE 1.2-continued

| Example | Structure | 1H NMR, LCMS, HPLC, rt | IC50 μM Cascade MEK1 | HPLC method |
|---|---|---|---|---|
| 3 | 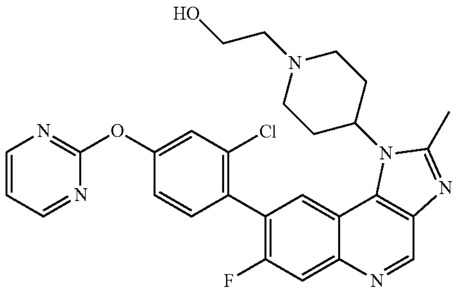 [SMILES: Cc1nc2cnc3cc(F)c(-c4ccc(Oc5ncccn5)cc4Cl)cc3c2n1C1CCN(CCO)CC1] | ¹H NMR (CDCl₃, 400 MHz): δ 9.26 (s, 1H), 8.63 (d, 2H), 8.35-8.25 (m, 1H), 8.04 (d, 1H), 7.56 (d, 1H), 7.50 (d, 1H), 7.30 (dd, 1H), 7.14 (t, 1H), 5.13-4.90 (m, 1H), 3.71-3.52 (m, 2H), 3.25-3.16 (m, 2H), 2.83 (s, 3H), 2.69-2.50 (m, 4H), 2.41-2.29 (m, 2H), 2.32-1.99 (m, 2H); LCMS: 100%, m/z = 533.4 (M + 1); HPLC: 97.69%, rt: 5.54 min. | 0.104 | 3 |
| 4 | 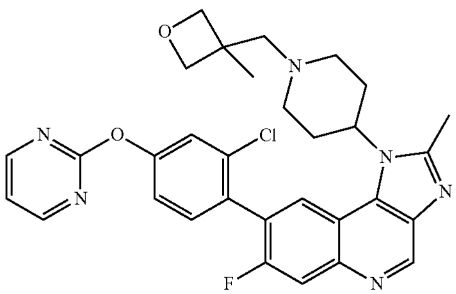 [SMILES: Cc1nc2cnc3cc(F)c(-c4ccc(Oc5ncccn5)cc4Cl)cc3c2n1C1CCN(CC2(C)COC2)CC1] | ¹H NMR (CDCl₃, 400 MHz): δ 9.26 (s, 1H), 8.64 (d, 2H), 8.04 (d, 1H), 7.55 (d, 1H), 7.50 (s, 1H), 7.29 (d, 2H), 7.13 (t, 1H), 4.54-4.22 (m, 4H), 2.99-2.79 (m, 6H), 2.61 (s, 3H), 2.34-2.22 (m, 2H), 2.18-1.85 (m, 2H), 1.45-0.90 (m, 4H); LCMS: 97.45%, m/z = 573.6 (M + 1); HPLC: 96.81%, rt: 3.58 min. | 0.309 | 4 |
| 5 | 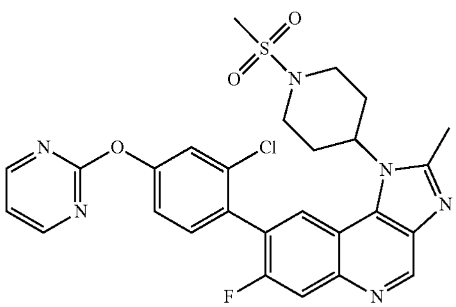 [SMILES: Cc1nc2cnc3cc(F)c(-c4ccc(Oc5ncccn5)cc4Cl)cc3c2n1C1CCN(S(C)(=O)=O)CC1] | ¹H NMR (DMSO-d₆, 400 MHz): δ 9.20 (s, 1H), 8.71 (d, 2H), 8.55-8.47 (m, 1H), 8.06 (d, 1H), 7.74 (d, 1H), 7.61 (s, 1H), 7.41-7.32 (m, 2H), 5.45-5.33 (m, 1H), 3.85-3.77 (m, 2H), 3.09-2.92 (m, 2H), 2.89 (s, 3H), 2.79 (s, 3H), 2.35-2.17 (m, 4H); LCMS: 98.33%, m/z = 567.4 (M + 1); HPLC: 94.22%, rt: 6.80 min. | 0.04 | 1 |
| 6 | 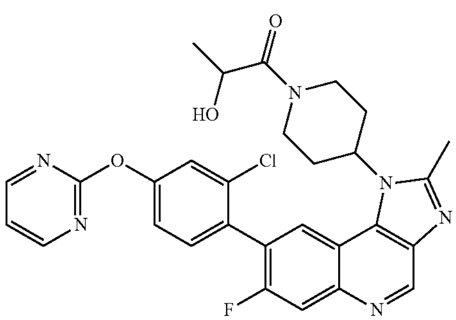 [SMILES: Cc1nc2cnc3cc(F)c(-c4ccc(Oc5ncccn5)cc4Cl)cc3c2n1C1CCN(C(=O)C(C)O)CC1] | ¹H NMR (CDCl₃, 400 MHz): δ 9.27 (s, 1H), 8.64 (d, 2H), 8.26 (d, 1H), 8.06 (d, 1H), 7.61-7.48 (m, 2H), 7.30 (d, 1H), 7.13 (t, 1H), 5.35-5.22 (m, 1H), 5.02-4.92 (m, 1H), 4.59-4.50 (m, 1H), 4.09-3.98 (m, 1H), 3.81-3.72 (m, 1H), 3.38-3.25 (m, 1H), 2.92-2.82 (m, 3H), 2.80 (s, 3H), 2.41-2.22 (m, 2H), 1.34 (s, 3H); LCMS: 96.69%, m/z = 561.5 (M + 1); HPLC: 95.29%, rt: 3.37 min. | 0.062 | 1 |
| 7 | 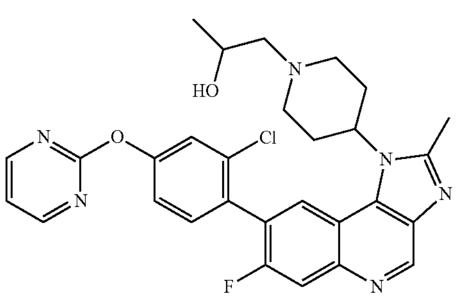 [SMILES: Cc1nc2cnc3cc(F)c(-c4ccc(Oc5ncccn5)cc4Cl)cc3c2n1C1CCN(CC(C)O)CC1] | ¹H NMR (DMSO-d₆, 400 MHz): δ 9.20 (s, 1H), 8.74 (d, 2H), 8.06 (d, 1H), 7.75-7.68 (m, 1H), 7.67-7.62 (m, 1H), 7.43-7.33 (m, 3H), 4.30-4.19 (m, 1H), 3.67-3.48 (m, 1H), 3.25-2.99 (m, 4H), 2.77 (s, 3H), 2.35-2.18 (m, 6H), 1.30-1.21 (m, 3H); LCMS: 92.41%, m/z = 547.2 (M + 1); HPLC: 96.85%, rt: 3.43 min. | 0.468 | 1 |

TABLE 1.2-continued

| Example | Structure | 1H NMR, LCMS, HPLC, rt | IC50 μM Cascade MEK1 | HPLC method |
|---|---|---|---|---|
| 8 | 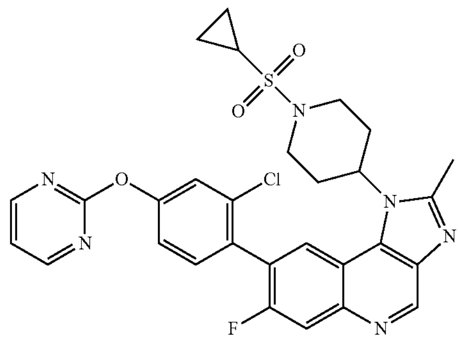 [SMILES: Cc1nc2cnc3cc(F)c(-c4ccc(Oc5ncccn5)cc4Cl)cc3c2n1C1CCN(S(=O)(=O)C2CC2)CC1] | ¹H NMR (CDCl₃, 400 MHz): δ 9.27 (s, 1H), 8.64 (d, 2H), 8.26 (bs, 1H), 8.06 (d, 1H), 7.59 (d, 1H), 7.49 (s, 1H), 7.33-7.30 (dd, 1H), 7.16-7.13 (m, 1H), 5.20 (m, 1H), 4.13 (d, 2H), 3.11 (m, 2H), 2.84 (s, 3H), 2.58 (bs, 2H), 2.30 (bs, 3H), 1.03 (m, 4H); LCMS: 99.23%, m/z = 592.95 (M + 1); HPLC: 97.12%, rt: 3.84 min. | 0.015 | 1 |
| 9 | 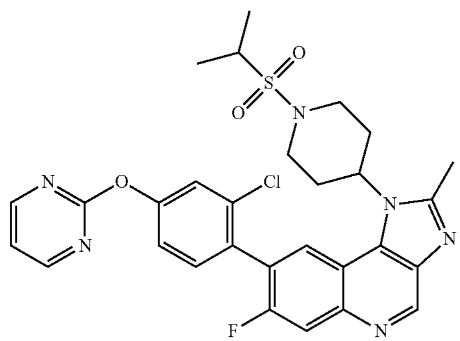 [SMILES: Cc1nc2cnc3cc(F)c(-c4ccc(Oc5ncccn5)cc4Cl)cc3c2n1C1CCN(S(=O)(=O)C(C)C)CC1] | ¹H NMR (DMSO-d₆, 400 MHz): δ 9.20 (s, 1H), 8.72 (d, 2H), 8.46 (d, 1H), 8.06 (d, 1H), 7.73 (d, 1H), 7.63 (s, 1H), 7.36-7.30 (dd, 2H), 5.31 (m, 1H), 3.85 (d, 2H), 3.23 (m, 2H), 2.78 (s, 3H), 2.19 (m, 2H), 2.30 (bs, 3H), 1.35 (s, 6H); LCMS: 96.70%, m/z = 595.00 (M + 1); HPLC: 92.43%, rt: 3.99 min. | 0.103 | 1 |
| 10 | 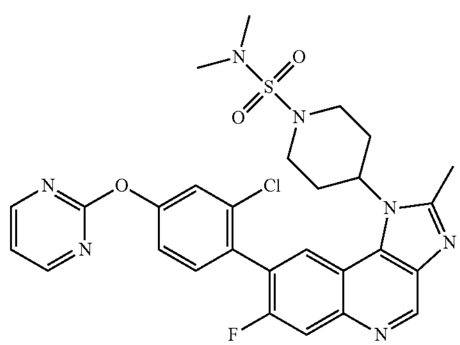 [SMILES: Cc1nc2cnc3cc(F)c(-c4ccc(Oc5ncccn5)cc4Cl)cc3c2n1C1CCN(S(=O)(=O)N(C)C)CC1] | ¹H NMR (CDCl₃, 400 MHz): δ 9.27 (s, 1H), 8.64 (d, 2H), 8.31 (bs, 1H) 8.06 (d, 1H), 7.57 (d, 1H), 7.50 (s, 1H), 7.32-7.30 (dd, 1H), 7.16 (dd, 1H) 5.23 (m, 1H), 3.99 (d, 2H), 3.07 (bs, 2H), 2.84 (s, 8H), 2.20 (dd, 2H), 2.30 (bs, 3H); LCMS: 99.20%, m/z = 595.95 (M + 1); HPLC: 98.14%, rt: 4.104 min. | 0.213 | 1 |
| 11 | 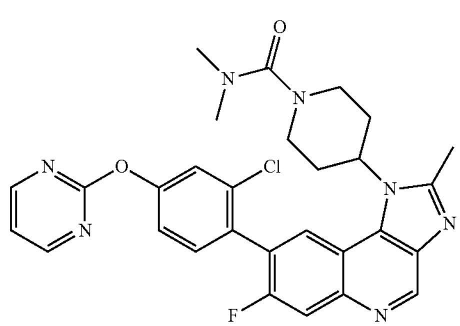 [SMILES: Cc1nc2cnc3cc(F)c(-c4ccc(Oc5ncccn5)cc4Cl)cc3c2n1C1CCN(C(=O)N(C)C)CC1] | ¹H NMR (CDCl₃, 400 MHz): δ 9.28 (s, 1H), 8.64 (d, 2H), 8.46 (bs, 1H), 8.06 (d, 1H), 7.52 (m, 1H), 7.49 (s, 1H), 7.30 (d, 1H), 7.13 (m, 1H), 4.83 (m, 1H), 3.91 (s, 2H), 2.91 (bs, 4H), 2.81 (m, 5H), 2.58 (bs, 3H), 2.16 (bs, 2H), 1.25 (s, 1H); LCMS: 98.22%, m/z = 560.35 (M + 1); HPLC: 97.56%, rt: 2.594 min. | 2.35 | 3 |

TABLE 1.2-continued

| Example | Structure | 1H NMR, LCMS, HPLC, rt | IC50 μM Cascade MEK1 | HPLC method |
|---|---|---|---|---|
| 12 | 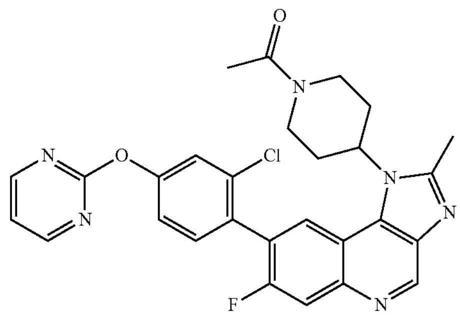 [SMILES: CC(=O)N1CCC(n2c(C)nc3cnc4cc(F)c(-c5ccc(Oc6ncccn6)cc5Cl)cc4c32)CC1] | ¹H NMR (CDCl₃, 400 MHz): δ 9.27 (s, 1H), 8.63 (d, 2H), 8.27 (d, 1H), 8.06 (d, 1H), 7.61-7.53 (m, 1H), 7.49 (s, 1H), 7.32 (d, 1H), 7.12 (t, 1H), 5.33-5.15 (m, 1H), 4.99 (d, 1H), 4.11 (d, 1H), 3.39-3.26 (m, 2H), 2.81 (s, 3H), 2.80-2.69 (m, 2H), 2.41-2.25 (m, 2H), 2.18 (m, 3H); LCMS: 98.09%, m/z = 531.4 (M + 1); HPLC: 95.65%, rt: 3.55 min. | 0.212 | 1 |
| 13 | 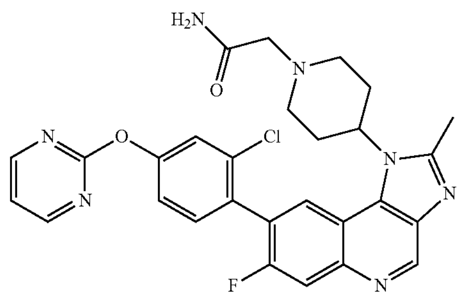 [SMILES: Cc1nc2cnc3cc(F)c(-c4ccc(Oc5ncccn5)cc4Cl)cc3c2n1C1CCN(CC(N)=O)CC1] | ¹H NMR (CDCl₃, 400 MHz): δ 9.31 (s, 1H), 8.89 (d, 1H), 8.81 (d, 1H), 8.06 (d, 1H), 7.58 (d, 1H), 7.47 (d, 1H), 7.30 (d, 1H), 7.28 (d, 1H), 7.19 (t, 1H), 4.62-4.51 (m, 1H), 3.21-3.07 (m, 2H), 3.05-2.95 (m, 2H), 2.82-2.96 (m, 2H), 2.78 (s, 3H), 2.62-2.46 (m, 2H), 2.05-1.92 (m, 2H); LCMS: 99.57%, m/z = 546.6 (M + 1); HPLC: 96.97%, rt: 3.03 min. | 0.515 | 1 |
| 14 | 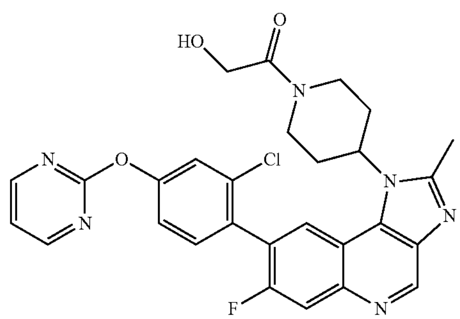 [SMILES: Cc1nc2cnc3cc(F)c(-c4ccc(Oc5ncccn5)cc4Cl)cc3c2n1C1CCN(C(=O)CO)CC1] | ¹H NMR (CDCl₃, 400 MHz): δ 9.28 (s, 1H), 8.65 (d, 2H), 8.25 (d, 1H), 8.05 (d, 1H), 7.51 (d, 2H), 7.32-7.30 (m, 1H), 7.15-7.13 (m, 1H), 5.6 (bs, 1H), 4.98-4.95 (m, 1H) 4.22-4.19 (m, 2H), 3.83 (d, 2H), 3.50 (d, 1H), 3.26 (d, 1H), 2.90 (s, 1H), 2.81 (s, 4H), 2.34 (dd, , 2H); LCMS: 99.8%, m/z = 547.4 (M + 1); HPLC: 95.8%, rt: 3.36 min. | 0.0071 | 1 |
| 15 | 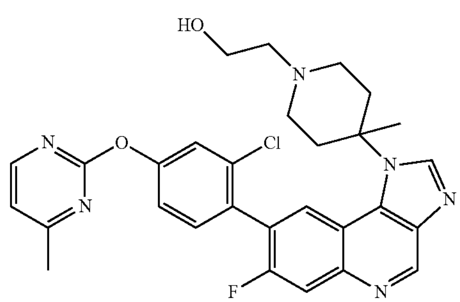 [SMILES: Cc1ccnc(Oc2ccc(-c3cc4c(cc3F)ncc3ncn(C5(C)CCN(CCO)CC5)c34)c(Cl)c2)n1] | ¹H NMR (CDCl₃, 400 MHz): δ 9.39 (s, 1H), 9.15 (s, 1H), 8.42 (d, 1H), 8.33 (d, 1H), 8.06 (d, 1H), 7.53 (d, 1H), 7.46 (m, 1H), 7.26-7.24 (dd, 1H), 7.01 (d, 1H), 3.49 (s, 2H), 3.32 (m, 2H), 2.95 (s, 3H), 2.81 (bs, 1H), 2.57 (s, 3H), 2.50-2.47 (m, 3H), 2.08 (d, 2H), 2.0 (s, 3H); LCMS: 97.08%, m/z = 547.2 (M + 1); HPLC: 99.6%, rt: 3.61 min. | 0.016 | 1 |
| 16 | 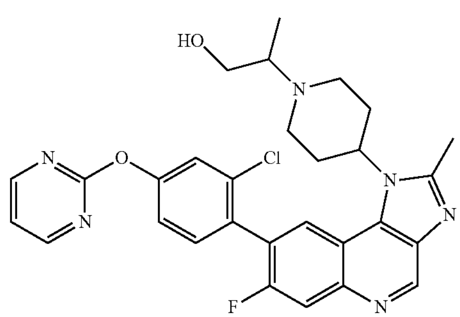 [SMILES: Cc1nc2cnc3cc(F)c(-c4ccc(Oc5ncccn5)cc4Cl)cc3c2n1C1CCN(C(C)CO)CC1] | ¹H NMR (CDCl₃, 400 MHz): δ 9.27 (s, 1H), 8.64 (d, 2H), 8.33-8.25 (m, 1H), 8.05 (d, 1H), 7.57 (d, 1H), 7.52 (d, 1H), 7.32 (dd, 1H), 7.14 (t, 1H), 3.89-3.82 (m, 1H), 3.50-3.45 (m, 1H), 3.29 (d, 1H), 3.10 (d, 1H), 2.84 (s, 3H), 2.61-2.50 (m, 2H), 2.43-2.13 (m, 6H), 1.14 (s, 3H); LCMS: 99.31%, m/z = 547.05 (M + 1); HPLC: 90.33%, rt: 5.89 min. | 0.059 | 1 |

TABLE 1.2-continued

| Example | Structure | 1H NMR, LCMS, HPLC, rt | IC50 μM Cascade MEK1 | HPLC method |
|---|---|---|---|---|
| 17 | 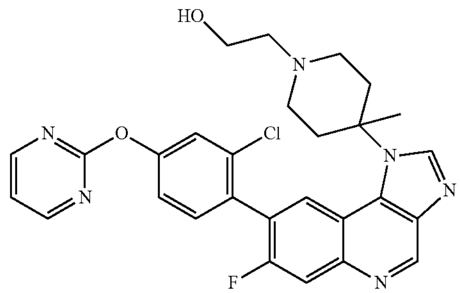 [SMILES: CC1(n2cnc3cnc4cc(F)c(-c5ccc(Oc6ncccn6)cc5Cl)cc4c32)CCN(CCO)CC1] | ¹H NMR (DMSO-d₆, 400 MHz): δ 9.33 (s, 1H), 9.29 (bs, 1H), 8.73 (m, 3H), 8.08 (d, 1H), 7.64 (d, 1H), 7.46 (dd, 1H), 7.26-7.34 (dd, 2H), 4.32 (m, 1H), 3.18-3.14 (q, 1H), 2.88 (m, 4H), 2.50 (s, 4H), 2.42-2.30 (m, 2H), 1.99 (d, 2H), 1.92 (m, 2H); LCMS: 99.71%, m/z = 533.7 (M + 1); HPLC: 98.32%, rt: 5.77 min. | 0.093 | 3 |
| 18 | 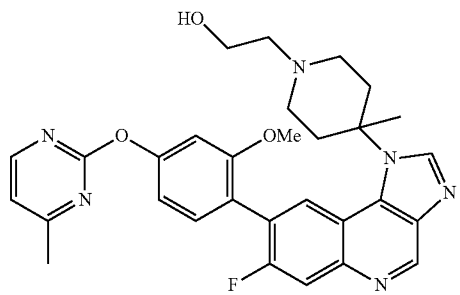 [SMILES: COc1cc(Oc2nccc(C)n2)ccc1-c1cc2c(cc1F)ncc1ncn(C3(C)CCN(CCO)CC3)c12] | ¹H NMR (CDCl₃, 400 MHz): δ 9.37 (s, 1H), 9.01 (s, 1H), 8.42 (d, 1H), 8.32 (s, 1H), 8.03 (d, 1H), 7.43 (d, 1H), 7.00-6.95 (m, 3H), 3.83 (s, 3H), 3.38 (t, 2H), 2.96 (t, 2H), 2.71 (m, 1H), 2.58 (s, 3H), 2.56-2.48 (m, 5H), 2.17 (d, 2H), 1.99 (s, 3H); LCMS: 99.41%, m/z = 543.7 (M + 1); HPLC: 99.00%, rt: 5.71 min. | 0.013 | 3 |
| 19 | 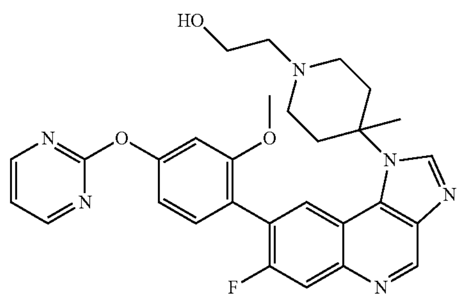 [SMILES: COc1cc(Oc2ncccn2)ccc1-c1cc2c(cc1F)ncc1ncn(C3(C)CCN(CCO)CC3)c12] | ¹H NMR (CDCl₃, 400 MHz): δ 9.37 (s, 1H), 8.95 (s, 1H), 8.64 (d, 1H), 8.32 (s, 1H), 8.03 (d, 1H), 7.45 (d, 1H), 7.27 (s, 1H), 7.14 (t, 1H), 7.01-6.91 (m, 2H), 3.83 (s, 3H), 3.49-3.39 (m, 2H), 2.99-2.88 (m, 2H), 2.79-2.55 (m, 4H), 2.55 (t, 2H), 2.25-2.15 (m, 2H), 1.99 (s, 3H); LCMS: 99.51%, m/z = 529.4 (M + 1); HPLC: 98.02%, rt: 5.66 min. | 0.333 | 1 |
| 20 | 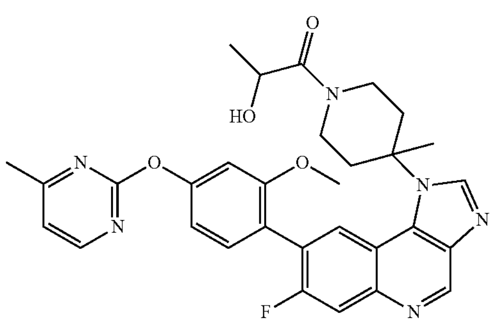 [SMILES: COc1cc(Oc2nccc(C)n2)ccc1-c1cc2c(cc1F)ncc1ncn(C3(C)CCN(C(=O)C(C)O)CC3)c12] | ¹H NMR (CDCl₃, 400 MHz): δ 9.37 (s, 1H), 8.50-8.45 (m, 1H), 8.43 (d, 1H), 8.28 (d, 1H), 8.05 (d, 1H), 7.43 (d, 1H), 7.01-6.95 (m, 3H), 4.46-4.39 (m, 1H), 3.82 (s, 3H), 3.71 (d, 1H), 3.52-3.43 (m, 3H), 2.92-2.69 (m, 2H), 2.57 (s, 3H), 2.55-2.50 (m, 2H), 2.06 (s, 3H), 1.34 (d, 1.5H), 1.17 (d, 1.5H); LCMS: 94.08%, m/z = 571.7 (M + 1); HPLC: 99.42%, rt: 4.03 min. | 0.157 | 1 |
| 21 | 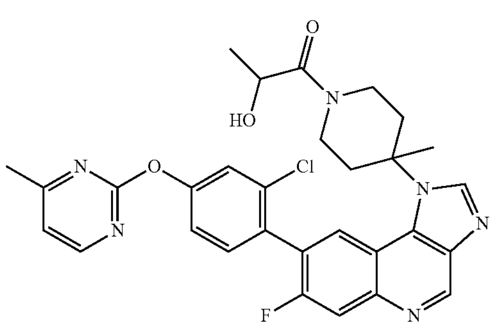 [SMILES: Cc1ccnc(Oc2ccc(-c3cc4c(cc3F)ncc3ncn(C5(C)CCN(C(=O)C(C)O)CC5)c34)c(Cl)c2)n1] | ¹H NMR (CDCl₃, 400 MHz): δ 9.41 (s, 1H), 8.46-8.39 (m, 2H), 8.29 (s, 1H), 8.10 (d, 1H), 7.53-7.49 (m, 2H), 7.30 (d, 1H), 7.01 (d, 1H), 4.49-4.40 (m, 1H), 3.81-3.80 (m, 1H), 3.79-3.69 (m, 1H), 3.59-3.45 (m, 2H), 2.83-2.67 (m, 2H), 2.57 (s, 3H), 2.43-2.35 (m, 2H), 2.50 (s, 3H), 1.39-1.28 (m, 3H); LCMS: 95.93%, m/z = 575.4 (M + 1); HPLC: 97.48%, rt: 4.42 min. | 0.028 | 1 |

TABLE 1.2-continued

| Example | Structure | 1H NMR, LCMS, HPLC, rt | IC50 µM Cascade MEK1 | HPLC method |
|---|---|---|---|---|
| 22 | 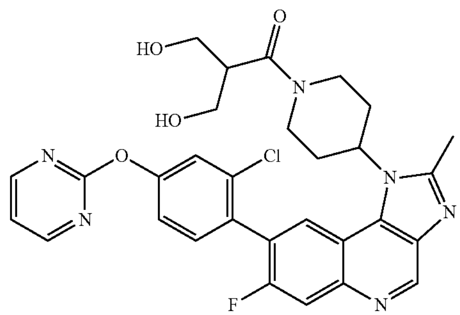 [SMILES: Cc1nc2cnc3cc(F)c(-c4ccc(Oc5ncccn5)cc4Cl)cc3c2n1C1CCN(C(=O)C(CO)CO)CC1] | ¹H NMR (CDCl₃, 400 MHz): δ 9.27 (s, 1H), 8.65 (d, 2H), 8.28 (s, 1H), 8.05 (d, 1H), 7.60-7.46 (m, 2H), 7.30 (d, 1H), 7.16 (s, 1H), 5.48-5.23 (m, 1H), 5.12-4.97 (m, 1H), 4.88-4.65 (m, 1H), 4.40-4.24 (m, 1H), 4.10-3.71 (m, 3H), 3.48-3.00 (m, 5H), 2.80 (s, 4H), 2.48-2.20 (m, 3H); LCMS: 99.45%, m/z = 591.05 (M + 1); HPLC: 98.66%, rt: 3.13 min. | 1.346 | 1 |
| 23 | 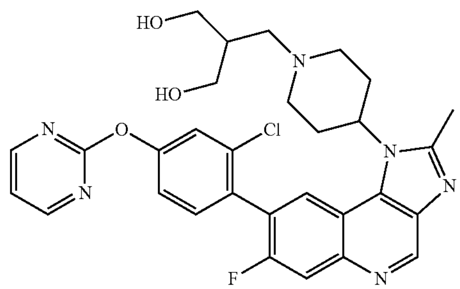 [SMILES: Cc1nc2cnc3cc(F)c(-c4ccc(Oc5ncccn5)cc4Cl)cc3c2n1C1CCN(CC(CO)CO)CC1] | ¹H NMR (CDCl₃, 400 MHz): δ 9.28 (s, 1H), 8.66 (d, 2H), 8.05 (d, 1H), 7.60-7.57 (m, 1H), 7.52-7.48 (m, 1H), 7.32-7.26 (m, 2H), 7.21-7.15 (m, 1H), 4.16-4.10 (m, 1H), 3.70-3.62 (m, 4H), 3.56-3.44 (m, 3H), 3.34-3.15 (m, 3H), 2.80 (s, 4H), 2.32-2.18 (m, 4H); LCMS: 98.20%, m/z = 576.85 (M + 1); HPLC: 98.61%, rt: 5.56 min. | 0.322 | 3 |
| 24 | 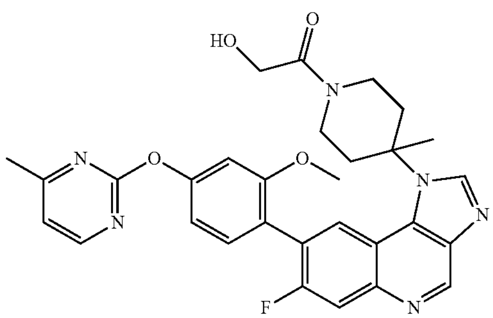 [SMILES: COc1cc(Oc2nccc(C)n2)ccc1-c1cc2c(cc1F)ncc1ncn(C3(C)CCN(C(=O)CO)CC3)c12] | ¹H NMR (CDCl₃, 400 MHz): δ 9.38 (s, 1H), 8.48 (d, 1H), 8.43 (d, 1H), 8.30 (s, 1H), 8.05 (d, 1H), 7.40 (d, 1H), 6.99-6.95 (m, 3H), 4.20-4.10 (m, 2H), 4.01-3.94 (m, 1H), 3.81 (s, 3H), 3.73 (t, 1H), 3.63-3.52 (m, 1H), 3.45-3.32 (m, 2H), 2.93-2.82 (m, 2H), 2.57 (s, 3H), 2.35-2.25 (m, 1H), 2.25-2.16 (m, 1H), 2.07 (s, 3H); LCMS: 97.44%, m/z = 557.3 (M + 1); HPLC: 94.48%, rt: 3.90 min. | 0.021 | 1 |
| 25 | 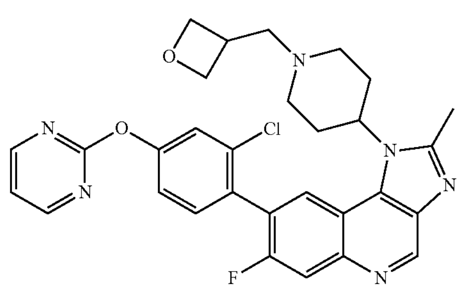 [SMILES: Cc1nc2cnc3cc(F)c(-c4ccc(Oc5ncccn5)cc4Cl)cc3c2n1C1CCN(CC2COC2)CC1] | ¹H NMR (CDCl₃, 400 MHz): δ 9.24 (s, 1H), 8.63 (d, 2H), 8.32-8.18 (m, 1H), 8.01 (d, 1H), 7.58-7.48 (m, 2H), 7.31-7.27 (m, 1H), 7.12 (t, 1H), 5.03-4.85 (m, 1H), 4.84-4.68 (m, 2H), 4.44-4.26 (m, 2H), 3.30-3.12 (m, 1H), 3.06-2.84 (m, 2H), 2.88-2.67 (m, 6H), 2.58-2.32 (m, 1H), 2.39-2.02 (m, 4H); LCMS: 53.64%, m/z = 559.35 (M + 1); HPLC: 98.77%, rt: 3.39 min. | 0.655 | 1 |
| 26 | 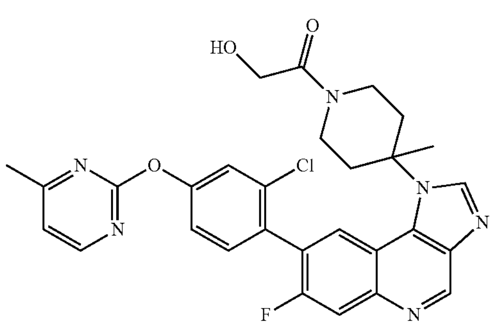 [SMILES: Cc1ccnc(Oc2ccc(-c3cc4c(cc3F)ncc3ncn(C5(C)CCN(C(=O)CO)CC5)c34)c(Cl)c2)n1] | ¹H NMR (CDCl₃, 400 MHz): δ 9.41 (s, 1H), 8.47-8.40 (m, 2H), 8.32 (s, 1H), 8.09 (d, 1H), 7.49 (d, 1H), 7.46 (s, 1H), 7.29 (dd, 1H), 6.99 (d, 1H), 4.30-4.20 (m, 1H), 4.16 (d, 1H), 4.03 (d, 1H), 3.73 (bs, 1H), 3.56-3.30 (m, 3H), 2.90-2.79 (m, 2H), 2.57 (s, 3H), 2.32-2.19 (m, 2H), 2.08 (s, 3H); LCMS: 99.11%, m/z = 561.2 (M + 1); HPLC: 99.47%, rt: 3.83 min. | 0.0043 | 1 |

TABLE 1.2-continued

| Example | Structure | 1H NMR, LCMS, HPLC, rt | IC50 μM Cascade MEK1 | HPLC method |
|---|---|---|---|---|
| 27 | 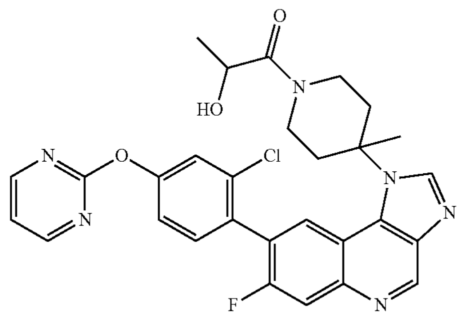 [SMILES: CC(O)C(=O)N1CCC(C)(n2cnc3cnc4cc(F)c(-c5ccc(Oc6ncccn6)cc5Cl)cc4c32)CC1] | ¹H NMR (CDCl₃, 400 MHz): δ 9.42 (s, 1H), 8.66-8.65 (d, 2H), 8.45-8.40 (d, 1H), 8.3 (s, 1H), 8.15-8.1 (d, 1H), 7.55-7.50 (d, 2H), 7.35-7.30 (d, 1H), 7.20-7.10 (t, 1H), 4.50-4.40 (t, 1H), 3.90-3.70 (m, 2H), 3.64-3.45 (m, 2H), 2.70-2.6 (m, 2H), 2.45-2.30 (bs, 2H), 2.09 (s, 3H), 1.40-1.15 (dd, 3H); LCMS: 93.23%, m/z = 561.4 (M + 1); HPLC: 98.04%, rt: 3.07 min. | 0.073 | 3 |
| 28 | 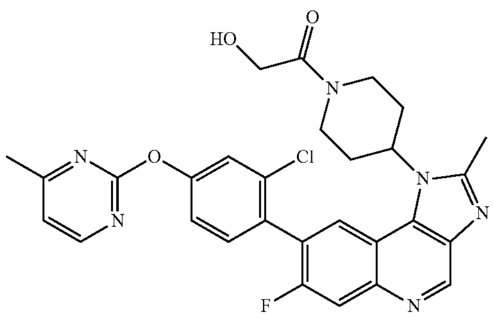 | ¹H NMR (CDCl₃, 400 MHz): δ 9.26 (s, 1H), 8.43 (d, 1H), 8.24 (d, 1H), 8.04 (d, 1H), 7.48 (d, 1H), 7.30-7.25 (m, 2H), 6.98 (d, 1H), 4.99-4.90 (m, 1H), 4.19 (d, 1H), 3.76 (d, 1H), 3.31-3.19 (m, 2H), 2.95-2.79 (m, 4H), 2.79 (s, 3H), 2.55 (s, 3H), 1.89-1.70 (m, 2H); LCMS: 87.67%, m/z = 561.1 (M + 1); HPLC: 99.29%, rt: 2.57 min. | 0.0037 | 5 |
| 29 | 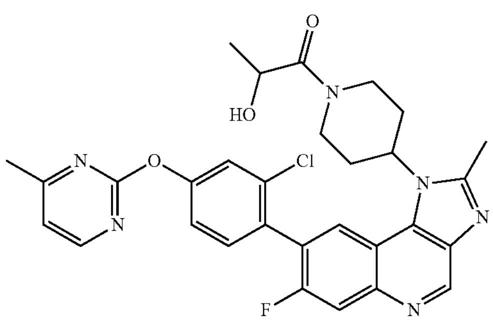 | ¹H NMR (CDCl₃, 400 MHz): δ 9.26 (s, 1H), 8.43 (d, 1H), 8.26 (d, 1H), 8.05 (d, 1H), 7.50 (s, 2H), 7.30-7.26 (m, 1H), 7.98 (d, 1H), 5.35-5.20 (m, 1H), 4.98 (d, 1H), 4.60-4.49 (m, 1H), 4.11-3.93 (m, 1H), 3.85-3.69 (m, 1H), 3.39-3.20 (m, 1H), 2.95-2.82 (m, 1H), 2.80 (s, 3H), 2.56 (s, 3H), 2.42-2.22 (m, 2H), 1.72-1.59 (m, 2H), 1.42-1.29 (m, 3H); LCMS: 90.37%, m/z = 575.03 (M + 1); HPLC: 95.04%, rt: 3.74 min. | 0.019 | 1 |
| 30 | 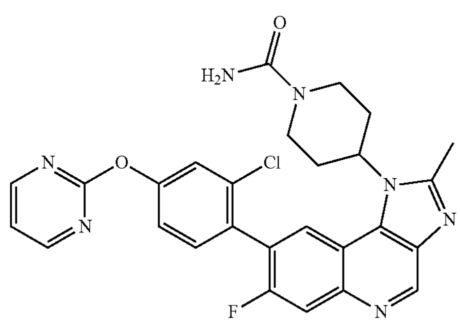 [SMILES: Cc1nc2cnc3cc(F)c(-c4ccc(Oc5ncccn5)cc4Cl)cc3c2n1C1CCN(C(N)=O)CC1] | ¹H NMR (DMSO-d₆, 300 MHz): δ 9.20 (s, 1H), 8.71 (d, 2H), 8.40 (d, 1H), 8.05 (d, 1H), 7.75-7.59 (m, 2H), 7.41 (d, 1H), 7.36 (t, 1H), 6.19-5.92 (m, 1H), 5.90-5.65 (m, 1H), 5.41-5.15 (m, 1H), 5.10-4.79 (m, 1H), 4.19 (d, 2H), 3.01-2.85 (m, 2H), 2.77 (s, 3H), 2.22-1.85 (m, 3H); LCMS: 99.43%, m/z = 532.3 (M + 1); HPLC: 96.63%, rt: 3.16 min. | 0.011 | 3 |

TABLE 1.2-continued

| Example | Structure | 1H NMR, LCMS, HPLC, rt | IC50 μM Cascade MEK1 | HPLC method |
|---|---|---|---|---|
| 31 | 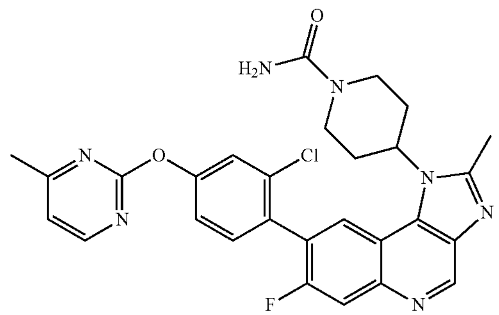 | ¹H NMR (DMSO-d₆, 400 MHz): δ 9.19 (s, 1H), 8.51 (d, 1H), 8.40 (m, 1H), 8.05 (d, 1H), 7.72-7.54 (m, 2H), 7.42-7.36 (m, 1H), 7.22 (d, 1H), 6.10-5.50 (m, 3H), 5.10-4.80 (m, 1H), 4.20 (m, 2H), 2.92 (t, 2H), 2.77 (s, 3H), 2.46 (s, 3H), 2.10-1.90 (m, 3H); LCMS: 99.6%, m/z = 546.5 (M + 1); HPLC: 96.6%, rt: 6.26 min. | 0.003 | 1 |
| 32 | 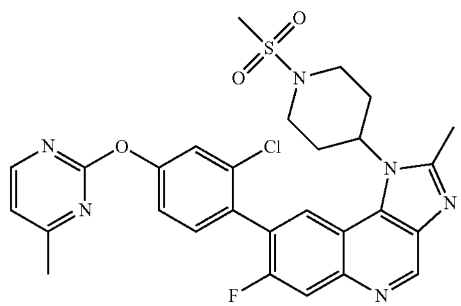 [SMILES: Cc1ccnc(Oc2ccc(-c3cc4c(cc3F)ncc3nc(C)n(C5CCN(S(C)(=O)=O)CC5)c34)c(Cl)c2)n1] | ¹H NMR (CDCl₃, 400 MHz): δ 9.52 (s, 1H), 8.64 (d, 1H), 8.55 (d, 1H), 8.22 (d, 1H), 7.78 (d, 1H), 7.63 (s, 1H), 7.40 (s, 1H), 7.26 (d, 1H), 3.89-3.81 (m, 1H), 3.79-3.50 (m, 4H), 3.16-3.02 (m, 2H), 2.99-2.80 (m, 2H), 2.88 (s, 3H), 2.48 (s, 3H), 2.45-2.20 (m, 3H); LCMS: 96.64%, m/z = 581.1 (M + 1); HPLC: 96.81%, rt: 2.68 min. | 0.032 | 5 |
| 33 | 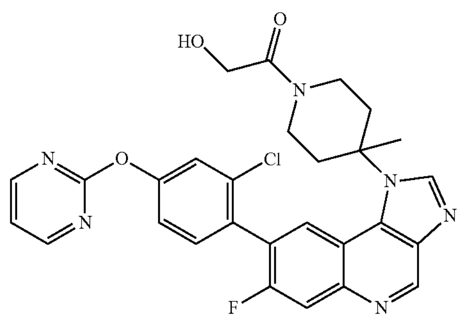 [SMILES: CC1(n2cnc3cnc4cc(F)c(-c5ccc(Oc6ncccn6)cc5Cl)cc4c32)CCN(C(=O)CO)CC1] | ¹H NMR (CDCl₃, 400 MHz): δ 9.43 (s, 1H), 8.67-8.66 (d, 2H), 8.44-8.42 (d, 1H), 8.33 (s, 1H), 8.12-8.1 (d, 1H), 7.51-7.49 (m, 2H), 7.32-7.27 (dd, 1H), 7.17-7.15 (t, 1H), 4.21-4.16 (m, 2H), 4.08-4.04 (d, 1H), 3.71 (s, 1H), 3.60-3.50 (m, 1H), 3.44-3.35 (m, 2H), 2.86-2.83 (bs, 2H), 2.28-2.24 (t, 2H), 2.09 (s, 3H); LCMS: 99.69%, m/z = 547.0 (M + 1); HPLC: 99.06%, rt: 3.72 min. | 0.028 | 1 |
| 34 | 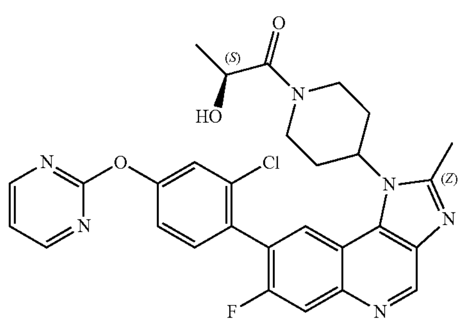 | ¹H NMR (CDCl₃, 400 MHz): δ 9.27 (s, 1H), 8.64 (d, 2H), 8.27 (d, 1H), 8.06 (d, 1H), 7.59-7.49 (m, 2H), 7.31 (d, 1H), 7.14 (t, 1H), 5.45-5.33 (m, 1H), 5.03-4.93 (m, 1H), 4.61-4.52 (m, 1H), 4.12-3.98 (m, 1H), 3.79 (d, 1H), 3.40-3.25 (m, 1H), 2.95-2.83 (m, 2H), 2.81 (s, 3H), 2.45-2.33 (m, 2H), 1.49-1.31 (m, 3H); LCMS: 98.63%, m/z = 561.4 (M + 1); HPLC: 96.79%, rt: 3.38 min. | 0.088 | 1 |
| 35 | 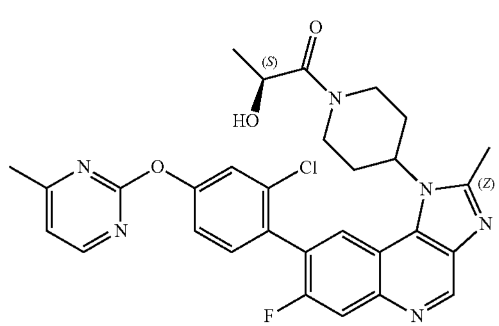 | ¹H NMR (CDCl₃, 400 MHz): δ 9.27 (s, 1H), 8.43 (d, 1H), 8.07 (d, 1H), 8.06 (d, 1H), 7.60-7.51 (m, 2H), 7.30-7.26 (m, 1H), 7.00 (d, 1H), 5.39-5.29 (m, 1H), 4.10-4.00 (m, 1H), 3.80-3.30 (m, 2H), 2.90-2.60 (m, 2H), 2.81 (s, 3H), 2.56 (s, 3H), 2.40-2.10 (m, 3H), 1.35-1.33 (m, 4H); LCMS: 98.74%, m/z = 575.60 (M + 1); HPLC: 90.71%, rt: 3.50 min. | 0.019 | 1 |

TABLE 1.2-continued

| Example | Structure | 1H NMR, LCMS, HPLC, rt | IC50 μM Cascade MEK1 | HPLC method |
|---|---|---|---|---|
| 36 | 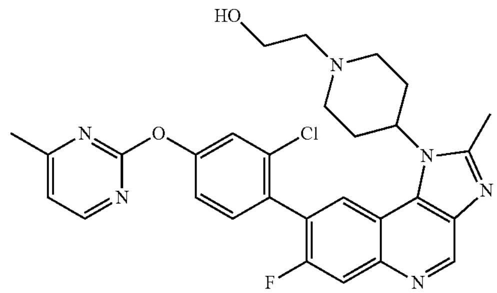 | 1H NMR (CDCl₃, 400 MHz): δ 9.25 (s, 1H), 8.41 (d, 1H), 8.02 (d, 1H), 7.54 (d, 1H), 7.48 (d, 1H), 7.30-7.24 (m, 2H), 6.98 (d, 1H), 3.75-3.30 (m, 3H), 3.25-3.15 (m, 2H), 2.82 (s, 3H), 2.70-2.59 (m, 4H), 2.55 (s, 3H), 2.42-2.30 (m, 2H), 2.25-1.90 (m, 2H); LCMS: 98.76%, m/z = 547.2 (M + 1); HPLC: 95.40%, rt: 3.02 min. | 0.026 | 1 |
| 37 | 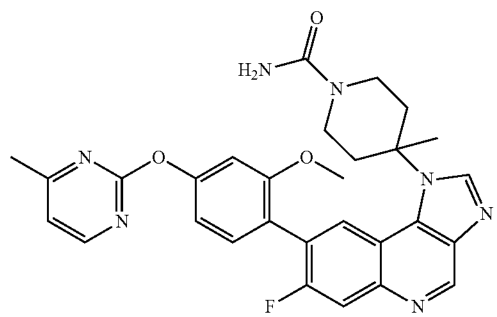 [SMILES: COc1cc(Oc2nccc(C)n2)ccc1-c1cc2c(cc1F)ncc1ncn(C3(C)CCN(C(N)=O)CC3)c12] | ¹H NMR (CDCl₃, 400 MHz): δ 9.39 (s, 1H), 8.73 (d, 1H), 8.40 (d, 1H), 8.35 (s, 1H), 8.05 (d, 1H), 7.40 (d, 1H), 7.18 (d, 1H), 6.99-6.91 (m, 2H), 4.74 (s, 2H), 3.97 (d, 2H), 3.81 (s, 3H), 3.25-2.98 (m, 4H), 2.56 (s, 3H), 2.08 (s, 3H), 1.94 (d, 2H); LCMS: 99.54%, m/z = 542.4 (M + 1); HPLC: 98.15%, rt: 3.30 min. | 0.0027 | 1 |
| 38 | 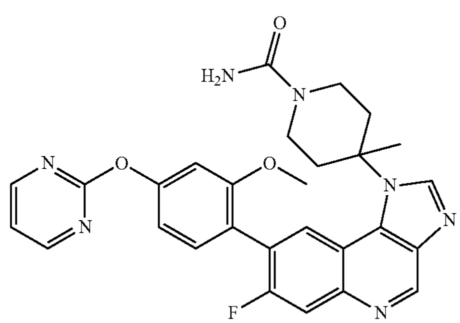 [SMILES: COc1cc(Oc2ncccn2)ccc1-c1cc2c(cc1F)ncc1ncn(C3(C)CCN(C(N)=O)CC3)c12] | ¹H NMR (CDCl₃, 400 MHz): δ 9.38 (s, 1H), 8.70 (d, 1H), 8.61 (d, 2H), 8.34 (s, 1H), 8.04 (d, 1H), 7.41 (dd, 1H), 7.11 (t, 1H), 6.95-6.90 (m, 2H), 4.73 (s, 2H), 3.95 (d, 2H), 3.81 (s, 3H), 3.20 (t, 2H), 3.11-2.94 (m, 2H), 2.07 (s, 3H), 1.96 (d, 2H); LCMS: 98.83%, m/z = 528.3 (M + 1); HPLC: 98.72%, rt: 3.06 min. | 0.0046 | 1 |
| 39 | 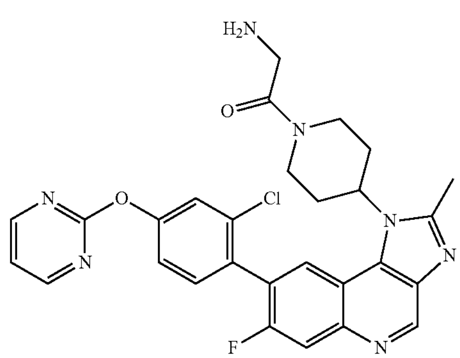 [SMILES: Cc1nc2cnc3cc(F)c(-c4ccc(Oc5ncccn5)cc4Cl)cc3c2n1C1CCN(C(=O)CN)CC1] | ¹H NMR (CDCl₃, 400 MHz): δ 9.27 (s, 1H), 8.64 (d, 2H), 8.27 (d, 1H), 8.06 (d, 1H), 7.61-7.52 (m, 1H), 7.51 (d, 1H), 7.32 (d, 1H), 7.14 (t, 1H), 5.35-5.16 (m, 1H), 5.15-4.92 (m, 1H), 4.09-3.99 (m, 1H), 3.61-3.51 (m, 2H), 3.33-3.20 (m, 2H), 2.81 (s, 3H), 2.41-2.19 (m, 4H); LCMS: 95.70%, m/z = 546.1 (M + 1); HPLC: 92.16%, rt: 3.39 min. | 0.455 | 1 |

TABLE 1.2-continued

| Example | Structure | 1H NMR, LCMS, HPLC, rt | IC50 μM Cascade MEK1 | HPLC method |
|---|---|---|---|---|
| 40 | 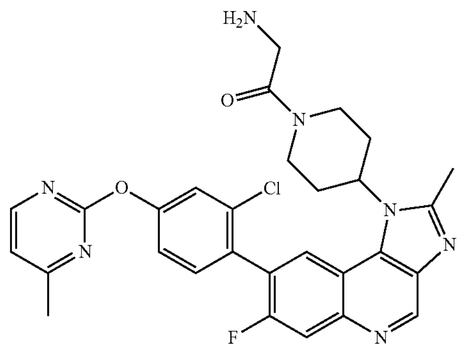 [SMILES: Cc1ccnc(Oc2ccc(-c3cc4c(cc3F)ncc3nc(C)n(C5CCN(C(=O)CN)CC5)c34)c(Cl)c2)n1] | ¹H NMR (CDCl₃, 400 MHz): δ 9.24 (s, 1H), 8.42 (d, 1H), 8.25 (d, 1H), 8.02 (d, 1H), 7.60-7.40 (m, 2H), 7.30-7.26 (m, 1H), 6.97 (s, 1H), 5.23 (s, 1H), 4.97 (d, 1H), 4.01 (d, 1H), 3.52-3.24 (m, 4H), 2.78 (s, 3H), 2.54 (s, 3H), 2.28-2.02 (m, 6H); LCMS: 97.47%, m/z = 560.1 (M + 1); HPLC: 95.25%, rt: 2.94 min. | 0.186 | 1 |
| 41 | 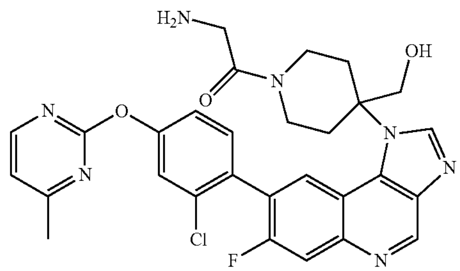 [SMILES: Cc1ccnc(Oc2ccc(-c3cc4c(cc3F)ncc3ncn(C5(CO)CCN(C(=O)CN)CC5)c34)c(Cl)c2)n1] | ¹H NMR (DMSO-d₆, 400 MHz): δ 9.34 (s, 1H), 8.68 (s, 1H), 8.53 (d, 1H), 8.44 (d, 1H), 8.11 (d, 1H), 7.67 (d, 1H), 7.60 (s, 1H), 7.37 (d, 1H), 7.23 (d, 1H), 5.58-5.48 (m, 1H), 4.49-4.38 (m, 1H), 4.13 (d, 2H), 4.12-4.01 (m, 1H), 3.98-3.87 (m, 1H), 3.82-3.69 (m, 1H), 3.58-3.43 (m, 2H), 3.23-3.10 (m, 1H), 2.81-2.63 (m, 2H), 2.47 (s, 3H), 2.35-2.15 (m, 2H); LCMS: 97.48%, m/z = 577.4 (M + 1); HPLC: 96.69%, rt: 3.51 min. | 0.022 | 1 |
| 42 | 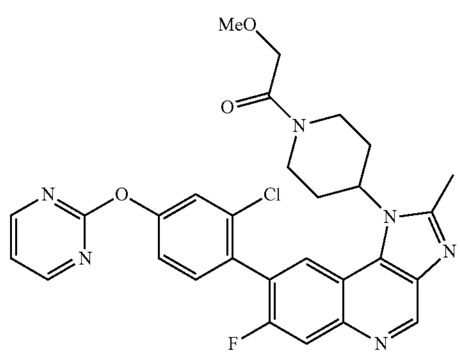 [SMILES: COCC(=O)N1CCC(n2c(C)nc3cnc4cc(F)c(-c5ccc(Oc6ncccn6)cc5Cl)cc4c32)CC1] | ¹H NMR (CDCl₃, 400 MHz): δ 9.25 (s, 1H), 8.62 (d, 2H), 8.29 (s, 1H), 8.24 (d, 1H), 7.61-7.46 (m, 2H), 7.30 (d, 1H), 7.13 (t, 1H), 5.35-5.16 (m, 1H), 4.99-4.87 (m, 1H), 4.30-4.19 (m, 2H), 3.52-3.38 (m, 2H), 2.26 (s, 3H), 2.80 (s, 3H), 2.41-1.89 (m, 5H); LCMS: 93.19%, m/z = 561.1 (M + 1); HPLC: 98.48%, rt: 3.63 min. | 0.085 | 1 |
| 43A | 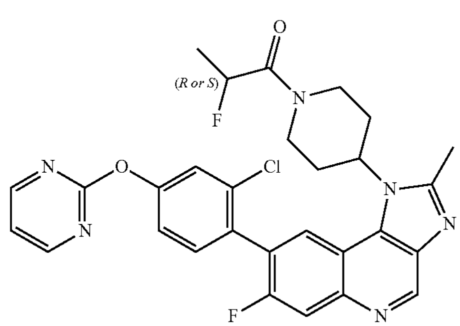 | ¹HNMR (CDCl₃, 400 MHz): δ 9.30 (s, 1H), 8.66 (d, 2H), 8.31 (d, 1H), 8.10 (d, 1H), 7.55-7.48 (m, 2H), 7.33 (dd, 1H), 7.16 (t, 1H), 5.48-5.31 (m, 1H), 5.10-4.95 (m, 1H), 4.52-4.31 (m, 1H), 3.38-3.24 (m, 1H), 2.95-2.85 (m, 2H), 2.83 (s, 3H), 2.50-2.18 (m, 3H), 1.70-1.49 (m, 4H); LCMS: 94.93%, m/z = 563.2 (M⁺); HPLC: 97.94%, rt: 28.93 min. | 0.06 | 1 |

Peak 1

TABLE 1.2-continued

| Example | Structure | 1H NMR, LCMS, HPLC, rt | IC50 µM Cascade MEK1 | HPLC method |
|---|---|---|---|---|
| 43B | 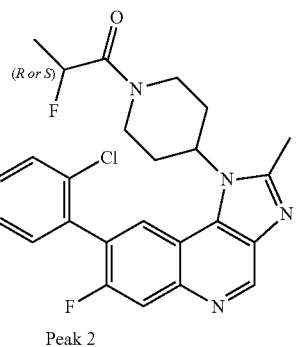<br>Peak 2 | ¹HNMR (CDCl₃, 400 MHz): δ 9.31 (s, 1H), 8.65 (d, 2H), 8.33 (d, 1H), 8.12 (d, 1H), 7.61-7.49 (m, 2H), 7.32 (dd, 1H), 7.16 (t, 1H), 5.45-5.17 (m, 1H), 5.04-4.88 (m, 1H), 4.50-4.31 (m, 1H), 3.40-3.22 (m, 1H), 2.95-2.85 (m, 2H), 2.84 (s, 3H), 2.56-2.19 (m, 3H) 1.72-1.52 (m, 4H); LCMS: 98.75%, m/z = 563.2 (M⁺); HPLC: 94.64%, rt: 32.55 min. | 0.547 | 1 |
| 44 | 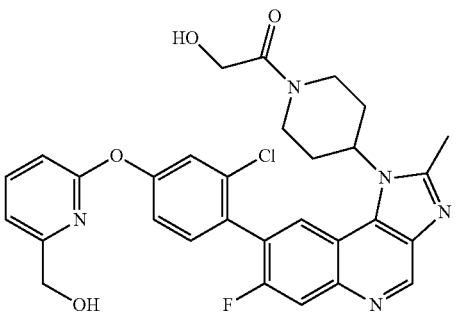 [SMILES: Cc1nc2cnc3cc(F)c(-c4ccc(Oc5cccc(CO)n5)cc4Cl)cc3c2n1C1CCN(C(=O)CO)CC1] | ¹HNMR (CDCl₃, 400 MHz): δ 9.31 (s, 1H), 8.28-8.17 (m, 1H), 8.05 (d, 1H), 7.79 (t, 1H), 7.45 (s, 1H), 7.28-7.24 (m, 2H), 7.07 (d, 1H), 7.00 (d, 1H), 5.08-4.96 (m, 1H), 4.93-4.77 (m, 1H), 4.75-4.16 (m, 1H), 4.63-4.54 (m, 1H), 4.31-4.21 (m, 2H), 3.86-3.75 (m, 2H), 3.33-3.21 (m, 2H), 2.95-2.83 (m, 3H), 2.81 (s, 3H), 2.18-1.96 (m, 2H); LCMS: m/z = 83.62%, 576.45 (M⁺); HPLC: 98.59%, rt: 3.58 min. | 0.002 | 1 |
| 45 | 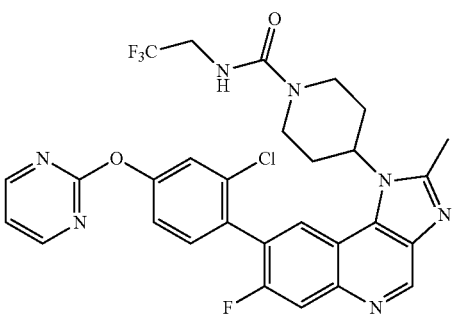 [SMILES: Cc1nc2cnc3cc(F)c(-c4ccc(Oc5ncccn5)cc4Cl)cc3c2n1C1CCN(C(=O)NCC(F)(F)F)CC1] | ¹HNMR (CDCl₃, 300 MHz): δ 9.26 (s, 1H), 8.64 (d, 2H), 8.35-8.25 (m, 1H), 8.10 (d, 1H), 7.59-7.46 (m, 2H), 7.31 (dd, 1H), 7.15 (t, 1H), 5.15-4.95 (m, 2H), 4.30 (d, 2H), 4.02-3.84 (m, 2H), 3.10 (t, 2H), 2.82 (s, 3H), 2.54-2.12 (m, 4H); LCMS: 94.87%, m/z = 614.5 (M + 1); HPLC: 96.46%, rt: 3.64 min. | 0.191 | 1 |
| 46 | 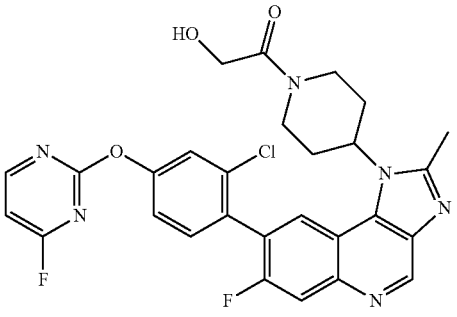 | ¹HNMR (CDCl₃, 400 MHz): δ 9.31 (s, 1H), 8.56 (d, 1H), 8.34-8.14 (m, 2H), 7.64-7.45 (m, 2H), 7.32 (dd, 1H), 7.01-6.98 (m, 1H), 5.45-4.77 (m, 2H), 4.41-4.10 (m, 2H), 3.85 (d, 1H), 3.47-3.29 (d, 1H), 3.04-3.87 (m, 2H), 2.84 (s, 3H), 2.54-2.00 (m, 4H); LCMS: 97.87%, m/z = 565.45 (M + 1); HPLC; 94.75%, rt: 3.74 min. | 0.01 | 1 |

TABLE 1.2-continued

| Example | Structure | 1H NMR, LCMS, HPLC, rt | IC50 μM Cascade MEK1 | HPLC method |
|---|---|---|---|---|
| 47 | 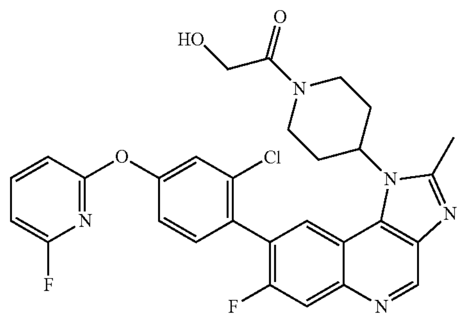 | ¹HNMR (DMSO-d₆, 400 MHz): δ 9.20 (s, 1H), 8.54-8.19 (m, 1H), 8.14-8.03 (m, 2H), 7.82-7.66 (m, 1H), 7.59-7.54 (m, 1H), 7.36-7.28 (m, 1H), 7.09 (d, 1H), 6.98 (dd, 1H), 5.48-5.24 (m, 1H), 4.65-4.55 (m, 2H), 4.16-4.03 (m, 2H), 3.97-3.86 (m, 2H), 2.95-2.80 (m, 2H), 2.77 (s, 3H), 2.28-2.01 (m, 2H); LCMS: 98.13%, m/z = 564.20 (M + 1); HPLC: 97.09%, rt: 3.97 min. | 0.0017 | 3 |
| 48 | 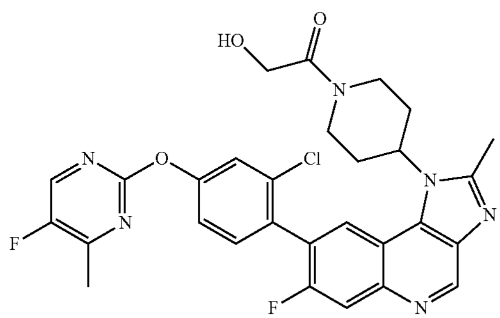 [SMILES: Cc1nc(Oc2ccc(-c3cc4c(cc3F)ncc3nc(C)n(C5CCN(C(=O)CO)CC5)c34)c(Cl)c2)ncc1F] | ¹HNMR (DMSO-d₆, 400 MHz): δ 9.18 (s, 1H), 8.62 (s, 1H), 8.32 (s, 1H), 8.05 (d, 1H), 7.78-67 (m, 1H), 7.63-7.55 (m, 1H), 7.41-7.53 (m, 1H), 5.50-4.92 (m, 1H), 4.66-4.54 (m, 2H), 4.16-4.02 (m, 2H), 3.96-3.87 (m, 2H), 2.96-2.82 (m, 1H), 2.78 (s, 3H), 2.47 (s, 3H), 2.49-2.05 (m, 3H); LCMS: 100%, m/z = 578.9 (M⁺); HPLC: 97.87%, rt: 4.27 min. | 0.011 | 1 |
| 49 | 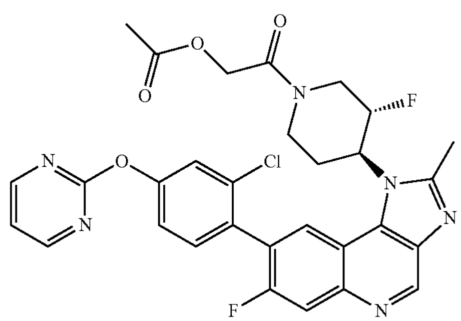 [SMILES: CC(=O)OCC(=O)N1CC[C@H](n2c(C)nc3cnc4cc(F)c(-c5ccc(Oc6ncccn6)cc5Cl)cc4c32)[C@@H](F)C1] | ¹HNMR (CDCl₃, 400 MHz): δ 9.31 (d, 1H), 8.68-8.60 (m, 2H), 8.34 (d, 0.5H), 8.12-8.01 (m, 1.5H), 7.59 (d, 0.5H), 7.54-7.45 (m, 1.5H), 7.37-7.30 (m, 1H), 7.18-7.11 (m, 1H), 5.69-5.16 (m, 2H), 4.99-4.61 (m, 3H), 4.37-4.25 (m, 0.5H), 4.01-3.88 (m, 0.5H), 3.50 (d, 1H), 3.03-2.90 (m, 2H), 2.88 (s, 1.5H), 2.81 (s, 1.5H), 2.50-2.33 (m, 1H), 2.22 (s, 1.5H), 2.07 (s, 1.5H); LCMS: 99.24%, m/z = 608.45 (M + 1); HPLC: 99.76%, rt: 4.32 min. | 0.232 | 1 |
| 50 | 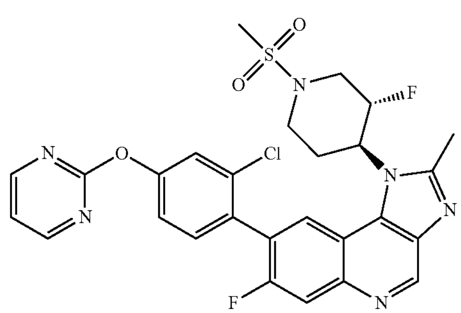 [SMILES: Cc1nc2cnc3cc(F)c(-c4ccc(Oc5ncccn5)cc4Cl)cc3c2n1[C@H]1CCN(S(C)(=O)=O)C[C@@H]1F] | ¹HNMR (CDCl₃, 300 MHz): δ 9.29 (d, 1H), 8.65-8.56 (m, 2H), 8.31-8.18 (m, 1H), 8.12-8.02 (m, 1H), 7.60-7.41 (m, 2H), 7.35-7.28 (m, 1H), 7.20-7.17 (m, 1H), 5.00-5.20 (m, 1.5H), 4.75-4.57 (m, 0.5H), 4.47-4.33 (m, 1H), 4.13-4.00 (m, 1H), 3.09-2.95 (m, 2H), 2.96 (s, 1.5H), 2.89 (s, 1.5H), 2.77 (s, 1.5H), 2.71 (s, 1.5H), 2.65-2.50 (m, 1H), 2.43-2.15 (m, 1H); LCMS: 97.71%, m/z = 585.1 (M⁺); HPLC: 98.58%, rt: 3.83 min. | 0.012 | 1 |
| 51 | 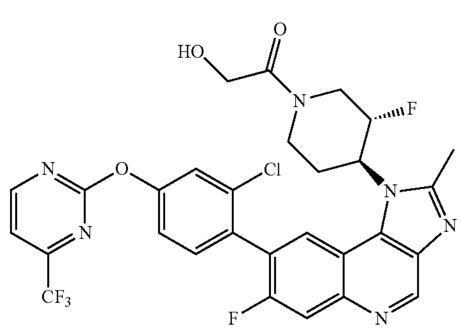 [SMILES: Cc1nc2cnc3cc(F)c(-c4ccc(Oc5nccc(C(F)(F)F)n5)cc4Cl)cc3c2n1[C@H]1CCN(C(=O)CO)C[C@@H]1F] | ¹HNMR (CDCl₃, 300 MHz): δ 9.32 (s, 1H), 8.85 (d, 1H), 8.08 (d, 2H), 7.95-7.87 (m, 1H), 7.52 (s, 1H), 7.46 (d, 1H), 7.32 (dd, 1H), 5.69-5.20 (m, 2H), 4.95-4.68 (m, 1H), 4.20-4.05 (m, 1H), 3.84-3.20 (m, 1H), 3.40-3.16 (m, 2H), 2.98-2.82 (m, 2H), 2.79 (s, 3H), 2.43-2.13 (m, 2H); LCMS: 94.03%, m/z = 633.1 (M + 1); HPLC: 97.16%, rt: 4.17 min. | 0.001 | 3 |

TABLE 1.2-continued

| Example | Structure | 1H NMR, LCMS, HPLC, rt | IC50 μM Cascade MEK1 | HPLC method |
|---|---|---|---|---|
| 52 | 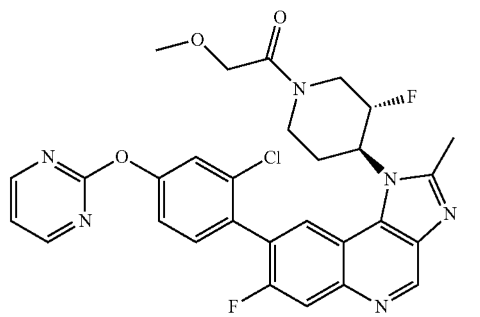 [SMILES: COCC(=O)N1CC[C@H](n2c(C)nc3cnc4cc(F)c(-c5ccc(Oc6ncccn6)cc5Cl)cc4c32)[C@@H](F)C1] | ¹HNMR (DMSO-d₆, 300 MHz): δ 9.21 (d, 1H), 8.80-8.56 (m, 2H), 8.15-7.95 (m, 2H), 7.78-7.48 (m, 2H), 7.44-7.24 (m, 2H), 5.71-5.07 (m, 2H), 4.95-4.78 (m, 1H), 4.55-4.45 (m, 1H), 4.38-4.10 (m, 1H), 3.95-3.73 (m, 2H), 3.09 (s, 3H), 2.89-2.68 (m, 4H), 2.39-2.15 (m, 2H); LCMS: 93.15%, m/z = 579.2 (M + 1); HPLC: 99.63%, rt: 3.99 min. | 0.009 | 1 |
| 53 | 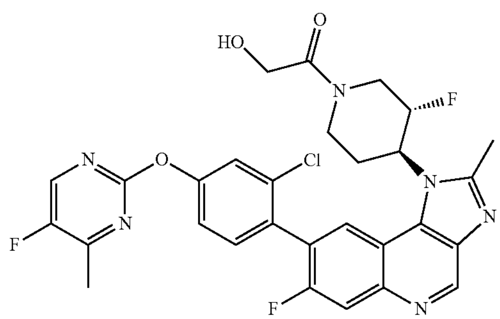 [SMILES: Cc1nc(Oc2ccc(-c3cc4c(cc3F)ncc3nc(C)n([C@H]5CCN(C(=O)CO)C[C@@H]5F)c34)c(Cl)c2)ncc1F] | ¹HNMR (CDCl₃, 300 MHz): δ 9.32 (s, 1H), 8.30 (s, 1H), 8.06 (d, 1H), 7.95-7.86 (m, 1H), 7.58-7.35 (m, 2H), 7.30-7.26 (m, 1H), 5.71-5.08 (m, 2H), 4.96-4.70 (m, 1H), 4.32-4.05 (m, 2H), 3.85-3.68 (m, 1H), 3.64-3.52 (m, 1H), 3.35-3.13 (m, 1H), 3.00-2.87 (m, 2H), 2.79 (s, 3H), 2.56 (d, 3H), 2.28-2.10 (m, 1H); LCMS: 98.34%, m/z = 597.1 (M + 1); HPLC: 98.81%, rt: 3.95 min. | 0.0062 | 3 |
| 54 | 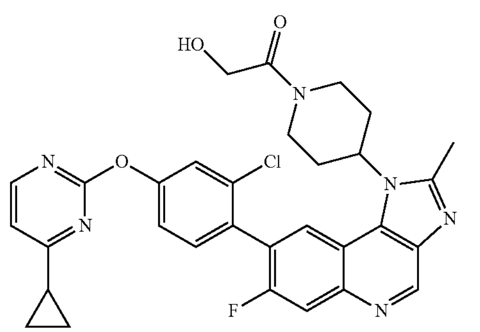 [SMILES: Cc1nc2cnc3cc(F)c(-c4ccc(Oc5nccc(C6CC6)n5)cc4Cl)cc3c2n1C1CCN(C(=O)CO)CC1] | ¹HNMR (CDCl₃, 300 MHz): δ 9.27 (s, 1H), 8.33 (d, 1H), 8.24 (d, 1H), 8.05 (d, 1H), 7.58-7.50 (m, 1H), 7.48 (d, 1H), 7.27 (dd, 1H), 7.97 (s, 1H), 5.35-5.24 (m, 0.5H), 4.97 (d, 1H), 4.88-4.75 (m, 0.5H), 4.35-4.14 (m, 1.5H), 3.82 (d, 1H), 3.15-3.04 (m, 0.5H), 3.33-3.21 (m, 1H), 2.96-2.83 (m, 2H), 2.81 (s, 3H), 2.41-2.25 (m, 2H), 2.06-1.98 (m, 2H), 1.28-1.10 (m, 5H); LCMS: 93.42%, m/z = 587.2 (M⁺); HPLC: 97.30%, rt: 3.89 min. | 0.0015 | 4 |
| 55 | 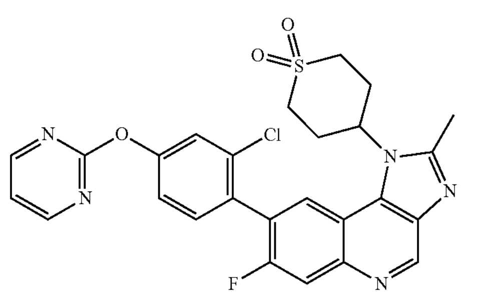 [SMILES: Cc1nc2cnc3cc(F)c(-c4ccc(Oc5ncccn5)cc4Cl)cc3c2n1C1CCS(=O)(=O)CC1] | ¹HNMR (DMSO-d₆, 400 MHz): δ 9.19 (d, 1H), 8.71 (d, 2H), 8.09-8.02 (m, 1H), 7.76-7.64 (m, 1H), 7.58 (d, 1H), 7.43 (d, 1H), 7.38-7.32 (m, 2H), 5.65-5.51 (m, 0.3H), 5.19-5.05 (m, 0.7H), 3.82-3.54 (m, 2H), 3.30-3.21 (m, 2H), 3.10-2.97 (m, 2H), 2.8-2.74 (m, 4H), 2.45-2.28 (m, 1H); LCMS: m/z = 93.88%, 538.40 (M + 1); HPLC: 95.13%, rt: 3.55 min. | 0.047 | 1 |
| 56 | 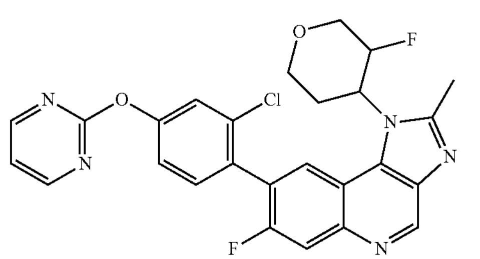 [SMILES: Cc1nc2cnc3cc(F)c(-c4ccc(Oc5ncccn5)cc4Cl)cc3c2n1C1CCOCC1F] | ¹HNMR (DMSO-d₆, 300 MHz): δ 9.21 (d, 1H), 8.73 (d, 2H), 8.62-8.34 (m, 1H), 8.15-8.05 (m, 1H), 7.81-7.73 (m, 1H), 7.70-7.66 (m, 1H), 7.41 (dd, 1H), 7.35 (t, 1H), 5.89-5.42 (m, 1H), 5.35-5.28 (m, 0.5H), 5.18-5.12 (m, 0.5H), 4.25-4.04 (m, 2H), 3.87-3.42 (m, 2H), 3.31-2.99 (m, 2H), 2.80 (s, 2.7H), 2.76 (s, 0.3H); LCMS: 53.05% +29.00%, m/z = 508.1 (M); HPLC: 72.37%, rt: 3.97 min, 27.62%, rt: 3.87 min. | 0.28 | 3 |

TABLE 1.2-continued

| Example | Structure | 1H NMR, LCMS, HPLC, rt | IC50 μM Cascade MEK1 | HPLC method |
|---|---|---|---|---|
| 57 | 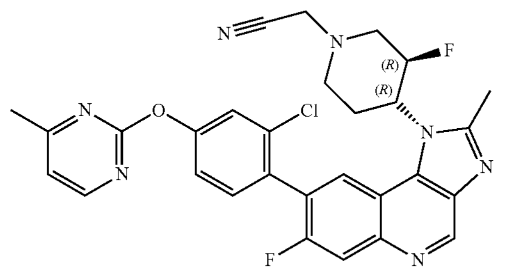 | ¹H NMR (CDCl₃, 400 MHz): δ 9.32 (s, 1H), 8.69-8.67 (d, 1H), 8.40-8.39 (d, 1H), 8.08-8.05 (d, 1H), 7.52-7.45 (m, 2H), 7.28-7.25 (m, 1H), 7.01-7.00 (d, 1H), 5.76-5.63 (m, 1H), 4.71-4.63 (m, 1H), 3.54-3.35 (m, 3H), 3.01-2.93 (m, 2H), 2.81-2.67 (m, 5H), 2.56 (s, 3H), 2.24-2.17 (m, 1H); LCMS: 99.48%, m/z = 559.7 (M + 1); HPLC: 99.10%, rt = 4.79 min.; Column: ZORBAX XDB C18, 5 micro (4.6 × 150 mm); Chiral HPLC: 99.64%, rt = 23.05 min.; Column: AG/CHIRALPAK AD-H/03. | 0.019 | 1 |
| 58 | 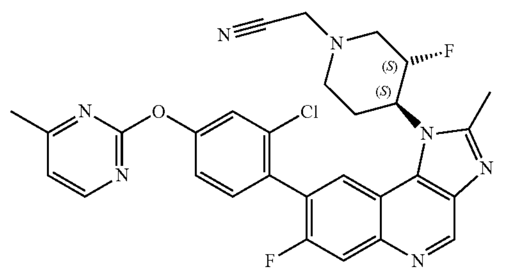 | ¹H NMR (CDCl₃, 400 MHz): δ 9.32 (s, 1H), 8.69-8.67 (d, 1H), 8.40-8.39 (d, 1H), 8.08-8.05 (d, 1H), 7.52-7.50 (d, 1H), 7.45-7.44 (d, 1H), 7.28-7.25 (m, 1H), 7.01-7.00 (d, 1H), 5.85-5.55 (m, 1H), 4.71-4.63 (m, 1H), 3.50-3.36 (m, 3H), 3.0-2.95 (m, 2H), 2.77 (s, 3H), 2.74-2.68 (m, 2H), 2.67 (s, 3H), 2.24-2.18 (m, 1H); LCMS: 98.75%, m/z = 559.8 (M + 1); HPLC: 99.47%, rt = 4.512 min.; Column: ZORBAX XDB C18, 5 micro (4.6 × 150 mm); Chiral HPLC: 99.31%, rt = 18.13 min.; Column: AG/CHIRALPAK AD-H/03. | 0.003 | 1 |
| 59 | 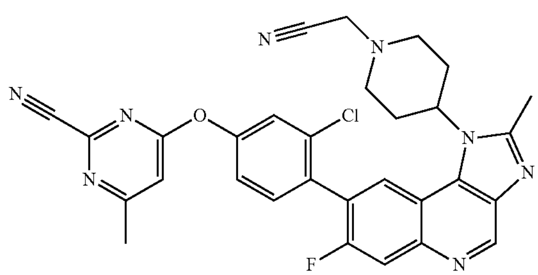 [SMILES: Cc1cc(Oc2ccc(-c3cc4c(cc3F)ncc3nc(C)n(C5CCN(CC#N)CC5)c34)c(Cl)c2)nc(C#N)n1] | ¹H NMR (CDCl₃, 400 MHz): δ 9.29 (s, 1H), 8.92 (bs, 1H), 8.06 (d, 1H), 7.61 (d, 1H), 7.41 (s, 1H), 7.26-7.22 (dd, 1H), 7.05 (s, 1H), 5.20 (m, 1H), 3.50 (s, 2H), 3.11 (d, 2H), 2.80 (bs, 4H), 2.62 (m, 6H), 2.05 (bs, 2H); LCMS: 94.69%, m/z = 566.7 (M + 1); HPLC: 95.03%, rt: 4.70 min. | 0.018 | 1 |
| 60 | 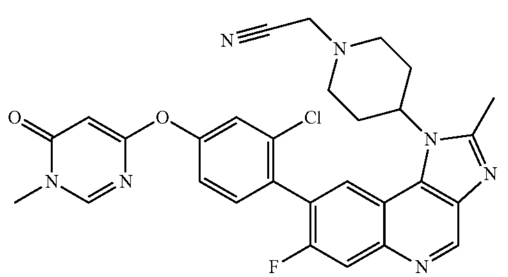 [SMILES: Cc1nc2cnc3cc(F)c(-c4ccc(Oc5cc(=O)n(C)cn5)cc4Cl)cc3c2n1C1CCN(CC#N)CC1] | ¹H NMR (CDCl₃, 400 MHz): δ 9.27 (s, 1H), 8.9 (bs, 1H), 8.04 (d, 2H), 7.53 (d, 1H), 7.37 (s, 1H), , 7.18 (dd, 1H), 5.86 (s, 1H), 3.53 (s, −3H), 3.06-3.05 (m, 2H), 2.80 (bs, 4H), 2.66-2.60 (t, 3H), 1.28 (d, 5H); LCMS: 93.39%, m/z = 558.30 (M + 1); HPLC: 91.5%, rt: 3.63 min. | 0.113 | 1 |
| 61 | 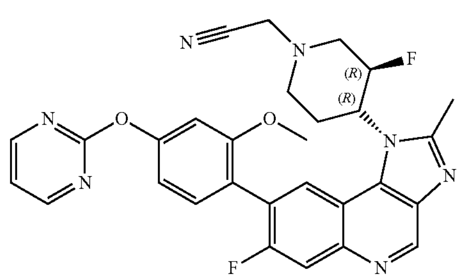 | ¹H NMR (CDCl₃, 400 MHz): δ 9.30 (s, 1H), 8.64-8.60 (m, 3H), 8.03-8.00 (d, 1H), 7.41-7.39 (d, 1H), 7.15-7.13 (m, 1H), 7.01-6.94 (m, 2H), 5.79-5.65 (m, 1H), 4.70-4.62 (m, 1H), 3.83 (s, 3H), 3.57-3.47 (m, 3H), 3.03-2.95 (m, 2H), 2.78 (s, 3H), 2.72-2.70 (m, 2H), 2.25-2.22 (m, 1H); LCMS: 96.23%, m/z = 542.5 (M + 1); HPLC: 98.31%, rt = 6.63 min.; Column: ZORBAX XDB C18, 5 micro (4.6 × 150 mm); Chiral HPLC: 97.35%, rt = 18.522 min.; Column: LUX 5 u AMYLOSE-2 (150 × 4.60 MM), 5 Micron. | 0.211 | 1 |

TABLE 1.2-continued

| Example | Structure | 1H NMR, LCMS, HPLC, rt | IC50 μM Cascade MEK1 | HPLC method |
|---|---|---|---|---|
| 62 | 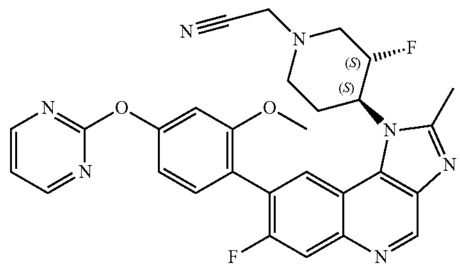 | ¹H NMR (CDCl₃, 400 MHz): δ 9.27 (s, 1H), 8.62-8.57 (m, 3H), 8.00-7.97 (d, 1H), 7.38-7.36 (d, 1H), 7.12-7.10 (m, 1H), 6.93-6.91 (d, 2H), 5.77-5.62 (m, 1H), 4.68-4.60 (m, 1H), 3.81 (s, 3H), 3.44-3.33 (m, 3H), 3.02-2.97 (m, 2H), 2.78 (s, 3H), 2.72-2.65 (m, 2H), 2.22-2.17 (m, 1H); LCMS: 95.36%, m/z = 542.5 (M + 1); HPLC: 96.54%, rt = 6.63 min.; Column: ZORBAX XDB C18, 5 micro (4.6 × 150 mm); Chiral HPLC: 96.18%, rt = 20.44 min.; Column: LUX 5 u AMYLOSE-2 (150 × 4.60 MM), 5 Micron. | 0.0037 | 1 |
| 63 | 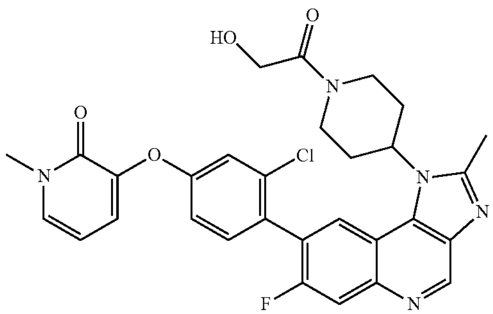 | ¹H NMR (CDCl₃, 400 MHz): δ 9.26 (s, 1H), 8.21-8.20 (d, 1H), 8.04-8.01 (d, 1H), 7.30 (s, 1H), 7.28-7.26 (m, 2H), 7.17-7.16 (d, 1H), 7.04-7.01 (dd, 1H), 6.26-6.22 (t, 1H), 5.35-5.30 (m, 1H), 4.90-5.00 (m, 2H), 4.25-4.28 (m, 1H), 3.89-3.78 (m, 1H), 3.66 (s, 3H), 3.39-3.20 (m, 1H), 3.02-2.90 (m, 1H), 2.80 (s, 3H), 2.41-2.25 (m, 4H); LCMS: 94.13%, m/z = 576.3 (M + 1); HPLC: 93.22%, rt: 3.28 min. | 0.0085 | 1 |
| 64 | 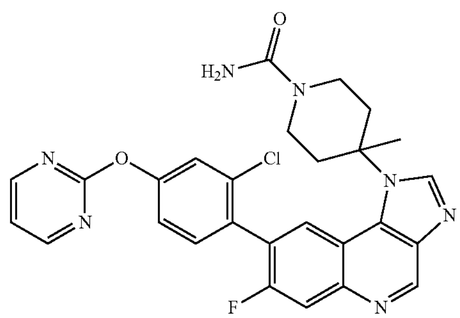 [SMILES: CC1(n2cnc3cnc4cc(F)c(-c5ccc(Oc6ncccn6)cc5Cl)cc4c32)CCN(C(N)=O)CC1] | ¹H NMR (DMSO-d₆, 400 MHz): δ 9.35 (s, 1H), 8.73 (d, 3H), 8.55 (d, 1H), 8.12 (d, 1H), 7.68 (d, 1H), 7.64 (d, 1H), 7.41 (dd, 1H), 7.39 (t, 1H), 5.91 (s, 2H), 3.65-3.56 (m, 2H), 3.44-3.32 (m, 2H), 2.52-2.50 (m, 2H), 2.25-2.15 (m, 2H), 1.94 (s, 3H); LCMS: 98.76%, m/z = 532.05 (M + 1); HPLC: 99.18%, rt: 3.90 min. | 0.0053 | 1 |
| 65 | 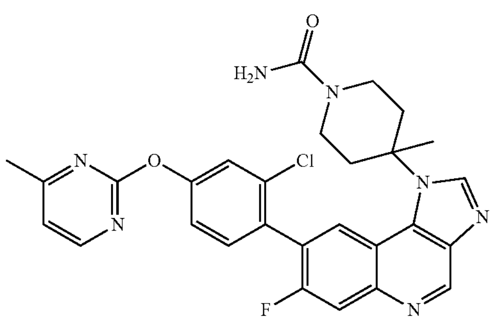 [SMILES: Cc1ccnc(Oc2ccc(-c3cc4c(cc3F)ncc3ncn(C5(C)CCN(C(N)=O)CC5)c34)c(Cl)c2)n1] | ¹H NMR (DMSO-d₆, 400 MHz): δ 9.35 (s, 1H), 8.72 (s, 1H), 8.53 (d, 2H), 8.11 (d, 1H), 7.66 (d, 1H), 7.59 (d, 1H), 7.38 (dd, 1H), 7.23 (d, 1H), 5.88 (s, 2H), 3.65-3.56 (m, 2H), 3.44-3.32 (m, 2H), 2.62-2.50 (m, 2H), 2.50 (s, 3H), 2.25-2.15 (m, 2H), 1.94 (s, 3H); LCMS: 100%, m/z = 545.90 (M + 1); HPLC: 98.82%, rt: 4.10 min. | 0.0024 | 1 |
| 66 | 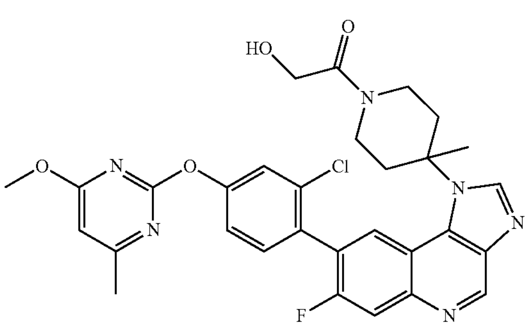 [SMILES: COc1cc(C)nc(Oc2ccc(-c3cc4c(cc3F)ncc3ncn(C5(C)CCN(C(=O)CO)CC5)c34)c(Cl)c2)n1] | ¹H NMR (CDCl₃, 400 MHz): δ 9.42 (s, 1H), 8.44-8.42 (d, 1H), 8.32 (s, 1H), 8.11-8.08 (d, 1H), 7.528-7.523 (d, 1H), 7.47-7.45 (d, 1H), 7.33-7.31 (dd, 1H), 6.40 (s, 1H), 4.3-4.1 (m, 2H), 3.97 (s, 3H), 3.7 (s, 1H), 3.56-3.3 (m, 4H), 2.90-2.75 (bs, 2H), 2.44 (s, 3H), 2.30-2.15 (bs, 2H), 2.09 (s, 3H); LCMS: 93.21%, m/z = 591.5 (M + 1); HPLC: 98.58%, rt: 4.62 min. | 0.01 | 1 |

TABLE 1.2-continued

| Example | Structure | 1H NMR, LCMS, HPLC, rt | IC50 µM Cascade MEK1 | HPLC method |
|---|---|---|---|---|
| 67 | 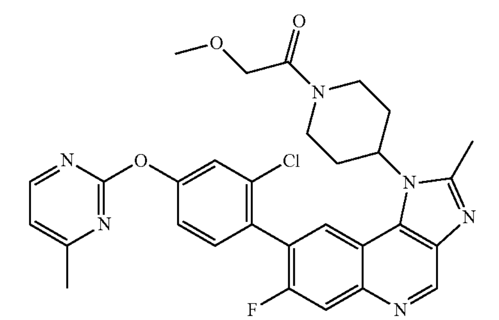 [SMILES: COCC(=O)N1CCC(n2c(C)nc3cnc4cc(F)c(-c5ccc(Oc6nccc(C)n6)cc5Cl)cc4c32)CC1] | ¹H NMR (CDCl₃, 400 MHz): δ 9.31 (s, 1H), 8.43 (d, 1H), 8.32 (d, 1H), 8.13 (d, 1H), 7.49 (s, 2H), 7.33 (d, 1H), 7.00 (t, 1H), 5.41-5.18 (m, 1H), 5.02-4.82 (m, 1H), 4.35-4.15 (m, 3H), 3.55-3.01 (m, 5H), 2.85-2.65 (m, 5H), 2.56 (s, 3H), 2.40-2.18 (m, 2H); LCMS: 96.42%, m/z = 575.4 (M + 1); HPLC: 95.10%, rt: 3.67 min. | 0.053 | 1 |
| 68 | 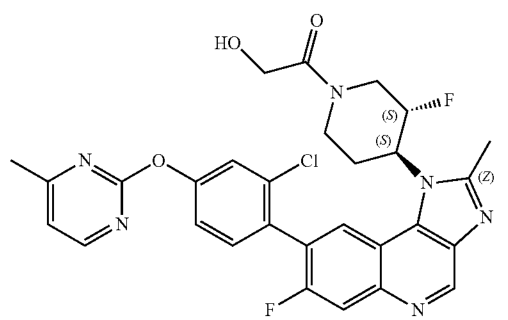 | ¹H NMR (CDCl₃, 400 MHz): δ 9.32 (s, 1H), 8.44 (d, 1H), 8.06 (d, 1H), 7.94 (s, 1H), 7.60-7.36 (m, 2H), 7.29 (s, 1H), 6.99 (d, 1H), 5.65-5.21 (m, 2H), 4.95-4.70 (m, 1H), 4.30-4.11 (m, 2H), 3.92-3.73 (m, 2H), 3.40-3.15 (m, 1H), 3.05-2.75 (m, 5H), 2.57 (s, 3H), 2.29-2.10 (m, 1H); LCMS: 99.65%, m/z = 579.25 (M+); HPLC: 97.96%, rt: 3.62 min. | 0.0047 | 1 |
| 69 | 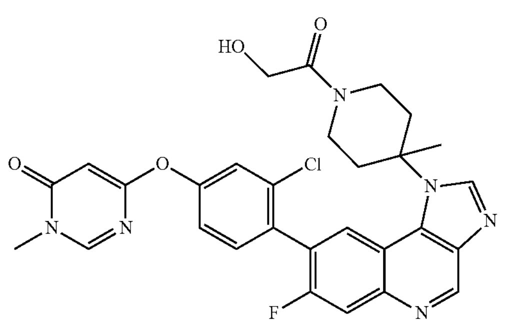 [SMILES: Cn1cnc(Oc2ccc(-c3cc4c(cc3F)ncc3ncn(C5(C)CCN(C(=O)CO)CC5)c34)c(Cl)c2)cc1=O] | ¹H NMR (CDCl₃, 400 MHz): δ 9.42 (s, 1H), 8.40 (d, 1H), 8.32 (s, 1H), 8.11-8.09 (m, 2H), 7.48 (d, 1H), 7.38 (d, 1H), 7.20-7.18 (m, 1H), 5.97 (s, 1H), 4.25-4.18 (m, 1H), 4.17 (s, 2H), 4.05 (d, 1H), 3.54 (s, 3H), 3.42-3.38 (m, 3H), 2.86-2.78 (m, 2H), 2.23 (t, 2H), 2.09 (s, 3H); LCMS: 85.3%, m/z = 576.90 (M+); HPLC: 93.5%, rt: 3.28 min. | 0.059 | 1 |
| 70 | 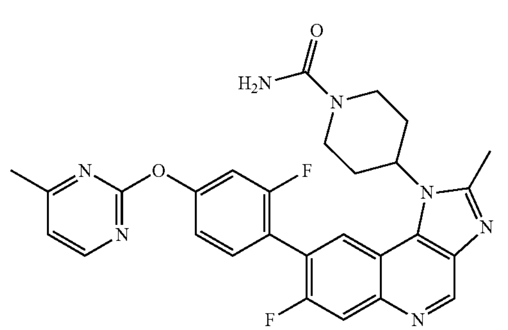 | ¹H NMR (CDCl₃, 400 MHz): δ 9.23 (s, 1H), 8.37 (s, 2H), 8.01 (d, 1H), 7.60-7.47 (m, 1H), 7.22-7.12 (m, 2H), 6.96 (d, 1H), 4.92-4.68 (m, 3H), 4.29-4.25 (m, 2H), 3.10-2.96 (m, 2H), 2.77 (s, 3H), 2.53 (s, 3H), 2.10-1.89 (m, 4H); LCMS: 99.78%, m/z = 530.35 (M + 1); HPLC: 95.11%, rt: 3.18 min. | 0.0043 | 1 |

TABLE 1.2-continued

| Example | Structure | 1H NMR, LCMS, HPLC, rt | IC50 μM Cascade MEK1 | HPLC method |
|---|---|---|---|---|
| 71 | 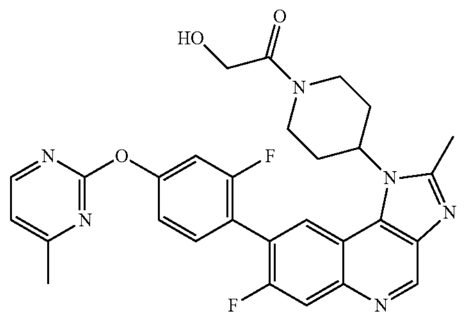 [SMILES: Cc1ccnc(Oc2ccc(-c3cc4c(cc3F)ncc3nc(C)n(C5CCN(C(=O)CO)CC5)c34)c(F)c2)n1] | ¹H NMR (DMSO-d₆, 400 MHz): δ 9.18 (s, 1H), 8.53 (d, 1H), 8.31 (s, 1H), 8.05 (d, 1H), 7.90-7.65 (m, 1H), 7.38-7.30 (m, 1H), 7.22 (dd, 2H), 5.10-4.95 (m, 1H), 4.75-4.55 (m, 1H), 4.20-3.90 (m, 3H), 3.40-3.22 (m, 2H), 2.98-2.80 (m, 2H), 2.78 (s, 3H), 2.50 (s, 3H), 2.30-2.00 (m, 2H); LCMS: 90.93%, m/z = 545.2 (M + 1); HPLC: 93.33%, rt: 3.29 min. | 0.039 | 1 |
| 72 | 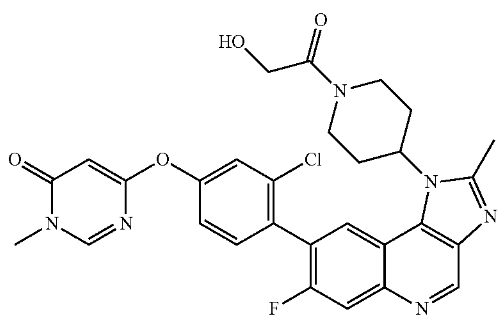 [SMILES: Cc1nc2cnc3cc(F)c(-c4ccc(Oc5cc(=O)n(C)cn5)cc4Cl)cc3c2n1C1CCN(C(=O)CO)CC1] | ¹H NMR (CDCl₃, 400 MHz): δ 9.28 (s, 1H), 8.21 (d, 1H), 8.09-8.04 (t, 2H), 7.39 (d, 1H), 7.26 (s, 1H), 7.20-7.18 (m, 1H), 5.97 (bs, 1H), 5.22 (m, 1H), 4.98 (d, 2H), 4.22 (m, 2H), 3.82 (d, 2H), 3.53 (s, 3H), 3.25 (t, 2H), 2.89 (s, 3H), 2.50-2.23 (m, 2H); LCMS: 99.3%, m/z = 577.2 (M + 1); HPLC: 97.37%, rt: 3.27 min. | 0.045 | 1 |
| 73 | 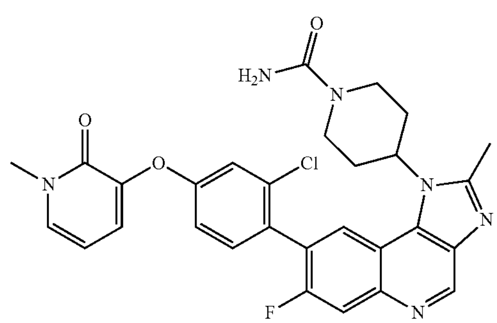 | ¹H NMR (CD₃OD, 400 MHz): δ 9.12 (s, 1H), 8.45-8.43 (d, 1H), 7.93-7.90 (d, 1H), 7.62-7.60 (d, 1H), 7.49-7.40 (m, 2H), 7.15 (s, 1H), 7.03-7.01 (d, 1H), 6.45-6.41 (t, 1H), 5.03-4.95 (m, 1H), 4.31-4.20 (m, 2H), 3.64 (s, 3H), 3.11-2.99 (m, 2H), 2.81 (s, 3H), 2.72-2.61 (m, 2H), 2.05-1.95 (m, 2H); LCMS: 99.72%, m/z = 560.95 (M+); HPLC: 95.59%, rt: 3.10 min. | 0.0036 | 1 |
| 74 | 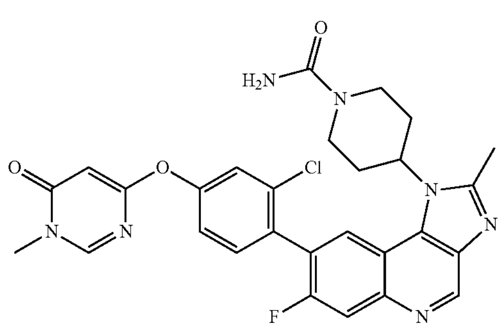 [SMILES: Cc1nc2cnc3cc(F)c(-c4ccc(Oc5cc(=O)n(C)cn5)cc4Cl)cc3c2n1C1CCN(C(N)=O)CC1] | ¹H NMR (CDCl₃, 400 MHz): δ 9.29 (s, 1H), 8.44 (d, 1H), 8.06 (d, 2H), 7.53 (d, 1H), 7.35 (s, 1H), 7.22 (d, 1H), 5.97 (bs, 1H), 4.88-4.55 (m, 3H), 4.35-4.15 (m, 2H), 3.53 (s, 3H), 3.05 (bs, 2H), 2.80 (s, 3H), 2.78-2.65 (m, 2H), 2.10-1.95 (m, 2H); LCMS: 90.8%, m/z = 562.2 (M + 1); HPLC: 97.04%, rt: 2.42 min. | 0.01 | 5 |

TABLE 1.2-continued

| Example | Structure | 1H NMR, LCMS, HPLC, rt | IC50 μM Cascade MEK1 | HPLC method |
|---|---|---|---|---|
| 75 | 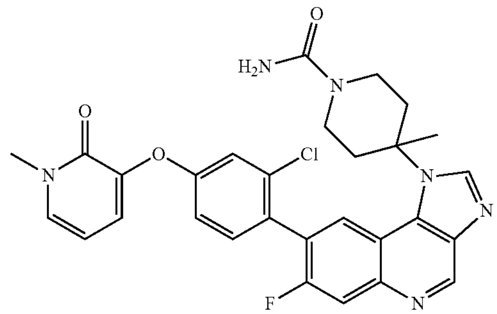 [SMILES: Cn1cccc(Oc2ccc(-c3cc4c(cc3F)ncc3ncn(C5(C)CCN(C(N)=O)CC5)c34)c(Cl)c2)c1=O] | ¹H NMR (CDCl₃, 400 MHz): δ 9.39 (s, 1H), 8.69 (d, 1H), 8.36 (s, 1H), 8.05 (d, 1H), 7.38-7.28 (m, 3H), 7.15-7.10 (m, 1H), 7.05-6.97 (m, 1H), 6.28 (t, 1H), 4.89 (bs, 2H), 4.02-3.93 (m, 2H), 3.68 (s, 3H), 3.18-2.96 (m, 4H), 2.07 (s, 3H), 1.96-1.87 (m, 2H); LCMS: 100%, m/z = 561.5 (M + 1); HPLC: 98.16%, rt: 6.36 min. | 0.0038 | 1 |
| 76 | 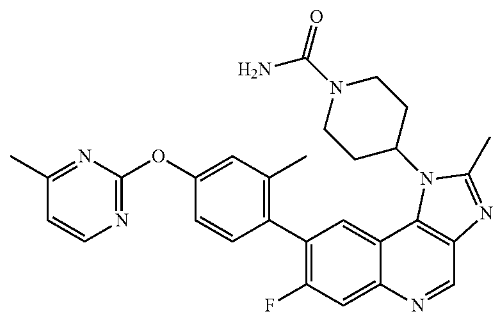 | ¹H NMR (CDCl₃, 400 MHz): δ 9.27 (s, 1H), 8.35 (s, 1H), 8.26 (bs, 1H), 8.02 (d, 1H), 7.36 (s, 1H), 7.26 (s, 2H), 6.93 (d, 1H), 5.25-5.05 (m, 1H), 4.78 (bs, 2H), 4.35-4.10 (m, 2H), 3.55-3.38 (m, 2H), 3.03 (t, 2H), 2.79 (s, 3H), 2.55 (s, 3H), 2.25 (s, 3H), 2.01-1.89 (m, 2H); LCMS: 100%, m/z = 526.4 (M + 1); HPLC; 98.8%, rt: 3.71 min. | 0.04 | 1 |
| 77 | 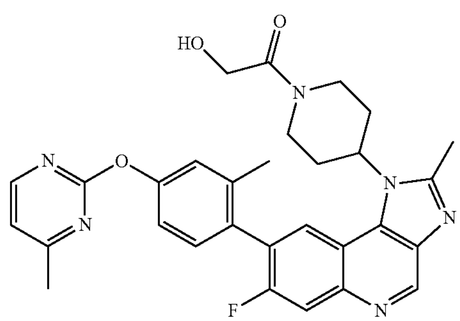 [SMILES: Cc1ccnc(Oc2ccc(-c3cc4c(cc3F)ncc3nc(C)n(C5CCN(C(=O)CO)CC5)c34)c(C)c2)n1] | ¹H NMR (CDCl₃, 400 MHz): δ 9.27 (s, 1H), 8.41 (d, 1H), 8.11 (bs, 1H), 8.03 (d, 1H), 7.31 (s, 1H), 7.35-7.18 (m, 2H), 6.95 (d, 1H), 5.40-5.20 (m, 1H), 5.02-4.90 (m, 1H), 4.25-4.10 (m, 1H), 3.90-3.78 (m, 2H), 3.30-3.15 (m, 2H), 2.95-2.70 (m, 5H), 2.56 (s, 3H), 2.29 (s, 3H), 2.01-1.89 (m, 2H); LCMS: 98.8%, m/z = 541.35 (M + 1); HPLC: 96.44%, rt: 3.82 min. | 0.08 | 1 |
| 78 | 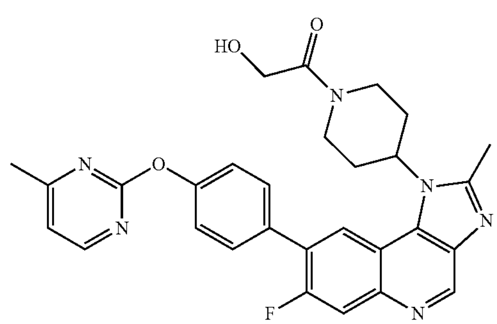 | ¹H NMR (DMSO-d₆, 300 MHz): δ 9.16 (s, 1H), 8.50 (td, 1H), 8.45 (d, 1H), 8.04 (d, 1H), 7.76-7.66 (m, 2H), 7.37 (d, 2H), 7.19 (d, 1H), 5.05-4.90 (m, 1H), 4.70 (d, 1H), 4.55-4.45 (m, 1H), 4.20-4.10 (m, 2H), 4.00 (d, 1H), 3.28-3.16 (m, 2H), 3.00-2.85 (m, 1H), 2.79 (s, 3H), 2.50 (s, 3H), 2.30-2.05 (m, 3H); LCMS: 93.23%, m/z = 527.20 (M + 1); HPLC: 96.31%, rt: 3.76 min. | 0.179 | 1 |

TABLE 1.2-continued

| Example | Structure | 1H NMR, LCMS, HPLC, rt | IC50 μM Cascade MEK1 | HPLC method |
|---|---|---|---|---|
| 79 | 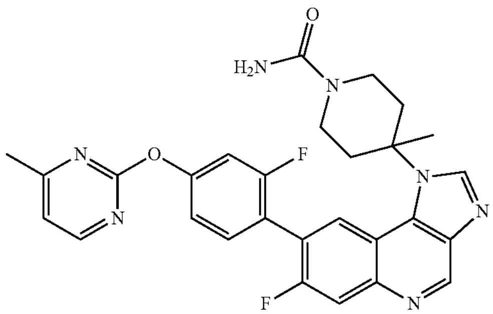 [SMILES: Cc1ccnc(Oc2ccc(-c3cc4c(cc3F)ncc3ncn(C5(C)CCN(C(N)=O)CC5)c34)c(F)c2)n1] | ¹H NMR (DMSO-d₆, 300 MHz): δ 9.37 (s, 1H), 8.75 (s, 1H), 8.63 (d, 1H), 8.53 (d, 1H), 8.14 (d, 1H), 7.69 (t, 1H), 7.41 (dd, 1H), 7.25 (dd, 2H), 5.93 (s, 2H), 3.70-3.55 (m, 2H), 3.38-3.20 (m, 2H), 2.69-2.58 (m, 2H), 2.47 (s, 3H), 2.22-2.07 (m, 2H), 1.97 (s, 3H); LCMS: 100%, m/z = 530.7 (M + 1); HPLC: 98.60%, rt: 3.99 min. | 0.0092 | 1 |
| 80 | 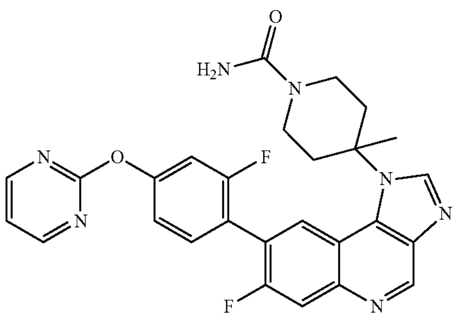 [SMILES: CC1(n2cnc3cnc4cc(F)c(-c5ccc(Oc6ncccn6)cc5F)cc4c32)CCN(C(N)=O)CC1] | ¹H NMR (DMSO-d₆, 300 MHz): δ 9.35 (s, 1H), 8.73 (d, 3H), 8.62 (d, 1H), 8.14 (d, 1H), 7.71 (t, 1H), 7.42 (dd, 1H), 7.36 (t, 1H), 7.28 (dd, 1H), 5.95 (s, 2H), 3.70-3.55 (m, 2H), 2.65-2.50 (m, 4H), 2.25-2.08 (m, 2H), 1.97 (s, 3H); LCMS: 93.81%, m/z = 516.2 (M + 1); HPLC: 99.37%, rt: 3.44 min. | 0.013 | 1 |
| 81 | 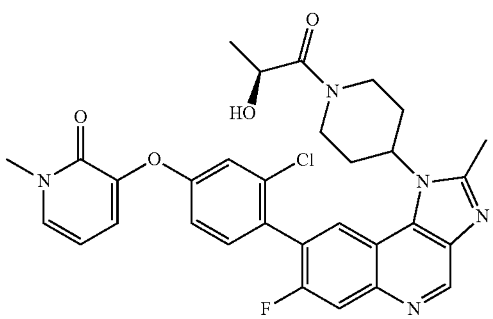 | ¹H NMR (CDCl₃, 300 MHz): δ 9.25 (s, 1H), 8.25-8.17 (m, 1H), 8.01 (d, 1H), 7.44-7.31 (m, 2H), 7.15 (s, 1H), 7.01 (d, 1H), 6.24 (t, 1H), 5.38-5.20 (m, 1H), 5.04-4.75 (m, 2H), 4.60-4.39 (m, 2H), 4.12-3.93 (m, 1H), 3.80-3.78 (m, 1H), 3.65 (s, 3H), 3.43-3.17 (m, 1H), 2.95-2.75 (m, 4H), 2.45-2.16 (m, 2H), 2.10-2.00 (m, 1H), 1.45-1.30 (m, 2H); LCMS: 100%, m/z = 590.5 (M + 1); HPLC: 98.96%, rt: 6.43 min. | 0.007 | 1 |
| 82 | 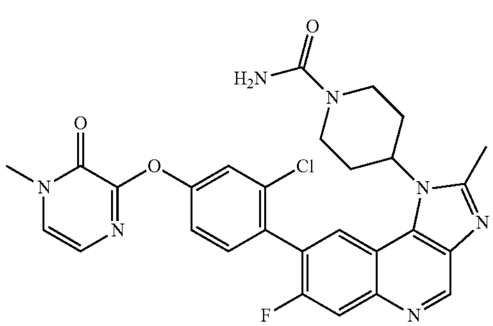 | ¹H NMR (DMSO-d₆, 400 MHz): δ 9.19 (s, 1H), 8.36 (m, 1H), 8.05 (d, 1H), 7.66 (m, 1H), 7.55 (m, 1H), 7.47 (d, 1H), 7.37 (d, 1H), 6.78 (s, 1H), 6.05-5.70 (m, 2H), 5.15-5.20 (m, 2H), 4.19 (d, 2H), 3.52 (s, 3H), 2.92-2.89 (m, 2H), 2.77 (s, 3H), 2.33 (m, 1H), 2.11-2.19 (m, 2H); LCMS: 96.41%, m/z = 562.1 (M + 1); HPLC: 97.48%, rt: 3.46 min. | 0.0045 | 1 |

TABLE 1.2-continued

| Example | Structure | 1H NMR, LCMS, HPLC, rt | IC50 μM Cascade MEK1 | HPLC method |
|---|---|---|---|---|
| 83 | 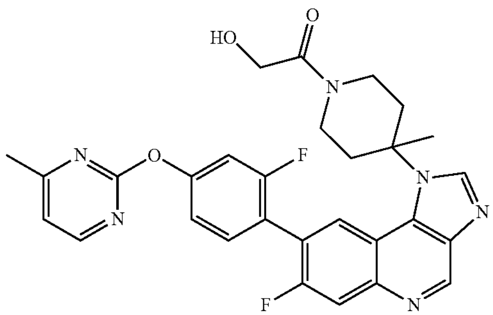 [SMILES: Cc1ccnc(Oc2ccc(-c3cc4c(cc3F)ncc3ncn(C5(C)CCN(C(=O)CO)CC5)c34)c(F)c2)n1] | ¹H NMR (DMSO-d₆, 300 MHz): δ 9.35 (s, 1H), 8.73 (s, 1H), 8.52 (t, 2H), 8.13 (d, 1H), 7.73 (t, 1H), 7.40 (d, 1H), 7.24 (t, 2H), 4.48 (t, 1H), 4.10 (d, 1H), 3.69 (d, 1H), 3.60-3.35 (m, 4H), 2.73-2.58 (m, 2H), 2.47 (s, 3H), 2.35-2.20 (m, 2H), 1.97 (s, 3H); LCMS: 68.16%, m/z = 544.85 (M + 1); HPLC: 98.85%, rt: 3.74 min. | 0.047 | 1 |
| 84 | 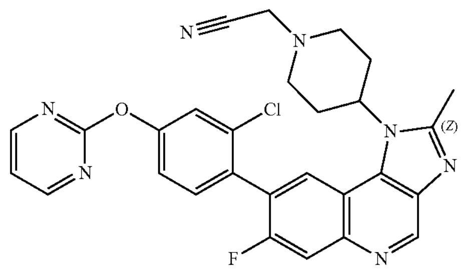 | 1H NMR (DMSO-d₆, 400 MHz): δ 9.21 (s, 1H), 8.73 (d, 2H), 8.06 (d, 1H), 7.73 (s, 1H), 7.64 (d, 1H), 7.43 (dd, 2H), 7.37 (t, 1H), 4.90 (s, 1H), 3.70 (s, 2H), 3.02 (d, 3H), 2.77 (s, 3H), 2.50-2.40 (m, 2H), 2.11 (s, 3H); LCMS: m/z = 96.73%, 528.1 (M + 1); HPLC: 96.48%, rt: 4.04 min. | 0.022 | 2 |
| 85 | 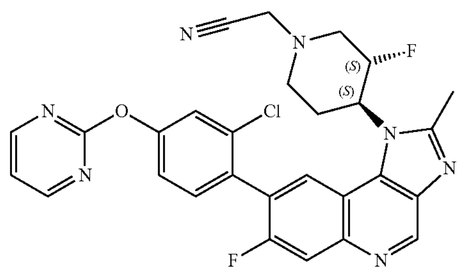 | 1H NMR (CDCl₃, 400 MHz): δ 9.33 (s, 1H), 8.70 (d, 1H), 8.63 (d, 2H), 8.08 (d, 1H), 7.53 (dd, 1H), 7.46 (d, 1H), 7.29 (d, 1H), 7.16 (, 1H), 5.70 (, 1H), 4.68 (q, 1H), 3.58-3.30 (m, 3H), 3.02 (s, 2H), 2.78 (s, 3H), 2.78-2.65 (m, 2H), 2.21 (dt, 1H); LCMS: m/z = 91.66%, 546.1 (M + 1); HPLC: 98.87%, rt: 4.65 min; 0.01% TFA in water, ACN:MeOH (1:1), Column: AG/C18/15-016. | 0.011 | 2 |
| 86 | 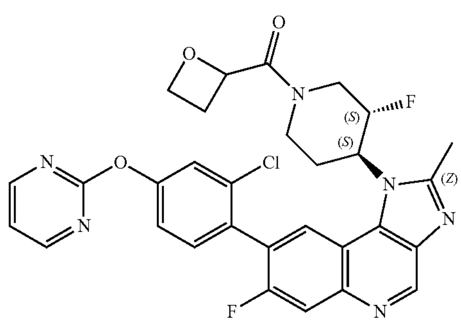 | ¹HNMR (DMSO-d₆, 300 MHz): δ 9.22 (d, 1H), 8.73 (d, 1.7H), 8.61 (d, 0.3H), 8.12-7.91 (m, 2H), 7.80-7.54 (m, 2H), 7.43 (dd, 1H), 7.37 (t, 1H), 5.72-5.50 (m, 1H), 5.41-5.15 (m, 2H), 4.61-4.45 (m, 3H), 3.82-3.65 (m, 1H), 3.13-2.95 (m, 2H), 2.85-2.80 (m, 2H), 2.76 (s, 3H), 2.37-2.21 (m, 2H); LCMS: 100%, m/z = 591.0 (M+); HPLC: 98.85%, rt: 4.41 min. | 0.011 | 1 |
| 87 | 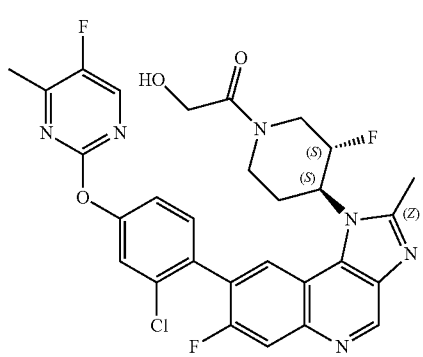 | ¹HNMR (CDCl₃, 300 MHz): δ 9.32 (s, 1H), 8.30 (s, 1H), 8.06 (d, 1H), 7.95-7.86 (m, 1H), 7.58-7.35 (m, 2H), 7.30-7.26 (m, 1H), 5.71-5.08 (m, 2H), 4.96-4.70 (m, 1H), 4.32-4.05 (m, 2H), 3.85-3.68 (m, 1H), 3.64-3.52 (m, 1H), 3.35-3.13 (m, 1H), 3.00-2.87 (m, 2H), 2.79 (s, 3H), 2.56 (d, 3H), 2.28-2.10 (m, 1H); LCMS: 98.34%, m/z = 597.1 (M + 1); HPLC: 98.81%, rt: 3.95 min. | 0.0062 | 3 |

TABLE 1.2-continued

| Example | Structure | 1H NMR, LCMS, HPLC, rt | IC50 μM Cascade MEK1 | HPLC method |
|---|---|---|---|---|
| 88 | 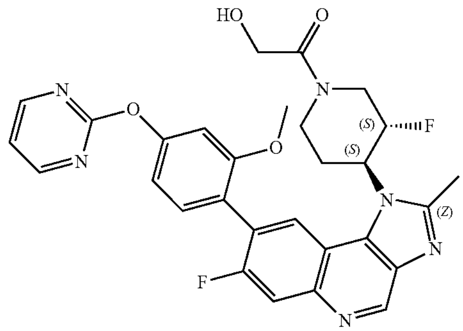 | 1HNMR (CDCl₃, 400 MHz): δ 9.31 (s, 1H), 8.65 (d, 2H), 8.03 (d, 2H), 7.44-7.35 (m, 1H), 7.12 (t, 1H), 7.02-6.96 (m, 2H), 5.83-5.58 (m, 1H), 5.20-4.67 (m, 2H), 4.32-4.01 (m, 2H), 3.85 (s, 3H), 3.78-3.67 (m, 1H), 3.35-3.11 (m, 1H), 3.08-2.82 (m, 2H), 2.80 (s, 3H), 2.50-2.22 (m, 1H), 2.21-1.98 (m, 1H); LCMS: 99.03%, m/z = 561.2 (M + 1); HPLC: 98.83%, rt: 3.20 min. | 0.0057 | 1 |
| 89 | 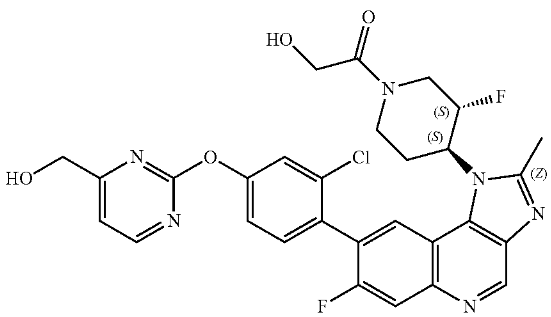 | ¹HNMR (CDCl₃, 400 MHz): δ 9.39 (s, 1H), 8.23 (d, 1H), 8.09 (d, 1H), 8.01-7.82 (m, 1H), 7.52 (s, 1H), 7.51-7.36 (m, 1H), 7.31 (d, 1H), 7.12 (d, 1H), 5.65-5.20 (m, 2H), 4.90-4.71 (m, 2H), 4.69 (d, 2H), 4.31-4.18 (m, 1H), 4.17-4.09 (m, 1H), 3.85-3.75 (m, 1H), 3.35-3.18 (m, 1H), 2.98-2.81 (m, 2H), 2.80 (s, 3H), 2.45-2.25 (m, 1H), 2.24-2.12 (m, 1H); LCMS: 98.12%, m/z = 595.1 (M + 1); HPLC: 95.34%, rt: 3.37 min. | 0.0026 | 1 |
| 90 | 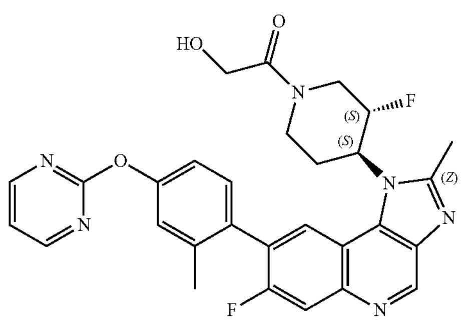 | ¹HNMR (CDCl₃, 300 MHz): δ 9.32 (s, 1H), 8.64 (d, 2H), 8.05 (d, 1H), 7.86 (d, 1H), 7.25-7.16 (m, 3H), 7.11 (t, 1H), 5.62-5.21 (m, 2H), 4.96-4.68 (m, 1H), 4.31-4.05 (m, 1H), 4.01-3.60 (m, 2H), 3.48-3.12 (m, 1H), 3.05-2.86 (m, 1H), 2.86 (s, 3H), 2.36 (s, 3H), 2.32-2.10 (m, 2H); LCMS: 99.20%, m/z = 545.2 (M + 1); HPLC: 98.15%, rt: 3.80 min. | 0.0026 | 1 |
| 91 | 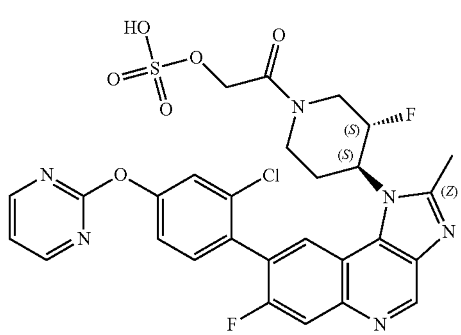 | ¹HNMR (DMSO-d₆, 600 MHz): δ 9.28 (d, 1H), 8.80-8.72 (m, 1.5H), 8.65 (d, 0.5H), 8.12-7.98 (m, 1.5H), 7.92-7.80 (m, 0.5H), 7.23 (d, 0.5H), 7.67 (d, 0.5H), 7.57-7.49 (m, 0.5H), 7.46-7.42 (m, 0.5H), 7.39-7.31 (m, 1H), 7.28-7.23 (m, 0.5H), 7.20-7.12 (m, 0.5H), 5.68-5.56 (m, 1H), 5.54-5.46 (m, 0.5H), 5.27-5.13 (m, 1H), 4.89-4.77 (m, 0.5H), 4.64-4.56 (m, 0.5H), 4.50-4.40 (m, 2H), 4.37-4.22 (m, 0.5H), 4.17-4.03 (m, 0.5H), 3.10-2.93 (m, 1H), 2.82 (s, 2H), 2.76 (s, 1H), 2.35-2.15 (m, 2H); LCMS: 100%, m/z = 645.3 (M+); HPLC: 93.03%, rt: 3.36 min. | 0.018 | 3 |

TABLE 1.2-continued

| Example | Structure | 1H NMR, LCMS, HPLC, rt | IC50 μM Cascade MEK1 | HPLC method |
|---|---|---|---|---|
| 92 | 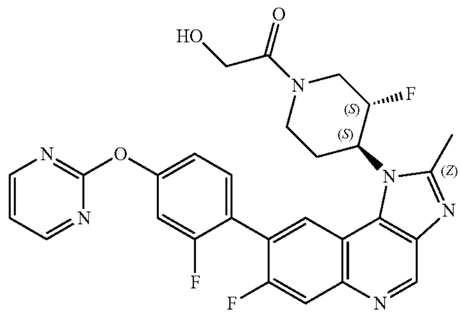 | ¹HNMR (CDCl₃, 300 MHz): δ 9.32 (s, 1H), 8.66 (d, 2H), 8.09 (dd, 2H), 7.57 (t, 1H), 7.21-7.13 (m, 3H), 5.71-5.15 (m, 2H), 5.10-4.65 (m, 1H), 4.42-4.05 (m, 2H), 4.01-3.63 (m, 1H), 3.55-3.10 (m, 1H), 3.08-2.90 (m, 1H), 2.81 (s, 3H), 2.50-1.97 (m, 2H); LCMS: 92.79%, m/z = 549.2 (M + 1); HPLC: 96.64%, rt: 4.13 min. | 0.032 | 1 |
| 93 | 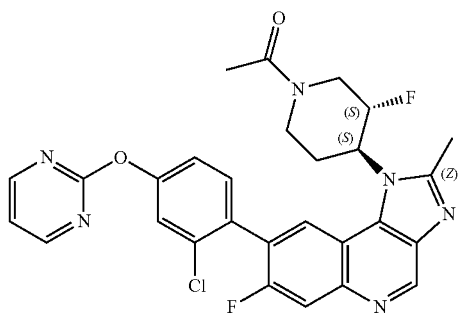 | ¹H NMR (DMSO-d₆, 400 MHz): δ 9.23 (s, 1H), 8.71 (d, 2H), 8.30 (s, 1H), 8.10-7.95 (m, 2H), 7.730-7.50 (m, 2H), 7.45-7.25 (m, 2H), 5.60-5.40 (m, 1H), 5.22-5.07 (m, 1H), 4.60-4.38 (m, 1H), 2.81 (s, 3H), 2.74 (s, 3H), 2.35-2.05 (m, 2H), 1.89-1.68 (m, 2H); LCMS: 97.71%, m/z = 549.3 (M + 1); HPLC: 96.77%, rt: 4.14 min. | 0.025 | 1 |
| 94 | 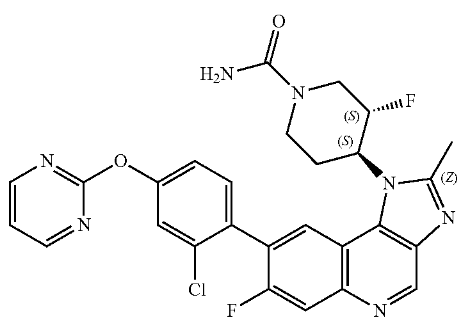 | ¹H NMR (CDCl₃, 400 MHz): δ 9.33 (s, 1H), 8.60 (d, 2H), 8.10-8.02 (m, 2H), 7.52 (d, 1H), 7.42 (s, 1H), 7.35-7.28 (m, 1H), 7.14 (t, 1H), 5.70-5.40 (m, 1H), 5.00 (s, 2H), 4.82-4.45 (m, 2H), 4.40-3.95 (m, 1H), 3.95-2.85 (m, 3H), 2.79 (s, 3H), 2.22-2.08 (m, 1H); LCMS: 97.71%, m/z = 550.2 (M + 1); HPLC: 99.09%, rt: 3.49 min. | 0.0027 | 1 |
| 95 | 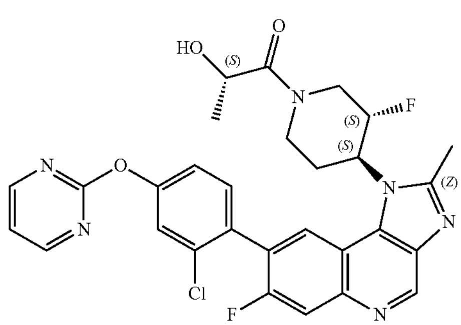 | ¹H NMR (DMSO-d₆, 400 MHz): δ 9.29 (s, 1H), 8.70 (d, 2H), 8.01 (d, 2H), 7.70-7.46 (m, 2H), 7.42-7.25 (m, 2H), 5.65-5.02 (m, 2H), 4.83-70 (m, 1H), 4.62-4.25 (m, 2H), 3.28-3.05 (m, 2H), 2.78 (s, 3H), 2.67-2.64 (m, 1H), 2.54-2.50 (m, 1H), 2.45-2.40 (m, 1H), 2.37-2.23 (m, 2H), 2.05-1.92 (m, 1H); LCMS: 98.84%, m/z = 578.75 (M+); HPLC: 98.71%, rt: 4.15 min | 0.0073 | 1 |

TABLE 1.2-continued

| Example | Structure | 1H NMR, LCMS, HPLC, rt | IC50 μM Cascade MEK1 | HPLC method |
|---|---|---|---|---|
| 96 | 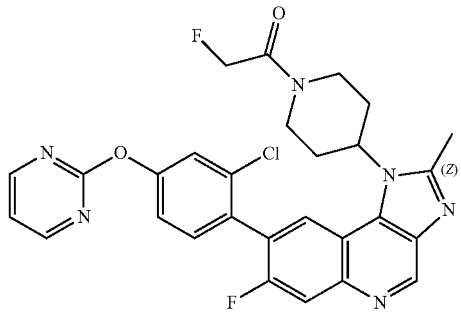 | ¹H NMR (CDCl₃, 400 MHz): δ 9.27 (s, 1H), 8.63 (d, 2H), 8.27 (d, 1H), 8.06 (d, 1H), 7.57-7.47 (m, 2H), 7.31 (dd, 1H), 7.13 (t, 1H), 5.38-5.21 (m, 1H), 5.10-4.88 (m, 3H), 4.22-4.10 (m, 1H), 3.37-3.23 (m, 1H), 2.92-2.83 (m, 2H), 2.81 (s, 3H), 2.48-2.21 (m, 3H); LCMS: 99.01%, m/z = 549.1 (M + 1); HPLC: 95.02%, rt: 3.95 min. | 0.04 | 1 |
| 97 | 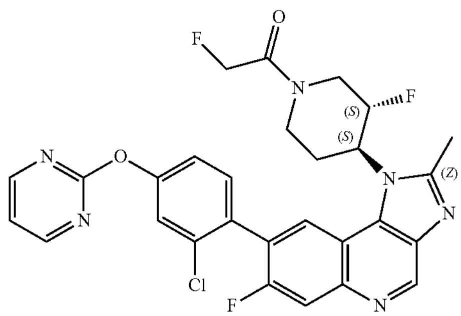 | ¹H NMR (CDCl₃, 300 MHz): δ 9.31 (s, 1H), 8.62 (d, 2H), 8.32 (d, 1H), 8.11-7.90 (m, 2H), 7.54-7.36 (m, 1H), 7.35-7.27 (m, 1H), 7.12 (t, 1H), 5.60-5.32 (m, 1H), 5.30-5.07 (m, 1H), 4.99-4.65 (m, 2H), 4.63-4.37 (m, 1H), 4.30-4.04 (m, 1H), 3.45-3.14 (m, 1H), 3.05-2.85 (m, 1H), 2.79 (s, 3H), 2.44-2.32 (m, 1H), 2.26-2.13 (m, 1H); LCMS: 96.27%, m/z = 567.0 (M + 1); HPLC: 98.21%, rt: 6.96 min. | 0.011 | 1 |
| 98 | 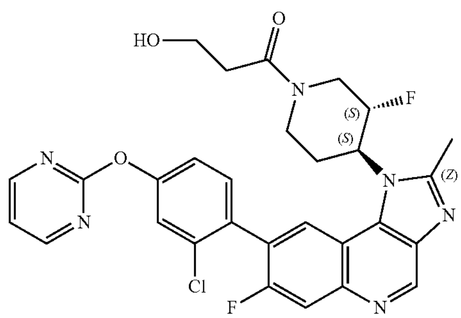 | ¹HNMR (CDCl₃, 400 MHz): δ 9.29 (d, 1H), 8.63 (d, 2H), 8.30 (d, 0.5H), 8.05 (d, 1H), 8.00 (d, 0.5H), 7.99 (d, 1H), 7.56 (d, 0.5H), 7.47 (d, 1.5H), 7.29 (d, 1H), 7.13 (t, 1H), 5.61-5.15 (m, 2H), 5.13-4.85 (m, 1H), 4.81-4.59 (m, 1H), 4.52-4.31 (m, 1H), 4.19-4.01 (m, 1H), 3.93 (brs, 1H), 3.79-3.41 (m, 1H), 3.39-3.10 (m, 1H), 3.00-2.87 (m, 2H), 2.83 (s, 3H), 2.68-2.48 (m, 2H); LCMS: 97.88%, m/z = 580.05 (M + 1); HPLC: 98.68%, rt: 3.58 min. | 0.04 | 1 |
| 99 | 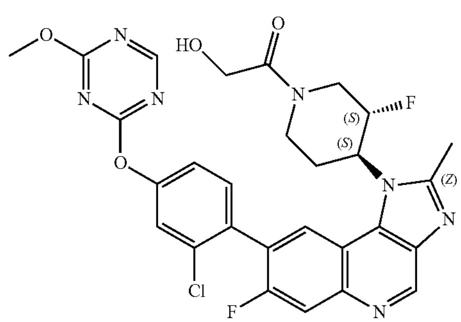 | ¹HNMR (CDCl₃, 400 MHz): δ 9.32 (s, 1H), 8.73 (s, 1H), 8.09 (d, 1H), 7.92 (brs, 1H), 7.55-7.45 (m, 2H), 7.31 (dd, 1H), 5.81-5.23 (m, 2H), 5.10-4.72 (m, 1H), 4.28-4.10 (m, 1H), 4.09 (s, 3H), 3.90-3.75 (m, 1H), 3.45 (brs, 1H), 3.39-3.15 (m, 1H), 3.10-2.91 (m, 1H), 2.82 (s, 3H), 2.50-2.15 (m, 2H); LCMS: 100%, m/z = 596.2 (M + 1); HPLC: 97.88%, rt: 3.83 min. | 0.0085 | 1 |

Assays

Compounds of the invention were assessed for their ability to inhibit MEK activity. The inhibitory properties of the compounds of the invention described herein can be evidenced by testing in any one of the following assays.

[MEK1 1 mM ATP 1050 uM]

A BRAF-MEK-ERK cascade assay is used to evaluate the effects of these compounds as inhibitors of the MAP kinase pathway. An enzymatic cascade assay is set up using recombinant human activated BRAF (V599E) kinase (Cat No. 14-557), human full length MEK1 kinase (Cat No. 14-706) and human full length active MAP Kinase 2/ERK2 (Cat No. 14-536) enzymes procured from Upstate. TR-FRET (Time resolved fluorescence resonance energy transfer) detection technology is used for the read out. The assay buffer solution contains 50 mM Tris pH 7.5, 10 mM MgCl2, 1 mM DTT, 0.01% Tween 20, 0.1 nM activated BRAF, 2 nM inactive MEK1, 10 nM inactive ERK2, 1 mM ATP and 500 nM long chain biotin-peptide substrate (LCB-FFKNIVTPRTPPP) in a 384 well format. The kinase reaction is stopped after 90 minutes with 10 mM EDTA and Lance detection mix (2 nM Eu-labeled phospho-serine/threonine antibody (Cat. No.

AD0176-Perkin Elmer), 20 nM SA-APC (Cat No. CR130-100-Perkin Elmer) is added. The TR-FRET signal (Excitation at 340 nm, Emission at 615 nm and 665 nm) is read with 50 μs delay time on a Victor3 V fluorimeter. The data is calculated using the ratio of readings at 665 nm to 615 nm. The final concentration of DMSO is 2.5% in the assay. Compounds are screened at 10 μM concentration with pre-incubation of the enzymes in the presence of test compound for 45 minutes.

Each individual $IC_{50}$ is determined using a 10 point dose response curve generated by GraphPad Prism software Version 4 (San Diego, Calif., USA) using non linear regression curve fit for sigmoidal dose response (variable slope). The $IC_{50}$ values obtained for the compounds of the invention are listed in Table 1.2 above.

An in-vitro MAP kinase assay is set up using activated MAP kinase 2/ERK2 (Cat. No. 14-550) obtained from Upstate. TR-FRET detection technology is used for the read out.

The assay buffer solution contains 50 mM Tris pH 7.5, 10 mM $MgCl_2$, 1 mM DTT, 0.01% Tween 20, 1 nM activated ERK2, 100 μM ATP and 500 nM long chain biotin-peptide substrate (LCB-FFKNIVTPRTPPP) in a 384 well format. The kinase reaction is stopped after 90 minutes with 10 mM EDTA and Lance detection mix (2 nM Eu-labeled phosphoserine/threonine antibody (Cat. No. AD0176-Perkin Elmer), 20 nM SA-APC (Cat. No. CR130-100-Perkin Elmer) is added. The TR-FRET signal (excitation at 340 nm, emission at 615 nm and 665 nm) is read with 50 μs delay time on Victor3 V fluorimeter. The data is calculated using the ratio of readings at 665 nm to 615 nm. The final concentration of DMSO is 2.5% in the assay. Compounds are screened at 10 μM concentration with pre-incubation of the enzymes in the presence of test compound for 45 minutes. Compounds of the invention were found to be inactive in this assy, e.g. ex. 14 (16% inhibition at 10 uM), ex. 1A (55% inhibition at 10 uM).

The radioactive filter binding assay is standardized using recombinant human activated BRAF (V599E) kinase (Cat No. 14-557) and kinase dead MEK1 (K97R) (Cat No. 14-737) procured from Upstate. The incorporation of 32P into MEK1 (K97R) by BRAF (V599E) is measured with final assay buffer conditions of 50 mM Tris pH 7.5, 10 mM MgCl2, 1 mM DTT, 100 mM sucrose, 100 μM sodium orthovanadate, 5 μM ATP and 2 μCi [γ 32P] ATP and 500 mg MEK1 Kinase dead substrate. The enzymatic reaction is stopped after 120 minutes with 8N HCl (hydrochloric acid) and 1 mM ATP. The solution is spotted on P81 filter paper and washed 4 times with 0.75% orthophosphoric acid and lastly with acetone. The dried P81 filter papers are read in a Micro-beta Trilux scintillation counter. The final concentration of DMSO is 1% in the assay. Compounds are screened at 10 μM concentration with pre-incubation of the enzymes in the presence of test compound for 45 minutes. Compounds of the invention were found to be inactive in this assy, e.g. ex. 33 (13% inhibition at 10 uM), ex. 1A (0% inhibition at 10 uM).

These assays described above are fully detailed in Han, Shulin, et. al., Bioorganic & Medicinal Chemistry Letters (2005) 15, 5467-5473, and in Yeh, et. al., Clin Cancer Res (2007) 13 (5), 1576-1583.

The cell viability assay in A375 cells (A375 ICW IC50 in Table 2) is set up in a 96-well plate format using XTT. XTT is a yellow tetrazolium salt that is cleaved to an orange formazan dye by the mitochondria of metabolically active cells. The procedure allows for rapid determination in a microtitre plate, to give reproducible and sensitive results.

A375 cells are grown in DMEM media containing 10% FBS and 1 mM sodium pyruvate. Cells are trypsinized and seeded at 1000 cells/well. After allowing the cells to adhere overnight, compound is added to the wells at the following final concentrations: 10, 3, 1, 0.3, 0.1, 0.03, 0.01, 0.001, and 0.0001 μM. The assay is set up in triplicates for each concentration. DMSO concentrations are kept at 0.5%/well. Three days after compound addition, the XTT assay is performed. Wells are washed once with PBS. 100 μL of DMEM media without phenol red or FBS is added to each well. A working solution of XTT containing 1 mg/ml XTT and 100 μL of PMS (stock concentration 0.383 mg/ml) per 5 ml is prepared. 50 μL of the working solution of XTT is added to each well. Absorbance of the plate is read at 465 nm using a Spectramax 190 (Molecular Devices). The absorbance from wells with media and XTT alone, but without cells is considered the blank and subtracted from readings from all wells. The cell viability assay is further described in Scudiero, et. al., Cancer Research (1988) 48, 4827-4833; Weislow, et. al., J. Natl. Cancer Institute, (1989) 81, 577-586; and Roehm, et. al., J. Immunol. Methods [1991]142:257-265. The $IC_{50}$ values obtained for the compounds of the invention are listed in Table 2 below.

TABLE 2

All $IC_{50}$ values are in uM.

| Example | MEK1 1 mM ATP IC50 | A375 ICW IC50 | A375 XTT IC50 uM |
|---|---|---|---|
| 1A | 0.005 | 0.0039 | 0.003 |
| 1B | 0.138 | | |
| 2 | 0.726 | 3.27 | 2.41 |
| 3 | 0.104 | 0.652 | 0.368 |
| 4 | 0.309 | | |
| 5 | 0.04 | 0.28 | 0.321 |
| 6 | 0.062 | 0.267 | 0.232 |
| 7 | 0.468 | | |
| 8 | 0.015 | 0.34 | 0.319 |
| 9 | 0.103 | 0.744 | 0.755 |
| 10 | 0.213 | 2.62 | 2.09 |
| 11 | 2.35 | >10 | 6.55 |
| 12 | 0.212 | 0.712 | 0.414 |
| 13 | 0.515 | 1.88 | 1.11 |
| 14 | 0.0071 | 0.053 | 0.076 |
| 15 | 0.016 | 0.118 | 0.088 |
| 16 | 0.059 | 0.667 | 0.587 |
| 17 | 0.093 | 0.224 | 0.132 |
| 18 | 0.013 | 0.247 | 0.14 |
| 19 | 0.333 | 1.7 | 0.643 |
| 20 | 0.157 | 0.669 | 0.683 |
| 21 | 0.028 | 0.071 | 0.085 |
| 22 | 1.346 | >10 | >10 |
| 23 | 0.322 | | |
| 24 | 0.021 | 0.22 | 0.161 |
| 25 | 0.655 | 3.05 | 1.72 |
| 26 | 0.0043 | 0.004 | 0.011 |
| 27 | 0.073 | 0.365 | 0.362 |
| 28 | 0.0037 | 0.0047 | 0.0048 |
| 29 | 0.019 | 0.081 | 0.091 |
| 30 | 0.011 | 0.017 | 0.014 |
| 31 | 0.003 | 0.006 | 0.0047 |
| 32 | 0.032 | 0.1 | 0.094 |
| 33 | 0.028 | 0.06 | 0.054 |
| 34 | 0.088 | 0.151 | 0.212 |
| 35 | 0.019 | 0.018 | 0.026 |
| 36 | 0.026 | 0.044 | 0.091 |
| 37 | 0.0027 | 0.009 | 0.008 |
| 38 | 0.0046 | 0.063 | 0.119 |
| 39 | 0.455 | | |
| 40 | 0.186 | | |
| 41 | 0.022 | 0.62 | 2.8 |
| 42 | 0.085 | 0.239 | 0.208 |
| 43A | 0.06 | 0.848 | 0.677 |
| 43B | 0.547 | 3.8 | 2.38 |
| 44 | 0.002 | 0.026 | 0.011 |
| 45 | 0.191 | >10 | 4.27 |
| 46 | 0.01 | 0.206 | 2.63 |
| 47 | 0.0017 | 0.016 | 0.011 |

TABLE 2-continued

All IC$_{50}$ values are in uM.

| Example | MEK1 1 mM ATP IC50 | A375 ICW IC50 | A375 XTT IC50 uM |
|---|---|---|---|
| 48 | 0.011 | 0.044 | 0.025 |
| 49 | 0.232 | 0.019 | 0.034 |
| 50 | 0.012 | 0.072 | 0.067 |
| 51 | 0.001 | 0.021 | 0.004 |
| 52 | 0.009 | 0.109 | 0.159 |
| 53 | 0.0062 | 0.029 | 0.012 |
| 54 | 0.0015 | 0.042 | 0.025 |
| 55 | 0.047 | 0.231 | 0.319 |
| 56 | 0.28 | | |
| 57 | 0.019 | 0.089 | 0.041 |
| 58 | 0.003 | 0.014 | 0.008 |
| 59 | 0.018 | 0.609 | 1.6 |
| 60 | 0.113 | 0.499 | 1.71 |
| 61 | 0.211 | 0.168 | 0.193 |
| 62 | 0.0037 | 0.049 | 0.055 |
| 63 | 0.0085 | 0.245 | 0.714 |
| 64 | 0.0053 | 0.007 | 0.016 |
| 65 | 0.0024 | 0.005 | 0.004 |
| 66 | 0.01 | | |
| 67 | 0.053 | 0.539 | 0.281 |
| 68 | 0.0047 | 0.007 | 0.0025 |
| 69 | 0.059 | 0.272 | 0.708 |
| 70 | 0.0043 | 0.033 | 0.06 |
| 71 | 0.039 | 0.076 | 0.144 |
| 72 | 0.045 | 0.197 | 0.623 |
| 73 | 0.0036 | 0.175 | 0.254 |
| 74 | 0.01 | 1.55 | 3.64 |
| 75 | 0.0038 | 0.259 | 0.194 |
| 76 | 0.04 | 0.022 | 0.013 |
| 77 | 0.08 | 0.065 | 0.09 |
| 78 | 0.179 | | |
| 79 | 0.0092 | 0.007 | 0.0056 |
| 80 | 0.013 | 0.06 | 0.08 |
| 81 | 0.007 | 0.381 | 1.148 |
| 82 | 0.0045 | 2.18 | 2.33 |
| 83 | 0.047 | 0.088 | 0.301 |
| 84 | 0.022 | 0.058 | 0.225 |
| 85 | 0.011 | 0.016 | 0.021 |
| 86 | 0.011 | 0.176 | 0.175 |
| 87 | 0.0062 | 0.029 | 0.012 |
| 88 | 0.0057 | 0.053 | 0.108 |
| 89 | 0.0026 | 0.04 | 0.045 |
| 90 | 0.0026 | 0.019 | 0.02 |
| 91 | 0.018 | >10 | >10 |
| 92 | 0.032 | 0.145 | 0.135 |
| 93 | 0.025 | 0.064 | 0.061 |
| 94 | 0.0027 | 0.006 | 0.005 |
| 95 | 0.0073 | 0.027 | 0.031 |
| 96 | 0.04 | 0.359 | 0.394 |
| 97 | 0.011 | 0.112 | 0.09 |
| 98 | 0.04 | 0.547 | 0.557 |
| 99 | 0.0085 | 0.035 | 0.531 |

Percentage viability is calculated considering the blank subtracted value from wells treated with DMSO alone as 100% viable. IC$_{50}$ values are calculated using Graphpad Prism, using non-linear regression curve fit for sigmoidal dose response (variable slope). Compounds of the invention were evaluated in this cell viability assay. The IC$_{50}$ values obtained for the compounds of the invention are listed in Table 2 above.

A375 P-Erk (In-Cell-Western) (A375 ICW IC50 in Table 2):

Human melanoma A375 cells were seeded at 50,000 cells per well in 100 µl growth medium in Costar 96 well black clear bottom plates and placed at 37° C./5% CO$_2$ over night. Test compounds were diluted in DMSO to generate a concentration curve. A 5 mM stock was used for the highest concentration at 500 times; to yield a final concentration of 10 µM with 3-fold dilutions down to 0.0001 µM. 1 µl of diluted compound was added to 500 µl cell culture media and mixed well. Media was removed from cells and 200 µl of media containing compound was added. Cells were treated for 3 hrs with compound at 37° C., 5% CO$_2$.

After the compound incubation, cells were washed once with PBS (Mg and fixed in 4% paraformaldehyde/PBS for 1 hr at room temperature. Following fixation, cells were washed three times with PBS/0.1% TritonX-100(PBST), and then blocked with 5% skimmed milk/PBST, for 1-2 hr. 50 µL per well primary antibody was added (rabbit-anti-phospho-ERK1/2) at 1:500 in 5% skimmed milk/PBST and incubated overnight at 4° C. Cells were washed four times with 100 µl DELFIA wash buffer and 50 µL per well secondary antibody was added (DELFIA-EU-N-1-labeled anti-rabbit antibody) at 1:3000 in DELFIA assay buffer and incubated for 2 hr at room temperature in the dark (covered). Cells were washed 4× with 100 ml DELFIA wash buffer. 50 µL per well Wallac-DELFIA enhancement solution was added. Plates were shaken at room temperature for 20 min and then read on the Perkin Elmer Victor3v reader on the Europium setting (emission/excitation of 615/340 nm).

IC$_{50}$ values were calculated using DMSO diluent values as 0% inhibition and counts of the highest tested concentration of the reference inhibitor as 100% inhibition. All the concentrations along with DMSO were done in triplicates. The IC$_{50}$ *values*s obtained for the compounds of the invention are listed in table 2.

It is understood that the examples and embodiments described herein are for illustrative purposes only and that various modifications or changes in light thereof will be suggested to persons skilled in the art and are to be included within the spirit and purview of this application and scope of the appended claims.

We claim:

1. A compound of formula I:

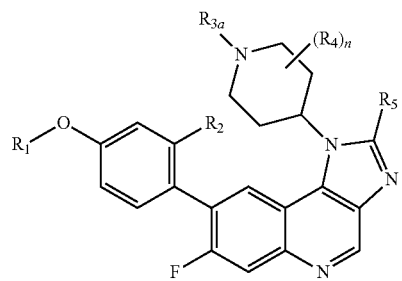

wherein n is selected from 0, 1, 2 and 3;

R$_1$ is selected from:

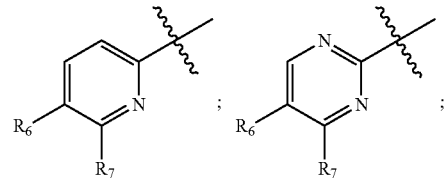

-continued

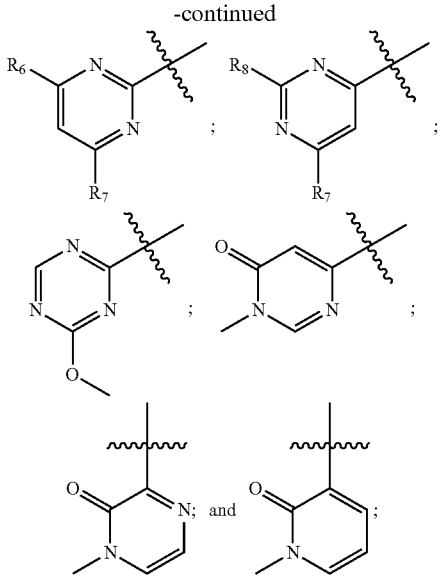

R$_2$ is selected from chloro, methyl, hydrogen, fluoro and methoxy;
R$_{3a}$ is selected from cyano-methyl, 2-hydroxy-ethyl, 1-hydroxypropan-2-yl, 3-hydroxy-2-(hydroxy-methyl)propanoyl, 2-methoxy-ethyl, 2-fluoropropanoyl, (3-methyloxetan-3-yl)-methyl, methyl-sulfonyl, amino-carbonyl-methyl, cyclopropyl-sulfonyl, isopropyl-sulfonyl, dimethylcarbamoyl, 3-hydroxy-2-(hydroxy-methyl)propyl, 2-hydroxy-propyl, 2-hydroxyacetyl, 2-acetoxyacetyl, 2-methoxyacetyl, (2,2,2-trifluoroethyl)carbamoyl, 2-aminoacetyl, oxetan-3-ylmethyl, (S)-2-hydroxypropanoyl, 2-hydroxypropanoyl, acetyl, 2-amino-2-oxoethyl, carbamoyl, (oxetan-2-yl)-methanoyl, 2-(sulfooxy)acetyl, 2-fluoroethanoyl, 3-hydroxypropanoyl, and N,N-dimethylsulfonamidyl;
each R$_4$ is independently selected from hydrogen, halo, methyl and hydroxy-methyl; and
optionally two R$_4$ groups together with the carbon atoms to which they are attached form —(CH$_2$)$_{2-3}$—;
R$_5$ is selected from hydrogen and methyl;
R$_6$ is selected from hydrogen, methoxy and halo;
R$_7$ is selected from hydrogen, fluoro, CF$_3$, CH$_2$OH, cyclopropyl and methyl; and
R$_8$ is cyano;
or the pharmaceutically acceptable salts thereof.

2. The compound of claim 1, wherein:
n is selected from 0 or 1;
R$_1$ is selected from:

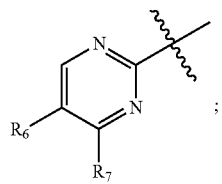

R$_2$ is selected from chloro, methyl, hydrogen, fluoro and methoxy;
R$_{3a}$ is selected from cyano-methyl, 3-hydroxy-2-(hydroxy-methyl)propanoyl, 2-methoxy-ethyl, 2-fluoropropanoyl, (3-methyloxetan-3-yl)-methyl, methyl-sulfonyl, amino-carbonyl-methyl, cyclopropyl-sulfonyl, isopropyl-sulfonyl, dimethylcarbamoyl, 2-hydroxyacetyl, 2-acetoxyacetyl, 2-methoxyacetyl, (2,2,2-trifluoroethyl)carbamoyl, 2-aminoacetyl, oxetan-3-ylmethyl, (S)-2-hydroxypropanoyl, 2-hydroxypropanoyl, acetyl, 2-amino-2-oxoethyl, carbamoyl, (oxetan-2-yl)-methanoyl, 2-(sulfooxy)acetyl, 2-fluoroethanoyl, 3-hydroxypropanoyl, and N,N-dimethylsulfonamidyl;
each R$_4$ is independently selected from halo, methyl and hydroxy-methyl;
R$_5$ is selected from hydrogen and methyl;
R$_6$ is selected from hydrogen and halo; and
R$_7$ is selected from hydrogen, fluoro, CF$_3$, CH$_2$OH, cyclopropyl and methyl;
or the pharmaceutically acceptable salts thereof.

3. The compound of claim 1, wherein:
n is selected from 0 or 1;
R$_1$ is selected from:

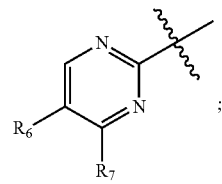

R$_2$ is selected from chloro, methyl, hydrogen, fluoro and methoxy;
R$_{3a}$ is selected from 3-hydroxy-2-(hydroxy-methyl)propanoyl, 2-fluoropropanoyl, methyl-sulfonyl, cyclopropyl-sulfonyl, isopropyl-sulfonyl, dimethylcarbamoyl, 2-hydroxyacetyl, 2-acetoxyacetyl, 2-methoxyacetyl, (2,2,2-trifluoroethyl)carbamoyl, 2-aminoacetyl, (S)-2-hydroxypropanoyl, 2-hydroxypropanoyl, acetyl, carbamoyl, 2-(sulfooxy)acetyl, 2-fluoroethanoyl, 3-hydroxypropanoyl, and N,N-dimethylsulfonamidyl;
each R$_4$ is independently selected from halo, methyl and hydroxy-methyl;
R$_5$ is selected from hydrogen and methyl;
R$_6$ is selected from hydrogen and halo; and
R$_7$ is selected from hydrogen, fluoro, CF$_3$, CH$_2$OH, cyclopropyl and methyl;
or the pharmaceutically acceptable salts thereof.

4. The compound of claim 1, wherein:
n is selected from 0 or 1;
R$_1$ is selected from:

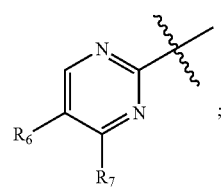

R$_2$ is selected from chloro and methoxy;
R$_{3a}$ is selected from 3-hydroxy-2-(hydroxy-methyl)propanoyl, 2-fluoropropanoyl, dimethylcarbamoyl, 2-hydroxyacetyl, 2-acetoxyacetyl, 2-methoxyacetyl, (2,2,2-trifluoroethyl)carbamoyl, 2-aminoacetyl, (S)-2-hydroxypropanoyl, 2-hydroxypropanoyl, acetyl, carbamoyl, 2-(sulfooxy)acetyl, 2-fluoroethanoyl and 3-hydroxypropanoyl;

each $R_4$ is independently selected from halo, methyl and hydroxy-methyl;

$R_5$ is selected from hydrogen and methyl;

$R_6$ is hydrogen; and $R_7$ is hydrogen;

or the pharmaceutically acceptable salts thereof.

5. The compound of claim 1 of formula Ie:

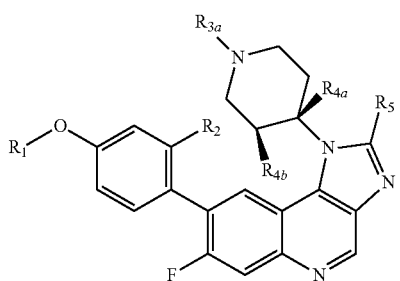

wherein:

$R_1$ is selected from:

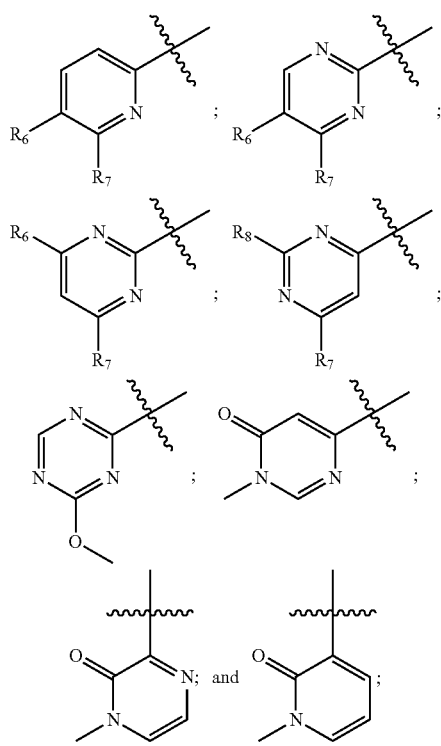

$R_2$ is selected from chloro, methyl, fluoro and methoxy;

$R_{3a}$ is selected from cyano-methyl, 2-hydroxy-ethyl, 1-hydroxypropan-2-yl, 3-hydroxy-2-(hydroxy-methyl)propanoyl, 2-methoxy-ethyl, 2-fluoropropanoyl, (3-methyloxetan-3-yl)-methyl, methyl-sulfonyl, amino-carbonyl-methyl, cyclopropyl-sulfonyl, isopropyl-sulfonyl, dimethylcarbamoyl, 3-hydroxy-2-(hydroxy-methyl)propyl, 2-hydroxy-propyl, 2-hydroxyacetyl, 2-acetoxyacetyl, 2-methoxyacetyl, (2,2,2-trifluoroethyl)carbamoyl, 2-aminoacetyl, oxetan-3-ylmethyl, (S)-2-hydroxypropanoyl, 2-hydroxypropanoyl, acetyl, 2-amino-2-oxoethyl, carbamoyl, (oxetan-2-yl)-methanoyl, 2-(sulfooxy)acetyl, 2-fluoroethanoyl, 3-hydroxypropanoyl, and N,N-dimethylsulfonamidyl;

$R_{4a}$ is selected from hydrogen and methyl;

$R_{4b}$ is selected from hydrogen and fluorine;

$R_5$ is selected from hydrogen and methyl;

$R_6$ is selected from hydrogen and fluoro;

$R_7$ is selected from hydrogen, fluoro, $CF_3$, $CH_2OH$, cyclopropyl and methyl; and $R_8$ is cyano;

or the pharmaceutically acceptable salts thereof.

6. The compound of claim 1 of formula Ie:

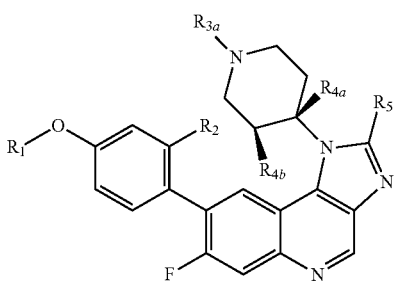

wherein $R_1$ is selected from:

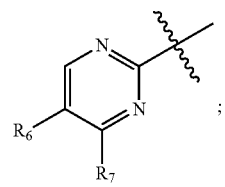

$R_2$ is selected from chloro, methyl, fluoro and methoxy;

$R_{3a}$ is selected from cyano-methyl, 3-hydroxy-2-(hydroxy-methyl)propanoyl, 2-methoxy-ethyl, 2-fluoropropanoyl, (3-methyloxetan-3-yl)-methyl, methyl-sulfonyl, amino-carbonyl-methyl, cyclopropyl-sulfonyl, isopropyl-sulfonyl, dimethylcarbamoyl, 2-hydroxyacetyl, 2-acetoxyacetyl, 2-methoxyacetyl, (2,2,2-trifluoroethyl)carbamoyl, 2-aminoacetyl, oxetan-3-ylmethyl, (S)-2-hydroxypropanoyl, 2-hydroxypropanoyl, acetyl, 2-amino-2-oxoethyl, carbamoyl, (oxetan-2-yl)-methanoyl, 2-(sulfooxy)acetyl, 2-fluoroethanoyl, 3-hydroxypropanoyl, and N,N-dimethylsulfonamidyl;

$R_{4a}$ is hydrogen;

$R_{4b}$ is fluorine;

$R_5$ is methyl;

$R_6$ is hydrogen and fluoro; and $R_7$ is selected from hydrogen, $CF_3$, $CH_2OH$, and methyl;

or the pharmaceutically acceptable salts thereof.

7. The compound of claim 1 of formula Ie:

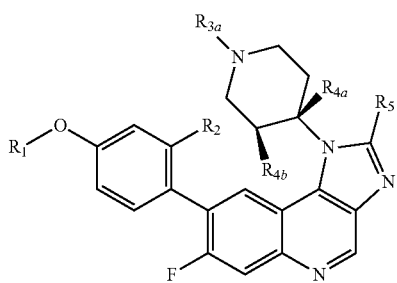

wherein
R₁ is selected from:

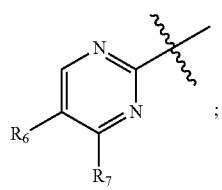

R₂ is selected from chloro, methyl, fluoro and methoxy;
R$_{3a}$ is selected from cyano-methyl, methyl-sulfonyl, 2-hydroxyacetyl, 2-acetoxyacetyl, 2-methoxyacetyl, (S)-2-hydroxypropanoyl, acetyl, carbamoyl, (oxetan-2-yl)-methanoyl, 2-(sulfooxy)acetyl, 2-fluoroethanoyl and 3-hydroxypropanoyl;
R$_{4a}$ is hydrogen;
R$_{4b}$ is fluorine;
R₅ is methyl;
R₆ is selected from hydrogen and fluoro; and
R₇ is selected from hydrogen, CF₃, CH₂OH, and methyl;
or the pharmaceutically acceptable salts thereof.

8. The compound of claim 1 selected from:
1-((3S,4S)-4-(8-(2-chloro-4-(pyrimidin-2-yloxy)phenyl)-7-fluoro-2-methyl-1H-imidazo[4,5-c]quinolin-1-yl)-3-fluoropiperidin-1-yl)-2-hydroxyethanone;
1-((3R,4R)-4-(8-(2-chloro-4-(pyrimidin-2-yloxy)phenyl)-7-fluoro-2-methyl-1H-imidazo[4,5-c]quinolin-1-yl)-3-fluoropiperidin-1-yl)-2-hydroxyethanone;
8-(2-chloro-4-(pyrimidin-2-yloxy)phenyl)-7-fluoro-1-(1-(2-methoxyethyl)piperidin-4-yl)-2-methyl-1H-imidazo[4,5-c]quinolone;
2-(4-(8-(2-chloro-4-(pyrimidin-2-yloxy)phenyl)-7-fluoro-2-methyl-1H-imidazo[4,5-c]quinolin-1-yl)piperidin-1-yl)ethanol;
8-(2-chloro-4-(pyrimidin-2-yloxy)phenyl)-7-fluoro-2-methyl-1-(1-((3-methyloxetan-3-yl)methyl)piperidin-4-yl)-1H-imidazo[4,5-c]quinolone;
8-(2-chloro-4-(pyrimidin-2-yloxy)phenyl)-7-fluoro-2-methyl-1-(1-(methylsulfonyl)piperidin-4-yl)-1H-imidazo[4,5-c]quinolone;
1-(4-(8-(2-chloro-4-(pyrimidin-2-yloxy)phenyl)-7-fluoro-2-methyl-1H-imidazo[4,5-c]quinolin-1-yl)piperidin-1-yl)-2-hydroxypropan-1-one;
1-(4-(8-(2-chloro-4-(pyrimidin-2-yloxy)phenyl)-7-fluoro-2-methyl-1H-imidazo[4,5-c]quinolin-1-yl)piperidin-1-yl)propan-2-ol;
8-(2-chloro-4-(pyrimidin-2-yloxy)phenyl)-1-(1-(cyclopropylsulfonyl)piperidin-4-yl)-7-fluoro-2-methyl-1H-imidazo[4,5-c]quinolone;
8-(2-chloro-4-(pyrimidin-2-yloxy)phenyl)-7-fluoro-1-(1-(isopropylsulfonyl)piperidin-4-yl)-2-methyl-1H-imidazo[4,5-c]quinolone;
4-(8-(2-chloro-4-(pyrimidin-2-yloxy)phenyl)-7-fluoro-2-methyl-1H-imidazo[4,5-c]quinolin-1-yl)-N,N-dimethylpiperidine-1-sulfonamide;
4-(8-(2-chloro-4-(pyrimidin-2-yloxy)phenyl)-7-fluoro-2-methyl-1H-imidazo[4,5-c]quinolin-1-yl)-N,N-dimethylpiperidine-1-carboxamide;
1-(4-(8-(2-chloro-4-(pyrimidin-2-yloxy)phenyl)-7-fluoro-2-methyl-1H-imidazo[4,5-c]quinolin-1-yl)piperidin-1-yl)ethanone;
2-(4-(8-(2-chloro-4-(pyrimidin-2-yloxy)phenyl)-7-fluoro-2-methyl-1H-imidazo[4,5-c]quinolin-1-yl)piperidin-1-yl)acetamide;
1-(4-(8-(2-chloro-4-(pyrimidin-2-yloxy)phenyl)-7-fluoro-2-methyl-1H-imidazo[4,5-c]quinolin-1-yl)piperidin-1-yl)-2-hydroxyethanone;
2-(4-(8-(2-chloro-4-((4-methylpyrimidin-2-yl)oxy)phenyl)-7-fluoro-1H-imidazo[4,5-c]quinolin-1-yl)-4-methylpiperidin-1-yl)ethanol;
2-(4-(8-(2-chloro-4-(pyrimidin-2-yloxy)phenyl)-7-fluoro-2-methyl-1H-imidazo[4,5-c]quinolin-1-yl)piperidin-1-yl)propan-1-ol;
2-(4-(8-(2-chloro-4-(pyrimidin-2-yloxy)phenyl)-7-fluoro-1H-imidazo[4,5-c]quinolin-1-yl)-4-methylpiperidin-1-yl)ethanol;
2-(4-(7-fluoro-8-(2-methoxy-4-((4-methylpyrimidin-2-yl)oxy)phenyl)-1H-imidazo[4,5-c]quinolin-1-yl)-4-methylpiperidin-1-yl)ethanol;
2-(4-(7-fluoro-8-(2-methoxy-4-(pyrimidin-2-yloxy)phenyl)-1H-imidazo[4,5-c]quinolin-1-yl)-4-methylpiperidin-1-yl)ethanol;
1-(4-(7-fluoro-8-(2-methoxy-4-((4-methylpyrimidin-2-yl)oxy)phenyl)-1H-imidazo[4,5-c]quinolin-1-yl)-4-methylpiperidin-1-yl)-2-hydroxypropan-1-one;
1-(4-(8-(2-chloro-4-((4-methylpyrimidin-2-yl)oxy)phenyl)-7-fluoro-1H-imidazo[4,5-c]quinolin-1-yl)-4-methylpiperidin-1-yl)-2-hydroxypropan-1-one;
1-(4-(8-(2-chloro-4-(pyrimidin-2-yloxy)phenyl)-7-fluoro-2-methyl-1H-imidazo[4,5-c]quinolin-1-yl)piperidin-1-yl)-3-hydroxy-2-(hydroxymethyl)propan-1-one;
2-((4-(8-(2-chloro-4-(pyrimidin-2-yloxy)phenyl)-7-fluoro-2-methyl-1H-imidazo[4,5-c]quinolin-1-yl)piperidin-1-yl)methyl)propane-1,3-diol;
1-(4-(7-fluoro-8-(2-methoxy-4-((4-methylpyrimidin-2-yl)oxy)phenyl)-1H-imidazo[4,5-c]quinolin-1-yl)-4-methylpiperidin-1-yl)-2-hydroxyethanone;
8-(2-chloro-4-(pyrimidin-2-yloxy)phenyl)-7-fluoro-2-methyl-1-(1-(oxetan-3-ylmethyl)piperidin-4-yl)-1H-imidazo[4,5-c]quinolone;
1-(4-(8-(2-chloro-4-((4-methylpyrimidin-2-yl)oxy)phenyl)-7-fluoro-1H-imidazo[4,5-c]quinolin-1-yl)-4-methylpiperidin-1-yl)-2-hydroxyethanone;
1-(4-(8-(2-chloro-4-(pyrimidin-2-yloxy)phenyl)-7-fluoro-1H-imidazo[4,5-c]quinolin-1-yl)-4-methylpiperidin-1-yl)-2-hydroxypropan-1-one;
1-(4-(8-(2-chloro-4-((4-methylpyrimidin-2-yl)oxy)phenyl)-7-fluoro-2-methyl-1H-imidazo[4,5-c]quinolin-1-yl)piperidin-1-yl)-2-hydroxyethanone;
1-(4-(8-(2-chloro-4-((4-methylpyrimidin-2-yl)oxy)phenyl)-7-fluoro-2-methyl-1H-imidazo[4,5-c]quinolin-1-yl)piperidin-1-yl)-2-hydroxypropan-1-one;
4-(8-(2-chloro-4-(pyrimidin-2-yloxy)phenyl)-7-fluoro-2-methyl-1H-imidazo[4,5-c]quinolin-1-yl)piperidine-1-carboxamide;

4-(8-(2-chloro-4-((4-methylpyrimidin-2-yl)oxy)phenyl)-7-fluoro-2-methyl-1H-imidazo[4,5-c]quinolin-1-yl)piperidine-1-carboxamide;

8-(2-chloro-4-((4-methylpyrimidin-2-yl)oxy)phenyl)-7-fluoro-2-methyl-1-(1-(methylsulfonyl)piperidin-4-yl)-1H-imidazo[4,5-c]quinolone;

1-(4-(8-(2-chloro-4-(pyrimidin-2-yloxy)phenyl)-7-fluoro-1H-imidazo[4,5-c]quinolin-1-yl)-4-methylpiperidin-1-yl)-2-hydroxyethanone;

(S)-1-(4-(8-(2-chloro-4-(pyrimidin-2-yloxy)phenyl)-7-fluoro-2-methyl-1H-imidazo[4,5-c]quinolin-1-yl)piperidin-1-yl)-2-hydroxypropan-1-one;

(S)-1-(4-(8-(2-chloro-4-(4-methylpyrimidin-2-yl)oxy)phenyl)-7-fluoro-2-methyl-1H-imidazo[4,5-c]quinolin-1-yl)piperidin-1-yl)-2-hydroxypropan-1-one;

2-(4-(8-(2-chloro-4-(4-methylpyrimidin-2-yl)oxy)phenyl)-7-fluoro-2-methyl-1H-imidazo[4,5-c]quinolin-1-yl)piperidin-1-yl)ethanol;

4-(7-fluoro-8-(2-methoxy-4-(4-methylpyrimidin-2-yl)oxy)phenyl)-1H-imidazo[4,5-c]quinolin-1-yl)-4-methylpiperidine-1-carboxamide;

4-(7-fluoro-8-(2-methoxy-4-(pyrimidin-2-yloxy)phenyl)-1H-imidazo[4,5-c]quinolin-1-yl)-4-methylpiperidine-1-carboxamide;

2-amino-1-(4-(8-(2-chloro-4-(pyrimidin-2-yloxy)phenyl)-7-fluoro-2-methyl-1H-imidazo[4,5-c]quinolin-1-yl)piperidin-1-yl)ethanone;

2-amino-1-(4-(8-(2-chloro-4-((4-methylpyrimidin-2-yl)oxy)phenyl)-7-fluoro-2-methyl-1H-imidazo[4,5-c]quinolin-1-yl)piperidin-1-yl)ethanone;

1-(4-(8-(2-chloro-4-((4-methylpyrimidin-2-yl)oxy)phenyl)-7-fluoro-1H-imidazo[4,5-c]quinolin-1-yl)-4-(hydroxymethyl)piperidin-1-yl)-2-hydroxyethanone;

1-(4-(8-(2-chloro-4-(pyrimidin-2-yloxy)phenyl)-7-fluoro-2-methyl-1H-imidazo[4,5-c]quinolin-1-yl)piperidin-1-yl)-2-methoxyethanone;

(S)-1-(4-(8-(2-chloro-4-(pyrimidin-2-yloxy)phenyl)-7-fluoro-2-methyl-1H-imidazo[4,5-c]quinolin-1-yl)piperidin-1-yl)-2-fluoropropan-1-one;

(R)-1-(4-(8-(2-chloro-4-(pyrimidin-2-yloxy)phenyl)-7-fluoro-2-methyl-1H-imidazo[4,5-c]quinolin-1-yl)piperidin-1-yl)-2-fluoropropan-1-one;

1-(4-(8-(2-chloro-4-((6-(hydroxymethyl)pyridin-2-yl)oxy)phenyl)-7-fluoro-2-methyl-1H-imidazo[4,5-c]quinolin-1-yl)piperidin-1-yl)-2-hydroxyethanone;

4-(8-(2-chloro-4-(pyrimidin-2-yloxy)phenyl)-7-fluoro-2-methyl-1H-imidazo[4,5-c]quinolin-1-yl)-N-(2,2,2-trifluoroethyl)piperidine-1-carboxamide;

1-(4-(8-(2-chloro-4-(4-fluoropyrimidin-2-yl)oxy)phenyl)-7-fluoro-2-methyl-1H-imidazo[4,5-c]quinolin-1-yl)piperidin-1-yl)-2-hydroxyethanone;

1-(4-(8-(2-chloro-4-(6-fluoropyridin-2-yl)oxy)phenyl)-7-fluoro-2-methyl-1H-imidazo[4,5-c]quinolin-1-yl)piperidin-1-yl)-2-hydroxyethanone;

1-(4-(8-(2-chloro-4-(5-fluoro-4-methylpyrimidin-2-yl)oxy)phenyl)-7-fluoro-2-methyl-1H-imidazo[4,5-c]quinolin-1-yl)piperidin-1-yl)-2-hydroxyethanone;

2-((3S,4S)-4-(8-(2-chloro-4-(pyrimidin-2-yloxy)phenyl)-7-fluoro-2-methyl-1H-imidazo[4,5-c]quinolin-1-yl)-3-fluoropiperidin-1-yl)-2-oxoethyl acetate;

8-(2-chloro-4-(pyrimidin-2-yloxy)phenyl)-7-fluoro-1-((3S,4S)-3-fluoro-1-(methylsulfonyl)piperidin-4-yl)-2-methyl-1H-imidazo[4,5-c]quinolone;

1-((3S,4S)-4-(8-(2-chloro-4-((4-(trifluoromethyl)pyrimidin-2-yl)oxy)phenyl)-7-fluoro-2-methyl-1H-imidazo[4,5-c]quinolin-1-yl)-3-fluoropiperidin-1-yl)-2-hydroxyethanone;

1-((3S,4S)-4-(8-(2-chloro-4-(pyrimidin-2-yloxy)phenyl)-7-fluoro-2-methyl-1H-imidazo[4,5-c]quinolin-1-yl)-3-fluoropiperidin-1-yl)-2-methoxyethanone;

1-((3S,4S)-4-(8-(2-chloro-4-(5-fluoro-4-methylpyrimidin-2-yl)oxy)phenyl)-7-fluoro-2-methyl-1H-imidazo[4,5-c]quinolin-1-yl)-3-fluoropiperidin-1-yl)-2-hydroxyethanone;

1-(4-(8-(2-chloro-4-(4-cyclopropylpyrimidin-2-yl)oxy)phenyl)-7-fluoro-2-methyl-1H-imidazo[4,5-c]quinolin-1-yl)piperidin-1-yl)-2-hydroxyethanone;

2-((3R,4R)-4-(8-(2-chloro-4-(4-methylpyrimidin-2-yl)oxy)phenyl)-7-fluoro-2-methyl-1H-imidazo[4,5-c]quinolin-1-yl)-3-fluoropiperidin-1-yl)acetonitrile;

2-((3S,4S)-4-(8-(2-chloro-4-(4-methylpyrimidin-2-yl)oxy)phenyl)-7-fluoro-2-methyl-1H-imidazo[4,5-c]quinolin-1-yl)-3-fluoropiperidin-1-yl)acetonitrile;

4-(3-chloro-4-(1-(1-(cyanomethyl)piperidin-4-yl)-7-fluoro-2-methyl-1H-imidazo[4,5-c]quinolin-8-yl)phenoxy)-6-methylpyrimidine-2-carbonitrile;

2-(4-(8-(2-chloro-4-((1-methyl-6-oxo-1,6-dihydropyrimidin-4-yl)oxy)phenyl)-7-fluoro-2-methyl-1H-imidazo[4,5-c]quinolin-1-yl)piperidin-1-yl)acetonitrile;

2-((3R,4R)-3-fluoro-4-(7-fluoro-8-(2-methoxy-4-(pyrimidin-2-yloxy)phenyl)-2-methyl-1H-imidazo[4,5-c]quinolin-1-yl)piperidin-1-yl)acetonitrile;

2-((3S,4S)-3-fluoro-4-(7-fluoro-8-(2-methoxy-4-(pyrimidin-2-yloxy)phenyl)-2-methyl-1H-imidazo[4,5-c]quinolin-1-yl)piperidin-1-yl)acetonitrile;

3-(3-chloro-4-(7-fluoro-1-(1-(2-hydroxyacetyl)piperidin-4-yl)-2-methyl-1H-imidazo[4,5-c]quinolin-8-yl)phenoxy)-1-methylpyridin-2(1H)-one;

4-(8-(2-chloro-4-(pyrimidin-2-yloxy)phenyl)-7-fluoro-1H-imidazo[4,5-c]quinolin-1-yl)-4-methylpiperidine-1-carboxamide;

4-(8-(2-chloro-4-((4-methylpyrimidin-2-yl)oxy)phenyl)-7-fluoro-1H-imidazo[4,5-c]quinolin-1-yl)-4-methylpiperidine-1-carboxamide;

1-(4-(8-(2-chloro-4-(4-methoxy-6-methylpyrimidin-2-yl)oxy)phenyl)-7-fluoro-1H-imidazo[4,5-c]quinolin-1-yl)-4-methylpiperidin-1-yl)-2-hydroxyethanone;

1-(4-(8-(2-chloro-4-(4-methylpyrimidin-2-yl)oxy)phenyl)-7-fluoro-2-methyl-1H-imidazo[4,5-c]quinolin-1-yl)piperidin-1-yl)-2-methoxyethanone;

1-((3S,4S)-4-(8-(2-chloro-4-((4-methylpyrimidin-2-yl)oxy)phenyl)-7-fluoro-2-methyl-1H-imidazo[4,5-c]quinolin-1-yl)-3-fluoropiperidin-1-yl)-2-hydroxyethanone;

6-(3-chloro-4-(7-fluoro-1-(1-(2-hydroxyacetyl)-4-methylpiperidin-4-yl)-1H-imidazo[4,5-c]quinolin-8-yl)phenoxy)-3-methylpyrimidin-4(3H)-one;

4-(7-fluoro-8-(2-fluoro-4-((4-methylpyrimidin-2-yl)oxy)phenyl)-2-methyl-1H-imidazo[4,5-c]quinolin-1-yl)piperidine-1-carboxamide;

1-(4-(7-fluoro-8-(2-fluoro-4-(4-methylpyrimidin-2-yl)oxy)phenyl)-2-methyl-1H-imidazo[4,5-c]quinolin-1-yl)piperidin-1-yl)-2-hydroxyethanone;

6-(3-chloro-4-(7-fluoro-1-(1-(2-hydroxyacetyl)piperidin-4-yl)-2-methyl-1H-imidazo[4,5-c]quinolin-8-yl)phenoxy)-3-methylpyrimidin-4(3H)-one;

4-(8-(2-chloro-4-((1-methyl-2-oxo-1,2-dihydropyridin-3-yl)oxy)phenyl)-7-fluoro-2-methyl-1H-imidazo[4,5-c]quinolin-1-yl)piperidine-1-carboxamide;

4-(8-(2-chloro-4-((1-methyl-6-oxo-1,6-dihydropyrimidin-4-yl)oxy)phenyl)-7-fluoro-2-methyl-1H-imidazo[4,5-c]quinolin-1-yl)piperidine-1-carboxamide;

4-(8-(2-chloro-4-((1-methyl-2-oxo-1,2-dihydropyridin-3-yl)oxy)phenyl)-7-fluoro-1H-imidazo[4,5-c]quinolin-1-yl)-4-methylpiperidine-1-carboxamide;
4-(7-fluoro-2-methyl-8-(2-methyl-4-(4-methylpyrimidin-2-yl)oxy)phenyl)-1H-imidazo[4,5-c]quinolin-1-yl)piperidine-1-carboxamide;
1-(4-(7-fluoro-2-methyl-8-(2-methyl-4-(4-methylpyrimidin-2-yl)oxy)phenyl)-1H-imidazo[4,5-c]quinolin-1-yl)piperidin-1-yl)-2-hydroxyethanone;
1-(4-(7-fluoro-2-methyl-8-(4-(4-methylpyrimidin-2-yl)oxy)phenyl)-1H-imidazo[4,5-c]quinolin-1-yl)piperidin-1-yl)-2-hydroxyethanone;
4-(7-fluoro-8-(2-fluoro-4-((4-methylpyrimidin-2-yl)oxy)phenyl)-1H-imidazo[4,5-c]quinolin-1-yl)-4-methylpiperidine-1-carboxamide;
4-(7-fluoro-8-(2-fluoro-4-(pyrimidin-2-yloxy)phenyl)-1H-imidazo[4,5-c]quinolin-1-yl)-4-methylpiperidine-1-carboxamide;
(S)-3-(3-chloro-4-(7-fluoro-1-(1-(2-hydroxypropanoyl)piperidin-4-yl)-2-methyl-1H-imidazo[4,5-c]quinolin-8-yl)phenoxy)-1-methylpyridin-2(1H)-one;
4-(8-(2-chloro-4-((4-methyl-3-oxo-3,4-dihydropyrazin-2-yl)oxy)phenyl)-7-fluoro-2-methyl-1H-imidazo[4,5-c]quinolin-1-yl)piperidine-1-carboxamide;
1-(4-(7-fluoro-8-(2-fluoro-4-(4-methylpyrimidin-2-yl)oxy)phenyl)-1H-imidazo[4,5-c]quinolin-1-yl)-4-methylpiperidin-1-yl)-2-hydroxyethanone;
2-(4-(8-(2-chloro-4-(pyrimidin-2-yloxy)phenyl)-7-fluoro-2-methyl-1H-imidazo[4,5-c]quinolin-1-yl)piperidin-1-yl)acetonitrile;
2-((3S,4S)-4-(8-(2-chloro-4-(pyrimidin-2-yloxy)phenyl)-7-fluoro-2-methyl-1H-imidazo[4,5-c]quinolin-1-yl)-3-fluoropiperidin-1-yl)acetonitrile;
((3S,4S)-4-(8-(2-chloro-4-(pyrimidin-2-yloxy)phenyl)-7-fluoro-2-methyl-1H-imidazo[4,5-c]quinolin-1-yl)-3-fluoropiperidin-1-yl)(oxetan-2-yl)methanone;
1-((3S,4S)-4-(8-(2-chloro-4-(5-fluoro-4-methylpyrimidin-2-yl)oxy)phenyl)-7-fluoro-2-methyl-1H-imidazo[4,5-c]quinolin-1-yl)-3-fluoropiperidin-1-yl)-2-hydroxyethanone;
1-((3S,4S)-3-fluoro-4-(7-fluoro-8-(2-methoxy-4-(pyrimidin-2-yloxy)phenyl)-2-methyl-1H-imidazo[4,5-c]quinolin-1-yl)piperidin-1-yl)-2-hydroxyethanone;
1-((3S,4S)-4-(8-(2-chloro-4-((4-(hydroxymethyl)pyrimidin-2-yl)oxy)phenyl)-7-fluoro-2-methyl-1H-imidazo[4,5-c]quinolin-1-yl)-3-fluoropiperidin-1-yl)-2-hydroxyethanone;
1-((3S,4S)-3-fluoro-4-(7-fluoro-2-methyl-8-(2-methyl-4-(pyrimidin-2-yloxy)phenyl)-1H-imidazo[4,5-c]quinolin-1-yl)piperidin-1-yl)-2-hydroxyethanone;
2-((3S,4S)-4-(8-(2-chloro-4-(pyrimidin-2-yloxy)phenyl)-7-fluoro-2-methyl-1H-imidazo[4,5-c]quinolin-1-yl)-3-fluoropiperidin-1-yl)-2-oxoethyl hydrogen sulfate;
1-((3S,4S)-3-fluoro-4-(7-fluoro-8-(2-fluoro-4-(pyrimidin-2-yloxy)phenyl)-2-methyl-1H-imidazo[4,5-c]quinolin-1-yl)piperidin-1-yl)-2-hydroxyethanone;
1-((3S,4S)-4-(8-(2-chloro-4-(pyrimidin-2-yloxy)phenyl)-7-fluoro-2-methyl-1H-imidazo[4,5-c]quinolin-1-yl)-3-fluoropiperidin-1-yl)ethanone;
(3S,4S)-4-(8-(2-chloro-4-(pyrimidin-2-yloxy)phenyl)-7-fluoro-2-methyl-1H-imidazo[4,5-c]quinolin-1-yl)-3-fluoropiperidine-1-carboxamide;
(S)-1-((3S,4S)-4-(8-(2-chloro-4-(pyrimidin-2-yloxy)phenyl)-7-fluoro-2-methyl-1H-imidazo[4,5-c]quinolin-1-yl)-3-fluoropiperidin-1-yl)-2-hydroxypropan-1-one;
1-(4-(8-(2-chloro-4-(pyrimidin-2-yloxy)phenyl)-7-fluoro-2-methyl-1H-imidazo[4,5-c]quinolin-1-yl)piperidin-1-yl)-2-fluoroethanone;
1-((3S,4S)-4-(8-(2-chloro-4-(pyrimidin-2-yloxy)phenyl)-7-fluoro-2-methyl-1H-imidazo[4,5-c]quinolin-1-yl)-3-fluoropiperidin-1-yl)-2-fluoroethanone;
1-((3S,4S)-4-(8-(2-chloro-4-(pyrimidin-2-yloxy)phenyl)-7-fluoro-2-methyl-1H-imidazo[4,5-c]quinolin-1-yl)-3-fluoropiperidin-1-yl)-3-hydroxypropan-1-one; and
1-((3S,4S)-4-(8-(2-chloro-4-((4-methoxy-1,3,5-triazin-2-yl)oxy)phenyl)-7-fluoro-2-methyl-1H-imidazo[4,5-c]quinolin-1-yl)-3-fluoropiperidin-1-yl)-2-hydroxyethanone.

9. A pharmaceutical composition comprising a compound according to claim 8, or a pharmaceutically acceptable salt thereof, and at least one pharmaceutically acceptable carrier.

10. A combination comprising a compound according to claim 8, or a pharmaceutically acceptable salt thereof, and one or more therapeutically active agents.

11. A pharmaceutical composition according to claim 9 for treating melanoma which is mediated by the activity of MEK.

12. A method of treatment of an MEK-mediated melanoma, comprising the step of administering to a patient in need thereof a therapeutically effective amount of a compound of claim 8, or a pharmaceutically acceptable salt thereof.

13. 1-((3S,4S)-4-(8-(2-chloro-4-(pyrimidin-2-yloxy)phenyl)-7-fluoro-2-methyl-1H-imidazo[4,5-c]quinolin-1-yl)-3-fluoropiperidin-1-yl)-2-hydroxyethanone:

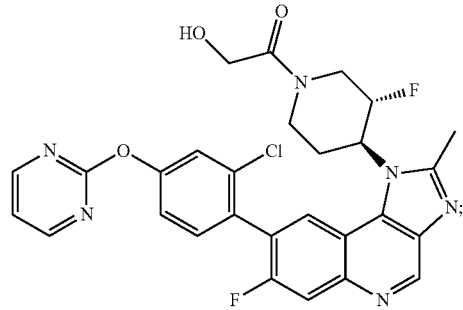 [SMILES: Cc1nc2cnc3cc(F)c(-c4ccc(Oc5ncccn5)cc4Cl)cc3c2n1[C@H]1CCN(C(=O)CO)C[C@@H]1F]

or a pharmaceutically acceptable salt thereof.

14. 1-(4-(8-(2-chloro-4-(pyrimidin-2-yloxy)phenyl)-7-fluoro-2-methyl-1H-imidazo[4,5-c]quinolin-1-yl)piperidin-1-yl)-2-hydroxyethanone:

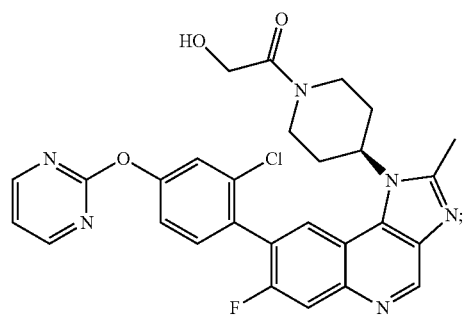

or a pharmaceutically acceptable salt thereof.

15. 1-(4-(8-(2-chloro-4-(4-methylpyrimidin-2-yl)oxy)phenyl)-7-fluoro-2-methyl-1H-imidazo[4,5-c]quinolin-1-yl)piperidin-1-yl)-2-hydroxyethanone:
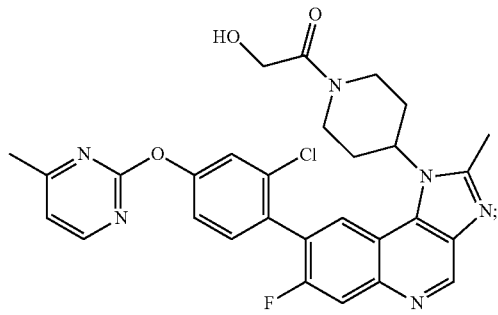
or a pharmaceutically acceptable salt thereof.
16. 1-((3S,4S)-4-(8-(2-chloro-4-((4-(trifluoromethyl)pyrimidin-2-yl)oxy)phenyl)-7-fluoro-2-methyl-1H-imidazo[4,5-c]quinolin-1-yl)-3-fluoropiperidin-1-yl)-2-hydroxyethanone:
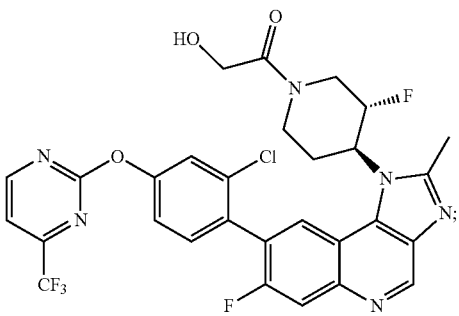 [SMILES: Cc1nc2cnc3cc(F)c(-c4ccc(Oc5nccc(C(F)(F)F)n5)cc4Cl)cc3c2n1[C@H]1CCN(C(=O)CO)C[C@@H]1F]
or a pharmaceutically acceptable salt thereof.
* * * * *

UNITED STATES PATENT AND TRADEMARK OFFICE
CERTIFICATE OF CORRECTION

PATENT NO. : 9,227,969 B2
APPLICATION NO. : 14/451563
DATED : January 5, 2016
INVENTOR(S) : Mark Gary Bock et al.

It is certified that error appears in the above-identified patent and that said Letters Patent is hereby corrected as shown below:

Claims

In column 175, the chemical name spanning from lines 47-49, Claim 7 that appears as "8-(2-chloro-4-(pyrimidin-2-yloxy)phenyl)-7-fluoro-1-(1-(2-methoxyethyl)piperidin-4-yl)-2-methyl-1H-imidazo[4,5-c]quinolone", should appear as --8-(2-chloro-4-(pyrimidin-2-yloxy)phenyl)-7-fluoro-1-(1-(2-methoxyethyl)piperidin-4-yl)-2-methyl-1H-imidazo[4,5-c]quinoline--.

In column 175, the chemical name spanning from lines 53-55, Claim 7 that appears as "8-(2-chloro-4-(pyrimidin-2-yloxy)phenyl)-7-fluoro-2-methyl-1-(1-((3-methyloxetan-3-yl)methyl)piperidin-4-yl)-1H-imidazo[4,5-c]quinolone", should appear as --8-(2-chloro-4-(pyrimidin-2-yloxy)phenyl)-7-fluoro-2-methyl-1-(1-((3-methyloxetan-3-yl)methyl)piperidin-4-yl)-1H-imidazo[4,5-c]quinoline--.

In column 175, the chemical name spanning from lines 56-58, Claim 7 that appears as "8-(2-chloro-4-(pyrimidin-2-yloxy)phenyl)-7-fluoro-2-methyl-1-(1-(methylsulfonyl)piperidin-4-yl)-1H-imidazo[4,5-c]quinolone", should appear as --8-(2-chloro-4-(pyrimidin-2-yloxy)phenyl)-7-fluoro-2-methyl-1-(1-(methylsulfonyl)piperidin-4-yl)-1H-imidazo[4,5-c]quinoline--.

In column 175, the chemical name spanning from lines 65-67, Claim 7 that appears as "8-(2-chloro-4-(pyrimidin-2-yloxy)phenyl)-1-(1-cyclopropylsulfonyl)piperidin-4-yl)-7-fluoro-2-methyl-1H-imidazo[4,5-c]quinolone", should appear as --8-(2-chloro-4-(pyrimidin-2-yloxy)phenyl)-1-(1-(cyclopropylsulfonyl)piperidin-4-yl)-7-fluoro-2-methyl-1H-imidazo[4,5-c]quinoline--.

Signed and Sealed this
Thirty-first Day of May, 2016

Michelle K. Lee
*Director of the United States Patent and Trademark Office*

Claims

In column 176, the chemical name spanning from lines 1-3, Claim 7 that appears as "8-(2-chloro-4-(pyrimidin-2-yloxy)phenyl)-7-fluoro-1-(1-(isopropylsulfonyl)piperidin-4-yl)-2-methyl-1H-imidazo[4,5-c]quinolone", should appear as --8-(2-chloro-4-(pyrimidin-2-yloxy)phenyl)-7-fluoro-1-(1-(isopropylsulfonyl)piperidin-4-yl)-2-methyl-1H-imidazo[4,5-c]quinoline--.

In column 176, the chemical name spanning from lines 50-52, Claim 7 that appears as "8-(2-chloro-4-(pyrimidin-2-yloxy)phenyl)-7-fluoro-2-methyl-1-(1-(oxetan-3-ylmethyl)piperidin-4-yl)-1H-imidazo[4,5-c]quinolone", should appear as --8-(2-chloro-4-(pyrimidin-2-yloxy)phenyl)-7-fluoro-2-methyl-1-(1-(oxetan-3-ylmethyl)piperidin-4-yl)-1H-imidazo[4,5-c]quinoline--.

In column 177, the chemical name spanning from lines 4-6, Claim 8 that appears as "8-(2-chloro-4-((4-methylpyrimidin-2-yl)oxy)phenyl)-7-fluoro-2-methyl-1-(1-(methylsulfonyl)piperidin-4-yl)-1H-imidazo[4,5-c]quinolone", should appear as --8-(2-chloro-4-((4-methylpyrimidin-2-yl)oxy)phenyl)-7-fluoro-2-methyl-1-(1-(methylsulfonyl)piperidin-4-yl)-1H-imidazo[4,5-c]quinoline--.

In column 177, the chemical name spanning from lines 61-63, Claim 8 that appears as "8-(2-chloro-4-(pyrimidin-2-yloxy)phenyl)-7-fluoro-1-((3S,4S)-3-fluoro-1-(methylsulfonyl)piperidin-4-yl)-2-methyl-1H-imidazo[4,5-c]quinolone", should appear as --8-(2-chloro-4-(pyrimidin-2-yloxy)phenyl)-7-fluoro-1-((3S,4S)-3-fluoro-1-(methylsulfonyl)piperidin-4-yl)-2-methyl-1H-imidazo[4,5-c]quinoline--.